United States Patent
Rousseau et al.

(10) Patent No.: US 9,453,076 B2
(45) Date of Patent: Sep. 27, 2016

(54) ANTI-TLR4 ANTIBODIES AND USES THEREOF

(71) Applicant: NovImmune S.A., Geneva (CH)

(72) Inventors: Francois Rousseau, Collonges Sous Saleve (FR); Jeremy Loyau, Annemasse (FR); Nicolas Fischer, Geneva (CH); Greg Elson, Collonges Sous Saleve (FR); Marie Kosco-Vilbois, Minzier (FR)

(73) Assignee: NOVIMMUNE S.A., Geneva (CH)

( * ) Notice: Subject to any disclaimer, the term of this patent is extended or adjusted under 35 U.S.C. 154(b) by 0 days.

(21) Appl. No.: 13/853,158

(22) Filed: Mar. 29, 2013

(65) Prior Publication Data

US 2013/0315914 A1 Nov. 28, 2013

Related U.S. Application Data

(60) Provisional application No. 61/617,164, filed on Mar. 29, 2012.

(51) Int. Cl.
| | |
|---|---|
| C07K 16/28 | (2006.01) |
| A61K 39/395 | (2006.01) |
| C07K 14/705 | (2006.01) |

(52) U.S. Cl.
CPC ....... C07K 16/2866 (2013.01); C07K 16/2896 (2013.01); *C07K 2316/96* (2013.01); *C07K 2317/24* (2013.01); *C07K 2317/33* (2013.01); *C07K 2317/34* (2013.01); *C07K 2317/51* (2013.01); *C07K 2317/515* (2013.01); *C07K 2317/565* (2013.01); *C07K 2317/75* (2013.01); *C07K 2317/92* (2013.01)

(58) Field of Classification Search
None
See application file for complete search history.

(56) References Cited

U.S. PATENT DOCUMENTS 7,674,884 B2   3/2010   Elson et al.

FOREIGN PATENT DOCUMENTS

| WO | WO-2005065015 A2 | * | 7/2005 |
|---|---|---|---|
| WO | WO-2006077471 A2 | * | 7/2006 |
| WO | WO-2007110678 A2 | * | 10/2007 |
| WO | WO-2009101479 A2 | * | 8/2009 |
| WO | WO 2009/138494 A2 | | 11/2009 |

OTHER PUBLICATIONS

Akashi-Takamura et al. Agonistic antibody to TLR4/MD-2 protects mice from acute lethal hepatitis induced by TNFalpha. J Immunol 176: 4244-4251, 2006.*
Bahrun et al. Preparation and characterization of agonistic monoclonal antibodies against toll-like receptor 4-MD-2 complex. Hybridoma 26(6): 393-400, 2007.*
Daubeuf et al. TLR4/MD-2 monoclonal antibody therapy affords protection in experimental models of septic shock. J Immunol 179: 6107-6114, 2007.*
Dunn-Siegrist et al. Pivotal involvement of Fcgamma receptor IIA in the neutralization of lipopolysaccharide signaling via a potent novel anti-TLR4 monoclonal antibody 15C1. J Biol Chem 282(48): 34817-34827, 2007.*
Loyau et al. Maximizing the potentcy of an anti-TLR4 monoclonal antibody by exploiting proximity to Fcgamma receptors. mAbs 6(6): 1621-1630, 2014.*
Pugin et al. Soluble MD-2 activity in plasma from patients with severe sepsis and septic shock. Blood 104: 4071-4079, 2004.*
Tsukamoto et al. Multople potential regulatory sites of TLR4 activation induced by LPS as revealed by novel inhibitory human TLR4 mAbs. Int Immunol 24(8): 495-506, Apr. 12, 2012.*
InvivoGen: "Mab-hTLR4" Retrieved from the Internet: URL:http://www.invivogen.corn/PDF/MAB_hTLR4TDS.pdf (Aug. 21, 2013).
Ravn et al., "By-passing in vitro screening—next generation sequencing technologies applied to antibody display and in silico candidate selection." Nucleic Acids Res. Nov. 2010; vol. 38(21):e193.
S. Spiller et al., "TLR4-induced I FN-production increases TLR2 sensitivity and drives Gram-negative sepsis in mice". J Exp Med. Aug. 4, 2008; vol. 205(8): pp. 1747-1754.
International Search Report and Written Opinion issued on Nov. 6, 2013 for PCT/US2013/034543, mailed Dec. 12, 2013; 22 pages.

* cited by examiner

*Primary Examiner* — Bridget E Bunner
(74) *Attorney, Agent, or Firm* — Cooley LLP; Ivor R. Elrifi

(57) ABSTRACT

Disclosed are antibodies that specifically bind Toll-like Receptor 4 (TLR-4), and to methods of using the anti-TLR4 antibodies as therapeutics and diagnostic agents.

13 Claims, 11 Drawing Sheets

```
15C1 CDRH3                    97 ARKDPSDAFPY 107
(SEQ ID NO:44)

Human TLR4   325 DFSYNFGWQHLELVNCKFGQFPTLKLKSLKRLTFTSNKGGNAFSEVSLPS 374
(From SEQ ID NO: 23)

1E11 CDRH3                    97 ARKDSGNYFPY 107
(SEQ ID NO:7)

Cyno TLR4    325 DFSYNFRWQHLELVNCKFEQFPTLELKSLKRLTFTANKGGNAFSEVSLPS 374
(From SEQ ID NO: 24)

1G12 CDRH3                    97 ARKDSGRYWPY 107
(SEQ ID NO:37)
```

FIGURE 15
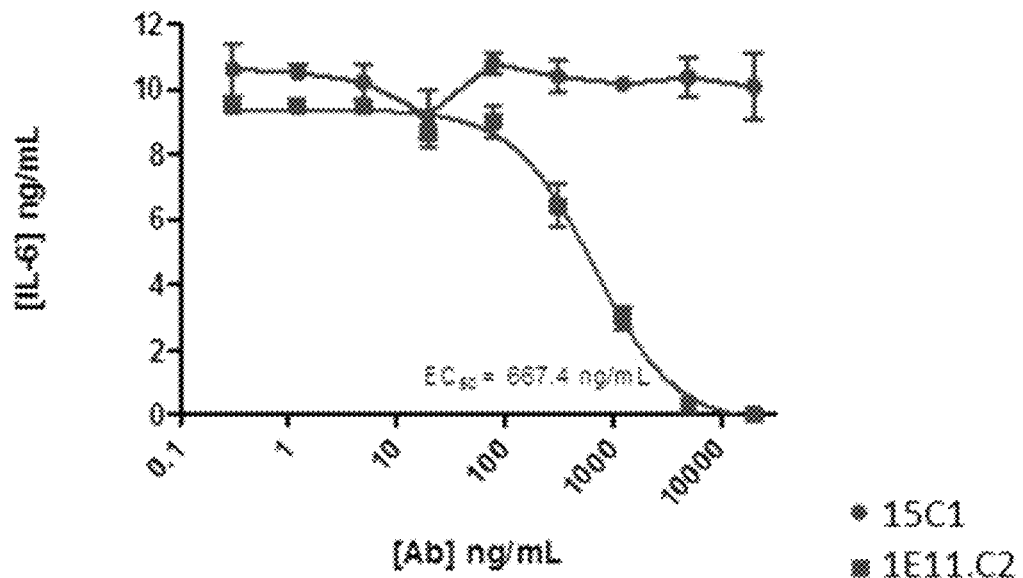
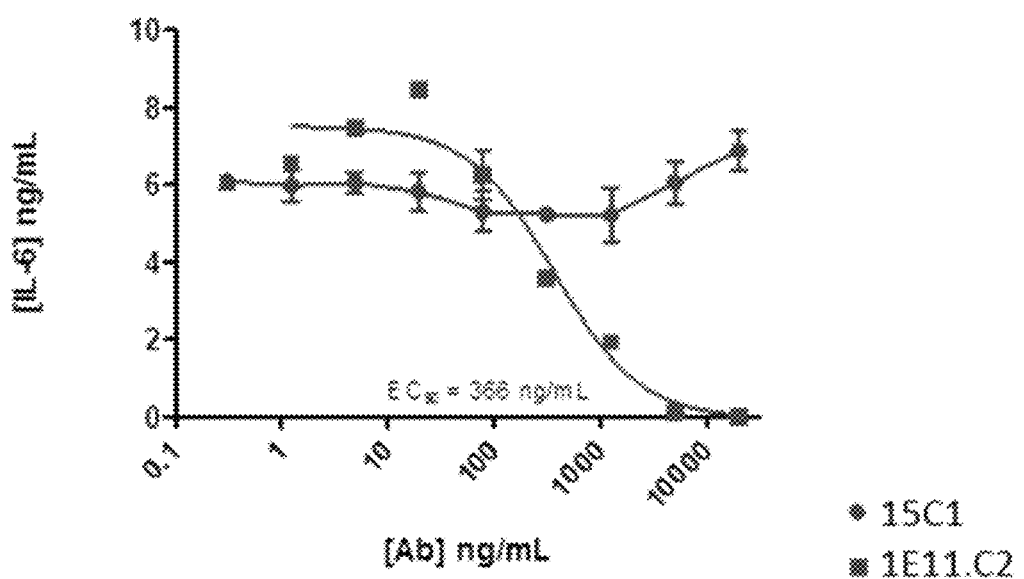

SEQUENCE LISTING

<160> NUMBER OF SEQ ID NOS: 112

<210> SEQ ID NO 1
<211> LENGTH: 354
<212> TYPE: DNA
<213> ORGANISM: Artificial Sequence
<220> FEATURE:
<223> OTHER INFORMATION: chemically synthesized

<400> SEQUENCE: 1

```
caggtgcagc ttcaggagtc cggcccagga ctggtgaagc cttcggacac cctgtccctc      60
acctgcgctg tctctggtta ctccatcacc ggtggttata gctggcactg gatacggcag     120
cccccaggga agggactgga gtggatgggg tatatccact acagtggtta cactgacttc     180
aaccccctccc tcaagactcg aatcaccata tcacgtgaca cgtccaagaa ccagttctcc    240
ctgaagctga gctctgtgac cgctgtggac actgcagtgt attactgtgc gagaaaagat    300
tcgggcaact acttccctta ctggggccaa gggactctgg tcactgtctc ttcc          354
```

<210> SEQ ID NO 2
<211> LENGTH: 118
<212> TYPE: PRT
<213> ORGANISM: Artificial Sequence
<220> FEATURE:
<223> OTHER INFORMATION: chemically synthesized

<400> SEQUENCE: 2

```
Gln Val Gln Leu Gln Glu Ser Gly Pro Gly Leu Val Lys Pro Ser Asp
  1               5                  10                  15
Thr Leu Ser Leu Thr Cys Ala Val Ser Gly Tyr Ser Ile Thr Gly Gly
             20                  25                  30
Tyr Ser Trp His Trp Ile Arg Gln Pro Pro Gly Lys Gly Leu Glu Trp
         35                  40                  45
Met Gly Tyr Ile His Tyr Ser Gly Tyr Thr Asp Phe Asn Pro Ser Leu
     50                  55                  60
Lys Thr Arg Ile Thr Ile Ser Arg Asp Thr Ser Lys Asn Gln Phe Ser
 65                  70                  75                  80
Leu Lys Leu Ser Ser Val Thr Ala Val Asp Thr Ala Val Tyr Tyr Cys
                 85                  90                  95
Ala Arg Lys Asp Ser Gly Asn Tyr Phe Pro Tyr Trp Gly Gln Gly Thr
                100                 105                 110
Leu Val Thr Val Ser Ser
            115
```

<210> SEQ ID NO 3
<211> LENGTH: 321
<212> TYPE: DNA
<213> ORGANISM: Artificial Sequence
<220> FEATURE:
<223> OTHER INFORMATION: chemically synthesized

<400> SEQUENCE: 3

```
gaaattgtgt tgacgcagtc tccagacttt cagtctgtga ctccaaagga aaaagtcacc      60
atcacctgca gggccagtca gagtatcagc gaccacttac actggtacca acagaaacct    120
gatcagtctc ccaagctcct catcaaatat gcttcccatg ccatttctgg ggtcccatcg    180
aggttcagtg gcagtgggtc tgggacagac ttcactctca ccatcaatag cctagaggct    240
gaagatgctg caacgtatta ctgtcagcag ggtcacagtt ttccgctcac tttcggcgga    300
gggaccaagg tggagatcaa a                                             321
```

<210> SEQ ID NO 4
<211> LENGTH: 107
<212> TYPE: PRT
<213> ORGANISM: Artificial Sequence
<220> FEATURE:
<223> OTHER INFORMATION: chemically synthesized

<400> SEQUENCE: 4

```
Glu Ile Val Leu Thr Gln Ser Pro Asp Phe Gln Ser Val Thr Pro Lys
 1               5                  10                  15

Glu Lys Val Thr Ile Thr Cys Arg Ala Ser Gln Ser Ile Ser Asp His
            20                  25                  30

Leu His Trp Tyr Gln Gln Lys Pro Asp Gln Ser Pro Lys Leu Leu Ile
         35                  40                  45

Lys Tyr Ala Ser His Ala Ile Ser Gly Val Pro Ser Arg Phe Ser Gly
     50                  55                  60

Ser Gly Ser Gly Thr Asp Phe Thr Leu Thr Ile Asn Ser Leu Glu Ala
 65                  70                  75                  80

Glu Asp Ala Ala Thr Tyr Tyr Cys Gln Gln Gly His Ser Phe Pro Leu
                 85                  90                  95

Thr Phe Gly Gly Gly Thr Lys Val Glu Ile Lys
            100                 105
```

<210> SEQ ID NO 5
<211> LENGTH: 354
<212> TYPE: DNA
<213> ORGANISM: Artificial Sequence
<220> FEATURE:
<223> OTHER INFORMATION: chemically synthesized

<400> SEQUENCE: 5

```
caggtgcagc ttcaggagtc cggcccagga ctggtgaagc cttcggacac cctgtccctc      60
acctgcgctg tctctggtta ctccatcacc ggtggttata ctggcactg gatacggcag     120
cccccaggga agggactgga gtggatgggg tatatccact acagtggtta cactgacttc     180
aaccctcccc tcaagactcg aatcaccata tcacgtgaca cgtccaagaa ccagttctcc     240
ctgaagctga gctctgtgac cgctgtggac actgcagtgt attactgtgc gagaaaagat     300
tccggccgcc tcctcccta ctggggccaa gggactctgg tcactgtctc ttcc             354
```

<210> SEQ ID NO 6
<211> LENGTH: 118
<212> TYPE: PRT
<213> ORGANISM: Artificial Sequence
<220> FEATURE:
<223> OTHER INFORMATION: chemically synthesized

<400> SEQUENCE: 6

```
Gln Val Gln Leu Gln Glu Ser Gly Pro Gly Leu Val Lys Pro Ser Asp
 1               5                  10                  15

Thr Leu Ser Leu Thr Cys Ala Val Ser Gly Tyr Ser Ile Thr Gly Gly
            20                  25                  30

Tyr Ser Trp His Trp Ile Arg Gln Pro Pro Gly Lys Gly Leu Glu Trp
         35                  40                  45

Met Gly Tyr Ile His Tyr Ser Gly Tyr Thr Asp Phe Asn Pro Ser Leu
     50                  55                  60

Lys Thr Arg Ile Thr Ile Ser Arg Asp Thr Ser Lys Asn Gln Phe Ser
 65                  70                  75                  80
```

```
Leu Lys Leu Ser Ser Val Thr Ala Val Asp Thr Ala Val Tyr Tyr Cys
             85                  90                  95

Ala Arg Lys Asp Ser Gly Arg Leu Leu Pro Tyr Trp Gly Gln Gly Thr
            100                 105                 110

Leu Val Thr Val Ser Ser
        115

<210> SEQ ID NO 7
<211> LENGTH: 354
<212> TYPE: DNA
<213> ORGANISM: Artificial Sequence
<220> FEATURE:
<223> OTHER INFORMATION: chemically synthesized

<400> SEQUENCE: 7
caggtgcagc ttcaggagtc cggcccagga ctggtgaagc cttcggacac cctgtccctc      60
acctgcgctg tctctggtta ctccatcacc ggtggttata gctggcactg gatacggcag     120
cccccaggga agggactgga gtggatgggg tatatccact acagtggtta cactgacttc     180 aaccccctccc tcaagactcg aatcaccata tcacgtgaca cgtccaagaa ccagttctcc    240
ctgaagctga gctctgtgac cgctgtggac actgcagtgt attactgtgc gagaaaagat    300
agcggcaagt ggttgcctta ctggggccaa gggactctgg tcactgtctc ttcc           354

<210> SEQ ID NO 8
<211> LENGTH: 118
<212> TYPE: PRT
<213> ORGANISM: Artificial Sequence
<220> FEATURE:
<223> OTHER INFORMATION: chemically synthesized

<400> SEQUENCE: 8

Gln Val Gln Leu Gln Glu Ser Gly Pro Gly Leu Val Lys Pro Ser Asp
1               5                   10                  15

Thr Leu Ser Leu Thr Cys Ala Val Ser Gly Tyr Ser Ile Thr Gly Gly
            20                  25                  30

Tyr Ser Trp His Trp Ile Arg Gln Pro Pro Gly Lys Gly Leu Glu Trp
        35                  40                  45

Met Gly Tyr Ile His Tyr Ser Gly Tyr Thr Asp Phe Asn Pro Ser Leu
    50                  55                  60

Lys Thr Arg Ile Thr Ile Ser Arg Asp Thr Ser Lys Asn Gln Phe Ser
65                  70                  75                  80

Leu Lys Leu Ser Ser Val Thr Ala Val Asp Thr Ala Val Tyr Tyr Cys
             85                  90                  95

Ala Arg Lys Asp Ser Gly Lys Trp Leu Pro Tyr Trp Gly Gln Gly Thr
            100                 105                 110

Leu Val Thr Val Ser Ser
        115

<210> SEQ ID NO 9
<211> LENGTH: 354
<212> TYPE: DNA
<213> ORGANISM: Artificial Sequence
<220> FEATURE:
<223> OTHER INFORMATION: chemically synthesized

<400> SEQUENCE: 9
caggtgcagc ttcaggagtc cggcccagga ctggtgaagc cttcggacac cctgtccctc      60
acctgcgctg tctctggtta ctccatcacc ggtggttata gctggcactg gatacggcag     120
```

```
cccccaggga agggactgga gtggatgggg tatatccact acagtggtta cactgacttc    180
aacccctccc tcaagactcg aatcaccata tcacgtgaca cgtccaagaa ccagttctcc    240
ctgaagctga gctctgtgac cgctgtggac actgcagtgt attactgtgc gagaaaagat    300
agcgggcacc tcatgcctta ctggggccaa gggactctgg tcactgtctc ttcc          354
```

<210> SEQ ID NO 10
<211> LENGTH: 118
<212> TYPE: PRT
<213> ORGANISM: Artificial Sequence
<220> FEATURE:
<223> OTHER INFORMATION: chemically synthesized

<400> SEQUENCE: 10

```
Gln Val Gln Leu Gln Glu Ser Gly Pro Gly Leu Val Lys Pro Ser Asp
1               5                   10                  15

Thr Leu Ser Leu Thr Cys Ala Val Ser Gly Tyr Ser Ile Thr Gly Gly
            20                  25                  30

Tyr Ser Trp His Trp Ile Arg Gln Pro Pro Gly Lys Gly Leu Glu Trp
        35                  40                  45

Met Gly Tyr Ile His Tyr Ser Gly Tyr Thr Asp Phe Asn Pro Ser Leu
    50                  55                  60

Lys Thr Arg Ile Thr Ile Ser Arg Asp Thr Ser Lys Asn Gln Phe Ser
65                  70                  75                  80

Leu Lys Leu Ser Ser Val Thr Ala Val Asp Thr Ala Val Tyr Tyr Cys
                85                  90                  95

Ala Arg Lys Asp Ser Gly His Leu Met Pro Tyr Trp Gly Gln Gly Thr
            100                 105                 110

Leu Val Thr Val Ser Ser
        115
```

<210> SEQ ID NO 11
<211> LENGTH: 354
<212> TYPE: DNA
<213> ORGANISM: Artificial Sequence
<220> FEATURE:
<223> OTHER INFORMATION: chemically synthesized

<400> SEQUENCE: 11

```
caggtgcagc ttcaggagtc cggcccagga ctggtgaagc cttcggacac cctgtccctc    60
acctgcgctg tctctggtta ctccatcacc ggtggttata gctggcactg gatacggcag    120
cccccaggga agggactgga gtggatgggg tatatccact acagtggtta cactgacttc    180
aacccctccc tcaagactcg aatcaccata tcacgtgaca cgtccaagaa ccagttctcc    240
ctgaagctga gctctgtgac cgctgtggac actgcagtgt attactgtgc gagaaaagat    300
tccgggcaca actaccctta ctggggccaa gggactctgg tcactgtctc ttcc          354
```

<210> SEQ ID NO 12
<211> LENGTH: 118
<212> TYPE: PRT
<213> ORGANISM: Artificial Sequence
<220> FEATURE:
<223> OTHER INFORMATION: chemically synthesized

<400> SEQUENCE: 12

```
Gln Val Gln Leu Gln Glu Ser Gly Pro Gly Leu Val Lys Pro Ser Asp
1               5                   10                  15

Thr Leu Ser Leu Thr Cys Ala Val Ser Gly Tyr Ser Ile Thr Gly Gly
            20                  25                  30
```

```
        Tyr Ser Trp His Trp Ile Arg Gln Pro Pro Gly Lys Gly Leu Glu Trp
                35                  40                  45

Met Gly Tyr Ile His Tyr Ser Gly Tyr Thr Asp Phe Asn Pro Ser Leu
         50                  55                  60

Lys Thr Arg Ile Thr Ile Ser Arg Asp Thr Ser Lys Asn Gln Phe Ser
         65                  70                  75                  80

Leu Lys Leu Ser Ser Val Thr Ala Val Asp Thr Ala Val Tyr Tyr Cys
                        85                  90                  95

Ala Arg Lys Asp Ser Gly His Asn Tyr Pro Tyr Trp Gly Gln Gly Thr
                    100                 105                 110

Leu Val Thr Val Ser Ser
                    115

<210> SEQ ID NO 13
<211> LENGTH: 354
<212> TYPE: DNA
<213> ORGANISM: Artificial Sequence
<220> FEATURE:
<223> OTHER INFORMATION: chemically synthesized

<400> SEQUENCE: 13
caggtgcagc ttcaggagtc cggcccagga ctggtgaagc cttcggacac cctgtccctc      60
acctgcgctg tctctggtta ctccatcacc ggtggttata ctggcactg gatacgcag     120 cccccaggga agggactgga gtggatgggg tatatccact acagtggtta cactgacttc     180
aacccctccc tcaagactcg aatcaccata tcacgtgaca cgtccaagaa ccagttctcc     240
ctgaagctga gctctgtgac cgctgtggac actgcagtgt attactgtgc gagaaaagat     300
agcggcaaga acttccctta ctggggccaa gggactctgg tcactgtctc ttcc           354

<210> SEQ ID NO 14
<211> LENGTH: 118
<212> TYPE: PRT
<213> ORGANISM: Artificial Sequence
<220> FEATURE:
<223> OTHER INFORMATION: chemically synthesized

<400> SEQUENCE: 14

Gln Val Gln Leu Gln Glu Ser Gly Pro Gly Leu Val Lys Pro Ser Asp
         1               5                  10                  15

Thr Leu Ser Leu Thr Cys Ala Val Ser Gly Tyr Ser Ile Thr Gly Gly
                        20                  25                  30

Tyr Ser Trp His Trp Ile Arg Gln Pro Pro Gly Lys Gly Leu Glu Trp
                    35                  40                  45

Met Gly Tyr Ile His Tyr Ser Gly Tyr Thr Asp Phe Asn Pro Ser Leu
         50                  55                  60

Lys Thr Arg Ile Thr Ile Ser Arg Asp Thr Ser Lys Asn Gln Phe Ser
         65                  70                  75                  80

Leu Lys Leu Ser Ser Val Thr Ala Val Asp Thr Ala Val Tyr Tyr Cys
                        85                  90                  95

Ala Arg Lys Asp Ser Gly Lys Asn Phe Pro Tyr Trp Gly Gln Gly Thr
                    100                 105                 110

Leu Val Thr Val Ser Ser
                    115

<210> SEQ ID NO 15
<211> LENGTH: 354
<212> TYPE: DNA
```

<210> SEQ ID NO 15
<211> LENGTH: 354
<212> TYPE: DNA
<213> ORGANISM: Artificial Sequence
<220> FEATURE:
<223> OTHER INFORMATION: chemically synthesized

<400> SEQUENCE: 15

```
caggtgcagc ttcaggagtc cggcccagga ctggtgaagc cttcggacac cctgtccctc      60
acctgcgctg tctctggtta ctccatcacc ggtggttata gctggcactg gatacggcag     120
cccccaggga agggactgga gtggatgggg tatatccact acagtggtta cactgacttc     180
aacccctccc tcaagactcg aatcaccata tcacgtgaca cgtccaagaa ccagttctcc     240
ctgaagctga gctctgtgac cgctgtggac actgcagtgt attactgtgc gagaaaagat     300
agcggccagt tgttcccctta ctggggccaa gggactctgg tcactgtctc ttcc          354
```

<210> SEQ ID NO 16
<211> LENGTH: 118
<212> TYPE: PRT
<213> ORGANISM: Artificial Sequence
<220> FEATURE:
<223> OTHER INFORMATION: chemically synthesized

<400> SEQUENCE: 16

```
Gln Val Gln Leu Gln Glu Ser Gly Pro Gly Leu Val Lys Pro Ser Asp
1               5                   10                  15
Thr Leu Ser Leu Thr Cys Ala Val Ser Gly Tyr Ser Ile Thr Gly Gly
            20                  25                  30
Tyr Ser Trp His Trp Ile Arg Gln Pro Pro Gly Lys Gly Leu Glu Trp
        35                  40                  45
Met Gly Tyr Ile His Tyr Ser Gly Tyr Thr Asp Phe Asn Pro Ser Leu
    50                  55                  60
Lys Thr Arg Ile Thr Ile Ser Arg Asp Thr Ser Lys Asn Gln Phe Ser
65                  70                  75                  80
Leu Lys Leu Ser Ser Val Thr Ala Val Asp Thr Ala Val Tyr Tyr Cys
                85                  90                  95
Ala Arg Lys Asp Ser Gly Gln Leu Phe Pro Tyr Trp Gly Gln Gly Thr
            100                 105                 110
Leu Val Thr Val Ser Ser
        115
```

<210> SEQ ID NO 17
<211> LENGTH: 354
<212> TYPE: DNA
<213> ORGANISM: Artificial Sequence
<220> FEATURE:
<223> OTHER INFORMATION: chemically synthesized

<400> SEQUENCE: 17

```
caggtgcagc ttcaggagtc cggcccagga ctggtgaagc cttcggacac cctgtccctc      60
acctgcgctg tctctggtta ctccatcacc ggtggttata gctggcactg gatacggcag     120
cccccaggga agggactgga gtggatgggg tatatccact acagtggtta cactgacttc     180
aacccctccc tcaagactcg aatcaccata tcacgtgaca cgtccaagaa ccagttctcc     240
ctgaagctga gctctgtgac cgctgtggac actgcagtgt attactgtgc gagaaaagat     300
agcggccaca acttgcctta ctggggccaa gggactctgg tcactgtctc ttcc           354
```

<210> SEQ ID NO 18
<211> LENGTH: 118
<212> TYPE: PRT
<213> ORGANISM: Artificial Sequence
<220> FEATURE:
<223> OTHER INFORMATION: chemically synthesized

<400> SEQUENCE: 18

Gln Val Gln Leu Gln Glu Ser Gly Pro Gly Leu Val Lys Pro Ser Asp
1               5                   10                  15

Thr Leu Ser Leu Thr Cys Ala Val Ser Gly Tyr Ser Ile Thr Gly Gly
            20                  25                  30

Tyr Ser Trp His Trp Ile Arg Gln Pro Pro Gly Lys Gly Leu Glu Trp
        35                  40                  45

Met Gly Tyr Ile His Tyr Ser Gly Tyr Thr Asp Phe Asn Pro Ser Leu
    50                  55                  60

Lys Thr Arg Ile Thr Ile Ser Arg Asp Thr Ser Lys Asn Gln Phe Ser
65                  70                  75                  80

Leu Lys Leu Ser Ser Val Thr Ala Val Asp Thr Ala Val Tyr Tyr Cys
                85                  90                  95

Ala Arg Lys Asp Ser Gly His Asn Leu Pro Tyr Trp Gly Gln Gly Thr
            100                 105                 110

Leu Val Thr Val Ser Ser
        115

<210> SEQ ID NO 19
<211> LENGTH: 354
<212> TYPE: DNA
<213> ORGANISM: Artificial Sequence
<220> FEATURE:
<223> OTHER INFORMATION: chemically synthesized

<400> SEQUENCE: 19
caggtgcagc ttcaggagtc cggcccagga ctggtgaagc cttcggacac cctgtccctc    60
acctgcgctg tctctggtta ctccatcacc ggtggttata gctggcactg gatacggcag   120
cccccaggga agggactgga gtggatgggg tatatccact acagtggtta cactgacttc   180
aaccccctccc tcaagactcg aatcaccata tcacgtgaca cgtccaagaa ccagttctcc   240
ctgaagctga gctctgtgac cgctgtggac actgcagtgt attactgtgc gagaaaagat   300
tcgggcgact acttccctta ctggggccaa gggactctgg tcactgtctc ttcc          354

<210> SEQ ID NO 20
<211> LENGTH: 118
<212> TYPE: PRT
<213> ORGANISM: Artificial Sequence
<220> FEATURE:
<223> OTHER INFORMATION: chemically synthesized

<400> SEQUENCE: 20

Gln Val Gln Leu Gln Glu Ser Gly Pro Gly Leu Val Lys Pro Ser Asp
1               5                   10                  15

Thr Leu Ser Leu Thr Cys Ala Val Ser Gly Tyr Ser Ile Thr Gly Gly
            20                  25                  30

Tyr Ser Trp His Trp Ile Arg Gln Pro Pro Gly Lys Gly Leu Glu Trp
        35                  40                  45

Met Gly Tyr Ile His Tyr Ser Gly Tyr Thr Asp Phe Asn Pro Ser Leu
    50                  55                  60

Lys Thr Arg Ile Thr Ile Ser Arg Asp Thr Ser Lys Asn Gln Phe Ser
65                  70                  75                  80

Leu Lys Leu Ser Ser Val Thr Ala Val Asp Thr Ala Val Tyr Tyr Cys
                85                  90                  95

Ala Arg Lys Asp Ser Gly Asp Tyr Phe Pro Tyr Trp Gly Gln Gly Thr
            100                 105                 110

Leu Val Thr Val Ser Ser
        115

<210> SEQ ID NO 21
<211> LENGTH: 354
<212> TYPE: DNA
<213> ORGANISM: Artificial Sequence
<220> FEATURE:
<223> OTHER INFORMATION: chemically synthesized

<400> SEQUENCE: 21
caggtgcagc ttcaggagtc cggcccagga ctggtgaagc cttcggacac cctgtccctc     60
acctgcgctg tctctggtta ctccatcacc ggtggttata gctggcactg gatacggcag    120
cccccaggga agggactgga gtggatgggg tatatccact acagtggtta cactgacttc    180
aaccccctcc tcaagactcg aatcaccata tcacgtgaca cgtccaagaa ccagttctcc    240
ctgaagctga gctctgtgac cgctgtggac actgcagtgt attactgtgc gagaaaagat    300
tccgggcggt actggcctta ctggggccaa gggactctgg tcactgtctc ttcc          354

<210> SEQ ID NO 22
<211> LENGTH: 118
<212> TYPE: PRT
<213> ORGANISM: Artificial Sequence
<220> FEATURE:
<223> OTHER INFORMATION: chemically synthesized

<400> SEQUENCE: 22

Gln Val Gln Leu Gln Glu Ser Gly Pro Gly Leu Val Lys Pro Ser Asp
1               5                   10                  15

Thr Leu Ser Leu Thr Cys Ala Val Ser Gly Tyr Ser Ile Thr Gly Gly
            20                  25                  30

Tyr Ser Trp His Trp Ile Arg Gln Pro Pro Gly Lys Gly Leu Glu Trp
        35                  40                  45

Met Gly Tyr Ile His Tyr Ser Gly Tyr Thr Asp Phe Asn Pro Ser Leu
    50                  55                  60

Lys Thr Arg Ile Thr Ile Ser Arg Asp Thr Ser Lys Asn Gln Phe Ser
65                  70                  75                  80

Leu Lys Leu Ser Ser Val Thr Ala Val Asp Thr Ala Val Tyr Tyr Cys
                85                  90                  95

Ala Arg Lys Asp Ser Gly Arg Tyr Trp Pro Tyr Trp Gly Gln Gly Thr
            100                 105                 110

Leu Val Thr Val Ser Ser
        115

<210> SEQ ID NO 23
<211> LENGTH: 489
<212> TYPE: DNA
<213> ORGANISM: Artificial Sequence
<220> FEATURE:
<223> OTHER INFORMATION: chemically synthesized
<220> FEATURE:
<221> NAME/KEY: misc_feature
<222> LOCATION: (23)..(23)
<223> OTHER INFORMATION: n is a, c, g, or t
<220> FEATURE:
<221> NAME/KEY: misc_feature
<222> LOCATION: (28)..(28)
<223> OTHER INFORMATION: n is a, c, g, or t
<220> FEATURE:
<221> NAME/KEY: misc_feature

```
<222> LOCATION: (32)..(32)
<223> OTHER INFORMATION: n is a, c, g, or t
<220> FEATURE:
<221> NAME/KEY: misc_feature
<222> LOCATION: (36)..(36)
<223> OTHER INFORMATION: n is a, c, g, or t
<220> FEATURE:
<221> NAME/KEY: misc_feature
<222> LOCATION: (39)..(39)
<223> OTHER INFORMATION: n is a, c, g, or t
<220> FEATURE:
<221> NAME/KEY: misc_feature
<222> LOCATION: (64)..(64)
<223> OTHER INFORMATION: n is a, c, g, or t
<220> FEATURE:
<221> NAME/KEY: misc_feature
<222> LOCATION: (78)..(78)
<223> OTHER INFORMATION: n is a, c, g, or t
<220> FEATURE:
<221> NAME/KEY: misc_feature
<222> LOCATION: (81)..(81)
<223> OTHER INFORMATION: n is a, c, g, or t
<220> FEATURE:
<221> NAME/KEY: misc_feature
<222> LOCATION: (87)..(87)
<223> OTHER INFORMATION: n is a, c, g, or t
<220> FEATURE:
<221> NAME/KEY: misc_feature
<222> LOCATION: (91)..(91)
<223> OTHER INFORMATION: n is a, c, g, or t
<220> FEATURE:
<221> NAME/KEY: misc_feature
<222> LOCATION: (96)..(96)
<223> OTHER INFORMATION: n is a, c, g, or t
<220> FEATURE:
<221> NAME/KEY: misc_feature
<222> LOCATION: (98)..(98)
<223> OTHER INFORMATION: n is a, c, g, or t
<220> FEATURE:
<221> NAME/KEY: misc_feature
<222> LOCATION: (103)..(103)
<223> OTHER INFORMATION: n is a, c, g, or t
<220> FEATURE:
<221> NAME/KEY: misc_feature
<222> LOCATION: (114)..(114)
<223> OTHER INFORMATION: n is a, c, g, or t
<220> FEATURE:
<221> NAME/KEY: misc_feature
<222> LOCATION: (118)..(118)
<223> OTHER INFORMATION: n is a, c, g, or t
<220> FEATURE:
<221> NAME/KEY: misc_feature
<222> LOCATION: (120)..(120)
<223> OTHER INFORMATION: n is a, c, g, or t
<220> FEATURE:
<221> NAME/KEY: misc_feature
<222> LOCATION: (129)..(130)
<223> OTHER INFORMATION: n is a, c, g, or t
<220> FEATURE:
<221> NAME/KEY: misc_feature
<222> LOCATION: (133)..(133)
<223> OTHER INFORMATION: n is a, c, g, or t
<220> FEATURE:
<221> NAME/KEY: misc_feature
<222> LOCATION: (148)..(148)
<223> OTHER INFORMATION: n is a, c, g, or t
<220> FEATURE:
<221> NAME/KEY: misc_feature
<222> LOCATION: (150)..(150)
<223> OTHER INFORMATION: n is a, c, g, or t
<220> FEATURE:
<221> NAME/KEY: misc_feature
<222> LOCATION: (158)..(158)
<223> OTHER INFORMATION: n is a, c, g, or t
<220> FEATURE:
<221> NAME/KEY: misc_feature
<222> LOCATION: (169)..(169)
<223> OTHER INFORMATION: n is a, c, g, or t
<220> FEATURE:
```

```
<221> NAME/KEY: misc_feature
<222> LOCATION: (172)..(172)
<223> OTHER INFORMATION: n is a, c, g, or t
<220> FEATURE:
<221> NAME/KEY: misc_feature
<222> LOCATION: (187)..(187)
<223> OTHER INFORMATION: n is a, c, g, or t
<220> FEATURE:
<221> NAME/KEY: misc_feature
<222> LOCATION: (192)..(192)
<223> OTHER INFORMATION: n is a, c, g, or t
<220> FEATURE:
<221> NAME/KEY: misc_feature
<222> LOCATION: (205)..(205)
<223> OTHER INFORMATION: n is a, c, g, or t
<220> FEATURE:
<221> NAME/KEY: misc_feature
<222> LOCATION: (209)..(209)
<223> OTHER INFORMATION: n is a, c, g, or t
<220> FEATURE:
<221> NAME/KEY: misc_feature
<222> LOCATION: (218)..(218)
<223> OTHER INFORMATION: n is a, c, g, or t
<220> FEATURE:
<221> NAME/KEY: misc_feature
<222> LOCATION: (236)..(236)
<223> OTHER INFORMATION: n is a, c, g, or t
<220> FEATURE:
<221> NAME/KEY: misc_feature
<222> LOCATION: (243)..(243)
<223> OTHER INFORMATION: n is a, c, g, or t
<220> FEATURE:
<221> NAME/KEY: misc_feature
<222> LOCATION: (249)..(249)
<223> OTHER INFORMATION: n is a, c, g, or t
<220> FEATURE:
<221> NAME/KEY: misc_feature
<222> LOCATION: (257)..(257)
<223> OTHER INFORMATION: n is a, c, g, or t
<220> FEATURE:
<221> NAME/KEY: misc_feature
<222> LOCATION: (268)..(268)
<223> OTHER INFORMATION: n is a, c, g, or t
<220> FEATURE:
<221> NAME/KEY: misc_feature
<222> LOCATION: (270)..(270)
<223> OTHER INFORMATION: n is a, c, g, or t
<220> FEATURE:
<221> NAME/KEY: misc_feature
<222> LOCATION: (279)..(279)
<223> OTHER INFORMATION: n is a, c, g, or t
<220> FEATURE:
<221> NAME/KEY: misc_feature
<222> LOCATION: (281)..(281)
<223> OTHER INFORMATION: n is a, c, g, or t
<220> FEATURE:
<221> NAME/KEY: misc_feature
<222> LOCATION: (285)..(285)
<223> OTHER INFORMATION: n is a, c, g, or t
<220> FEATURE:
<221> NAME/KEY: misc_feature
<222> LOCATION: (293)..(293)
<223> OTHER INFORMATION: n is a, c, g, or t
<220> FEATURE:
<221> NAME/KEY: misc_feature
<222> LOCATION: (298)..(298)
<223> OTHER INFORMATION: n is a, c, g, or t
<220> FEATURE:
<221> NAME/KEY: misc_feature
<222> LOCATION: (302)..(303)
<223> OTHER INFORMATION: n is a, c, g, or t
<220> FEATURE:
<221> NAME/KEY: misc_feature
<222> LOCATION: (310)..(310)
<223> OTHER INFORMATION: n is a, c, g, or t
<220> FEATURE:
<221> NAME/KEY: misc_feature
<222> LOCATION: (316)..(316)
<223> OTHER INFORMATION: n is a, c, g, or t
```

<220> FEATURE:
<221> NAME/KEY: misc_feature
<222> LOCATION: (327)..(327)
<223> OTHER INFORMATION: n is a, c, g, or t
<220> FEATURE:
<221> NAME/KEY: misc_feature
<222> LOCATION: (329)..(329)
<223> OTHER INFORMATION: n is a, c, g, or t
<220> FEATURE:
<221> NAME/KEY: misc_feature
<222> LOCATION: (355)..(355)
<223> OTHER INFORMATION: n is a, c, g, or t
<220> FEATURE:
<221> NAME/KEY: misc_feature
<222> LOCATION: (359)..(359)
<223> OTHER INFORMATION: n is a, c, g, or t
<220> FEATURE:
<221> NAME/KEY: misc_feature
<222> LOCATION: (389)..(389)
<223> OTHER INFORMATION: n is a, c, g, or t
<220> FEATURE:
<221> NAME/KEY: misc_feature
<222> LOCATION: (402)..(402)
<223> OTHER INFORMATION: n is a, c, g, or t
<220> FEATURE:
<221> NAME/KEY: misc_feature
<222> LOCATION: (405)..(405)
<223> OTHER INFORMATION: n is a, c, g, or t
<220> FEATURE:
<221> NAME/KEY: misc_feature
<222> LOCATION: (418)..(418)
<223> OTHER INFORMATION: n is a, c, g, or t
<220> FEATURE:
<221> NAME/KEY: misc_feature
<222> LOCATION: (456)..(456)
<223> OTHER INFORMATION: n is a, c, g, or t
<220> FEATURE:
<221> NAME/KEY: misc_feature
<222> LOCATION: (477)..(477)
<223> OTHER INFORMATION: n is a, c, g, or t
<220> FEATURE:
<221> NAME/KEY: misc_feature
<222> LOCATION: (485)..(485)
<223> OTHER INFORMATION: n is a, c, g, or t

<400> SEQUENCE: 23
mmsasragta mascvrswcv vvntycmnyk dnstkndsnr hgsyssvdsr ctdgaysshs 60
ttgnsagasg sskvavtnas nghktknvah nskysntnhd ssnksyctdr vhmnsdsnmn 120
gakrhktrnn dsnvmktcga gvhrvgrngn kdksagcntr aydyydddnc tnvsssvsvt 180
rvkdsyngwh vnckgtkksk rttsnkggna svdsdsrngs kgccssdgtt skydsngvtm 240
ssnghdhsnk mssvsrnyds hthtrvangn gssvkmagns ndtrntdscs tansssvnms 300
hnnsdtykcn svdysnhmts kkhssantnd actchswkdr vvrmcatsdk gmvsntcmnk 360
tgvsvsvvvs vvavvykyhm agckygrgny davyssddwv rnvkngvchy rdgvaaanhg 420
hksrkvvvvs hsrwcyatws sragvkvktr vyrsrntywd svgrhwrrrk adgkswngtv 480 gtgcnwats 489

<210> SEQ ID NO 24
<211> LENGTH: 826
<212> TYPE: PRT
<213> ORGANISM: Artificial Sequence
<220> FEATURE:
<223> OTHER INFORMATION: chemically synthesized

<400> SEQUENCE: 24

Met Thr Ser Ala Leu Arg Leu Ala Gly Thr Leu Ile Pro Ala Met Ala
1 5 10 15

Phe Leu Ser Cys Val Arg Pro Glu Ser Trp Glu Pro Cys Val Glu Val

```
                20                  25                  30
Val Pro Asn Ile Thr Tyr Gln Cys Met Glu Leu Lys Phe Tyr Lys Ile
            35                  40                  45

Pro Asp Asn Ile Pro Phe Ser Thr Lys Asn Leu Asp Leu Ser Phe Asn
50                  55                  60

Pro Leu Arg His Leu Gly Ser Tyr Ser Phe Leu Arg Phe Pro Glu Leu
65                  70                  75                  80

Gln Val Leu Asp Leu Ser Arg Cys Glu Ile Gln Thr Ile Glu Asp Gly
                85                  90                  95

Ala Tyr Gln Ser Leu Ser His Leu Ser Thr Leu Ile Leu Thr Gly Asn
            100                 105                 110

Pro Ile Gln Ser Leu Ala Leu Gly Ala Phe Ser Gly Leu Ser Ser Leu
        115                 120                 125

Gln Lys Leu Val Ala Val Glu Thr Asn Leu Ala Ser Leu Glu Asn Phe
    130                 135                 140

Pro Ile Gly His Leu Lys Thr Leu Lys Glu Leu Asn Val Ala His Asn
145                 150                 155                 160

Leu Ile Gln Ser Phe Lys Leu Pro Glu Tyr Phe Ser Asn Leu Thr Asn
                165                 170                 175

Leu Glu His Leu Asp Leu Ser Ser Asn Lys Ile Gln Asn Ile Tyr Cys
            180                 185                 190

Lys Asp Leu Gln Val Leu His Gln Met Pro Leu Ser Asn Leu Ser Leu
        195                 200                 205

Asp Leu Ser Leu Asn Pro Ile Asn Phe Ile Gln Pro Gly Ala Phe Lys
    210                 215                 220

Glu Ile Arg Leu His Lys Leu Thr Leu Arg Ser Asn Phe Asp Asp Leu
225                 230                 235                 240

Asn Val Met Lys Thr Cys Ile Gln Gly Leu Ala Gly Leu Glu Val His
                245                 250                 255

Arg Leu Val Leu Gly Glu Phe Arg Asn Glu Arg Asn Leu Glu Glu Phe
            260                 265                 270

Asp Lys Ser Ser Leu Glu Gly Leu Cys Asn Leu Thr Ile Glu Glu Phe
        275                 280                 285

Arg Leu Thr Tyr Leu Asp Cys Tyr Leu Asp Asn Ile Ile Asp Leu Phe
    290                 295                 300

Asn Cys Leu Ala Asn Val Ser Ser Phe Ser Leu Val Ser Val Asn Ile
305                 310                 315                 320

Lys Arg Val Glu Asp Phe Ser Tyr Asn Phe Arg Trp Gln His Leu Glu
                325                 330                 335

Leu Val Asn Cys Lys Phe Glu Gln Phe Pro Thr Leu Glu Leu Lys Ser
            340                 345                 350

Leu Lys Arg Leu Thr Phe Thr Ala Asn Lys Gly Gly Asn Ala Phe Ser
        355                 360                 365

Glu Val Asp Leu Pro Ser Leu Glu Phe Leu Asp Leu Ser Arg Asn Gly
    370                 375                 380

Leu Ser Phe Lys Gly Cys Cys Ser Gln Ser Asp Phe Gly Thr Thr Ser
385                 390                 395                 400

Leu Lys Tyr Leu Asp Leu Ser Phe Asn Asp Val Ile Thr Met Ser Ser
                405                 410                 415

Asn Phe Leu Gly Leu Glu Gln Leu Glu His Leu Asp Phe Gln His Ser
            420                 425                 430

Asn Leu Lys Gln Met Ser Gln Phe Ser Val Phe Leu Ser Leu Arg Asn
        435                 440                 445
```

Leu Ile Tyr Leu Asp Ile Ser His Thr His Thr Arg Val Ala Phe Asn
    450                 455                 460

Gly Ile Phe Asp Gly Leu Leu Ser Leu Lys Val Leu Lys Met Ala Gly
465                 470                 475                 480

Asn Ser Phe Gln Glu Asn Phe Leu Pro Asp Ile Phe Thr Asp Leu Lys
                485                 490                 495

Asn Leu Thr Phe Leu Asp Leu Ser Gln Cys Gln Leu Glu Gln Leu Ser
            500                 505                 510

Pro Thr Ala Phe Asp Thr Leu Asn Lys Leu Gln Val Leu Asn Met Ser
        515                 520                 525

His Asn Asn Phe Phe Ser Leu Asp Thr Phe Pro Tyr Lys Cys Leu Pro
    530                 535                 540

Ser Leu Gln Val Leu Asp Tyr Ser Leu Asn His Ile Met Thr Ser Asn
545                 550                 555                 560

Asn Gln Glu Leu Gln His Phe Pro Ser Leu Ala Phe Leu Asn Leu
                565                 570                 575

Thr Gln Asn Asp Phe Ala Cys Thr Cys Glu His Gln Ser Phe Leu Gln
                580                 585                 590

Trp Ile Lys Asp Gln Arg Gln Leu Leu Val Glu Ala Glu Arg Met Glu
        595                 600                 605

Cys Ala Thr Pro Ser Asp Lys Gln Gly Met Pro Val Leu Ser Leu Asn
    610                 615                 620

Ile Thr Cys Gln Met Asn Lys Thr Ile Ile Gly Val Ser Val Phe Ser
625                 630                 635                 640

Val Leu Val Val Ser Val Val Ala Val Leu Val Tyr Lys Phe Tyr Phe
                645                 650                 655

His Leu Met Leu Leu Ala Gly Cys Ile Lys Tyr Gly Arg Gly Glu Asn
            660                 665                 670

Ile Tyr Asp Ala Phe Val Ile Tyr Ser Ser Gln Asp Glu Asp Trp Val
        675                 680                 685

Arg Asn Glu Leu Val Lys Asn Leu Glu Glu Gly Val Pro Pro Phe Gln
    690                 695                 700

Leu Cys Leu His Tyr Arg Asp Phe Ile Pro Gly Val Ala Ile Ala Ala
705                 710                 715                 720

Asn Ile Ile His Glu Gly Phe His Lys Ser Arg Lys Val Ile Val Val
                725                 730                 735

Val Ser Gln His Phe Ile Gln Ser Arg Trp Cys Ile Phe Glu Tyr Glu
            740                 745                 750

Ile Ala Gln Thr Trp Gln Phe Leu Ser Ser Arg Ala Gly Ile Ile Phe
        755                 760                 765

Ile Val Leu Gln Lys Val Glu Lys Thr Leu Leu Arg Gln Gln Val Glu
    770                 775                 780

Leu Tyr Arg Leu Leu Ser Arg Asn Thr Tyr Leu Glu Trp Glu Asp Ser
785                 790                 795                 800

Val Leu Gly Gln His Ile Phe Trp Arg Arg Leu Arg Lys Ala Leu Leu
                805                 810                 815

Asp Gly Lys Ser Trp Asn Pro Glu Glu Gln
            820                 825

<210> SEQ ID NO 25
<211> LENGTH: 9
<212> TYPE: PRT
<213> ORGANISM: Artificial Sequence
<220> FEATURE:

```
<223> OTHER INFORMATION: chemically synthesized

<400> SEQUENCE: 25

Gly Tyr Ser Ile Thr Gly Gly Tyr Ser
1               5

<210> SEQ ID NO 26
<211> LENGTH: 7
<212> TYPE: PRT
<213> ORGANISM: Artificial Sequence
<220> FEATURE:
<223> OTHER INFORMATION: chemically synthesized

<400> SEQUENCE: 26

Ile His Tyr Ser Gly Tyr Thr
1               5

<210> SEQ ID NO 27
<211> LENGTH: 11
<212> TYPE: PRT
<213> ORGANISM: Artificial Sequence
<220> FEATURE:
<223> OTHER INFORMATION: chemically synthesized

<400> SEQUENCE: 27

Ala Arg Lys Asp Ser Gly Asn Tyr Phe Pro Tyr
1               5                   10

<210> SEQ ID NO 28
<211> LENGTH: 11
<212> TYPE: PRT
<213> ORGANISM: Artificial Sequence
<220> FEATURE:
<223> OTHER INFORMATION: chemically synthesized

<400> SEQUENCE: 28

Ala Arg Lys Asp Ser Gly Arg Leu Leu Pro Tyr
1               5                   10

<210> SEQ ID NO 29
<211> LENGTH: 11
<212> TYPE: PRT
<213> ORGANISM: Artificial Sequence
<220> FEATURE:
<223> OTHER INFORMATION: chemically synthesized

<400> SEQUENCE: 29

Ala Arg Lys Asp Ser Gly Lys Trp Leu Pro Tyr
1               5                   10

<210> SEQ ID NO 30
<211> LENGTH: 11
<212> TYPE: PRT
<213> ORGANISM: Artificial Sequence
<220> FEATURE:
<223> OTHER INFORMATION: chemically synthesized

<400> SEQUENCE: 30

Ala Arg Lys Asp Ser Gly His Leu Met Pro Tyr
1               5                   10

<210> SEQ ID NO 31
<211> LENGTH: 11
<212> TYPE: PRT
<213> ORGANISM: Artificial Sequence
<220> FEATURE:
<223> OTHER INFORMATION: chemically synthesized
```

<400> SEQUENCE: 31

Ala Arg Lys Asp Ser Gly His Asn Tyr Pro Tyr
1               5                   10

<210> SEQ ID NO 32
<211> LENGTH: 11
<212> TYPE: PRT
<213> ORGANISM: Artificial Sequence
<220> FEATURE:
<223> OTHER INFORMATION: chemically synthesized

<400> SEQUENCE: 32

Ala Arg Lys Asp Ser Gly Lys Asn Phe Pro Tyr
1               5                   10

<210> SEQ ID NO 33
<211> LENGTH: 11
<212> TYPE: PRT
<213> ORGANISM: Artificial Sequence
<220> FEATURE:
<223> OTHER INFORMATION: chemically synthesized

<400> SEQUENCE: 33

Ala Arg Lys Asp Ser Gly Gln Leu Phe Pro Tyr
1               5                   10

<210> SEQ ID NO 34
<211> LENGTH: 11
<212> TYPE: PRT
<213> ORGANISM: Artificial Sequence
<220> FEATURE:
<223> OTHER INFORMATION: chemically synthesized

<400> SEQUENCE: 34

Ala Arg Lys Asp Ser Gly His Asn Leu Pro Tyr
1               5                   10

<210> SEQ ID NO 35
<211> LENGTH: 11
<212> TYPE: PRT
<213> ORGANISM: Artificial Sequence
<220> FEATURE:
<223> OTHER INFORMATION: chemically synthesized

<400> SEQUENCE: 35

Ala Arg Lys Asp Ser Gly Asp Tyr Phe Pro Tyr
1               5                   10

<210> SEQ ID NO 36
<211> LENGTH: 11
<212> TYPE: PRT
<213> ORGANISM: Artificial Sequence
<220> FEATURE:
<223> OTHER INFORMATION: chemically synthesized

<400> SEQUENCE: 36

Ala Arg Lys Asp Ser Gly Arg Tyr Trp Pro Tyr
1               5                   10

<210> SEQ ID NO 37
<211> LENGTH: 6
<212> TYPE: PRT
<213> ORGANISM: Artificial Sequence
<220> FEATURE:
<223> OTHER INFORMATION: chemically synthesized

```
<400> SEQUENCE: 37

Gln Ser Ile Ser Asp His
1               5

<210> SEQ ID NO 38
<211> LENGTH: 3
<212> TYPE: PRT
<213> ORGANISM: Artificial Sequence
<220> FEATURE:
<223> OTHER INFORMATION: chemically synthesized

<400> SEQUENCE: 38

Tyr Ala Ser
1

<210> SEQ ID NO 39
<211> LENGTH: 9
<212> TYPE: PRT
<213> ORGANISM: Artificial Sequence
<220> FEATURE:
<223> OTHER INFORMATION: chemically synthesized

<400> SEQUENCE: 39

Gln Gln Gly His Ser Phe Pro Leu Thr
1               5

<210> SEQ ID NO 40
<211> LENGTH: 447
<212> TYPE: PRT
<213> ORGANISM: Artificial Sequence
<220> FEATURE:
<223> OTHER INFORMATION: chemically synthesized

<400> SEQUENCE: 40

Gln Val Gln Leu Gln Glu Ser Gly Pro Gly Leu Val Lys Pro Ser Asp
1               5                   10                  15

Thr Leu Ser Leu Thr Cys Ala Val Ser Gly Tyr Ser Ile Thr Gly Gly
            20                  25                  30

Tyr Ser Trp His Trp Ile Arg Gln Pro Pro Gly Lys Gly Leu Glu Trp
        35                  40                  45

Met Gly Tyr Ile His Tyr Ser Gly Tyr Thr Asp Phe Asn Pro Ser Leu
    50                  55                  60

Lys Thr Arg Ile Thr Ile Ser Arg Asp Thr Ser Lys Asn Gln Phe Ser
65                  70                  75                  80

Leu Lys Leu Ser Ser Val Thr Ala Val Asp Thr Ala Val Tyr Tyr Cys
                85                  90                  95

Ala Arg Lys Asp Ser Gly Asn Tyr Phe Pro Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205
```

Asn Thr Lys Val Asp Lys Arg Val Glu Pro Lys Ser Cys Asp Lys Thr
            210                 215                 220
His Thr Cys Pro Pro Cys Pro Ala Pro Glu Leu Leu Gly Gly Pro Ser
225                 230                 235                 240
Val Phe Leu Phe Pro Pro Lys Pro Lys Asp Thr Leu Met Ile Ser Arg
                245                 250                 255
Thr Pro Glu Val Thr Cys Val Val Val Asp Val Ser His Glu Asp Pro
            260                 265                 270
Glu Val Lys Phe Asn Trp Tyr Val Asp Gly Val Glu Val His Asn Ala
        275                 280                 285
Lys Thr Lys Pro Arg Glu Glu Gln Tyr Asn Ser Thr Tyr Arg Val Val
    290                 295                 300
Ser Val Leu Thr Val Leu His Gln Asp Trp Leu Asn Gly Lys Glu Tyr
305                 310                 315                 320
Lys Cys Lys Val Ser Asn Lys Ala Leu Pro Ala Pro Ile Glu Lys Thr
                325                 330                 335
Ile Ser Lys Ala Lys Gly Gln Pro Arg Glu Pro Gln Val Tyr Thr Leu
            340                 345                 350
Pro Pro Ser Arg Glu Glu Met Thr Lys Asn Gln Val Ser Leu Thr Cys
        355                 360                 365
Leu Val Lys Gly Phe Tyr Pro Ser Asp Ile Ala Val Glu Trp Glu Ser
    370                 375                 380
Asn Gly Gln Pro Glu Asn Asn Tyr Lys Thr Thr Pro Pro Val Leu Asp
385                 390                 395                 400
Ser Asp Gly Ser Phe Phe Leu Tyr Ser Lys Leu Thr Val Asp Lys Ser
                405                 410                 415
Arg Trp Gln Gln Gly Asn Val Phe Ser Cys Ser Val Met His Glu Ala
            420                 425                 430
Leu His Asn His Tyr Thr Gln Lys Ser Leu Ser Leu Ser Pro Gly
        435                 440                 445

<210> SEQ ID NO 41
<211> LENGTH: 214
<212> TYPE: PRT
<213> ORGANISM: Artificial Sequence
<220> FEATURE:
<223> OTHER INFORMATION: chemically synthesized

<400> SEQUENCE: 41

Glu Ile Val Leu Thr Gln Ser Pro Asp Phe Gln Ser Val Thr Pro Lys
1               5                   10                  15
Glu Lys Val Thr Ile Thr Cys Arg Ala Ser Gln Ser Ile Ser Asp His
            20                  25                  30
Leu His Trp Tyr Gln Gln Lys Pro Asp Gln Ser Pro Lys Leu Leu Ile
        35                  40                  45
Lys Tyr Ala Ser His Ala Ile Ser Gly Val Pro Ser Arg Phe Ser Gly
    50                  55                  60
Ser Gly Ser Gly Thr Asp Phe Thr Leu Thr Ile Asn Ser Leu Glu Ala
65                  70                  75                  80
Glu Asp Ala Ala Thr Tyr Tyr Cys Gln Gln Gly His Ser Phe Pro Leu
                85                  90                  95
Thr Phe Gly Gly Gly Thr Lys Val Glu Ile Lys Arg Thr Val Ala Ala
            100                 105                 110
Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 42
<211> LENGTH: 4
<212> TYPE: PRT
<213> ORGANISM: Artificial Sequence
<220> FEATURE:
<223> OTHER INFORMATION: chemically synthesized

<400> SEQUENCE: 42

Ser Lys Ala Phe
1

<210> SEQ ID NO 43
<211> LENGTH: 118
<212> TYPE: PRT
<213> ORGANISM: Artificial Sequence
<220> FEATURE:
<223> OTHER INFORMATION: chemically synthesized

<400> SEQUENCE: 43

Gln Val Gln Leu Gln Glu Ser Gly Pro Gly Leu Val Lys Pro Ser Asp
1               5                   10                  15

Thr Leu Ser Leu Thr Cys Ala Val Ser Gly Tyr Ser Ile Thr Gly Gly
            20                  25                  30

Tyr Ser Trp His Trp Ile Arg Gln Pro Pro Gly Lys Gly Leu Glu Trp
        35                  40                  45

Met Gly Tyr Ile His Tyr Ser Gly Tyr Thr Asp Phe Asn Pro Ser Leu
    50                  55                  60

Lys Thr Arg Ile Thr Ile Ser Arg Asp Thr Ser Lys Asn Gln Phe Ser
65                  70                  75                  80

Leu Lys Leu Ser Ser Val Thr Ala Val Asp Thr Ala Val Tyr Tyr Cys
                85                  90                  95

Ala Arg Lys Asp Pro Ser Asp Ala Phe Pro Tyr Trp Gly Gln Gly Thr
            100                 105                 110

Leu Val Thr Val Ser Ser
        115

<210> SEQ ID NO 44
<211> LENGTH: 11
<212> TYPE: PRT
<213> ORGANISM: Artificial Sequence
<220> FEATURE:
<223> OTHER INFORMATION: chemically synthesized

<400> SEQUENCE: 44

Ala Arg Lys Asp Pro Ser Asp Ala Phe Pro Tyr
1               5                   10

```
<210> SEQ ID NO 45
<211> LENGTH: 11
<212> TYPE: PRT
<213> ORGANISM: Artificial Sequence
<220> FEATURE:
<223> OTHER INFORMATION: chemically synthesized
<220> FEATURE:
<221> NAME/KEY: MISC_FEATURE
<222> LOCATION: (3)..(7)
<223> OTHER INFORMATION: X is any amino acid

<400> SEQUENCE: 45

Ala Arg Xaa Xaa Xaa Xaa Xaa Ala Phe Pro Tyr
1               5                   10

<210> SEQ ID NO 46
<211> LENGTH: 11
<212> TYPE: PRT
<213> ORGANISM: Artificial Sequence
<220> FEATURE:
<223> OTHER INFORMATION: chemically synthesized
<220> FEATURE:
<221> NAME/KEY: MISC_FEATURE
<222> LOCATION: (7)..(11)
<223> OTHER INFORMATION: X is any amino acid

<400> SEQUENCE: 46

Ala Arg Lys Asp Pro Ser Xaa Xaa Xaa Xaa Xaa
1               5                   10

<210> SEQ ID NO 47
<211> LENGTH: 11
<212> TYPE: PRT
<213> ORGANISM: Artificial Sequence
<220> FEATURE:
<223> OTHER INFORMATION: chemically synthesized
<220> FEATURE:
<221> NAME/KEY: MISC_FEATURE
<222> LOCATION: (5)..(9)
<223> OTHER INFORMATION: X is any amino acid

<400> SEQUENCE: 47

Ala Arg Lys Asp Xaa Xaa Xaa Xaa Xaa Pro Tyr
1               5                   10

<210> SEQ ID NO 48
<211> LENGTH: 9
<212> TYPE: PRT
<213> ORGANISM: Artificial Sequence
<220> FEATURE:
<223> OTHER INFORMATION: chemically synthesized

<400> SEQUENCE: 48

Gln Gln Gly His Ser Phe Pro Leu Thr
1               5

<210> SEQ ID NO 49
<211> LENGTH: 9
<212> TYPE: PRT
<213> ORGANISM: Artificial Sequence
<220> FEATURE:
<223> OTHER INFORMATION: chemically synthesized
<220> FEATURE:
<221> NAME/KEY: MISC_FEATURE
<222> LOCATION: (3)..(7)
<223> OTHER INFORMATION: X is any amino acid

<400> SEQUENCE: 49

Gln Gln Xaa Xaa Xaa Xaa Xaa Leu Thr
```

<210> SEQ ID NO 50
<211> LENGTH: 9
<212> TYPE: PRT
<213> ORGANISM: Artificial Sequence
<220> FEATURE:
<223> OTHER INFORMATION: chemically synthesized
<220> FEATURE:
<221> NAME/KEY: MISC_FEATURE
<222> LOCATION: (5)..(9)
<223> OTHER INFORMATION: X is any amino acid

<400> SEQUENCE: 50

Gln Gln Gly His Xaa Xaa Xaa Xaa Xaa
1               5

<210> SEQ ID NO 51
<211> LENGTH: 9
<212> TYPE: PRT
<213> ORGANISM: Artificial Sequence
<220> FEATURE:
<223> OTHER INFORMATION: chemically synthesized
<220> FEATURE:
<221> NAME/KEY: MISC_FEATURE
<222> LOCATION: (3)..(6)
<223> OTHER INFORMATION: X is any amino acid
<220> FEATURE:
<221> NAME/KEY: misc_feature
<222> LOCATION: (8)..(8)
<223> OTHER INFORMATION: Xaa can be any naturally occurring amino acid

<400> SEQUENCE: 51

Gln Gln Xaa Xaa Xaa Xaa Pro Xaa Thr
1               5

<210> SEQ ID NO 52
<211> LENGTH: 705
<212> TYPE: DNA
<213> ORGANISM: Artificial Sequence
<220> FEATURE:
<223> OTHER INFORMATION: chemically synthesized

<400> SEQUENCE: 52

```
atgagtgtgc ccactcaggt cctggggttg ctgctgctgt ggcttacaga tgccagatgt      60
gaaattgtgt tgacgcagtc tccagacttt cagtctgtga ctccaaagga aaaagtcacc     120
atcacctgca gggccagtca gagtatcagc gaccacttac actggtacca acagaaacct     180
gatcagtctc ccaagctcct catcaaatat gcttcccatg ccatttctgg ggtcccatcg     240
aggttcagtg gcagtgggtc tgggacagac ttcactctca ccatcaatag cctagaggct     300
gaagatgctg caacgtatta ctgtcagcag ggtcacagtt ttccgctcac tttcggcgga     360
gggaccaagg tggagatcaa acgtacggtg gctgcaccat ctgtcttcat cttcccgcca     420
tctgatgagc agttgaaatc tggaactgcc tctgttgtgt gcctgctgaa taacttctat     480
cccagagagg ccaaagtaca gtggaaggtg gataacgccc tccaatcggg taactcccag     540
gagagtgtca cagagcagga cagcaaggac agcacctaca gcctcagcag caccctgacg     600
ctgagcaaag cagactacga gaaacacaaa gtctacgcct gcgaagtcac ccatcagggc     660
ctgagctcgc ccgtcacaaa gagcttcaac aggggagagt gttaa                    705
```

<210> SEQ ID NO 53
<211> LENGTH: 1398
<212> TYPE: DNA
<213> ORGANISM: Artificial Sequence -continued

```
<220> FEATURE:
<223> OTHER INFORMATION: chemically synthesized

<400> SEQUENCE: 53
atggaatgga gctgggtctt tctcttcttc ctgtcagtaa ctacaggtgt ccaccaggtg      60
cagcttcagg agtccggccc aggactggtg aagccttcgg acaccctgtc cctcacctgc     120
gctgtctctg gttactccat caccggtggt tatagctggc actggatacg cagcccccca     180
gggaagggac tggagtggat ggggtatatc cactacagtg gttacactga cttcaacccc     240
tccctcaaga ctcgaatcac catatcacgt gacacgtcca agaaccagtt ctccctgaag     300
ctgagctctg tgaccgctgt ggacactgca gtgtattact gtgcgagaaa agatccgtcc     360
gacgcctttc cttactgggg ccaagggact ctggtcactg tctcttccgc ctccaccaag     420
ggcccatcgg tcttcccccct ggcacccctcc tccaagagca cctctggggg cacagcggcc     480
ctgggctgcc tggtcaagga ctacttcccc gaaccggtga cagtctcgtg aactcagga     540
gccctgacca gcggcgtgca caccttcccg gctgtcctac agtcctcagg actctactcc     600
ctcagcagcg tggtgactgt gccctccagc agcttgggca cccagaccta catctgcaac     660
gtgaatcaca gcccagcaa caccaaggtg gacaagagag ttgagcccaa atcttgtgac     720
aaaactcaca catgcccacc gtgcccagca cctgaactcc tgggggggacc gtcagtcttc     780
ctcttccccc caaaacccaa ggacaccctc atgatctccc ggaccccctga ggtcacatgc     840
gtggtggtgg acgtgagcca cgaagaccct gaggtcaagt tcaactggta cgtggacggc     900
gtggaggtgc ataatgccaa gacaaagccg cgggaggagc agtacaacag cacgtaccgt     960
gtggtcagcg tcctcaccgt cctgcaccag gactggctga atggcaagga gtacaagtgc    1020
aaggtctcca acaaagccct cccagccccc atcgagaaaa ccatctccaa agccaaaggg    1080
cagccccgag aaccacaggt gtatccctg cccccatctc gggaggagat gaccaagaac    1140
caggtcagcc tgacttgcct ggtcaaaggc ttctatccca gcgacatcgc cgtggagtgg    1200
gagagcaacg ggcagccgga gaacaactac aagaccacgc ctcccgtgct ggactccgac    1260
ggctccttct cctctatag caagctcacc gtggacaagt ccaggtggca gcagggaac    1320
gtcttctcat gctccgtgat gcatgaggct ctgcacaacc actacacgca gaagagcctc    1380
tccctgtctc cgggttaa                                                  1398

<210> SEQ ID NO 54
<211> LENGTH: 12
<212> TYPE: PRT
<213> ORGANISM: Artificial Sequence
<220> FEATURE:
<223> OTHER INFORMATION: chemically synthesized
<220> FEATURE:
<221> NAME/KEY: MISC_FEATURE
<222> LOCATION: (8)..(8)
<223> OTHER INFORMATION: X is N, Q or D
<220> FEATURE:
<221> NAME/KEY: MISC_FEATURE
<222> LOCATION: (9)..(9)
<223> OTHER INFORMATION: X is Y or L

<400> SEQUENCE: 54

Cys Ala Arg Lys Asp Ser Gly Xaa Xaa Phe Pro Tyr
1               5                   10

<210> SEQ ID NO 55
<211> LENGTH: 9
<212> TYPE: PRT
<213> ORGANISM: Artificial Sequence
```

-continued

```
<220> FEATURE:
<223> OTHER INFORMATION: chemically synthesized

<400> SEQUENCE: 55

Gly Phe Pro Ile Arg Tyr Gly Tyr Ser
1               5

<210> SEQ ID NO 56
<211> LENGTH: 9
<212> TYPE: PRT
<213> ORGANISM: Artificial Sequence
<220> FEATURE:
<223> OTHER INFORMATION: chemically synthesized

<400> SEQUENCE: 56

Gly Tyr Pro Ile Arg Phe Gly Tyr Ser
1               5

<210> SEQ ID NO 57
<211> LENGTH: 9
<212> TYPE: PRT
<213> ORGANISM: Artificial Sequence
<220> FEATURE:
<223> OTHER INFORMATION: chemically synthesized

<400> SEQUENCE: 57

Gly Tyr Pro Ile Arg His Gly Tyr Ser
1               5

<210> SEQ ID NO 58
<211> LENGTH: 9
<212> TYPE: PRT
<213> ORGANISM: Artificial Sequence
<220> FEATURE:
<223> OTHER INFORMATION: chemically synthesized

<400> SEQUENCE: 58

Gly Phe Pro Ile Gly Gln Gly Tyr Ser
1               5

<210> SEQ ID NO 59
<211> LENGTH: 9
<212> TYPE: PRT
<213> ORGANISM: Artificial Sequence
<220> FEATURE:
<223> OTHER INFORMATION: chemically synthesized

<400> SEQUENCE: 59

Gly Tyr Pro Ile Trp Gly Gly Tyr Ser
1               5

<210> SEQ ID NO 60
<211> LENGTH: 9
<212> TYPE: PRT
<213> ORGANISM: Artificial Sequence
<220> FEATURE:
<223> OTHER INFORMATION: chemically synthesized

<400> SEQUENCE: 60

Gly Tyr Pro Ile Gly Gly Gly Tyr Ser
1               5

<210> SEQ ID NO 61
<211> LENGTH: 9
<212> TYPE: PRT
<213> ORGANISM: Artificial Sequence
<220> FEATURE:
```

<223> OTHER INFORMATION: chemically synthesized

<400> SEQUENCE: 61

Gln Gln Gly Asn Asp Phe Pro Val Thr
1               5

<210> SEQ ID NO 62
<211> LENGTH: 9
<212> TYPE: PRT
<213> ORGANISM: Artificial Sequence
<220> FEATURE:
<223> OTHER INFORMATION: chemically synthesized

<400> SEQUENCE: 62

Gln Gln Gly Tyr Asp Glu Pro Phe Thr
1               5

<210> SEQ ID NO 63
<211> LENGTH: 9
<212> TYPE: PRT
<213> ORGANISM: Artificial Sequence
<220> FEATURE:
<223> OTHER INFORMATION: chemically synthesized

<400> SEQUENCE: 63

Gln Gln Gly Tyr Asp Phe Pro Phe Thr
1               5

<210> SEQ ID NO 64
<211> LENGTH: 9
<212> TYPE: PRT
<213> ORGANISM: Artificial Sequence
<220> FEATURE:
<223> OTHER INFORMATION: chemically synthesized

<400> SEQUENCE: 64

Gln Gln Gly Tyr Asp Tyr Pro Phe Thr
1               5

<210> SEQ ID NO 65
<211> LENGTH: 9
<212> TYPE: PRT
<213> ORGANISM: Artificial Sequence
<220> FEATURE:
<223> OTHER INFORMATION: chemically synthesized

<400> SEQUENCE: 65

Gln Gln Gly Tyr Glu Phe Pro Phe Thr
1               5

<210> SEQ ID NO 66
<211> LENGTH: 354
<212> TYPE: DNA
<213> ORGANISM: Artificial Sequence
<220> FEATURE:
<223> OTHER INFORMATION: chemically synthesized

<400> SEQUENCE: 66
caggtgcagc ttcaggagtc cggcccagga ctggtgaagc cttcggacac cctgtccctc    60
acctgcgctg tctctggttt cccgatccgc tacgggtata gctggcactg gatacggcag   120
cccccaggga agggactgga gtggatgggg tatatccact acagtggtta cactgacttc   180 aaccccctccc tcaagactcg aatcaccata tcacgtgaca cgtccaagaa ccagttctcc   240
ctgaagctga gctctgtgac cgctgtggac actgcagtgt attactgtgc gagaaaagat   300
tcgggcaact acttcccttta ctggggccaa gggactctgg tcactgtctc ttcc      354

<210> SEQ ID NO 67
<211> LENGTH: 118
<212> TYPE: PRT
<213> ORGANISM: Artificial Sequence
<220> FEATURE:
<223> OTHER INFORMATION: chemically synthesized

<400> SEQUENCE: 67

Gln Val Gln Leu Gln Glu Ser Gly Pro Gly Leu Val Lys Pro Ser Asp
1               5                   10                  15

Thr Leu Ser Leu Thr Cys Ala Val Ser Gly Phe Pro Ile Arg Tyr Gly
            20                  25                  30

Tyr Ser Trp His Trp Ile Arg Gln Pro Pro Gly Lys Gly Leu Glu Trp
        35                  40                  45

Met Gly Tyr Ile His Tyr Ser Gly Tyr Thr Asp Phe Asn Pro Ser Leu
    50                  55                  60

Lys Thr Arg Ile Thr Ile Ser Arg Asp Thr Ser Lys Asn Gln Phe Ser
65                  70                  75                  80

Leu Lys Leu Ser Ser Val Thr Ala Val Asp Thr Ala Val Tyr Tyr Cys
                85                  90                  95

Ala Arg Lys Asp Ser Gly Asn Tyr Phe Pro Tyr Trp Gly Gln Gly Thr
            100                 105                 110

Leu Val Thr Val Ser Ser
        115

<210> SEQ ID NO 68
<211> LENGTH: 354
<212> TYPE: DNA
<213> ORGANISM: Artificial Sequence
<220> FEATURE:
<223> OTHER INFORMATION: chemically synthesized

<400> SEQUENCE: 68
caggtgcagc ttcaggagtc cggcccagga ctggtgaagc cttcggacac cctgtccctc      60
acctgcgctg tctctggtta cccgatccgg ttcggctata gctggcactg gatacggcag     120
cccccaggga agggactgga gtggatgggg tatatccact acagtggtta cactgacttc     180
aaccctcccc tcaagactcg aatcaccata tcacgtgaca cgtccaagaa ccagttctcc     240
ctgaagctga gctctgtgac cgctgtggac actgcagtgt attactgtgc gagaaaagat     300
tcgggcaact acttcccctta ctggggccaa gggactctgg tcactgtctc ttcc           354

<210> SEQ ID NO 69
<211> LENGTH: 118
<212> TYPE: PRT
<213> ORGANISM: Artificial Sequence
<220> FEATURE:
<223> OTHER INFORMATION: chemically synthesized

<400> SEQUENCE: 69

Gln Val Gln Leu Gln Glu Ser Gly Pro Gly Leu Val Lys Pro Ser Asp
1               5                   10                  15

Thr Leu Ser Leu Thr Cys Ala Val Ser Gly Tyr Pro Ile Arg Phe Gly
            20                  25                  30

Tyr Ser Trp His Trp Ile Arg Gln Pro Pro Gly Lys Gly Leu Glu Trp
        35                  40                  45

Met Gly Tyr Ile His Tyr Ser Gly Tyr Thr Asp Phe Asn Pro Ser Leu
    50                  55                  60

```
Lys Thr Arg Ile Thr Ile Ser Arg Asp Thr Ser Lys Asn Gln Phe Ser
 65                  70                  75                  80

Leu Lys Leu Ser Ser Val Thr Ala Val Asp Thr Ala Val Tyr Tyr Cys
                 85                  90                  95

Ala Arg Lys Asp Ser Gly Asn Tyr Phe Pro Tyr Trp Gly Gln Gly Thr
            100                 105                 110

Leu Val Thr Val Ser Ser
        115

<210> SEQ ID NO 70
<211> LENGTH: 354
<212> TYPE: DNA
<213> ORGANISM: Artificial Sequence
<220> FEATURE:
<223> OTHER INFORMATION: chemically synthesized

<400> SEQUENCE: 70
caggtgcagc ttcaggagtc cggcccagga ctggtgaagc cttcggacac cctgtccctc      60
acctgcgctg tctctggtta ccccatccgg cacgggtaca gctggcactg gatacggcag     120
cccccaggga agggactgga gtggatgggg tatatccact acagtggtta cactgacttc     180
aacccctccc tcaagactcg aatcaccata tcacgtgaca cgtccaagaa ccagttctcc     240
ctgaagctga gctctgtgac cgctgtggac actgcagtgt attactgtgc gagaaaagat     300
tcgggcaact acttcccta ctggggccaa gggactctgg tcactgtctc ttcc            354

<210> SEQ ID NO 71
<211> LENGTH: 118
<212> TYPE: PRT
<213> ORGANISM: Artificial Sequence
<220> FEATURE:
<223> OTHER INFORMATION: chemically synthesized

<400> SEQUENCE: 71

Gln Val Gln Leu Gln Glu Ser Gly Pro Gly Leu Val Lys Pro Ser Asp
  1               5                  10                  15

Thr Leu Ser Leu Thr Cys Ala Val Ser Gly Tyr Pro Ile Arg His Gly
             20                  25                  30

Tyr Ser Trp His Trp Ile Arg Gln Pro Pro Gly Lys Gly Leu Glu Trp
         35                  40                  45

Met Gly Tyr Ile His Tyr Ser Gly Tyr Thr Asp Phe Asn Pro Ser Leu
     50                  55                  60

Lys Thr Arg Ile Thr Ile Ser Arg Asp Thr Ser Lys Asn Gln Phe Ser
 65                  70                  75                  80

Leu Lys Leu Ser Ser Val Thr Ala Val Asp Thr Ala Val Tyr Tyr Cys
                 85                  90                  95

Ala Arg Lys Asp Ser Gly Asn Tyr Phe Pro Tyr Trp Gly Gln Gly Thr
            100                 105                 110

Leu Val Thr Val Ser Ser
        115

<210> SEQ ID NO 72
<211> LENGTH: 354
<212> TYPE: DNA
<213> ORGANISM: Artificial Sequence
<220> FEATURE:
<223> OTHER INFORMATION: chemically synthesized

<400> SEQUENCE: 72
```

```
caggtgcagc ttcaggagtc cggcccagga ctggtgaagc cttcggacac cctgtccctc    60
acctgcgctg tctctggttt cccgatcggc caggggtata gctggcactg gatacggcag   120
cccccaggga agggactgga gtggatgggg tatatccact acagtggtta cactgacttc   180
aacccctccc tcaagactcg aatcaccata tcacgtgaca cgtccaagaa ccagttctcc   240
ctgaagctga gctctgtgac cgctgtggac actgcagtgt attactgtgc gagaaaagat   300
tcgggcaact acttcccttta ctggggccaa gggactctgg tcactgtctc ttcc         354
```

```
<210> SEQ ID NO 73
<211> LENGTH: 118
<212> TYPE: PRT
<213> ORGANISM: Artificial Sequence
<220> FEATURE:
<223> OTHER INFORMATION: chemically synthesized

<400> SEQUENCE: 73
```

Gln Val Gln Leu Gln Glu Ser Gly Pro Gly Leu Val Lys Pro Ser Asp
1               5                   10                  15

Thr Leu Ser Leu Thr Cys Ala Val Ser Gly Phe Pro Ile Gly Gln Gly
            20                  25                  30

Tyr Ser Trp His Trp Ile Arg Gln Pro Pro Gly Lys Gly Leu Glu Trp
        35                  40                  45

Met Gly Tyr Ile His Tyr Ser Gly Tyr Thr Asp Phe Asn Pro Ser Leu
    50                  55                  60

Lys Thr Arg Ile Thr Ile Ser Arg Asp Thr Ser Lys Asn Gln Phe Ser
65                  70                  75                  80

Leu Lys Leu Ser Ser Val Thr Ala Val Asp Thr Ala Val Tyr Tyr Cys
                85                  90                  95

Ala Arg Lys Asp Ser Gly Asn Tyr Phe Pro Tyr Trp Gly Gln Gly Thr
            100                 105                 110

Leu Val Thr Val Ser Ser
        115

```
<210> SEQ ID NO 74
<211> LENGTH: 363
<212> TYPE: DNA
<213> ORGANISM: Artificial Sequence
<220> FEATURE:
<223> OTHER INFORMATION: chemically synthesized

<400> SEQUENCE: 74
caggtgcagc ttcaggagtc cggcccagga ctggtgaagc cttcggacac cctgtccctc    60
acctgcgctg tctctggtta cccgatctgg ggggctata gctggcactg gatacggcag   120
cccccaggga agggactgga gtggatgggg tatatccact acagtggtta cactgacttc   180
aacccctccc tcaagactcg aatcaccata tcacgtgaca cgtccaagaa ccagttctcc   240
ctgaagctga gctctgtgac cgctgtggac actgcagtgt attactgtgc gagaaaagat   300
tcgggcaact acttcccttta ctggggccaa gggactctgg tcactgtctc ttccgcctcc   360
acc                                                                 363
```

```
<210> SEQ ID NO 75
<211> LENGTH: 118
<212> TYPE: PRT
<213> ORGANISM: Artificial Sequence
<220> FEATURE:
<223> OTHER INFORMATION: chemically synthesized

<400> SEQUENCE: 75
```

Gln Val Gln Leu Gln Glu Ser Gly Pro Gly Leu Val Lys Pro Ser Asp
1               5                   10                  15

Thr Leu Ser Leu Thr Cys Ala Val Ser Gly Tyr Pro Ile Trp Gly Gly
            20                  25                  30

Tyr Ser Trp His Trp Ile Arg Gln Pro Pro Gly Lys Gly Leu Glu Trp
        35                  40                  45

Met Gly Tyr Ile His Tyr Ser Gly Tyr Thr Asp Phe Asn Pro Ser Leu
    50                  55                  60

Lys Thr Arg Ile Thr Ile Ser Arg Asp Thr Ser Lys Asn Gln Phe Ser
65                  70                  75                  80

Leu Lys Leu Ser Ser Val Thr Ala Val Asp Thr Ala Val Tyr Tyr Cys
                85                  90                  95

Ala Arg Lys Asp Ser Gly Asn Tyr Phe Pro Tyr Trp Gly Gln Gly Thr
            100                 105                 110

Leu Val Thr Val Ser Ser
        115

<210> SEQ ID NO 76
<211> LENGTH: 354
<212> TYPE: DNA
<213> ORGANISM: Artificial Sequence
<220> FEATURE:
<223> OTHER INFORMATION: chemically synthesized

<400> SEQUENCE: 76
caggtgcagc ttcaggagtc cggcccagga ctggtgaagc cttcggacac cctgtccctc      60
acctgcgctg tctctggtta ccccatcggc ggcggctata gctggcactg gatacggcag     120
cccccaggga agggactgga gtggatgggg tatatccact acagtggtta cactgacttc     180
aaccccctcc ctcaagactc gaatcaccat atcacgtgac acgtccaaga accagttctcc    240 ctgaagctga gctctgtgac cgctgtggac actgcagtgt attactgtgc gagaaaagat     300
tcgggcaact acttcccttta ctggggccaa gggactctgg tcactgtctc ttcc          354

<210> SEQ ID NO 77
<211> LENGTH: 118
<212> TYPE: PRT
<213> ORGANISM: Artificial Sequence
<220> FEATURE:
<223> OTHER INFORMATION: chemically synthesized

<400> SEQUENCE: 77

Gln Val Gln Leu Gln Glu Ser Gly Pro Gly Leu Val Lys Pro Ser Asp
1               5                   10                  15

Thr Leu Ser Leu Thr Cys Ala Val Ser Gly Tyr Pro Ile Gly Gly Gly
            20                  25                  30

Tyr Ser Trp His Trp Ile Arg Gln Pro Pro Gly Lys Gly Leu Glu Trp
        35                  40                  45

Met Gly Tyr Ile His Tyr Ser Gly Tyr Thr Asp Phe Asn Pro Ser Leu
    50                  55                  60

Lys Thr Arg Ile Thr Ile Ser Arg Asp Thr Ser Lys Asn Gln Phe Ser
65                  70                  75                  80

Leu Lys Leu Ser Ser Val Thr Ala Val Asp Thr Ala Val Tyr Tyr Cys
                85                  90                  95

Ala Arg Lys Asp Ser Gly Asn Tyr Phe Pro Tyr Trp Gly Gln Gly Thr
            100                 105                 110

Leu Val Thr Val Ser Ser

-continued

115

<210> SEQ ID NO 78
<211> LENGTH: 321
<212> TYPE: DNA
<213> ORGANISM: Artificial Sequence
<220> FEATURE:
<223> OTHER INFORMATION: chemically synthesized

<400> SEQUENCE: 78
gaaattgtgt tgacgcagtc tccagacttt cagtctgtga ctccaaagga aaaagtcacc      60
atcacctgca gggccagtca gagtatcagc gaccacttac actggtacca acagaaacct     120
gatcagtctc ccaagctcct catcaaatat gcttcccatg ccatttctgg ggtcccatcg     180
aggttcagtg gcagtgggtc tgggacagac ttcactctca ccatcaatag cctagaggct     240
gaagatgctg caacgtatta ctgtcagcag gggaacgact cccggtgac tttcggcgga      300 gggaccaagg tggagatcaa a                                               321

<210> SEQ ID NO 79
<211> LENGTH: 107
<212> TYPE: PRT
<213> ORGANISM: Artificial Sequence
<220> FEATURE:
<223> OTHER INFORMATION: chemically synthesized

<400> SEQUENCE: 79

Glu Ile Val Leu Thr Gln Ser Pro Asp Phe Gln Ser Val Thr Pro Lys
1               5                   10                  15

Glu Lys Val Thr Ile Thr Cys Arg Ala Ser Gln Ser Ile Ser Asp His
            20                  25                  30

Leu His Trp Tyr Gln Gln Lys Pro Asp Gln Ser Pro Lys Leu Leu Ile
        35                  40                  45

Lys Tyr Ala Ser His Ala Ile Ser Gly Val Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys Gln Gln Gly Asn Asp Phe Pro Val
                85                  90                  95

Thr Phe Gly Gly Gly Thr Lys Val Glu Ile Lys
            100                 105

<210> SEQ ID NO 80
<211> LENGTH: 321
<212> TYPE: DNA
<213> ORGANISM: Artificial Sequence
<220> FEATURE:
<223> OTHER INFORMATION: chemically synthesized

<400> SEQUENCE: 80
gaaattgtgt tgacgcagtc tccagacttt cagtctgtga ctccaaagga aaaagtcacc      60
atcacctgca gggccagtca gagtatcagc gaccacttac actggtacca acagaaacct     120
gatcagtctc ccaagctcct catcaaatat gcttcccatg ccatttctgg ggtcccatcg     180
aggttcagtg gcagtgggtc tgggacagac ttcactctca ccatcaatag cctagaggct     240
gaagatgctg caacgtatta ctgtcagcag gggtacgacg agccgttcac tttcggcgga     300
gggaccaagg tggagatcaa a                                               321

<210> SEQ ID NO 81

```
<211> LENGTH: 107
<212> TYPE: PRT
<213> ORGANISM: Artificial Sequence
<220> FEATURE:
<223> OTHER INFORMATION: chemically synthesized

<400> SEQUENCE: 81

Glu Ile Val Leu Thr Gln Ser Pro Asp Phe Gln Ser Val Thr Pro Lys
 1               5                  10                  15

Glu Lys Val Thr Ile Thr Cys Arg Ala Ser Gln Ser Ile Ser Asp His
            20                  25                  30

Leu His Trp Tyr Gln Gln Lys Pro Asp Gln Ser Pro Lys Leu Leu Ile
        35                  40                  45

Lys Tyr Ala Ser His Ala Ile Ser Gly Val Pro Ser Arg Phe Ser Gly
 50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys Gln Gln Gly Tyr Asp Glu Pro Phe
                85                  90                  95

Thr Phe Gly Gly Gly Thr Lys Val Glu Ile Lys
            100                 105

<210> SEQ ID NO 82
<211> LENGTH: 321
<212> TYPE: DNA
<213> ORGANISM: Artificial Sequence
<220> FEATURE:
<223> OTHER INFORMATION: chemically synthesized

<400> SEQUENCE: 82
gaaattgtgt tgacgcagtc tccagacttt cagtctgtga ctccaaagga aaaagtcacc      60
atcacctgca gggccagtca gagtatcagc gaccacttac actggtacca acagaaacct    120
gatcagtctc ccaagctcct catcaaatat gcttcccatg ccatttctgg ggtcccatcg    180
aggttcagtg gcagtgggtc tgggacagac ttcactctca ccatcaatag cctagaggct    240
gaagatgctg caacgtatta ctgtcagcag ggctacgact cccgttgac tttcggcgga     300 gggaccaagg tggagatcaa a                                              321

<210> SEQ ID NO 83
<211> LENGTH: 107
<212> TYPE: PRT
<213> ORGANISM: Artificial Sequence
<220> FEATURE:
<223> OTHER INFORMATION: chemically synthesized

<400> SEQUENCE: 83

Glu Ile Val Leu Thr Gln Ser Pro Asp Phe Gln Ser Val Thr Pro Lys
 1               5                  10                  15

Glu Lys Val Thr Ile Thr Cys Arg Ala Ser Gln Ser Ile Ser Asp His
            20                  25                  30

Leu His Trp Tyr Gln Gln Lys Pro Asp Gln Ser Pro Lys Leu Leu Ile
        35                  40                  45

Lys Tyr Ala Ser His Ala Ile Ser Gly Val Pro Ser Arg Phe Ser Gly
 50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys Gln Gln Gly Tyr Asp Phe Pro Leu
                85                  90                  95
```

```
Thr Phe Gly Gly Gly Thr Lys Val Glu Ile Lys
            100                 105
```

<210> SEQ ID NO 84
<211> LENGTH: 321
<212> TYPE: DNA
<213> ORGANISM: Artificial Sequence
<220> FEATURE:
<223> OTHER INFORMATION: chemically synthesized

<400> SEQUENCE: 84

```
gaaattgtgt tgacgcagtc tccagacttt cagtctgtga ctccaaagga aaaagtcacc      60
atcacctgca gggccagtca gagtatcagc gaccacttac actggtacca acagaaacct     120
gatcagtctc ccaagctcct catcaaatat gcttcccatg ccatttctgg ggtcccatcg     180
aggttcagtg gcagtgggtc tgggacagac ttcactctca ccatcaatag cctagaggct     240
gaagatgctg caacgtatta ctgtcagcag ggctacgact acccgctcac tttcggcgga     300
gggaccaagg tggagatcaa a                                               321
```

<210> SEQ ID NO 85
<211> LENGTH: 107
<212> TYPE: PRT
<213> ORGANISM: Artificial Sequence
<220> FEATURE:
<223> OTHER INFORMATION: chemically synthesized

<400> SEQUENCE: 85

```
Glu Ile Val Leu Thr Gln Ser Pro Asp Phe Gln Ser Val Thr Pro Lys
1               5                   10                  15

Glu Lys Val Thr Ile Thr Cys Arg Ala Ser Gln Ser Ile Ser Asp His
            20                  25                  30

Leu His Trp Tyr Gln Gln Lys Pro Asp Gln Ser Pro Lys Leu Leu Ile
        35                  40                  45

Lys Tyr Ala Ser His Ala Ile Ser Gly Val Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys Gln Gln Gly Tyr Asp Tyr Pro Leu
                85                  90                  95

Thr Phe Gly Gly Gly Thr Lys Val Glu Ile Lys
            100                 105
```

<210> SEQ ID NO 86
<211> LENGTH: 321
<212> TYPE: DNA
<213> ORGANISM: Artificial Sequence
<220> FEATURE:
<223> OTHER INFORMATION: chemically synthesized

<400> SEQUENCE: 86

```
gaaattgtgt tgacgcagtc tccagacttt cagtctgtga ctccaaagga aaaagtcacc      60
atcacctgca gggccagtca gagtatcagc gaccacttac actggtacca acagaaacct     120
gatcagtctc ccaagctcct catcaaatat gcttcccatg ccatttctgg ggtcccatcg     180
aggttcagtg gcagtgggtc tgggacagac ttcactctca ccatcaatag cctagaggct     240
gaagatgctg caacgtatta ctgtcagcag ggctacgagt cccgttgac tttcggcgga      300
gggaccaagg tggagatcaa a                                               321
```

<210> SEQ ID NO 87
<211> LENGTH: 107
<212> TYPE: PRT
<213> ORGANISM: Artificial Sequence
<220> FEATURE:
<223> OTHER INFORMATION: chemically synthesized

<400> SEQUENCE: 87

```
Glu Ile Val Leu Thr Gln Ser Pro Asp Phe Gln Ser Val Thr Pro Lys
1               5                   10                  15

Glu Lys Val Thr Ile Thr Cys Arg Ala Ser Gln Ser Ile Ser Asp His
            20                  25                  30

Leu His Trp Tyr Gln Gln Lys Pro Asp Gln Ser Pro Lys Leu Leu Ile
        35                  40                  45

Lys Tyr Ala Ser His Ala Ile Ser Gly Val Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys Gln Gln Tyr Glu Phe Pro Leu
                85                  90                  95

Thr Phe Gly Gly Gly Thr Lys Val Glu Ile Lys
            100                 105
```

<210> SEQ ID NO 88
<211> LENGTH: 354
<212> TYPE: DNA
<213> ORGANISM: Artificial Sequence
<220> FEATURE:
<223> OTHER INFORMATION: chemically synthesized

<400> SEQUENCE: 88

```
caggtgcagc ttcaggagtc cggcccagga ctggtgaagc cttcggacac cctgtccctc      60
acctgcgctg tctctggtta cccgatccgg ttcggctata gctggcactg gatacggcag     120
cccccaggga agggactgga gtggatgggg tatatccact acagtggtta cactgacttc     180
aaccccctccc tcaagactcg aatcaccata tcacgtgaca cgtccaagaa ccagttctcc    240
ctgaagctga gctctgtgac cgctgtggac actgcagtgt attactgtgc gagaaaagat    300
tcgggcaact acttccctta ctggggccaa gggactctgg tcactgtctc ttcc           354
```

<210> SEQ ID NO 89
<211> LENGTH: 118
<212> TYPE: PRT
<213> ORGANISM: Artificial Sequence
<220> FEATURE:
<223> OTHER INFORMATION: chemically synthesized

<400> SEQUENCE: 89

```
Gln Val Gln Leu Gln Glu Ser Gly Pro Gly Leu Val Lys Pro Ser Asp
1               5                   10                  15

Thr Leu Ser Leu Thr Cys Ala Val Ser Gly Tyr Pro Ile Arg Phe Gly
            20                  25                  30

Tyr Ser Trp His Trp Ile Arg Gln Pro Pro Gly Lys Gly Leu Glu Trp
        35                  40                  45

Met Gly Tyr Ile His Tyr Ser Gly Tyr Thr Asp Phe Asn Pro Ser Leu
    50                  55                  60

Lys Thr Arg Ile Thr Ile Ser Arg Asp Thr Ser Lys Asn Gln Phe Ser
65                  70                  75                  80

Leu Lys Leu Ser Ser Val Thr Ala Val Asp Thr Ala Val Tyr Tyr Cys
                85                  90                  95
```

Ala Arg Lys Asp Ser Gly Asn Tyr Phe Pro Tyr Trp Gly Gln Gly Thr
            100                 105                 110

Leu Val Thr Val Ser Ser
        115

<210> SEQ ID NO 90
<211> LENGTH: 321
<212> TYPE: DNA
<213> ORGANISM: Artificial Sequence
<220> FEATURE:
<223> OTHER INFORMATION: chemically synthesized

<400> SEQUENCE: 90
gaaattgtgt tgacgcagtc tccagacttt cagtctgtga ctccaaagga aaaagtcacc      60
atcacctgca gggccagtca gagtatcagc gaccacttac actggtacca acagaaacct     120
gatcagtctc ccaagctcct catcaaatat gcttcccatg ccatttctgg ggtcccatcg     180
aggttcagtg gcagtgggtc tgggacagac ttcactctca ccatcaatag cctagaggct     240
gaagatgctg caacgtatta ctgtcagcag gggaacgact cccggtgac tttcggcgga     300 gggaccaagg tggagatcaa a                                                321

<210> SEQ ID NO 91
<211> LENGTH: 107
<212> TYPE: PRT
<213> ORGANISM: Artificial Sequence
<220> FEATURE:
<223> OTHER INFORMATION: chemically synthesized

<400> SEQUENCE: 91

Glu Ile Val Leu Thr Gln Ser Pro Asp Phe Gln Ser Val Thr Pro Lys
1               5                   10                  15

Glu Lys Val Thr Ile Thr Cys Arg Ala Ser Gln Ser Ile Ser Asp His
            20                  25                  30

Leu His Trp Tyr Gln Gln Lys Pro Asp Gln Ser Pro Lys Leu Leu Ile
        35                  40                  45

Lys Tyr Ala Ser His Ala Ile Ser Gly Val Pro Ser Arg Phe Ser Gly
50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys Gln Gln Gly Asn Asp Phe Pro Val
            85                  90                  95

Thr Phe Gly Gly Gly Thr Lys Val Glu Ile Lys
            100                 105

<210> SEQ ID NO 92
<211> LENGTH: 354
<212> TYPE: DNA
<213> ORGANISM: Artificial Sequence
<220> FEATURE:
<223> OTHER INFORMATION: chemically synthesized

<400> SEQUENCE: 92
caggtgcagc ttcaggagtc cggcccagga ctggtgaagc cttcggacac cctgtccctc      60
acctgcgctg tctctggtta cccgatccgg ttcggctata gctggcactg gatacggcag     120
cccccaggga agggactgga gtggatgggg tatatccact acagtggtta cactgacttc     180
aacccctccc tcaagactcg aatcaccata tcacgtgaca cgtccaagaa ccagttctcc     240
ctgaagctga gctctgtgac cgctgtggac actgcagtgt attactgtgc gagaaaagat     300
tcgggcaact acttccctta ctggggccaa gggactctgg tcactgtctc ttcc    354

<210> SEQ ID NO 93
<211> LENGTH: 118
<212> TYPE: PRT
<213> ORGANISM: Artificial Sequence
<220> FEATURE:
<223> OTHER INFORMATION: chemically synthesized

<400> SEQUENCE: 93

Gln Val Gln Leu Gln Glu Ser Gly Pro Gly Leu Val Lys Pro Ser Asp
1               5                   10                  15

Thr Leu Ser Leu Thr Cys Ala Val Ser Gly Tyr Pro Ile Arg Phe Gly
            20                  25                  30

Tyr Ser Trp His Trp Ile Arg Gln Pro Pro Gly Lys Gly Leu Glu Trp
        35                  40                  45

Met Gly Tyr Ile His Tyr Ser Gly Tyr Thr Asp Phe Asn Pro Ser Leu
    50                  55                  60

Lys Thr Arg Ile Thr Ile Ser Arg Asp Thr Ser Lys Asn Gln Phe Ser
65                  70                  75                  80

Leu Lys Leu Ser Ser Val Thr Ala Val Asp Thr Ala Val Tyr Tyr Cys
                85                  90                  95

Ala Arg Lys Asp Ser Gly Asn Tyr Phe Pro Tyr Trp Gly Gln Gly Thr
            100                 105                 110

Leu Val Thr Val Ser Ser
        115

<210> SEQ ID NO 94
<211> LENGTH: 321
<212> TYPE: DNA
<213> ORGANISM: Artificial Sequence
<220> FEATURE:
<223> OTHER INFORMATION: chemically synthesized

<400> SEQUENCE: 94
gaaattgtgt tgacgcagtc tccagacttt cagtctgtga ctccaaagga aaaagtcacc    60
atcacctgca gggccagtca gagtatcagc gaccacttac actggtacca acagaaacct   120
gatcagtctc ccaagctcct catcaaatat gcttcccatg ccatttctgg ggtcccatcg   180
aggttcagtg gcagtgggtc tgggacagac ttcactctca ccatcaatag cctagaggct   240
gaagatgctg caacgtatta ctgtcagcag ggctacgact cccgttgac tttcggcgga   300 gggaccaagg tggagatcaa a                                              321

<210> SEQ ID NO 95
<211> LENGTH: 107
<212> TYPE: PRT
<213> ORGANISM: Artificial Sequence
<220> FEATURE:
<223> OTHER INFORMATION: chemically synthesized

<400> SEQUENCE: 95

Glu Ile Val Leu Thr Gln Ser Pro Asp Phe Gln Ser Val Thr Pro Lys
1               5                   10                  15

Glu Lys Val Thr Ile Thr Cys Arg Ala Ser Gln Ser Ile Ser Asp His
            20                  25                  30

Leu His Trp Tyr Gln Gln Lys Pro Asp Gln Ser Pro Lys Leu Leu Ile
        35                  40                  45

Lys Tyr Ala Ser His Ala Ile Ser Gly Val Pro Ser Arg Phe Ser Gly

```
                 50                  55                  60

Ser Gly Ser Gly Thr Asp Phe Thr Leu Thr Ile Asn Ser Leu Glu Ala
 65                  70                  75                  80

Glu Asp Ala Ala Thr Tyr Tyr Cys Gln Gln Gly Tyr Asp Phe Pro Leu
                 85                  90                  95

Thr Phe Gly Gly Gly Thr Lys Val Glu Ile Lys
                100                 105

<210> SEQ ID NO 96
<211> LENGTH: 354
<212> TYPE: DNA
<213> ORGANISM: Artificial Sequence
<220> FEATURE:
<223> OTHER INFORMATION: chemically synthesized

<400> SEQUENCE: 96
caggtgcagc ttcaggagtc cggcccagga ctggtgaagc cttcggacac cctgtccctc     60
acctgcgctg tctctggtta cccgatccgg ttcggctata ctggcactg gatacggcag    120 cccccaggga agggactgga gtggatgggg tatatccact acagtggtta cactgacttc    180
aaccctcccc tcaagactcg aatcaccata tcacgtgaca cgtccaagaa ccagttctcc    240
ctgaagctga gctctgtgac cgctgtggac actgcagtgt attactgtgc gagaaaagat    300
tcgggcaact acttccctta ctggggccaa gggactctgg tcactgtctc ttcc          354

<210> SEQ ID NO 97
<211> LENGTH: 118
<212> TYPE: PRT
<213> ORGANISM: Artificial Sequence
<220> FEATURE:
<223> OTHER INFORMATION: chemically synthesized

<400> SEQUENCE: 97

Gln Val Gln Leu Gln Glu Ser Gly Pro Gly Leu Val Lys Pro Ser Asp
 1               5                  10                  15

Thr Leu Ser Leu Thr Cys Ala Val Ser Gly Tyr Pro Ile Arg Phe Gly
                20                  25                  30

Tyr Ser Trp His Trp Ile Arg Gln Pro Pro Gly Lys Gly Leu Glu Trp
            35                  40                  45

Met Gly Tyr Ile His Tyr Ser Gly Tyr Thr Asp Phe Asn Pro Ser Leu
         50                  55                  60

Lys Thr Arg Ile Thr Ile Ser Arg Asp Thr Ser Lys Asn Gln Phe Ser
 65                  70                  75                  80

Leu Lys Leu Ser Ser Val Thr Ala Val Asp Thr Ala Val Tyr Tyr Cys
                85                  90                  95

Ala Arg Lys Asp Ser Gly Asn Tyr Phe Pro Tyr Trp Gly Gln Gly Thr
            100                 105                 110

Leu Val Thr Val Ser Ser
        115

<210> SEQ ID NO 98
<211> LENGTH: 321
<212> TYPE: DNA
<213> ORGANISM: Artificial Sequence
<220> FEATURE:
<223> OTHER INFORMATION: chemically synthesized

<400> SEQUENCE: 98
gaaattgtgt tgacgcagtc tccagacttt cagtctgtga ctccaaagga aaaagtcacc     60
```
atcacctgca gggccagtca gagtatcagc gaccacttac actggtacca acagaaacct    120
gatcagtctc ccaagctcct catcaaatat gcttcccatg ccatttctgg ggtcccatcg    180
aggttcagtg gcagtgggtc tgggacagac ttcactctca ccatcaatag cctagaggct    240
gaagatgctg caacgtatta ctgtcagcag ggctacgact acccgctcac tttcggcgga    300
gggaccaagg tggagatcaa a    321

<210> SEQ ID NO 99
<211> LENGTH: 107
<212> TYPE: PRT
<213> ORGANISM: Artificial Sequence
<220> FEATURE:
<223> OTHER INFORMATION: chemically synthesized

<400> SEQUENCE: 99

Glu Ile Val Leu Thr Gln Ser Pro Asp Phe Gln Ser Val Thr Pro Lys
1               5                   10                  15

Glu Lys Val Thr Ile Thr Cys Arg Ala Ser Gln Ser Ile Ser Asp His
            20                  25                  30

Leu His Trp Tyr Gln Gln Lys Pro Asp Gln Ser Pro Lys Leu Leu Ile
        35                  40                  45

Lys Tyr Ala Ser His Ala Ile Ser Gly Val Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys Gln Gln Gly Tyr Asp Tyr Pro Leu
                85                  90                  95

Thr Phe Gly Gly Gly Thr Lys Val Glu Ile Lys
            100                 105

<210> SEQ ID NO 100
<211> LENGTH: 354
<212> TYPE: DNA
<213> ORGANISM: Artificial Sequence
<220> FEATURE:
<223> OTHER INFORMATION: chemically synthesized

<400> SEQUENCE: 100
caggtgcagc ttcaggagtc cggcccagga ctggtgaagc cttcggacac cctgtccctc     60
acctgcgctg tctctggtta cccgatccgg ttcggctata gctggcactg gatacggcag    120
cccccaggga agggactgga gtggatgggg tatatccact acagtggtta cactgacttc    180
aaccccctcc ctcaagactc gatcaccata tcacgtgaca cgtccaagaa ccagttctcc    240
ctgaagctga gctctgtgac cgctgtggac actgcagtgt attactgtgc gagaaaagat    300
tcgggcaact acttccctta ctggggccaa gggactctgg tcactgtctc ttcc          354

<210> SEQ ID NO 101
<211> LENGTH: 118
<212> TYPE: PRT
<213> ORGANISM: Artificial Sequence
<220> FEATURE:
<223> OTHER INFORMATION: chemically synthesized

<400> SEQUENCE: 101

Gln Val Gln Leu Gln Glu Ser Gly Pro Gly Leu Val Lys Pro Ser Asp
1               5                   10                  15

Thr Leu Ser Leu Thr Cys Ala Val Ser Gly Tyr Pro Ile Arg Phe Gly
            20                  25                  30

```
Tyr Ser Trp His Trp Ile Arg Gln Pro Pro Gly Lys Gly Leu Glu Trp
         35                  40                  45

Met Gly Tyr Ile His Tyr Ser Gly Tyr Thr Asp Phe Asn Pro Ser Leu
 50                  55                  60

Lys Thr Arg Ile Thr Ile Ser Arg Asp Thr Ser Lys Asn Gln Phe Ser
 65                  70                  75                  80

Leu Lys Leu Ser Ser Val Thr Ala Val Asp Thr Ala Val Tyr Tyr Cys
                 85                  90                  95

Ala Arg Lys Asp Ser Gly Asn Tyr Phe Pro Tyr Trp Gly Gln Gly Thr
                100                 105                 110

Leu Val Thr Val Ser Ser
                115

<210> SEQ ID NO 102
<211> LENGTH: 321
<212> TYPE: DNA
<213> ORGANISM: Artificial Sequence
<220> FEATURE:
<223> OTHER INFORMATION: chemically synthesized

<400> SEQUENCE: 102
gaaattgtgt tgacgcagtc tccagacttt cagtctgtga ctccaaagga aaaagtcacc    60
atcacctgca gggccagtca gagtatcagc gaccacttac actggtacca acagaaacct   120
gatcagtctc ccaagctcct catcaaatat gcttcccatg ccattctctgg ggtcccatcg   180 aggttcagtg gcagtgggtc tgggacagac ttcactctca ccatcaatag cctagaggct   240
gaagatgctg caacgtatta ctgtcagcag ggctacgagt tcccgttgac tttcggcgga   300
gggaccaagg tggagatcaa a                                              321

<210> SEQ ID NO 103
<211> LENGTH: 107
<212> TYPE: PRT
<213> ORGANISM: Artificial Sequence
<220> FEATURE:
<223> OTHER INFORMATION: chemically synthesized

<400> SEQUENCE: 103

Glu Ile Val Leu Thr Gln Ser Pro Asp Phe Gln Ser Val Thr Pro Lys
  1               5                  10                  15

Glu Lys Val Thr Ile Thr Cys Arg Ala Ser Gln Ser Ile Ser Asp His
                 20                  25                  30

Leu His Trp Tyr Gln Gln Lys Pro Asp Gln Ser Pro Lys Leu Leu Ile
             35                  40                  45

Lys Tyr Ala Ser His Ala Ile Ser Gly Val Pro Ser Arg Phe Ser Gly
 50                  55                  60

Ser Gly Ser Gly Thr Asp Phe Thr Leu Thr Ile Asn Ser Leu Glu Ala
 65                  70                  75                  80

Glu Asp Ala Ala Thr Tyr Tyr Cys Gln Gln Gly Tyr Glu Phe Pro Leu
                 85                  90                  95

Thr Phe Gly Gly Gly Thr Lys Val Glu Ile Lys
                100                 105

<210> SEQ ID NO 104
<211> LENGTH: 8
<212> TYPE: PRT
<213> ORGANISM: Artificial Sequence
<220> FEATURE:
<223> OTHER INFORMATION: chemically synthesized
<220> FEATURE:
```

```
<221> NAME/KEY: MISC_FEATURE
<222> LOCATION: (2)..(3)
<223> OTHER INFORMATION: X is any amino acid
<220> FEATURE:
<221> NAME/KEY: MISC_FEATURE
<222> LOCATION: (5)..(7)
<223> OTHER INFORMATION: X is any amino acid

<400> SEQUENCE: 104

Gly Xaa Xaa Ile Xaa Xaa Xaa Tyr
1               5

<210> SEQ ID NO 105
<211> LENGTH: 8
<212> TYPE: PRT
<213> ORGANISM: Artificial Sequence
<220> FEATURE:
<223> OTHER INFORMATION: chemically synthesized
<220> FEATURE:
<221> NAME/KEY: MISC_FEATURE
<222> LOCATION: (3)..(3)
<223> OTHER INFORMATION: X is any amino acid
<220> FEATURE:
<221> NAME/KEY: MISC_FEATURE
<222> LOCATION: (5)..(8)
<223> OTHER INFORMATION: X is any amino acid

<400> SEQUENCE: 105

Gly Tyr Xaa Ile Xaa Xaa Xaa Xaa
1               5

<210> SEQ ID NO 106
<211> LENGTH: 214
<212> TYPE: PRT
<213> ORGANISM: Artificial Sequence
<220> FEATURE:
<223> OTHER INFORMATION: chemically synthesized

<400> SEQUENCE: 106

Glu Ile Val Leu Thr Gln Ser Pro Asp Phe Gln Ser Val Thr Pro Lys
1               5                   10                  15

Glu Lys Val Thr Ile Thr Cys Arg Ala Ser Gln Ser Ile Ser Asp His
            20                  25                  30

Leu His Trp Tyr Gln Gln Lys Pro Asp Gln Ser Pro Lys Leu Leu Ile
        35                  40                  45

Lys Tyr Ala Ser His Ala Ile Ser Gly Val Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys Gln Gln Gly His Ser Phe Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190
```

Ala Cys Glu Val Thr His Gln Gly Leu Ser Ser Pro Val Thr Lys Ser
            195                 200                 205
Phe Asn Arg Gly Glu Cys
    210

<210> SEQ ID NO 107
<211> LENGTH: 705
<212> TYPE: DNA
<213> ORGANISM: Artificial Sequence
<220> FEATURE:
<223> OTHER INFORMATION: chemically synthesized

<400> SEQUENCE: 107

```
atgagtgtgc ccactcaggt cctggggttg ctgctgctgt ggcttacaga tgccagatgt      60
gaaattgtgt tgacgcagtc tccagacttt cagtctgtga ctccaaagga aaaagtcacc     120
atcacctgca gggccagtca gagtatcagc gaccacttac actggtacca acagaaacct     180
gatcagtctc ccaagctcct catcaaatat gcttcccatg ccatttctgg ggtcccatcg     240
aggttcagtg gcagtgggtc tgggacagac ttcactctca ccatcaatag cctagaggct     300
gaagatgctg caacgtatta ctgtcagcag ggtcacagtt ttccgctcac tttcggcgga     360
gggaccaagg tggagatcaa acgtacggtg gctgcaccat ctgtcttcat cttcccgcca     420
tctgatgagc agttgaaatc tggaactgcc tctgttgtgt gcctgctgaa taacttctat     480
cccagagagg ccaaagtaca gtggaaggtg gataacgccc tccaatcggg taactcccag     540
gagagtgtca cagagcagga cagcaaggac agcacctaca gcctcagcag caccctgacg     600
ctgagcaaag cagactacga aaacacaaaa gtctacgcct gcgaagtcac ccatcagggc     660
ctgagctcgc ccgtcacaaa gagcttcaac aggggagagt gttaa                    705
```

<210> SEQ ID NO 108
<211> LENGTH: 446
<212> TYPE: PRT
<213> ORGANISM: Artificial Sequence
<220> FEATURE:
<223> OTHER INFORMATION: chemically synthesized

<400> SEQUENCE: 108

Gln Val Gln Leu Gln Glu Ser Gly Pro Gly Leu Val Lys Pro Ser Asp
1               5                   10                  15

Thr Leu Ser Leu Thr Cys Ala Val Ser Gly Phe Pro Ile Arg Tyr Gly
            20                  25                  30

Tyr Ser Trp His Trp Ile Arg Gln Pro Pro Gly Lys Gly Leu Glu Trp
        35                  40                  45

Met Gly Tyr Ile His Tyr Ser Gly Tyr Thr Asp Phe Asn Pro Leu Lys
    50                  55                  60

Thr Arg Ile Thr Ile Ser Arg Asp Thr Ser Lys Asn Gln Phe Ser Leu
65                  70                  75                  80

Lys Leu Ser Ser Val Thr Ala Val Asp Thr Ala Val Tyr Tyr Cys Ala
            85                  90                  95

Arg Lys Asp Ser Gly Asn Tyr Phe Pro Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser

|     |     |     |     | 145 |     |     |     |     | 150 |     |     |     |     | 155 |     |     |     |     | 160 |
| --- | --- | --- | --- | --- | --- | --- | --- | --- | --- | --- | --- | --- | --- | --- | --- | --- | --- | --- | --- |

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
                180                 185                 190

Leu Gly Thr Gln Thr Tyr Ile Cys Asn Val Asn His Lys Pro Ser Asn
                195                 200                 205

Thr Lys Val Asp Lys Arg Val Glu Pro Lys Ser Cys Asp Lys Thr His
210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
                260                 265                 270

Val Lys Phe Asn Trp Tyr Val Asp Gly Val Glu Val His Asn Ala Lys
                275                 280                 285

Thr Lys Pro Arg Glu Glu Gln Tyr Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
                340                 345                 350

Pro Ser Arg Glu Glu Met Thr Lys Asn Gln Val Ser Leu Thr Cys Leu
                355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
                420                 425                 430

His Asn His Tyr Thr Gln Lys Ser Leu Ser Leu Ser Pro Gly
                435                 440                 445

<210> SEQ ID NO 109
<211> LENGTH: 1398
<212> TYPE: DNA
<213> ORGANISM: Artificial Sequence
<220> FEATURE:
<223> OTHER INFORMATION: chemically synthesized

<400> SEQUENCE: 109

```
atggaatgga gctgggtctt tctcttcttc ctgtcagtaa ctacaggtgt ccaccaggtg    60
cagcttcagg agtccggccc aggactggtg aagccttcgg acaccctgtc cctcacctgc   120
gctgtctctg gtttcccgat ccgctacggg tatagctggc actggatacg cagcccccca   180
gggaagggac tggagtggat ggggtatatc cactacagtg gttacactga cttcaacccc   240
tccctcaaga ctcgaatcac catatcacgt gacacgtcca agaaccagtt ctccctgaag   300
ctgagctctg tgaccgctgt ggacactgca gtgtattact gtgcgagaaa agattcgggc   360
aactacttcc cttactgggg ccaagggact ctggtcactg tctcttccgc tccaccaag   420
```

```
ggcccatcgg tcttcccct ggcaccctcc tccaagagca cctctggggg cacagcggcc    480
ctgggctgcc tggtcaagga ctacttcccc gaaccggtga cagtctcgtg gaactcagga    540
gccctgacca gcggcgtgca caccttcccg gctgtcctac agtcctcagg actctactcc    600
ctcagcagcg tggtgactgt gccctccagc agcttgggca cccagaccta catctgcaac    660
gtgaatcaca gcccagcaa caccaaggtg gacaagagag ttgagcccaa atcttgtgac    720
aaaactcaca catgcccacc gtgcccagca cctgaactcc tggggggacc gtcagtcttc    780
ctcttccccc caaaacccaa ggacaccctc atgatctccc ggacccctga ggtcacatgc    840
gtggtggtgg acgtgagcca cgaagaccct gaggtcaagt tcaactggta cgtggacggc    900
gtggaggtgc ataatgccaa gacaaagccg cgggaggagc agtacaacag cacgtaccgt    960
gtggtcagcg tcctcaccgt cctgcaccag gactggctga atggcaagga gtacaagtgc   1020
aaggtctcca acaaagccct cccagccccc atcgagaaaa ccatctccaa agccaaaggg   1080
cagccccgag aaccacaggt gtataccctg cccccatctc gggaggagat gaccaagaac   1140
caggtcagcc tgacttgcct ggtcaaaggc ttctatccca gcgacatcgc cgtggagtgg   1200
gagagcaacg ggcagccgga gaacaactac aagaccacgc ctcccgtgct ggactccgac   1260
ggctccttct tcctctatag caagctcacc gtggacaagt ccaggtggca gcaggggaac   1320
gtcttctcat gctccgtgat gcatgaggct ctgcacaacc actacacgca gaagagcctc   1380
tccctgtctc cgggttaa                                                 1398

<210> SEQ ID NO 110
<211> LENGTH: 9
<212> TYPE: PRT
<213> ORGANISM: Artificial Sequence
<220> FEATURE:
<223> OTHER INFORMATION: chemically synthesized
<220> FEATURE:
<221> NAME/KEY: MISC_FEATURE
<222> LOCATION: (2)..(2)
<223> OTHER INFORMATION: X is F or Y
<220> FEATURE:
<221> NAME/KEY: MISC_FEATURE
<222> LOCATION: (5)..(5)
<223> OTHER INFORMATION: X is R, G or W
<220> FEATURE:
<221> NAME/KEY: MISC_FEATURE
<222> LOCATION: (6)..(6)
<223> OTHER INFORMATION: X is Y, F or G

<400> SEQUENCE: 110

Gly Xaa Pro Ile Xaa Xaa Gly Tyr Ser
1               5

<210> SEQ ID NO 111
<211> LENGTH: 11
<212> TYPE: PRT
<213> ORGANISM: Artificial Sequence
<220> FEATURE:
<223> OTHER INFORMATION: chemically synthesized
<220> FEATURE:
<221> NAME/KEY: MISC_FEATURE
<222> LOCATION: (7)..(7)
<223> OTHER INFORMATION: X is N, Q, D or E
<220> FEATURE:
<221> NAME/KEY: MISC_FEATURE
<222> LOCATION: (8)..(9)
<223> OTHER INFORMATION: X is any hydrophobic amino acid

<400> SEQUENCE: 111

Ala Arg Lys Asp Ser Gly Xaa Xaa Xaa Pro Tyr
```

-continued

```
<210> SEQ ID NO 112
<211> LENGTH: 9
<212> TYPE: PRT
<213> ORGANISM: Artificial Sequence
<220> FEATURE:
<223> OTHER INFORMATION: chemically synthesized
<220> FEATURE:
<221> NAME/KEY: MISC_FEATURE
<222> LOCATION: (4)..(4)
<223> OTHER INFORMATION: X is Y or N
<220> FEATURE:
<221> NAME/KEY: MISC_FEATURE
<222> LOCATION: (5)..(5)
<223> OTHER INFORMATION: X is D or E
<220> FEATURE:
<221> NAME/KEY: MISC_FEATURE
<222> LOCATION: (6)..(6)
<223> OTHER INFORMATION: X is F or Y
<220> FEATURE:
<221> NAME/KEY: MISC_FEATURE
<222> LOCATION: (8)..(8)
<223> OTHER INFORMATION: X is any hydrophobic amino acid

<400> SEQUENCE: 112

Gln Gln Gly Xaa Xaa Xaa Pro Xaa Thr
1               5
```

ANTI-TLR4 ANTIBODIES AND USES THEREOF

RELATED APPLICATIONS

This claims the benefit of U.S. Provisional Application No. 61/617,164, filed Mar. 29, 2012; which is incorporated herein by reference in its entirety.

INCORPORATION OF SEQUENCE LISTING

The contents of the text file named "428001USSeqList-.txt", which was created on Aug. 7, 2013 and is 89.5 KB in size, are hereby incorporated by reference in their entirety.

FIELD OF THE INVENTION

This invention relates generally to antibodies that specifically bind Toll-like Receptor 4 (TLR-4), and to methods of using the anti-TLR4 antibodies as therapeutics and diagnostic agents.

BACKGROUND OF THE INVENTION

Toll receptors, first discovered in *Drosophila*, are type I transmembrane protein having leucine-rich repeats (LRRs) in the extracellular portion of the protein, and one or two cysteine-rich domains. The mammalian homologs of the *Drosophila* Toll receptors are known as "Toll-like receptors" (TLRs). TLRs play a role in innate immunity by recognizing microbial particles and activating immune cells against the source of these microbial particles.

In humans, eleven Toll-like receptors, TLRs 1-11, have been identified and are characterized by the homology of their intracellular domains to that of the IL-1 receptor, and by the presence of extracellular leucine-rich repeats. The different types of TLRs are activated by different types of microbial particles. For example, TLR4 is primarily activated by lipopolysaccharide (LPS), while TLR2 is activated by lipoteichoic (LTA), lipoarabinomannan (LAM); lipoprotein (BLP), and peptideglycans (PGN). Toll receptor homologs, such as RP105, have also been identified.

TLR4 has been shown to associate with an accessory protein, myeloid differentiation protein-2 (MD-2). This protein has been found to interact directly with TLR4, and MD-2 has the ability to enable post-translational modifications of TLR4, as well as facilitate its transport to the cell surface. TLR4 and MD-2 form a complex on the cell surface.

Lipopolysaccharide (LPS), a component of gram-negative bacteria, is a microbial particle capable of strongly activating the innate immune system. LPS delivers signals to immune cells via its multi-chain receptor, comprising the TLR4/MD-2 complex as the principle signaling component.

Accordingly, there exists a need for methods and compositions that bind to TLR4 and modulate signaling that is mediated by the TLR4/MD-2 complex.

SUMMARY OF THE INVENTION

The invention provides monoclonal antibodies recognizing human and/or cynomolgus monkey TLR4/MD-2 receptor expressed on the cell surface. The antibodies are capable of blocking, e.g., neutralizing, receptor activation and subsequent intracellular signaling induced TLR4 ligands, e.g., LPS. Antibodies of the invention include antibodies that bind human and cynomolgus monkey TLR4/MD-2 receptor complex and also bind TLR4 independently of the presence of MD-2.

The present invention provides monoclonal antibodies that specifically bind to human and/or cynomolgus monkey TLR4/MD-2 receptor expressed on the cell surface and capable of blocking receptor activation and subsequent intracellular signaling induced by LPS. Exemplary monoclonal antibodies include: 1A1, 1A6, 1B12, 1C7, 1C10, 1C12, 1D10, 1E11, 1E11 N103D, 1G12, 1E11.C1, 1E11.C2, 1E11.C3, 1E11.C4, 1E11.C5, 1E11.C6, 1E11.E1, 1E11.E2, 1E11.E3, 1E11.E4, 1E11.E5, 1E11.C2E1, 1E11.C2E3, 1E11.C2E4 and 1E11.C2E5.

These antibodies have distinct specificities. Some antibodies show specificity for both the human and cynomolgus monkey TLR4 and/or both the human and cynomolgus monkey TLR4/MD-2 receptor complex, and they have been shown to inhibit receptor activation and subsequent intracellular signaling via LPS. For example, 1C12, 1E11, 1E11 N103D, 1E11.C1, 1E11.C2, 1E11.C3, 1E11.C4, 1E11.C5, 1E11.C6, 1E11.C2E1, 1E11.C2E2, 1E11.C2E3, 1E11.C2E4 and 1E11.C2E5 bind both human and cynomolgus monkey TLR4 independently of the presence of human or cynomolgus monkey MD-2. 1A1, 1A6, 1B12, 1C7, 1C10, 1D10 and 1G12 only bind to cynomolgus monkey TLR4 independently of the presence of cynomolgus monkey MD-2. 1E11.E1, 1E11.E2, 1E11.E3, 1E11.E4 and 1E11.E5 bind only to human TLR4 independently of the presence of human MD-2. These antibodies are respectively referred to herein as TLR4 antibodies.

The humanized antibodies of the invention contain a heavy chain variable region having the amino acid sequence of SEQ ID NO: 2, 6, 8, 10, 12, 14, 16, 18, 20, 22, 67, 69, 71, 73, 75, 77, 89, 93, 97 or 101. The humanized antibodies of the invention contain a light chain variable region having the amino acid sequence of SEQ ID NO: 4, 79, 81, 83, 85 or 87.

The three heavy chain CDRs include an amino acid sequence at least 90%, 92%, 95%, 97% 98%, 99% or more identical to a variable heavy chain complementarity determining region 1 (VH CDR1, also referred to herein as CDRH1) amino acid sequence selected from the group consisting of G(F/Y)PI(R/G/W)(Y/F/G)GYS (SEQ ID NO: 110), GYSITGGYS (SEQ ID NO: 25); GFPIRYGYS (SEQ ID NO: 55); GYPIRFGYS (SEQ ID NO: 56); GYPIRHGYS (SEQ ID NO: 57); GFPIGQGYS (SEQ ID NO: 58); GYPIWGGYS (SEQ ID NO: 59) and GYPIGGGYS (SEQ ID NO: 60), a variable heavy chain complementarity determining region 2 (VH CDR2, also referred to herein as CDRH2) amino acid sequence of IHYSGYT (SEQ ID NO: 26); and a variable heavy chain complementarity determining region 3 (VH CDR3, also referred to herein as CDRH3) amino acid sequence selected from the group consisting of ARKDSG(N/Q/D/E)$X_1X_2$PY (SEQ ID NO: 111) where $X_1$ and $X_2$ are each independently any hydrophobic amino acid, ARKDSGNYFPY (SEQ ID NO: 27); ARKDSGRLLPY (SEQ ID NO: 28); ARKDSGKWLPY (SEQ ID NO: 29); ARKDSGHLMPY (SEQ ID NO: 30); ARKDSGHNYPY (SEQ ID NO: 31); ARKDSGKNFPY (SEQ ID NO: 32); ARKDSGQLFPY (SEQ ID NO: 33); ARKDSGHNLPY (SEQ ID NO: 34); ARKDSGDYFPY (SEQ ID NO: 35) and ARKDSGRYWPY (SEQ ID NO: 36). The three light chain CDRs include an amino acid sequence at least 90%, 92%, 95%, 97% 98%, 99% or more identical to a variable light chain complementarity determining region 1 (VL CDR1, also referred to herein as CDRL1) amino acid sequence of QSISDH (SEQ ID NO: 37); a variable light chain complementarity determining region 2 (VL CDR2, also referred to herein as CDRL2) amino acid sequence of YAS (SEQ ID NO: 38); and a variable light chain complementarity determining region 3 (VL CDR3, also referred to herein as CDRL3) amino acid sequence selected from the group consisting of QQG(Y/N)(D/E)(F/Y)PXT (SEQ ID NO: 112) where X is any hydrophobic amino acid, QQGHSFPLT (SEQ ID NO: 39); QQGNDFPVT (SEQ ID NO: 61); QQGYDEPFT (SEQ ID NO: 62); QQGYDFPFT (SEQ ID NO: 63); QQGYDYPFT (SEQ ID NO: 64) and QQGYEF-PFT (SEQ ID NO: 65). The antibodies bind to human and cynomolgus monkey TLR4/MD-2 complex, to human and cynomolgus TLR4 when not complexed with human and cynomolgus MD-2, to human TLR4/MD-2 complex, to human TLR4 when not complexed with human MD-2, to cynomolgus monkey TLR4/MD-2 complex or cynomolgus TLR4 when not complexed with cynomolgus MD-2.

The anti-TLR4 antibodies of the invention also include antibodies that include a heavy chain variable amino acid sequence that is at least 90%, 92%, 95%, 97%, 98%, 99% or more identical the amino acid sequence of SEQ ID NO: 2, 6, 8, 10, 12, 14, 16, 18, 20, 22, 67, 69, 71, 73, 75, 77, 89, 93, 97 or 101, and/or a light chain variable amino acid that is at least 90%, 92%, 95%, 97%, 98%, 99% or more identical the amino acid sequence of SEQ ID NO: 4, 79, 81, 83, 85 or 87.

Antibodies of the invention specifically bind human and/or cynomolgus monkey TLR4 and/or human and/or cynomolgus monkey TLR4/MD-2 complexes, wherein the antibody binds to an epitope that includes one or more amino acid residues on human and/or cynomolgus monkey TLR4 between residues 289 and 375 of SEQ ID NO: 23 (human TLR4) and/or SEQ ID NO: 24 (cynomolgus TLR4). For example, TLR4 antibodies specifically bind to an epitope that includes residue 349 of SEQ ID NO: 23 (human) and/or SEQ ID NO: 24 (cynomolgus). In some embodiments, the epitope also includes additional residues, for example, residues selected from the group consisting of at least residues 328 and 329 of SEQ ID NO: 23 (human) and/or SEQ ID NO: 24 (cynomolgus); at least residue 351 of SEQ ID NO: 23 (human) and/or SEQ ID NO: 24 (cynomolgus); and at least residues 369 through 371 of SEQ ID NO: 23 (human) and/or SEQ ID NO: 24 (cynomolgus), and any combination thereof.

In some embodiments, the invention provides an isolated antibody that specifically binds Toll-like receptor 4 (TLR4), wherein the antibody binds to an epitope that includes at least residue 349 of SEQ ID NO: 23 and an epitope that includes at least residue 349 of SEQ ID NO: 24. In some embodiments, the antibody includes a heavy chain with three complementarity determining regions (CDRs) including a variable heavy chain complementarity determining region 1 (CDRH1) amino acid sequence of GYSITGGYS (SEQ ID NO: 25); a variable heavy chain complementarity determining region 2 (CDRH2) amino acid sequence of IHYSGYT (SEQ ID NO: 26); and a variable heavy chain complementarity determining region 3 (CDRH3) amino acid sequence of ARKDSG($X_1$)($X_2$)($X_3$)PY (SEQ ID NO: 111), where $X_1$ is N, Q, D or E, $X_2$ is any hydrophobic amino acid, and $X_3$ is any hydrophobic amino acid; and a light chain with three CDRs including a variable light chain complementarity determining region 1 (CDRL1) amino acid sequence of QSISDH (SEQ ID NO: 37); a variable light chain complementarity determining region 2 (CDRL2) amino acid sequence of YAS (SEQ ID NO: 38); and a variable light chain complementarity determining region 3 (CDRL3) amino acid sequence of QQGHSFPLT (SEQ ID NO: 39). In some embodiments, the epitope further includes at least residues 328 and 329 of SEQ ID NO: 23 and SEQ ID NO: 24. In some embodiments, the epitope further includes at least residue 351 of SEQ ID NO: 23 and SEQ ID NO: 24. In some embodiments, the epitope further includes one or more residues between residues 369 through 371 of SEQ ID NO: 23 and SEQ ID NO: 24. In some embodiments, the epitope further includes at least residues 369 through 371 of SEQ ID NO: 23 and SEQ ID NO: 24. In some embodiments, the antibody specifically binds to an epitope that includes at least residues 328, 329, 349, 351 and 369 through 371 of SEQ ID NO: 23 and SEQ ID NO: 24. In some embodiments, the antibody further includes an amino acid substitution in the gamma heavy chain constant region at EU amino acid position 325 and an amino acid substitution at EU amino acid position 328. In some embodiments, the amino acid substituted at EU amino acid position 325 is serine, and wherein the amino acid substituted at EU amino acid position 328 is phenylalanine.

The invention also provides isolated antibodies that specifically bind Toll-like receptor 4 (TLR4), wherein the antibody binds to an epitope that includes at least residue 349 of SEQ ID NO: 23, and wherein the antibody exhibits an $EC_{50}$ value for binding to human TLR4 that is lower than the $EC_{50}$ value exhibited by a reference antibody having the variable heavy chain amino acid sequence of SEQ ID NO: 43 and the variable light chain amino acid sequence of SEQ ID NO: 4. In some embodiments, the $EC_{50}$ value for binding to human TLR4 is determined by a competitive ELISA. In some embodiments, the antibody exhibits an $EC_{50}$ value for binding to human TLR4 that is at least tenfold lower than the $EC_{50}$ value exhibited by the reference antibody. In some embodiments, the antibody further specifically binds an epitope that includes at least residue 349 of SEQ ID NO: 24. In some embodiments, the antibody includes a heavy chain with three complementarity determining regions (CDRs) including a variable heavy chain complementarity determining region 1 (CDRH1) amino acid sequence of G($X_1$)PI($X_2$)($X_3$)GYS (SEQ ID NO: 110), where $X_1$ is F or Y, $X_2$ is R, G or W, $X_3$ is Y, F or G; a variable heavy chain complementarity determining region 2 (CDRH2) amino acid sequence of IHYSGYT (SEQ ID NO: 26); and a variable heavy chain complementarity determining region 3 (CDRH3) amino acid sequence of ARKDSG($X_1$)($X_2$)($X_3$)PY (SEQ ID NO: 111), where $X_1$ is N, Q, D or E, $X_2$ is any hydrophobic amino acid, and $X_3$ is any hydrophobic amino acid; and a light chain with three CDRs including a variable light chain complementarity determining region 1 (CDRL1) amino acid sequence of QSISDH (SEQ ID NO: 37); a variable light chain complementarity determining region 2 (CDRL2) amino acid sequence of YAS (SEQ ID NO: 38); and a variable light chain complementarity determining region 3 (CDRL3) including the amino acid sequence of QQG($X_1$)($X_2$)($X_3$)P($X_4$)T (SEQ ID NO: 112), where $X_1$ is Y or N, $X_2$ is D or E, $X_3$ is F or Y, and $X_4$ is any hydrophobic amino acid, or the amino acid sequence of QQGHSFPLT (SEQ ID NO: 39). In some embodiments, the antibody further includes an amino acid substitution in the gamma heavy chain constant region at EU amino acid position 325 and an amino acid substitution at EU amino acid position 328. In some embodiments, the amino acid substituted at EU amino acid position 325 is serine, and wherein the amino acid substituted at EU amino acid position 328 is phenylalanine. In some embodiments, the TLR4 antibodies also bind the human and/or cynomolgus monkey TLR4/MD-2 complex.

The invention also provides isolated antibodies that specifically bind Toll-like receptor 4 (TLR4), wherein the antibody binds to an epitope that includes at least residue 349 of SEQ ID NO: 23 and binds to an epitope that includes at least residue 349 of SEQ ID NO: 24, and wherein the antibody exhibits an $EC_{50}$ value for binding to human TLR4 that is lower than the $EC_{50}$ value exhibited by a reference antibody having the variable heavy chain amino acid sequence of SEQ ID NO: 43 and the variable light chain amino acid sequence of SEQ ID NO: 4. In some embodiments, the $EC_{50}$ value for binding to human TLR4 is determined by a competitive ELISA. In some embodiments, the antibody exhibits an $EC_{50}$ value for binding to human TLR4 that is at least tenfold lower than the $EC_{50}$ value exhibited by the reference antibody. In some embodiments, the antibody further specifically binds an epitope that includes at least residue 349 of SEQ ID NO: 24. In some embodiments, the antibody includes a heavy chain with three complementarity determining regions (CDRs) including a variable heavy chain complementarity determining region 1 (CDRH1) amino acid sequence of $G(X_1)PI(X_2)(X_3)GYS$ (SEQ ID NO: 110), where $X_1$ is F or Y, $X_2$ is R, G or W, $X_3$ is Y, F or G; a variable heavy chain complementarity determining region 2 (CDRH2) amino acid sequence of IHYSGYT (SEQ ID NO: 26); and a variable heavy chain complementarity determining region 3 (CDRH3) amino acid sequence of $ARKDSG(X_1)(X_2)(X_3)PY$ (SEQ ID NO: 111), where $X_1$ is N, Q, D or E, $X_2$ is any hydrophobic amino acid, and $X_3$ is any hydrophobic amino acid; and a light chain with three CDRs including a variable light chain complementarity determining region 1 (CDRL1) amino acid sequence of QSISDH (SEQ ID NO: 37); a variable light chain complementarity determining region 2 (CDRL2) amino acid sequence of YAS (SEQ ID NO: 38); and a variable light chain complementarity determining region 3 (CDRL3) including the amino acid sequence of $QQG(X_1)(X_2)(X_3)P(X_4)T$ (SEQ ID NO: 112), where $X_1$ is Y or N, $X_2$ is D or E, $X_3$ is F or Y, and $X_4$ is any hydrophobic amino acid, or the amino acid sequence of QQGHSFPLT (SEQ ID NO: 39). In some embodiments, the antibody further includes an amino acid substitution in the gamma heavy chain constant region at EU amino acid position 325 and an amino acid substitution at EU amino acid position 328. In some embodiments, the amino acid substituted at EU amino acid position 325 is serine, and wherein the amino acid substituted at EU amino acid position 328 is phenylalanine. In some embodiments, the TLR4 antibodies also bind the human and/or cynomolgus monkey TLR4/MD-2 complex.

The invention also provides isolated antibodies that specifically bind Toll-like receptor 4 (TLR4) of SEQ ID NO: 23, wherein the antibody on a wild-type human IgG1 Fc backbone exhibits an $IC_{50}$ value for inhibition of LPS activation of human TLR4 in a human whole blood assay that is lower than the $IC_{50}$ value exhibited by a reference antibody having the variable heavy chain amino acid sequence of SEQ ID NO: 43 and the variable light chain amino acid sequence of SEQ ID NO: 4. In some embodiments, the antibody exhibits an $IC_{50}$ value for inhibition of LPS activation of human TLR4 that is at least twofold lower than the $IC_{50}$ value exhibited by the reference antibody. In some embodiments, the antibody includes a heavy chain with three complementarity determining regions (CDRs) including a variable heavy chain complementarity determining region 1 (CDRH1) amino acid sequence of $G(X_1)PI(X_2)(X_3)GYS$ (SEQ ID NO: 110), where $X_1$ is F or Y, $X_2$ is R, G or W, $X_3$ is Y, F or G; a variable heavy chain complementarity determining region 2 (CDRH2) amino acid sequence of IHYSGYT (SEQ ID NO: 26); and a variable heavy chain complementarity determining region 3 (CDRH3) amino acid sequence of $ARKDSG(X_1)(X_2)(X_3)PY$ (SEQ ID NO: 111), where $X_1$ is N, Q, D or E, $X_2$ is any hydrophobic amino acid, and $X_3$ is any hydrophobic amino acid; and a light chain with three CDRs including a variable light chain complementarity determining region 1 (CDRL1) amino acid sequence of QSISDH (SEQ ID NO: 37); a variable light chain complementarity determining region 2 (CDRL2) amino acid sequence of YAS (SEQ ID NO: 38); and a variable light chain complementarity determining region 3 (CDRL3) including the amino acid sequence of $QQG(X_1)(X_2)(X_3)P(X_4)T$ (SEQ ID NO: 112), where $X_1$ is Y or N, $X_2$ is D or E, $X_3$ is F or Y, and $X_4$ is any hydrophobic amino acid, or the amino acid sequence of QQGHSFPLT (SEQ ID NO: 39). In some embodiments, the antibody binds to an epitope that includes at least residue 349 of SEQ ID NO: 23. In some embodiments, the antibody binds to an epitope that includes at least residue 349 of SEQ ID NO: 23 and binds to an epitope that includes at least residue 349 of SEQ ID NO: 24. In some embodiments, the antibody further includes an amino acid substitution in the gamma heavy chain constant region at EU amino acid position 325 and an amino acid substitution at EU amino acid position 328. In some embodiments, the amino acid substituted at EU amino acid position 325 is serine, and wherein the amino acid substituted at EU amino acid position 328 is phenylalanine. In some embodiments, the TLR4 antibodies also bind the human and/or cynomolgus monkey TLR4/MD-2 complex.

The invention also provides isolated antibodies that specifically bind to Toll-like receptor 4 (TLR4), wherein the antibody includes a heavy chain with three complementarity determining regions (CDRs) including a variable heavy chain complementarity determining region 1 (CDRH1) amino acid sequence of $G(X_1)PI(X_2)(X_3)GYS$ (SEQ ID NO: 110), where $X_1$ is F or Y, $X_2$ is R, G or W, $X_3$ is Y, F or G; a variable heavy chain complementarity determining region 2 (CDRH2) amino acid sequence of IHYSGYT (SEQ ID NO: 26); and a variable heavy chain complementarity determining region 3 (CDRH3) amino acid sequence of $ARKDSG(X_1)(X_2)(X_3)PY$ (SEQ ID NO: 111), where $X_1$ is N, Q, D or E, $X_2$ is any hydrophobic amino acid, and $X_3$ is any hydrophobic amino acid; and a light chain with three CDRs including a variable light chain complementarity determining region 1 (CDRL1) amino acid sequence of QSISDH (SEQ ID NO: 37); a variable light chain complementarity determining region 2 (CDRL2) amino acid sequence of YAS (SEQ ID NO: 38); and a variable light chain complementarity determining region 3 (CDRL3) amino acid sequence of $QQG(X_1)(X_2)(X_3)P(X_4)T$ (SEQ ID NO: 112), where $X_1$ is Y or N, $X_2$ is D or E, $X_3$ is F or Y, and $X_4$ is any hydrophobic amino acid. In some embodiments, the antibody includes a CDRH1 amino acid sequence of GYSITGGYS (SEQ ID NO: 25); GFPIRYGYS (SEQ ID NO: 55), GYPIRFGYS (SEQ ID NO: 56), GYPIRHGYS (SEQ ID NO: 57), GFPIGQGYS (SEQ ID NO: 58), GYPIWGGYS (SEQ ID NO: 59) or GYPIGGGYS (SEQ ID NO: 60); a CDRH2 amino acid sequence of IHYSGYT (SEQ ID NO: 26); and a CDRH3 amino acid sequence selected from the group consisting of ARKDSGNYFPY (SEQ ID NO: 27); ARKDSGQLFPY (SEQ ID NO: 33); and ARKDSGDYFPY (SEQ ID NO: 35); a CDRL1 amino acid sequence of QSISDH (SEQ ID NO: 37); a CDRL2 amino acid sequence of YAS (SEQ ID NO: 38); and a CDRL3 amino acid sequence of QQGHSFPLT (SEQ ID NO: 39), QQGNDFPVT (SEQ ID NO: 61), QQGYDEPFT (SEQ ID NO: 62), QQGYDFPLT (SEQ ID NO: 63), QQGYDYPLT (SEQ ID NO: 64) or QQGYEFPLT (SEQ ID NO: 65). In some embodiments, the antibody further includes an amino acid substitution in the gamma heavy chain constant region at EU amino acid position 325 and an amino acid substitution at EU amino acid position 328. In some embodiments, the amino acid substituted at EU amino acid position 325 is serine, and wherein the amino acid substituted at EU amino acid position 328 is phenylalanine. In some embodiments, the TLR4 antibodies also bind the human and/or cynomolgus monkey TLR4/MD-2 complex.

The invention also provides isolated antibodies that specifically bind a Toll-like receptor 4 (TLR4)/MD-2 complex, wherein the antibody includes a heavy chain variable amino acid sequence selected from the group consisting of SEQ ID NOs: 2, 6, 8, 10, 12, 14, 16, 18, 20, 22, 67, 69, 71, 73, 75 or 77 and includes a light chain variable amino acid including the amino acid sequence of SEQ ID NO: 4, 79, 81, 83, 85 or 87. In some embodiments, the antibody includes a combination of a variable heavy chain amino acid sequence and a variable light chain amino acid sequence selected from the group consisting of: (a) a heavy chain variable region including the amino acid sequence of SEQ ID NO: 6 and a light chain variable region including the amino acid sequence of SEQ ID NO: 4; (b) a heavy chain variable region including the amino acid sequence of SEQ ID NO: 8 and a light chain variable region including the amino acid sequence of SEQ ID NO: 4; (c) a heavy chain variable region including the amino acid sequence of SEQ ID NO: 10 and a light chain variable region including the amino acid sequence of SEQ ID NO: 4; (d) a heavy chain variable region including the amino acid sequence of SEQ ID NO: 12 and a light chain variable region including the amino acid sequence of SEQ ID NO: 4; (e) a heavy chain variable region including the amino acid sequence of SEQ ID NO: 14 and a light chain variable region including the amino acid sequence of SEQ ID NO: 4; (f) a heavy chain variable region including the amino acid sequence of SEQ ID NO: 16 and a light chain variable region including the amino acid sequence of SEQ ID NO: 4; (g) a heavy chain variable region including the amino acid sequence of SEQ ID NO: 18 and a light chain variable region including the amino acid sequence of SEQ ID NO: 4; (h) a heavy chain variable region including the amino acid sequence of SEQ ID NO: 2 and a light chain variable region including the amino acid sequence of SEQ ID NO: 4; (i) a heavy chain variable region including the amino acid sequence of SEQ ID NO: 20 and a light chain variable region including the amino acid sequence of SEQ ID NO: 4; (j) a heavy chain variable region including the amino acid sequence of SEQ ID NO: 22 and a light chain variable region including the amino acid sequence of SEQ ID NO: 4; (k) a heavy chain variable region including the amino acid sequence of SEQ ID NO: 67 and a light chain variable region including the amino acid sequence of SEQ ID NO: 4; (l) a heavy chain variable region including the amino acid sequence of SEQ ID NO: 69 and a light chain variable region including the amino acid sequence of SEQ ID NO: 4; (m) a heavy chain variable region including the amino acid sequence of SEQ ID NO: 71 and a light chain variable region including the amino acid sequence of SEQ ID NO: 4; (n) a heavy chain variable region including the amino acid sequence of SEQ ID NO: 73 and a light chain variable region including the amino acid sequence of SEQ ID NO: 4; (o) a heavy chain variable region including the amino acid sequence of SEQ ID NO: 75 and a light chain variable region including the amino acid sequence of SEQ ID NO: 4; (p) a heavy chain variable region including the amino acid sequence of SEQ ID NO: 77 and a light chain variable region including the amino acid sequence of SEQ ID NO: 4; (q) a heavy chain variable region including the amino acid sequence of SEQ ID NO: 2 and a light chain variable region including the amino acid sequence of SEQ ID NO: 79; (r) a heavy chain variable region including the amino acid sequence of SEQ ID NO: 2 and a light chain variable region including the amino acid sequence of SEQ ID NO: 81; (s) a heavy chain variable region including the amino acid sequence of SEQ ID NO: 2 and a light chain variable region including the amino acid sequence of SEQ ID NO: 83; (t) a heavy chain variable region including the amino acid sequence of SEQ ID NO: 2 and a light chain variable region including the amino acid sequence of SEQ ID NO: 85; (u) a heavy chain variable region including the amino acid sequence of SEQ ID NO: 2 and a light chain variable region including the amino acid sequence of SEQ ID NO: 87 (v) a heavy chain variable region including the amino acid sequence of SEQ ID NO: 69 and a light chain variable region including the amino acid sequence of SEQ ID NO: 79; (w) a heavy chain variable region including the amino acid sequence of SEQ ID NO: 69 and a light chain variable region including the amino acid sequence of SEQ ID NO: 83; (x) a heavy chain variable region including the amino acid sequence of SEQ ID NO: 69 and a light chain variable region including the amino acid sequence of SEQ ID NO: 85; and (y) a heavy chain variable region including the amino acid sequence of SEQ ID NO: 69 and a light chain variable region including the amino acid sequence of SEQ ID NO: 87. In some embodiments, the antibody further includes an amino acid substitution in the gamma heavy chain constant region at EU amino acid position 325 and an amino acid substitution at EU amino acid position 328. In some embodiments, the amino acid substituted at EU amino acid position 325 is serine, and wherein the amino acid substituted at EU amino acid position 328 is phenylalanine. In some embodiments, the TLR4 antibodies also bind the human and/or cynomolgus monkey TLR4/MD-2 complex.

Preferably, the TLR4 antibodies are formatted in an IgG isotype. More preferably, the TLR4 antibodies are formatted in an IgG1 isotype. An exemplary IgG1-formatted antibody is the IgG1-formatted 1E11 antibody comprising the heavy chain sequence of SEQ ID NO: 40 and the light chain sequence of SEQ ID NO: 41, as shown below:

```
>1E11 Heavy Chain Amino Acid Sequence
                                    (SEQ ID NO: 40)
QVQLQESGPGLVKPSDTLSLTCAVSGYSITGGYSWHWIRQPPGKGLEWM
GYIHYSGYTDFNPSLKTRITISRDTSKNQFSLKLSSVTAVDTAVYYCAR
KDSGNYFPYWGQGTLVTVSSASTKGPSVFPLAPSSKSTSGGTAALGCLV
KDYFPEPVTVSWNSGALTSGVHTFPAVLQSSGLYSLSSVVTVPSSSLGT
QTYICNVNHKPSNTKVDKRVEPKSCDKTHTCPPCPAPELLGGPSVFLFP
PKPKDTLMISRTPEVTCVVVDVSHEDPEVKFNWYVDGVEVHNAKTKPRE
EQYNSTYRVVSVLTVLHQDWLNGKEYKCKVSNKALPAPIEKTISKAKGQ
PREPQVYTLPPSREEMTKNQVSLTCLVKGFYPSDIAVEWESNGQPENNY
KTTPPVLDSDGSFFLYSKLTVDKSRWQQGNVFSCSVMHEALHNHYTQKS
LSLSPG >1E11 Light Chain Amino Acid Sequence
                                    (SEQ ID NO: 41)
EIVLTQSPDFQSVTPKEKVTITCRASQSISDHLHWYQQKPDQSPKLLIK
YASHAISGVPSRFSGSGSGTDFTLTINSLEAEDAATYYCQQGHSFPLTF
GGGTKVEIKRTVAAPSVFIFPPSDEQLKSGTASVVCLLNNFYPREAKVQ
WKVDNALQSGNSQESVTEQDSKDSTYSLSSTLTLSKADYEKHKVYACEV
THQGLSSPVTKSFNRGEC
```

The anti-TLR4 antibodies described herein also include at least one specific amino acid substitution within, for example, an Fc region or an FcR binding fragment thereof (e.g., a polypeptide having amino acid substitutions within an IgG constant domain) such that the modified antibody elicits alterations in antigen-dependent effector function while retaining binding to antigen as compared to an unaltered antibody. For example, the altered antibodies elicit the prevention of proinflammatory mediator release. In a preferred embodiment, the altered antibodies are human and of the IgG1 isotype.

The anti-TLR4 antibodies of the invention include an altered antibody in which at least one amino acid residue in the constant region of the Fc portion of the antibody has been modified. For example, at least one amino acid in the CH2 domain of the Fc portion has been replaced by a different residue, i.e., an amino acid substitution. In the altered antibodies described herein, one or more of the amino acid residues that correspond to residues 325, 326 and 328 is substituted with a different residue as compared to an unaltered antibody. The numbering of the residues in the gamma heavy chain is that of the EU index (see Edelman, G. M. et al., 1969; Kabat, E, A., T. T. Wu, H. M. Perry, K. S. Gottesman, and C. Foeller., 1991. *Sequences of Proteins of Immunological Interest*, 5$^{th}$ Ed. U.S. Dept. of Health and Human Services, Bethesda, Md., NIH Publication n. 91-3242). In a preferred embodiment, EU amino acid position 325 of the gamma heavy chain constant region is substituted with serine, and EU amino acid position 328 of the gamma heavy chain constant region is substituted with phenylalanine, such that the EU positions 325 to 328 of the gamma heavy chain constant region of the altered human IgG1 antibody comprise the amino acid sequence SKAF (SEQ ID NO: 42).

The present invention also provides methods of treating or preventing pathologies associated with aberrant TLR4/MD-2 activation and/or aberrant LPS activity (e.g., aberrant pro-inflammatory cytokine production such as aberrant IL-8 production), or alleviating a symptom associated with such pathologies, by administering a monoclonal antibody of the invention (e.g., a murine monoclonal or humanized monoclonal antibody) to a subject in which such treatment or prevention is desired. The subject to be treated is, e.g., human. The monoclonal antibody is administered in an amount sufficient to treat, prevent or alleviate a symptom associated with the pathology. The amount of monoclonal antibody sufficient to treat or prevent the pathology in the subject is, for example, an amount that is sufficient to reduce LPS-induced production of one or more pro-inflammatory cytokines (e.g., IL-6, IL-8). As used herein, the term "reduced" refers to a decreased production of a pro-inflammatory cytokine in the presence of a monoclonal antibody of the invention, wherein the production is, for example, local pro-inflammatory cytokine production (e.g., at a site of inflamed tissue) or systemic pro-inflammatory cytokine production. LPS-induced production of a pro-inflammatory cytokine is decreased when the level of pro-inflammatory cytokine production in the presence of a monoclonal antibody of the invention is greater than or equal to 5%, 10%, 20%, 25%, 30%, 40%, 50%, 60%, 70%, 75%, 80%, 90%, 95%, 99%, or 100% lower than a control level of pro-inflammatory cytokine production (i.e., the level of pro-inflammatory cytokine production in the absence of the monoclonal antibody). Level of pro-inflammatory cytokine production is measured. Those skilled in the art will appreciate that the level of pro-inflammatory cytokine production can be measured using a variety of assays, including, for example, the methods described herein as well as commercially available ELISA kits.

Pathologies treated and/or prevented using the monoclonal antibodies of the invention (e.g., a murine monoclonal or humanized monoclonal antibody) include, for example, sepsis induced by microbial products, acute inflammation, chronic inflammation (e.g., chronic inflammation associated with allergic conditions and asthma), autoimmune diseases (e.g., IBD and atherosclerosis), ischemic injury with and without transplantation, kidney diseases (e.g., diabetic nephropathy), acute kidney injury and diseases in which stress, for example, cellular stress, induces the expression of endogenous soluble stress factors (e.g., Hsp60, fibronectin, heparan sulphate, hyaluronan, gp96, β-Defensin-2 and surfactant protein A). Pathologies in which stress, for example, cellular stress induces the expression of endogenous soluble stress factors include, for example, osteoarthritis and rheumatoid arthritis. Pathologies associated with stress, for example, cellular stress, can also occur in subjects and patients placed on respirators, ventilators and other respiratory-assist devices. Such pathologies include, for example, ventilator-induced lung injury ("VILI"), also referred to as ventilation-associated lung injury ("VALI").

Pharmaceutical compositions according to the invention can include an anti-TLR4 antibody of the invention and a carrier. These pharmaceutical compositions can be included in kits, such as, for example, diagnostic kits.

BRIEF DESCRIPTION OF THE DRAWINGS

FIG. 15 is a series of graphs depicting the inhibition of IL-6 production induced by TLR4 activation in cynomolgus monkey whole blood assay by purified antibodies, referred to herein "15C1, 1E11C2". This experiment was conducted with blood of 2 different animals. Cynomolgus monkey blood was diluted with decreased concentration of antibodies and subsequently incubated with LPS. Levels of IL-6 were assessed 24 hours post LPS-treatment using Milliplex kit. The results obtained with parental antibody 15C1 are shown with circle symbols, while the results using 1E11.C2 antibody are shown in square symbols.

DETAILED DESCRIPTION OF THE INVENTION

Figure 1:
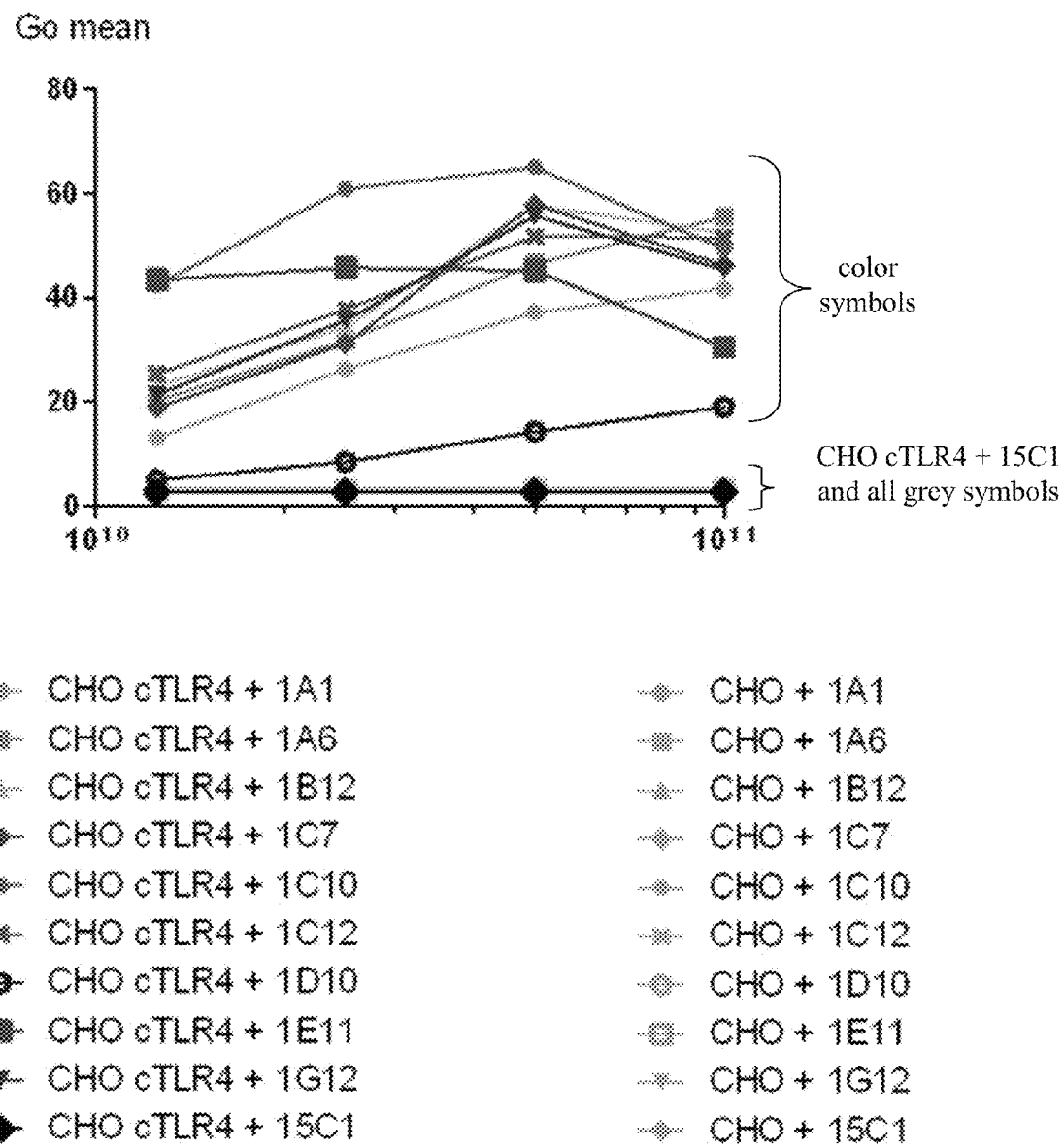
FIG. 1 is a graph depicting the binding by monoclonal phages expressing scFv, referred to herein as "1A1, 1A6, 1B12, 1C7, 1C10, 1C12, 1D10, 1E11, 1G12, 15C1", to the cynomolgus monkey TLR4. Specificity of binding is shown by flow cytometry using CHO cells mock transfected or transfected with cynomolgus monkey TLR4. The results using mock-transfected cells are shown with grey symbols (key on right), while the results using cynomolgus monkey TLR4 transfected cells are shown in other colored symbols (key on left).

The present invention provides monoclonal antibodies (MAbs) that specifically bind the human and/or cynomolgus monkey TLR4/MD-2 receptor complex. This receptor complex is activated by lipopolysaccharide (LPS), the major component of the outer membrane of gram-negative bacteria. It is also activated by additional ligands, including by way of non-limiting example, Respiratory Syncytial Virus Fusion protein, OxPL, Ox-LDL, Amyloid-β, β-Defensin 2, Nickel, HMGB1, HSP, S100A8/S100A9, Tenascin C, Fibronectin-EDA, Biglycan and Hyaluronan. The monoclonal antibodies of the invention inhibit receptor activation and subsequent intracellular signaling via LPS. Thus, the monoclonal antibodies neutralize the activation of the TLR4/MD-2 receptor complex. In particular, the invention provides monoclonal antibodies that recognize the TLR4/MD-2 receptor complex expressed on the cell surface. In addition, the monoclonal antibodies of the invention also recognize human and cynomolgus monkey TLR4 when not complexed with MD-2. The monoclonal antibody is, e.g., a humanized antibody.

Antibodies of the invention specifically bind human and/or cynomolgus monkey TLR4/MD-2 complex, wherein the antibody binds to an epitope that includes one or more amino acid residues on human TLR4 and/or cynomolgus TLR4 between residues 289 and 375 of SEQ ID NO: 23 (human) and SEQ ID NO: 24 (cynomolgus).

Exemplary antibodies of the invention include, 1A1, 1A6, 1B12, 1C7, 1C10, 1C12, 1D10, 1E11, 1E11 N103D, 1G12, 1E11.C1, 1E11.C2, 1E11.C3, 1E11.C4, 1E11.C5, 1E11.C6, 1E11.E1, 1E11.E2, 1E11.E3, 1E11.E4, 1E11.E5, 1E11.C2E1, 1E11.C2E2, 1E11.C2E3, 1E11.C2E4 and 1E11.C2E5. Some antibodies show specificity for both the human and cynomolgus monkey TLR4/MD-2 receptor complex, and they have been shown to inhibit receptor activation and subsequent intracellular signaling via LPS. For example, 1C12, 1E11, 1E11 N103D, 1E11.C1, 1E11.C2, 1E11.C3, 1E11.C4, 1E11.C5, 1E11.C6, 1E11.C2E1, 1E11.C2E2, 1E11.C2E3, 1E11.C2E4 and 1E11.C2E5 bind both human and cynomolgus monkey TLR4 independently of the presence of human or cynomolgus monkey MD-2. Exemplary antibodies 1A1, 1A6, 1B12, 1C7, 1C10, 1D10 and 1G12 only bind to cynomolgus monkey TLR4 independently of the presence of cynomolgus monkey MD-2. 1E11.E1, 1E11.E2, 1E11.E3, 1E11.E4 and 1E11.E5 bind only to human TLR4 independently of the presence of human MD-2.

TLRs recognize microbial particles and activate immune cells against the source of these microbial particles. (See Takeda et al., Annu. Rev. Immunol., 21: 335-76 (2003), hereby incorporated by reference in its entirety). TLR4 and MD-2 have been shown to form a complex on the cell surface, and the presence of MD-2 appears essential for the responsiveness of TLR4 to various ligands, including by way of non-limiting example, LPS, Respiratory Syncytial Virus Fusion protein, OxPL, Ox-LDL, Amyloid-β, β-Defensin 2, Nickel, HMGB1, HSP, S100A8/S100A9, Tenascin C, Fibronectin-EDA, Biglycan and Hyaluronan.

LPS delivers signals to immune cells via its multi-chain receptor in which the TLR4/MD-2 complex is the principle signaling component. LPS has been shown to exert its effects on the immune system via signaling through TLR4. LPS rapidly binds to the lipopolysaccharide-binding protein (LBP) in the bloodstream, and in this form, LPS interacts with the GPI-anchored cell surface protein CD14. LPS is then transferred to TLR4 which transduces an intracellular activation signal. Recently, another protein, MD-2, was found to be necessary for signal transduction via TLR4 to occur. MD-2 interacts directly with TLR4 and plays an important role in its post-translational modification and intracellular trafficking. In addition, MD-2 has been shown to directly bind LPS, which demonstrates the importance of this accessory protein in the LPS receptor complex (See Miyake K., Int. Immunopharmacol. 3:119-128 (2003), hereby incorporated by reference in its entirety). Accordingly, neutralization of LPS signaling mediated by the TLR4/MD-2 complex is a potential therapeutic strategy in the treatment of disorders such as, for example, acute systemic inflammation and sepsis induced by gram-negative bacterial infection.

TLR4 antibodies of the invention include, for example, the heavy chain complementarity determining regions (CDRs) shown below in Table 1A, the light chain CDRs shown in Table 1B, and combinations thereof.

TABLE 1

VH CDR sequences from antibody clones that bind and neutralize TLR4

| Clone ID | Heavy CDR1 | Heavy CDR2 | Heavy CDR3 |
| --- | --- | --- | --- |
| 1A1 | GYSIT...GGYS (SEQ ID NO: 25) | IHYS...GYT (SEQ ID NO: 26) | ARKDSGRLLPY (SEQ ID NO: 28) |
| 1A6 | GYSIT...GGYS (SEQ ID NO: 25) | IHYS...GYT (SEQ ID NO: 26) | ARKDSGKWLPY (SEQ ID NO: 29) |
| 1B12 | GYSIT...GGYS (SEQ ID NO: 25) | IHYS...GYT (SEQ ID NO: 26) | ARKDSGHLMPY (SEQ ID NO: 30) |
| 1C7 | GYSIT...GGYS (SEQ ID NO: 25) | IHYS...GYT (SEQ ID NO: 26) | ARKDSGHNYPY (SEQ ID NO: 31) |
| 1C10 | GYSIT...GGYS (SEQ ID NO: 25) | IHYS...GYT (SEQ ID NO: 26) | ARKDSGKNFPY (SEQ ID NO: 32) |
| 1C12 | GYSIT...GGYS (SEQ ID NO: 25) | IHYS...GYT (SEQ ID NO: 26) | ARKDSGQLFPY (SEQ ID NO: 33) |
| 1D10 | GYSIT...GGYS (SEQ ID NO: 25) | IHYS...GYT (SEQ ID NO: 26) | ARKDSGHNLPY (SEQ ID NO: 34) |
| 1E11 | GYSIT...GGYS (SEQ ID NO: 25) | IHYS...GYT (SEQ ID NO: 26) | ARKDSGNYFPY (SEQ ID NO: 27) |
| 1E11 N103D | GYSIT...GGYS (SEQ ID NO: 25) | IHYS...GYT (SEQ ID NO: 26) | ARKDSGDYFPY (SEQ ID NO: 35) |
| 1G12 | GYSIT...GGYS (SEQ ID NO: 25) | IHYS...GYT (SEQ ID NO: 26) | ARKDSGRYWPY (SEQ ID NO: 36) |
| 1E11.C1 | GFPIR...YGYS (SEQ ID NO: 55) | IHYS...GYT (SEQ ID NO: 26) | ARKDSGNYFPY (SEQ ID NO: 27) |
| 1E11.C2 | GYPIR...FGYS (SEQ ID NO: 56) | IHYS...GYT (SEQ ID NO: 26) | ARKDSGNYFPY (SEQ ID NO: 27) |

TABLE 1-continued

VH CDR sequences from antibody clones
that bind and neutralize TLR4

| Clone ID | Heavy CDR1 | Heavy CDR2 | Heavy CDR3 |
|---|---|---|---|
| 1E11.C3 | GYPIR...HGYS (SEQ ID NO: 57) | IHYS...GYT (SEQ ID NO: 26) | ARKDSGNYFPY (SEQ ID NO: 27) |
| 1E11.C4 | GFPIG...QGYS (SEQ ID NO: 58) | IHYS...GYT (SEQ ID NO: 26) | ARKDSGNYFPY (SEQ ID NO: 27) |
| 1E11.C5 | GYPIW...GGYS (SEQ ID NO: 59) | IHYS...GYT (SEQ ID NO: 26) | ARKDSGNYFPY (SEQ ID NO: 27) |
| 1E11.C6 | GYPIG...GGYS (SEQ ID NO: 60) | IHYS...GYT (SEQ ID NO: 26) | ARKDSGNYFPY (SEQ ID NO: 27) |
| 1E11.E1 | GYSIT...GGYS (SEQ ID NO: 25) | IHYS...GYT (SEQ ID NO: 26) | ARKDSGNYFPY (SEQ ID NO: 27) |
| 1E11.E2 | GYSIT...GGYS (SEQ ID NO: 25) | IHYS...GYT (SEQ ID NO: 26) | ARKDSGNYFPY (SEQ ID NO: 27) |
| 1E11.E3 | GYSIT...GGYS (SEQ ID NO: 25) | IHYS...GYT (SEQ ID NO: 26) | ARKDSGNYFPY (SEQ ID NO: 27) |
| 1E11.E4 | GYSIT...GGYS (SEQ ID NO: 25) | IHYS...GYT (SEQ ID NO: 26) | ARKDSGNYFPY (SEQ ID NO: 27) |
| 1E11.E5 | GYSIT...GGYS (SEQ ID NO: 25) | IHYS...GYT (SEQ ID NO: 26) | ARKDSGNYFPY (SEQ ID NO: 27) |
| 1E11.C2E1 | GYPIR...FGYS (SEQ ID NO: 56) | IHYS...GYT (SEQ ID NO: 26) | ARKDSGNYFPY (SEQ ID NO: 27) |
| 1E11.C2E3 | GYPIR...FGYS (SEQ ID NO: 56) | IHYS...GYT (SEQ ID NO: 26) | ARKDSGNYFPY (SEQ ID NO: 27) |
| 1E11.C2E4 | GYPIR...FGYS (SEQ ID NO: 56) | IHYS...GYT (SEQ ID NO: 26) | ARKDSGNYFPY (SEQ ID NO: 27) |
| 1E11.C2E5 | GYPIR...FGYS (SEQ ID NO: 56) | IHYS...GYT (SEQ ID NO: 26) | ARKDSGNYFPY (SEQ ID NO: 27) |

TABLE 1B

VL CDR sequences from antibody clones
that bind and neutralize TLR4

| Clone ID | Light CDR1 | Light CDR2 | Light CDR3 |
|---|---|---|---|
| 1A1 | QSI......SDH (SEQ ID NO: 37) | YA.......S (SEQ ID NO: 38) | QQGHSFPLT (SEQ ID NO: 39) |
| 1A6 | QSI......SDH (SEQ ID NO: 37) | YA.......S (SEQ ID NO: 38) | QQGHSFPLT (SEQ ID NO: 39) |
| 1B12 | QSI......SDH (SEQ ID NO: 37) | YA.......S (SEQ ID NO: 38) | QQGHSFPLT (SEQ ID NO: 39) |
| 1C7 | QSI......SDH (SEQ ID NO: 37) | YA.......S (SEQ ID NO: 38) | QQGHSFPLT (SEQ ID NO: 39) |
| 1C10 | QSI......SDH (SEQ ID NO: 37) | YA.......S (SEQ ID NO: 38) | QQGHSFPLT (SEQ ID NO: 39) |
| 1E11 | QSI......SDH (SEQ ID NO: 37) | YA.......S (SEQ ID NO: 38) | QQGHSFPLT (SEQ ID NO: 39) |
| 1E11 N103D | QSI......SDH (SEQ ID NO: 37) | YA.......S (SEQ ID NO: 38) | QQGHSFPLT (SEQ ID NO: 39) |
| 1G12 | QSI......SDH (SEQ ID NO: 37) | YA.......S (SEQ ID NO: 38) | QQGHSFPLT (SEQ ID NO: 39) |

TABLE 1B-continued

VL CDR sequences from antibody clones that bind and neutralize TLR4

| Clone ID | Light CDR1 | Light CDR2 | Light CDR3 |
|---|---|---|---|
| 1E11.C1 | QSI......SDH (SEQ ID NO: 37) | YA.......S (SEQ ID NO: 38) | QQGHSFPLT (SEQ ID NO: 39) |
| 1E11.C2 | QSI......SDH (SEQ ID NO: 37) | YA.......S (SEQ ID NO: 38) | QQGHSFPLT (SEQ ID NO: 39) |
| 1E11.C3 | QSI......SDH (SEQ ID NO: 37) | YA.......S (SEQ ID NO: 38) | QQGHSFPLT (SEQ ID NO: 39) |
| 1E11.C4 | QSI......SDH (SEQ ID NO: 37) | YA.......S (SEQ ID NO: 38) | QQGHSFPLT (SEQ ID NO: 39) |
| 1E11.C5 | QSI......SDH (SEQ ID NO: 37) | YA.......S (SEQ ID NO: 38) | QQGHSFPLT (SEQ ID NO: 39) |
| 1E11.C6 | QSI......SDH (SEQ ID NO: 37) | YA.......S (SEQ ID NO: 38) | QQGHSFPLT (SEQ ID NO: 39) |
| 1E11.E1 | QSI......SDH (SEQ ID NO: 37) | YA.......S (SEQ ID NO: 38) | QQGNDFPVT (SEQ ID NO: 61) |
| 1E11.E2 | QSI......SDH (SEQ ID NO: 37) | YA.......S (SEQ ID NO: 38) | QQGYDEPFT (SEQ ID NO: 62) |
| 1E11.E3 | QSI......SDH (SEQ ID NO: 37) | YA.......S (SEQ ID NO: 38) | QQGYDFPLT (SEQ ID NO: 63) |
| 1E11.E4 | QSI......SDH (SEQ ID NO: 37) | YA.......S (SEQ ID NO: 38) | QQGYDYPLT (SEQ ID NO: 64) |
| 1E11.E5 | QSI......SDH (SEQ ID NO: 37) | YA.......S (SEQ ID NO: 38) | QQGYEFPLT (SEQ ID NO: 65) |
| 1E11.C2E1 | QSI......SDH (SEQ ID NO: 37) | YA.......S (SEQ ID NO: 38) | QQGNDFPVT (SEQ ID NO: 61) |
| 1E11.C2E3 | QSI......SDH (SEQ ID NO: 37) | YA.......S (SEQ ID NO: 38) | QQGYDFPLT (SEQ ID NO: 63) |
| 1E11.C2E4 | QSI......SDH (SEQ ID NO: 37) | YA.......S (SEQ ID NO: 38) | QQGYDYPLT (SEQ ID NO: 64) |
| 1E11.C2E5 | QSI......SDH (SEQ ID NO: 37) | YA.......S (SEQ ID NO: 38) | QQGYEFPLT (SEQ ID NO: 65) |

TLR4 antibodies of the invention include, for example, antibodies having the combination of heavy chain and light chain sequences shown below in Table 2.

TABLE 2

VH and VL sequences from antibody clones that bind and neutralize TLR4

| Clone ID | Variable heavy chain | Variable light chain |
|---|---|---|
| 1A1 | SEQ ID NO: 6 | SEQ ID NO: 4 |
| 1A6 | SEQ ID NO: 8 | SEQ ID NO: 4 |
| 1B12 | SEQ ID NO: 10 | SEQ ID NO: 4 |
| 1C7 | SEQ ID NO: 12 | SEQ ID NO: 4 |
| 1C10 | SEQ ID NO: 14 | SEQ ID NO: 4 |
| 1C12 | SEQ ID NO: 16 | SEQ ID NO: 4 |
| 1D10 | SEQ ID NO: 18 | SEQ ID NO: 4 |
| 1E11 | SEQ ID NO: 2 | SEQ ID NO: 4 |
| 1E11 N103D | SEQ ID NO: 20 | SEQ ID NO: 4 |
| 1G12 | SEQ ID NO: 22 | SEQ ID NO: 4 |
| 1E11.C1 | SEQ ID NO: 67 | SEQ ID NO: 4 |
| 1E11.C2 | SEQ ID NO: 69 | SEQ ID NO: 4 |
| 1E11.C3 | SEQ ID NO: 71 | SEQ ID NO: 4 |
| 1E11.C4 | SEQ ID NO: 73 | SEQ ID NO: 4 |
| 1E11.C5 | SEQ ID NO: 75 | SEQ ID NO: 4 |
| 1E11.C6 | SEQ ID NO: 77 | SEQ ID NO: 4 |
| 1E11.E1 | SEQ ID NO: 2 | SEQ ID NO: 79 |
| 1E11.E2 | SEQ ID NO: 2 | SEQ ID NO: 81 |
| 1E11.E3 | SEQ ID NO: 2 | SEQ ID NO: 83 |
| 1E11.E4 | SEQ ID NO: 2 | SEQ ID NO: 85 |
| 1E11.E5 | SEQ ID NO: 2 | SEQ ID NO: 87 |
| 1E11.C2E1 | SEQ ID NO: 89 | SEQ ID NO: 91 |
| 1E11.C2E3 | SEQ ID NO: 93 | SEQ ID NO: 95 |
| 1E11.C2E4 | SEQ ID NO: 97 | SEQ ID NO: 99 |
| 1E11.C2E5 | SEQ ID NO: 101 | SEQ ID NO: 103 |

An exemplary TLR4 monoclonal antibody is the 1E11 antibody described herein. As shown below, the 1E11 antibody includes a heavy chain variable region (SEQ ID NO: 2) encoded by the nucleic acid sequence shown in SEQ ID NO: 1, and a light chain variable region (SEQ ID NO: 4) encoded by the nucleic acid sequence shown in SEQ ID NO: 3.

>1E11 VH nucleic acid sequence
(SEQ ID NO: 1)
CAGGTGCAGCTTCAGGAGTCCGGCCCAGGACTGGTGAAGCCTTCGGACA
CCCTGTCCCTCACCTGCGCTGTCTCTGGTTACTCCATCACCGGTGGTTA
TAGCTGGCACTGGATACGGCAGCCCCCAGGGAAGGGACTGGAGTGGATG
GGGTATATCCACTACAGTGGTTACACTGACTTCAACCCCTCCCTCAAGA
CTCGAATCACCATATCACGTGACACGTCCAAGAACCAGTTCTCCCTGAA
GCTGAGCTCTGTGACCGCTGTGGACACTGCAGTGTATTACTGTGCGAGA
AAAGATTCGGGCAACTACTTCCCTTACTGGGGCCAAGGGACTCTGGTCA
CTGTCTCTTCC >1E11 VH amino acid sequence
(SEQ ID NO: 2)
QVQLQESGPGLVKPSDTLSLTCAVSGYSITGGYSWHWIRQPPGKGLEWM
GYIHYSGYTDFNPSLKTRITISRDTSKNQFSLKLSSVTAVDTAVYYCAR
KDSGNYFPYWGQGTLVTVSS >1E11 VL nucleic acid sequence
(SEQ ID NO: 3)
GAAATTGTGTTGACGCAGTCTCCAGACTTTCAGTCTGTGACTCCAAAGG
AAAAAGTCACCATCACCTGCAGGGCCAGTCAGAGTATCAGCGACCACTT
ACACTGGTACCAACAGAAACCTGATCAGTCTCCCAAGCTCCTCATCAAA
TATGCTTCCCATGCCATTTCTGGGGTCCCATCGAGGTTCAGTGGCAGTG
GGTCTGGGACAGACTTCACTCTCACCATCAATAGCCTAGAGGCTGAAGA
TGCTGCAACGTATTACTGTCAGCAGGGTCACAGTTTTCCGCTCACTTTC
GGCGGAGGGACCAAGGTGGAGATCAAA >1E11 VL amino acid sequence
(SEQ ID NO: 4)
EIVLTQSPDFQSVTPKEKVTITCRASQSISDHLHWYQQKPDQSPKLLIK
YASHAISGVPSRFSGSGSGTDFTLTINSLEAEDAATYYCQQGHSFPLTF
GGGTKVEIK The amino acids encompassing the complementarity determining regions (CDR) are as defined by M. P. Lefranc (See Lefranc, M.-P., Current Protocols in Immunology, J. Wiley and Sons, New York supplement 40, A1.P.1-A.1P.37 (2000) LIGM:230). The heavy chain CDRs of the 1E11 antibody have the following sequences: GYSITGGYS (SEQ ID NO: 25); IHYSGYT (SEQ ID NO: 26); and ARKDS-GNYFPY (SEQ ID NO: 27). The light chain CDRs of the 1E11 antibody have the following sequences: QSISDH (SEQ ID NO: 37); YAS (SEQ ID NO: 38); and QQGHSF-PLT (SEQ ID NO: 39).

An exemplary TLR4 monoclonal antibody is the 1A1 antibody described herein. As shown below, the 1A1 antibody includes a heavy chain variable region (SEQ ID NO: 6) encoded by the nucleic acid sequence shown in SEQ ID NO: 5, and a light chain variable region (SEQ ID NO: 4) encoded by the nucleic acid sequence shown in SEQ ID NO: 3.

>1A1 VH nucleic acid sequence
(SEQ ID NO: 5)
CAGGTGCAGCTTCAGGAGTCCGGCCCAGGACTGGTGAAGCCTTCGGACA
CCCTGTCCCTCACCTGCGCTGTCTCTGGTTACTCCATCACCGGTGGTTA
TAGCTGGCACTGGATACGGCAGCCCCCAGGGAAGGGACTGGAGTGGATG
GGGTATATCCACTACAGTGGTTACACTGACTTCAACCCCTCCCTCAAGA
CTCGAATCACCATATCACGTGACACGTCCAAGAACCAGTTCTCCCTGAA
GCTGAGCTCTGTGACCGCTGTGGACACTGCAGTGTATTACTGTGCGAGA
AAAGATTCCGGCCGCCTCCTCCCTTACTGGGGCCAAGGGACTCTGGTCA
CTGTCTCTTCC >1A1 VH amino acid sequence
(SEQ ID NO: 6)
QVQLQESGPGLVKPSDTLSLTCAVSGYSITGGYSWHWIRQPPGKGLEWM
GYIHYSGYTDFNPSLKTRITISRDTSKNQFSLKLSSVTAVDTAVYYCAR
KDSGRLLPYWGQGTLVTVSS >1A1 VL nucleic acid sequence
(SEQ ID NO: 3)
GAAATTGTGTTGACGCAGTCTCCAGACTTTCAGTCTGTGACTCCAAAGG
AAAAAGTCACCATCACCTGCAGGGCCAGTCAGAGTATCAGCGACCACTT
ACACTGGTACCAACAGAAACCTGATCAGTCTCCCAAGCTCCTCATCAAA
TATGCTTCCCATGCCATTTCTGGGGTCCCATCGAGGTTCAGTGGCAGTG
GGTCTGGGACAGACTTCACTCTCACCATCAATAGCCTAGAGGCTGAAGA
TGCTGCAACGTATTACTGTCAGCAGGGTCACAGTTTTCCGCTCACTTTC
GGCGGAGGGACCAAGGTGGAGATCAAA >1A1 VL amino acid sequence
(SEQ ID NO: 4)
EIVLTQSPDFQSVTPKEKVTITCRASQSISDHLHWYQQKPDQSPKLLIK
YASHAISGVPSRFSGSGSGTDFTLTINSLEAEDAATYYCQQGHSFPLTF
GGGTKVEIK The amino acids encompassing the complementarity determining regions (CDR) are as defined by M. P. Lefranc (See Lefranc, M.-P., Current Protocols in Immunology, J. Wiley and Sons, New York supplement 40, A1.P.1-A.1P.37 (2000) LIGM:230). The heavy chain CDRs of the 1A1 antibody have the following sequences: GYSITGGYS (SEQ ID NO: 25); IHYSGYT (SEQ ID NO: 26); and ARKDS-GRLLPY (SEQ ID NO: 28). The light chain CDRs of the 1A1 antibody have the following sequences: QSISDH (SEQ ID NO: 37); YAS (SEQ ID NO: 38); and QQGHSFPLT (SEQ ID NO: 39).

An exemplary TLR4 monoclonal antibody is the 1A6 antibody described herein. As shown below, the 1A6 antibody includes a heavy chain variable region (SEQ ID NO: 8) encoded by the nucleic acid sequence shown in SEQ ID NO: 7, and a light chain variable region (SEQ ID NO: 4) encoded by the nucleic acid sequence shown in SEQ ID NO: 3.

>1A6 VH nucleic acid sequence
(SEQ ID NO: 7)
CAGGTGCAGCTTCAGGAGTCCGGCCCAGGACTGGTGAAGCCTTCGGACA
CCCTGTCCCTCACCTGCGCTGTCTCTGGTTACTCCATCACCGGTGGTTA
TAGCTGGCACTGGATACGGCAGCCCCCAGGGAAGGGACTGGAGTGGATG
GGGTATATCCACTACAGTGGTTACACTGACTTCAACCCCTCCCTCAAGA
CTCGAATCACCATATCACGTGACACGTCCAAGAACCAGTTCTCCCTGAA
GCTGAGCTCTGTGACCGCTGTGGACACTGCAGTGTATTACTGTGCGAGA
AAAGATAGCGGCAAGTGGTTGCCTTACTGGGGCCAAGGGACTCTGGTCA
CTGTCTCTTCC >1A6 VH amino acid sequence
(SEQ ID NO: 8)
QVQLQESGPGLVKPSDTLSLTCAVSGYSITGGYSWHWIRQPPGKGLEWM
GYIHYSGYTDFNPSLKTRITISRDTSKNQFSLKLSSVTAVDTAVYYCAR
KDSGKWLPYWGQGTLVTVSS >1A6 VL nucleic acid sequence
(SEQ ID NO: 3)
GAAATTGTGTTGACGCAGTCTCCAGACTTTCAGTCTGTGACTCCAAAGG
AAAAAGTCACCATCACCTGCAGGGCCAGTCAGAGTATCAGCGACCACTT
ACACTGGTACCAACAGAAACCTGATCAGTCTCCCAAGCTCCTCATCAAA
TATGCTTCCCATGCCATTTCTGGGGTCCCATCGAGGTTCAGTGGCAGTG
GGTCTGGGACAGACTTCACTCTCACCATCAATAGCCTAGAGGCTGAAGA
TGCTGCAACGTATTACTGTCAGCAGGGTCACAGTTTTCCGCTCACTTTC
GGCGGAGGGACCAAGGTGGAGATCAAA >1A6 VL amino acid sequence
(SEQ ID NO: 4)
EIVLTQSPDFQSVTPKEKVTITCRASQSISDHLHWYQQKPDQSPKLLIK
YASHAISGVPSRFSGSGSGTDFTLTINSLEAEDAATYYCQQGHSFPLTF
GGGTKVEIK The amino acids encompassing the complementarity determining regions (CDR) are as defined by M. P. Lefranc (See Lefranc, M.-P., Current Protocols in Immunology, J. Wiley and Sons, New York supplement 40, A1.P.1-A.1P.37 (2000) LIGM:230). The heavy chain CDRs of the 1A6 antibody have the following sequences: GYSITGGYS (SEQ ID NO: 25); IHYSGYT (SEQ ID NO: 26); and ARKDS-GKWLPY (SEQ ID NO: 29). The light chain CDRs of the 1A6 antibody have the following sequences: QSISDH (SEQ ID NO: 37); YAS (SEQ ID NO: 38); and QQGHSFPLT (SEQ ID NO: 39).

An exemplary TLR4 monoclonal antibody is the 1B12 antibody described herein. As shown below, the 1B12 antibody includes a heavy chain variable region (SEQ ID NO: 10) encoded by the nucleic acid sequence shown in SEQ ID NO: 9, and a light chain variable region (SEQ ID NO: 4) encoded by the nucleic acid sequence shown in SEQ ID NO: 3.

>1B12 VH nucleic acid sequence
(SEQ ID NO: 9)
CAGGTGCAGCTTCAGGAGTCCGGCCCAGGACTGGTGAAGCCTTCGGACA
CCCTGTCCCTCACCTGCGCTGTCTCTGGTTACTCCATCACCGGTGGTTA
TAGCTGGCACTGGATACGGCAGCCCCCAGGGAAGGGACTGGAGTGGATG
GGGTATATCCACTACAGTGGTTACACTGACTTCAACCCCTCCCTCAAGA
CTCGAATCACCATATCACGTGACACGTCCAAGAACCAGTTCTCCCTGAA
GCTGAGCTCTGTGACCGCTGTGGACACTGCAGTGTATTACTGTGCGAGA
AAAGATAGCGGGCACCTCATGCCTTACTGGGGCCAAGGGACTCTGGTCA
CTGTCTCTTCC >1B12 VH amino acid sequence
(SEQ ID NO: 10)
QVQLQESGPGLVKPSDTLSLTCAVSGYSITGGYSWHWIRQPPGKGLEWM
GYIHYSGYTDFNPSLKTRITISRDTSKNQFSLKLSSVTAVDTAVYYCAR
KDSGHLMPYWGQGTLVTVSS >1B12 VL nucleic acid sequence
(SEQ ID NO: 3)
GAAATTGTGTTGACGCAGTCTCCAGACTTTCAGTCTGTGACTCCAAAGG
AAAAAGTCACCATCACCTGCAGGGCCAGTCAGAGTATCAGCGACCACTT
ACACTGGTACCAACAGAAACCTGATCAGTCTCCCAAGCTCCTCATCAAA
TATGCTTCCCATGCCATTTCTGGGGTCCCATCGAGGTTCAGTGGCAGTG
GGTCTGGGACAGACTTCACTCTCACCATCAATAGCCTAGAGGCTGAAGA
TGCTGCAACGTATTACTGTCAGCAGGGTCACAGTTTTCCGCTCACTTTC
GGCGGAGGGACCAAGGTGGAGATCAAA >1B12 VL amino acid sequence
(SEQ ID NO: 4)
EIVLTQSPDFQSVTPKEKVTITCRASQSISDHLHWYQQKPDQSPKLLIK
YASHAISGVPSRFSGSGSGTDFTLTINSLEAEDAATYYCQQGHSFPLTF
GGGTKVEIK The amino acids encompassing the complementarity determining regions (CDR) are as defined by M. P. Lefranc (See Lefranc, M.-P., Current Protocols in Immunology, J. Wiley and Sons, New York supplement 40, A1.P.1-A.1P.37 (2000) LIGM:230). The heavy chain CDRs of the 1A6 antibody have the following sequences: GYSITGGYS (SEQ ID NO: 25); IHYSGYT (SEQ ID NO: 26); and ARKDS-GHLMPY (SEQ ID NO: 30). The light chain CDRs of the 1B12 antibody have the following sequences: QSISDH (SEQ ID NO: 37); YAS (SEQ ID NO: 38); and QQGHSFPLT (SEQ ID NO: 39).

An exemplary TLR4 monoclonal antibody is the 1C7 antibody described herein. As shown below, the 1C7 antibody includes a heavy chain variable region (SEQ ID NO: 12) encoded by the nucleic acid sequence shown in SEQ ID NO: 11, and a light chain variable region (SEQ ID NO: 4) encoded by the nucleic acid sequence shown in SEQ ID NO: 3.

>1C7 VH nucleic acid sequence
(SEQ ID NO: 11)
CAGGTGCAGCTTCAGGAGTCCGGCCCAGGACTGGTGAAGCCTTCGGACA
CCCTGTCCCTCACCTGCGCTGTCTCTGGTTACTCCATCACCGGTGGTTA
TAGCTGGCACTGGATACGGCAGCCCCCAGGGAAGGGACTGGAGTGGATG
GGGTATATCCACTACAGTGGTTACACTGACTTCAACCCCTCCCTCAAGA
CTCGAATCACCATATCACGTGACACGTCCAAGAACCAGTTCTCCCTGAA
GCTGAGCTCTGTGACCGCTGTGGACACTGCAGTGTATTACTGTGCGAGA
AAAGATTCCGGGCACAACTACCCTTACTGGGGCCAAGGGACTCTGGTCA
CTGTCTCTTCC >1C7 VH amino acid sequence
(SEQ ID NO: 12)
QVQLQESGPGLVKPSDTLSLTCAVSGYSITGGYSWHWIRQPPGKGLEWM
GYIHYSGYTDFNPSLKTRITISRDTSKNQFSLKLSSVTAVDTAVYYCAR
KDSGHNYPYWGQGTLVTVSS >1C7 VL nucleic acid sequence
(SEQ ID NO: 3)
GAAATTGTGTTGACGCAGTCTCCAGACTTTCAGTCTGTGACTCCAAAGG
AAAAAGTCACCATCACCTGCAGGGCCAGTCAGAGTATCAGCGACCACTT
ACACTGGTACCAACAGAAACCTGATCAGTCTCCCAAGCTCCTCATCAAA
TATGCTTCCCATGCCATTTCTGGGGTCCCATCGAGGTTCAGTGGCAGTG
GGTCTGGGACAGACTTCACTCTCACCATCAATAGCCTAGAGGCTGAAGA
TGCTGCAACGTATTACTGTCAGCAGGGTCACAGTTTTCCGCTCACTTTC
GGCGGAGGGACCAAGGTGGAGATCAAA >1C7 VL amino acid sequence
(SEQ ID NO: 4)
EIVLTQSPDFQSVTPKEKVTITCRASQSISDHLHWYQQKPDQSPKLLIK
YASHAISGVPSRFSGSGSGTDFTLTINSLEAEDAATYYCQQGHSFPLTF
GGGTKVEIK The amino acids encompassing the complementarity determining regions (CDR) are as defined by M. P. Lefranc (See Lefranc, M.-P., Current Protocols in Immunology, J. Wiley and Sons, New York supplement 40, A1.P.1-A.1P.37 (2000) LIGM:230). The heavy chain CDRs of the 1C7 antibody have the following sequences: GYSITGGYS (SEQ ID NO: 25); IHYSGYT (SEQ ID NO: 26); and ARKDS-GHNYPY (SEQ ID NO: 31). The light chain CDRs of the 1C7 antibody have the following sequences: QSISDH (SEQ ID NO: 37); YAS (SEQ ID NO: 38); and QQGHSFPLT (SEQ ID NO: 39).

An exemplary TLR4 monoclonal antibody is the 1C10 antibody described herein. As shown below, the 1C10 antibody includes a heavy chain variable region (SEQ ID NO: 14) encoded by the nucleic acid sequence shown in SEQ ID NO: 13, and a light chain variable region (SEQ ID NO: 4) encoded by the nucleic acid sequence shown in SEQ ID NO: 3.

>1C10 VH nucleic acid sequence
(SEQ ID NO: 13)
CAGGTGCAGCTTCAGGAGTCCGGCCCAGGACTGGTGAAGCCTTCGGACA
CCCTGTCCCTCACCTGCGCTGTCTCTGGTTACTCCATCACCGGTGGTTA
TAGCTGGCACTGGATACGGCAGCCCCCAGGGAAGGGACTGGAGTGGATG
GGGTATATCCACTACAGTGGTTACACTGACTTCAACCCCTCCCTCAAGA
CTCGAATCACCATATCACGTGACACGTCCAAGAACCAGTTCTCCCTGAA
GCTGAGCTCTGTGACCGCTGTGGACACTGCAGTGTATTACTGTGCGAGA
AAAGATAGCGGCAAGAACTTCCCTTACTGGGGCCAAGGGACTCTGGTCA
CTGTCTCTTCC >1C10 VH amino acid sequence
(SEQ ID NO: 14)
QVQLQESGPGLVKPSDTLSLTCAVSGYSITGGYSWHWIRQPPGKGLEWM
GYIHYSGYTDFNPSLKTRITISRDTSKNQFSLKLSSVTAVDTAVYYCAR
KDSGKNFPYWGQGTLVTVSS >1C10 VL nucleic acid sequence
(SEQ ID NO: 3)
GAAATTGTGTTGACGCAGTCTCCAGACTTTCAGTCTGTGACTCCAAAGG
AAAAAGTCACCATCACCTGCAGGGCCAGTCAGAGTATCAGCGACCACTT
ACACTGGTACCAACAGAAACCTGATCAGTCTCCCAAGCTCCTCATCAAA
TATGCTTCCCATGCCATTTCTGGGGTCCCATCGAGGTTCAGTGGCAGTG
GGTCTGGGACAGACTTCACTCTCACCATCAATAGCCTAGAGGCTGAAGA
TGCTGCAACGTATTACTGTCAGCAGGGTCACAGTTTTCCGCTCACTTTC
GGCGGAGGGACCAAGGTGGAGATCAAA >1C10 VL amino acid sequence
(SEQ ID NO: 4)
EIVLTQSPDFQSVTPKEKVTITCRASQSISDHLHWYQQKPDQSPKLLIK
YASHAISGVPSRFSGSGSGTDFTLTINSLEAEDAATYYCQQGHSFPLTF
GGGTKVEIK The amino acids encompassing the complementarity determining regions (CDR) are as defined by M. P. Lefranc (See Lefranc, M.-P., Current Protocols in Immunology, J. Wiley and Sons, New York supplement 40, A1.P.1-A.1P.37 (2000) LIGM:230). The heavy chain CDRs of the 1C10 antibody have the following sequences: GYSITGGYS (SEQ ID NO: 25); IHYSGYT (SEQ ID NO: 26); and ARKDS-GKNFPY (SEQ ID NO: 32). The light chain CDRs of the 1C10 antibody have the following sequences: QSISDH (SEQ ID NO: 37); YAS (SEQ ID NO: 38); and QQGHSF-PLT (SEQ ID NO: 39).

An exemplary TLR4 monoclonal antibody is the 1C12 antibody described herein. As shown below, the 1C12 antibody includes a heavy chain variable region (SEQ ID NO: 16) encoded by the nucleic acid sequence shown in SEQ ID NO: 15, and a light chain variable region (SEQ ID NO: 4) encoded by the nucleic acid sequence shown in SEQ ID NO: 3.

>1C12 VH nucleic acid sequence
(SEQ ID NO: 15)
CAGGTGCAGCTTCAGGAGTCCGGCCCAGGACTGGTGAAGCCTTCGGACAC
CCTGTCCCTCACCTGCGCTGTCTCTGGTTACTCCATCACCGGTGGTTATA
GCTGGCACTGGATACGGCAGCCCCCAGGGAAGGGACTGGAGTGGATGGG
GTATATCCACTACAGTGGTTACACTGACTTCAACCCCTCCCTCAAGACTC
GAATCACCATATCACGTGACACGTCCAAGAACCAGTTCTCCCTGAAGCT
GAGCTCTGTGACCGCTGTGGACACTGCAGTGTATTACTGTGCGAGAAAA
GATAGCGGCCAGTTGTTCCCTTACTGGGGCCAAGGGACTCTGGTCACT
GTCTCTTCC >1C12 VH amino acid sequence
(SEQ ID NO: 16)
QVQLQESGPGLVKPSDTLSLTCAVSGYSITGGYSWHWIRQPPGKGLEWM
GYIHYSGYTDFNPSLKTRITISRDTSKNQFSLKLSSVTAVDTAVYYCARK
DSGQLFPYWGQGTLVTVSS >1C12 VL nucleic acid sequence
(SEQ ID NO: 3)
GAAATTGTGTTGACGCAGTCTCCAGACTTTCAGTCTGTGACTCCAAAGG
AAAAAGTCACCATCACCTGCAGGGCCAGTCAGAGTATCAGCGACCAC
TTACACTGGTACCAACAGAAACCTGATCAGTCTCCCAAGCTCCTCATC
AAATATGCTTCCCATGCCATTTCTGGGGTCCCATCGAGGTTCAGTGGC
AGTGGGTCTGGGACAGACTTCACTCTCACCATCAATAGCCTAGAGGCT
GAAGATGCTGCAACGTATTACTGTCAGCAGGGTCACAGTTTTCCGCTC
ACTTTCGGCGGAGGGACCAAGGTGGAGATCAA
A >1C12 VL amino acid sequence
(SEQ ID NO: 4)
EIVLTQSPDFQSVTPKEKVTITCRASQSISDHLHWYQQKPDQSPKLLIK
YASHAISGVPSRFSGSGSGTDFTLTINSLEAEDAATYYCQQGHSFPLT
FGGGTKVEIK The amino acids encompassing the complementarity determining regions (CDR) are as defined by M. P. Lefranc (See Lefranc, M.-P., Current Protocols in Immunology, J. Wiley and Sons, New York supplement 40, A1.P.1-A.1P.37 (2000) LIGM:230). The heavy chain CDRs of the 1C12 antibody have the following sequences: GYSITGGYS (SEQ ID NO: 25); IHYSGYT (SEQ ID NO: 26); and ARKDS-GQLFPY (SEQ ID NO: 33). The light chain CDRs of the 1C12 antibody have the following sequences: QSISDH (SEQ ID NO: 37); YAS (SEQ ID NO: 38); and QQGHSF-PLT (SEQ ID NO: 39).

An exemplary TLR4 monoclonal antibody is the 1D10 antibody described herein. As shown below, the 1D10 antibody includes a heavy chain variable region (SEQ ID NO: 18) encoded by the nucleic acid sequence shown in SEQ ID NO: 17, and a light chain variable region (SEQ ID NO: 4) encoded by the nucleic acid sequence shown in SEQ ID NO: 3.

>1D10 VH nucleic acid sequence
(SEQ ID NO: 17)
CAGGTGCAGCTTCAGGAGTCCGGCCCAGGACTGGTGAAGCCTTCGGAC
ACCCTGTCCCTCACCTGCGCTGTCTCTGGTTACTCCATCACCGGTGG
TTATAGCTGGCACTGGATACGGCAGCCCCCAGGGAAGGGACTGGAGT
GGATGGGGTATATCCACTACAGTGGTTACACTGACTTCAACCCCTCC
CTCAAGACTCGAATCACCATATCACGTGACACGTCCAAGAACCAGTT
CTCCCTGAAGCTGAGCTCTGTGACCGCTGTGGACACTGCAGTGTATT
ACTGTGCGAGAAAAGATAGCGGCCACAACTTGCCTTA
CTGGGGCCAAGGGACTCTGGTCACTGTCTCTTCC >1D10 VH amino acid sequence
(SEQ ID NO: 18)
QVQLQESGPGLVKPSDTLSLTCAVSGYSITGGYSWHWIRQPPGKGLEWM
GYIHYSGYTDFNPSLKTRITISRDTSKNQFSLKLSSVTAVDTAVYY
CARKDSGHNLPYWGQGTLVTVSS >1D10 VL nucleic acid sequence
(SEQ ID NO: 3)
GAAATTGTGTTGACGCAGTCTCCAGACTTTCAGTCTGTGACTCCAAAG
GAAAAAGTCACCATCACCTGCAGGGCCAGTCAGAGTATCAGCGACCA
CTTACACTGGTACCAACAGAAACCTGATCAGTCTCCCAAGCTCCTCA
TCAAATATGCTTCCCATGCCATTTCTGGGGTCCCATCGAGGTTCAGT
GGCAGTGGGTCTGGGACAGACTTCACTCTCACCATCAATAGCCTAGA
GGCTGAAGATGCTGCAACGTATTACTGTCAGCAGGGTCACAGTTTT
CCGCTCACTTTCGGCGGAGGGACCAAGGTGGAGATCAAA >1D10 VL amino acid sequence
(SEQ ID NO: 4)
EIVLTQSPDFQSVTPKEKVTITCRASQSISDHLHWYQQKPDQSPKLL
IKYASHAISGVPSRFSGSGSGTDFTLTINSLEAEDAATYYCQQGHSF
PLTFGGGTKVEIK The amino acids encompassing the complementarity determining regions (CDR) are as defined by M. P. Lefranc (See Lefranc, M.-P., Current Protocols in Immunology, J. Wiley and Sons, New York supplement 40, A1.P.1-A.1P.37 (2000) LIGM:230). The heavy chain CDRs of the 1D10 antibody have the following sequences: GYSITGGYS (SEQ ID NO: 25); IHYSGYT (SEQ ID NO: 26); and ARKDS-GHNLPY (SEQ ID NO: 34). The light chain CDRs of the 1D10 antibody have the following sequences: QSISDH (SEQ ID NO: 37); YAS (SEQ ID NO: 38); and QQGHSF-PLT (SEQ ID NO: 39).

An exemplary TLR4 monoclonal antibody is the 1E11 N103D antibody described herein. As shown below, the 1E11 N103D antibody includes a heavy chain variable region (SEQ ID NO: 20) encoded by the nucleic acid sequence shown in SEQ ID NO: 19, and a light chain variable region (SEQ ID NO: 4) encoded by the nucleic acid sequence shown in SEQ ID NO: 3.

>1E11 N103D VH nucleic acid sequence
(SEQ ID NO: 19)
CAGGTGCAGCTTCAGGAGTCCGGCCCAGGACTGGTGAAGCCTTCGGACA
CCCTGTCCCTCACCTGCGCTGTCTCTGGTTACTCCATCACCGGTGGTT
ATAGCTGGCACTGGATACGGCAGCCCCCAGGGAAGGGACTGGAGTGGA
TGGGGTATATCCACTACAGTGGTTACACTGACTTCAACCCCTCCCTC
AAGACTCGAATCACCATATCACGTGACACGTCCAAGAACCAGTTCTCC
CTGAAGCTGAGCTCTGTGACCGCTGTGGACACTGCAGTGTATTACTGT
GCGAGAAAAGATTCGGGCGACTACTTCCCTTA
CTGGGGCCAAGGGACTCTGGTCACTGTCTCTTCC >1E11 N103D VH amino acid sequence
(SEQ ID NO: 20)
QVQLQESGPGLVKPSDTLSLTCAVSGYSITGGYSWHWIRQPPGKGLEW
MGYIHYSGYTDFNPSLKTRITISRDTSKNQFSLKLSSVTAVDTAVYY
CARKDSGDYFPYWGQGTLVTVSS >1E11 N103D VL nucleic acid sequence
(SEQ ID NO: 3)
GAAATTGTGTTGACGCAGTCTCCAGACTTTCAGTCTGTGACTCCAAAGG
AAAAAGTCACCATCACCTGCAGGGCCAGTCAGAGTATCAGCGACCACT
TACACTGGTACCAACAGAAACCTGATCAGTCTCCCAAGCTCCTCATC
AAATATGCTTCCCATGCCATTTCTGGGGTCCCATCGAGGTTCAGTGGC -continued
```
AGTGGGTCTGGGACAGACTTCACTCTCACCATCAATAGCCTAGAGGC
TGAAGATGCTGCAACGTATTACTGTCAGCAGGGTCACAGTTTTCCGCT
CACTTTCGGCGGAGGGACCAAGGTGGAGATCAAA >1E11 N103D VL amino acid sequence
                                            (SEQ ID NO: 4)
EIVLTQSPDFQSVTPKEKVTITCRASQSISDHLHWYQQKPDQSPKLL
IKYASHAISGVPSRFSGSGSGTDFTLTINSLEAEDAATYYCQQGHSF
PLTFGGGTKVEIK
```

The amino acids encompassing the complementarity determining regions (CDR) are as defined by M. P. Lefranc (See Lefranc, M.-P., Current Protocols in Immunology, J. Wiley and Sons, New York supplement 40, A1.P.1-A.1P.37 (2000) LIGM:230). The heavy chain CDRs of the 1E11 N103D antibody have the following sequences: GYSITG-GYS (SEQ ID NO: 25); IHYSGYT (SEQ ID NO: 26); and ARKDSGDYFPY (SEQ ID NO: 35). The light chain CDRs of the 1E11 N103D antibody have the following sequences: QSISDH (SEQ ID NO: 37); YAS (SEQ ID NO: 38); and QQGHSFPLT (SEQ ID NO: 39).

An exemplary TLR4 monoclonal antibody is the 1G12 antibody described herein. As shown below, the 1G12 antibody includes a heavy chain variable region (SEQ ID NO: 22) encoded by the nucleic acid sequence shown in SEQ ID NO: 21, and a light chain variable region (SEQ ID NO: 4) encoded by the nucleic acid sequence shown in SEQ ID NO: 3.

```
>1G12 VH nucleic acid sequence
                                           (SEQ ID NO: 21)
CAGGTGCAGCTTCAGGAGTCCGGCCCAGGACTGGTGAAGCCTTCGGACA
CCCTGTCCCTCACCTGCGCTGTCTCTGGTTACTCCATCACCGGTGGT
TATAGCTGGCACTGGATACGGCAGCCCCCAGGGAAGGGACTGGAGT
GGATGGGGTATATCCACTACAGTGGTTACACTGACTTCAACCCCTCC
CTCAAGACTCGAATCACCATATCACGTGACACGTCCAAGAACCAGTT
CTCCCTGAAGCTGAGCTCTGTGACCGCTGTGGACACTGCAGTGTAT
TACTGTGCGAGAAAAGATTCCGGGCGGTACTGGCCTTA
CTGGGGCCAAGGGACTCTGGTCACTGTCTCTTCC >1G12 VH amino acid sequence
                                           (SEQ ID NO: 22)
QVQLQESGPGLVKPSDTLSLTCAVSGYSITGGYSWHWIRQPPGKGLEW
MGYIHYSGYTDFNPSLKTRITISRDTSKNQFSLKLSSVTAVDTAVYY
CARKDSGRYWPYWGQGTLVTVSS >1G12 VL nucleic acid sequence
                                            (SEQ ID NO: 3)
GAAATTGTGTTGACGCAGTCTCCAGACTTTCAGTCTGTGACTCCAAAG
GAAAAAGTCACCATCACCTGCAGGGCCAGTCAGAGTATCAGCGACCAC
TTACACTGGTACCAACAGAAACCTGATCAGTCTCCCAAGCTCCTCA
TCAAATATGCTTCCCATGCCATTTCTGGGGTCCCATCGAGGTTCAGTG
GCAGTGGGTCTGGGACAGACTTCACTCTCACCATCAATAGCCTAGAGG
CTGAAGATGCTGCAACGTATTACTGTCAGCAGGGTCACAGTTTTCCG
CTCACTTTCGGCGGAGGGACCAAGGTGGAGATCAAA >1G12 VL amino acid sequence
                                            (SEQ ID NO: 4)
EIVLTQSPDFQSVTPKEKVTITCRASQSISDHLHWYQQKPDQSPKLLI
KYASHAISGVPSRFSGSGSGTDFTLTINSLEAEDAATYYCQQGHSFP
LTFGGGTKVEIK
```

The amino acids encompassing the complementarity determining regions (CDR) are as defined by M. P. Lefranc (See Lefranc, M.-P., Current Protocols in Immunology, J. Wiley and Sons, New York supplement 40, A1.P.1-A.1P.37 (2000) LIGM:230). The heavy chain CDRs of the 1G12 antibody have the following sequences: GYSITGGYS (SEQ ID NO: 25); IHYSGYT (SEQ ID NO: 26); and ARKDS-GRYWPY (SEQ ID NO: 36). The light chain CDRs of the 1E11 N103D antibody have the following sequences: QSISDH (SEQ ID NO: 37); YAS (SEQ ID NO: 38); and QQGHSFPLT (SEQ ID NO: 39).

An exemplary TLR4 monoclonal antibody is the 1E11.C1 antibody described herein. As shown below, the 1E11.C1 antibody includes a heavy chain variable region (SEQ ID NO: 67) encoded by the nucleic acid sequence shown in SEQ ID NO: 66, and a light chain variable region (SEQ ID NO: 4) encoded by the nucleic acid sequence shown in SEQ ID NO: 3.

```
>1E11.C1 VH nucleic acid sequence
                                           (SEQ ID NO: 66)
CAGGTGCAGCTTCAGGAGTCCGGCCCAGGACTGGTGAAGCCTTCGGAC
ACCCTGTCCCTCACCTGCGCTGTCTCTGGTTTCCCGATCCGCTACGG
GTATAGCTGGCACTGGATACGGCAGCCCCCAGGGAAGGGACTGGAG
TGGATGGGGTATATCCACTACAGTGGTTACACTGACTTCAACCCCTC
CCTCAAGACTCGAATCACCATATCACGTGACACGTCCAAGAACCAGT
TCTCCCTGAAGCTGAGCTCTGTGACCGCTGTGGACACTGCAGTGTA
TTACTGTGCGAGAAAAGATTCGGGCAACTACTTCCCTTA
CTGGGGCCAAGGGACTCTGGTCACTGTCTCTTCC >1E11.C1 VH amino acid sequence
                                           (SEQ ID NO: 67)
QVQLQESGPGLVKPSDTLSLTCAVSGFPIRYGYSWHWIRQPPGKGLE
WMGYIHYSGYTDFNPSLKTRITISRDTSKNQFSLKLSSVTAVDTA
VYYCARKDSGNYFPYWGQGTLVTVSS >1E11.C1 VL amino acid sequence
                                            (SEQ ID NO: 3)
GAAATTGTGTTGACGCAGTCTCCAGACTTTCAGTCTGTGACTCCAA
AGGAAAAAGTCACCATCACCTGCAGGGCCAGTCAGAGTATCAGCGA
CCACTTACACTGGTACCAACAGAAACCTGATCAGTCTCCCAAGCT
CCTCATCAAATATGCTTCCCATGCCATTTCTGGGGTCCCATCGAG
GTTCAGTGGCAGTGGGTCTGGGACAGACTTCACTCTCACCATCAA
TAGCCTAGAGGCTGAAGATGCTGCAACGTATTACTGTCAGCAGGG
TCACAGTTTTCCGCTCACTTTCGGCGGAGGGACCAAGGTGGAGAT
CAAA >1E11.C1 VL amino acid sequence
                                            (SEQ ID NO: 4)
EIVLTQSPDFQSVTPKEKVTITCRASQSISDHLHWYQQKPDQSPK
LLIKYASHAISGVPSRFSGSGSGTDFTLTINSLEAEDAATYYCQQ
GHSFPLTFGGGTKVEIK
```

The amino acids encompassing the complementarity determining regions (CDR) are as defined by M. P. Lefranc (See Lefranc, M.-P., Current Protocols in Immunology, J. Wiley and Sons, New York supplement 40, A1.P.1-A.1P.37 (2000) LIGM:230). The heavy chain CDRs of the 1E11.C1 antibody have the following sequences: GFPIRYGYS (SEQ ID NO: 55); IHYSGYT (SEQ ID NO: 26); and ARKDS-GNYFPY (SEQ ID NO: 27). The light chain CDRs of the 1E11.C1 antibody have the following sequences: QSISDH (SEQ ID NO: 37); YAS (SEQ ID NO: 38); and QQGHSF-PLT (SEQ ID NO: 39).

An exemplary TLR4 monoclonal antibody is the 1E11.C2 antibody described herein. As shown below, the 1E11.C2 antibody includes a heavy chain variable region (SEQ ID NO: 69) encoded by the nucleic acid sequence shown in SEQ ID NO: 68, and a light chain variable region (SEQ ID NO: 4) encoded by the nucleic acid sequence shown in SEQ ID NO: 3.

```
>1E11.C2 VH nucleic acid sequence
                                           (SEQ ID NO: 68)
CAGGTGCAGCTTCAGGAGTCCGGCCCAGGACTGGTGAAGCCTTCGGACA
CCCTGTCCCTCACCTGCGCTGTCTCTGGTTACCCGATCCGGTTCGGC
TATAGCTGGCACTGGATACGGCAGCCCCCAGGGAAGGGACTGGAGTG
GATGGGGTATATCCACTACAGTGGTTACACTGACTTCAACCCCTCC
CTCAAGACTCGAATCACCATATCACGTGACACGTCCAAGAACCAGT
TCTCCCTGAAGCTGAGCTCTGTGACCGCTGTGGACACTGCAGTGTA
TTACTGTGCGAGAAAAGATTCGGGCAACTACTTCCCTTA
CTGGGGCCAAGGGACTCTGGTCACTGTCTCTTCC
```

>1E11.C2 VH amino acid sequence
(SEQ ID NO: 69)
QVQLQESGPGLVKPSDTLSLTCAVSGYPIRFGYSWHWIRQPPGKGL
EWMGYIHYSGYTDFNPSLKTRITISRDTSKNQFSLKLSSVTAVD
TAVYYCARKDSGNYFPYWGQGTLVTVSS >1E11.C2 VL nucleic acid sequence
(SEQ ID NO: 3)
GAAATTGTGTTGACGCAGTCTCCAGACTTTCAGTCTGTGACTCCAAA
GGAAAAAGTCACCATCACCTGCAGGGCCAGTCAGAGTATCAGCGAC
CACTTACACTGGTACCAACAGAAACCTGATCAGTCTCCCAAGCTC
CTCATCAAATATGCTTCCCATGCCATTTCTGGGGTCCCATCGAGG
TTCAGTGGCAGTGGGTCTGGGACAGACTTCACTCTCACCATCAAT
AGCCTAGAGGCTGAAGATGCTGCAACGTATTACTGTCAGCAGGGT
CACAGTTTTCCGCTCACTTTCGGCGGAGGGACCAAGGTGGAGATCAAA >1E11.C2 VL amino acid sequence
(SEQ ID NO: 4)
EIVLTQSPDFQSVTPKEKVTITCRASQSISDHLHWYQQKPDQSPKLL
IKYASHAISGVPSRFSGSGSGTDFTLTINSLEAEDAATYYCQQGH
SFPLTFGGGTKVEIK The amino acids encompassing the complementarity determining regions (CDR) are as defined by M. P. Lefranc (See Lefranc, M.-P., Current Protocols in Immunology, J. Wiley and Sons, New York supplement 40, A1.P.1-A.1P.37 (2000) LIGM:230). The heavy chain CDRs of the 1E11.C2 antibody have the following sequences: GYPIRFGYS (SEQ ID NO: 56); IHYSGYT (SEQ ID NO: 26); and ARKDS-GNYFPY (SEQ ID NO: 27). The light chain CDRs of the 1E11.C1 antibody have the following sequences: QSISDH (SEQ ID NO: 37); YAS (SEQ ID NO: 38); and QQGHSF-PLT (SEQ ID NO: 39).

An exemplary TLR4 monoclonal antibody is the 1E11.C3 antibody described herein. As shown below, the 1E11.C3 antibody includes a heavy chain variable region (SEQ ID NO: 71) encoded by the nucleic acid sequence shown in SEQ ID NO: 70, and a light chain variable region (SEQ ID NO: 4) encoded by the nucleic acid sequence shown in SEQ ID NO: 3.

>1E11.C3 VH nucleic acid sequence
(SEQ ID NO: 70)
CAGGTGCAGCTTCAGGAGTCCGGCCCAGGACTGGTGAAGCCTTCGGAC
ACCCTGTCCCTCACCTGCGCTGTCTCTGGTTACCCCATCCGGCACGGG
TACAGCTGGCACTGGATACGGCAGCCCCCAGGGAAGGGACTGGAGTG
GATGGGGTATATCCACTACAGTGGTTACACTGACTTCAACCCCTCCC
TCAAGACTCGAATCACCATATCACGTGACACGTCCAAGAACCAGTTC
TCCCTGAAGCTGAGCTCTGTGACCGCTGTGGACACTGCAGTGTATTA
CTGTGCGAGAAAAGATTCGGGCAACTACTTCCCTTA
CTGGGGCCAAGGGACTCTGGTCACTGTCTCTTCC >1E11.C3 VH amino acid sequence
(SEQ ID NO: 71)
QVQLQESGPGLVKPSDTLSLTCAVSGYPIRHGYSWHWIRQPPGKGLEW
MGYIHYSGYTDFNPSLKTRITISRDTSKNQFSLKLSSVTAVDTAVYYC
ARKDSGNYFPYWGQGTLVTVSS >1E11.C3 VL nucleic acid sequence
(SEQ ID NO: 3)
GAAATTGTGTTGACGCAGTCTCCAGACTTTCAGTCTGTGACTCCAAA
GGAAAAAGTCACCATCACCTGCAGGGCCAGTCAGAGTATCAGCGACC
ACTTACACTGGTACCAACAGAAACCTGATCAGTCTCCCAAGCTCCTC
ATCAAATATGCTTCCCATGCCATTTCTGGGGTCCCATCGAGGTTCAG
TGGCAGTGGGTCTGGGACAGACTTCACTCTCACCATCAATAGCCTAG
AGGCTGAAGATGCTGCAACGTATTACTGTCAGCAGGGTCACAGTTTT
CCGCTCACTTTCGGCGGAGGGACCAAGGTGGAGATCAAA >1E11.C3 VL amino acid sequence
(SEQ ID NO: 4)
EIVLTQSPDFQSVTPKEKVTITCRASQSISDHLHWYQQKPDQSPKL
LIKYASHAISGVPSRFSGSGSGTDFTLTINSLEAEDAATYYCQQGH
SFPLTFGGGTKVEIK The amino acids encompassing the complementarity determining regions (CDR) are as defined by M. P. Lefranc (See Lefranc, M.-P., Current Protocols in Immunology, J. Wiley and Sons, New York supplement 40, A1.P.1-A.1P.37 (2000) LIGM:230). The heavy chain CDRs of the 1E11.C3 antibody have the following sequences: GYPIRHGYS (SEQ ID NO: 57); IHYSGYT (SEQ ID NO: 26); and ARKDS-GNYFPY (SEQ ID NO: 27). The light chain CDRs of the 1E11.C1 antibody have the following sequences: QSISDH (SEQ ID NO: 37); YAS (SEQ ID NO: 38); and QQGHSF-PLT (SEQ ID NO: 39).

An exemplary TLR4 monoclonal antibody is the 1E11.C4 antibody described herein. As shown below, the 1E11.C4 antibody includes a heavy chain variable region (SEQ ID NO: 73) encoded by the nucleic acid sequence shown in SEQ ID NO: 72, and a light chain variable region (SEQ ID NO: 4) encoded by the nucleic acid sequence shown in SEQ ID NO: 3.

>1E11.C4 VH nucleic acid sequence
(SEQ ID NO: 72)
CAGGTGCAGCTTCAGGAGTCCGGCCCAGGACTGGTGAAGCCTTCGGACA
CCCTGTCCCTCACCTGCGCTGTCTCTGGTTTCCCGATCGGCCAGGGG
TATAGCTGGCACTGGATACGGCAGCCCCCAGGGAAGGGACTGGAGTGG
ATGGGGTATATCCACTACAGTGGTTACACTGACTTCAACCCCTCCCTC
AAGACTCGAATCACCATATCACGTGACACGTCCAAGAACCAGTTCTCC
CTGAAGCTGAGCTCTGTGACCGCTGTGGACACTGCAGTGTATTACTGT
GCGAGAAAAGATTCGGGCAACTACTTCCCTTA
CTGGGGCCAAGGGACTCTGGTCACTGTCTCTTCC >1E11.C4 VH amino acid sequence
(SEQ ID NO: 73)
QVQLQESGPGLVKPSDTLSLTCAVSGFPIGQGYSWHWIRQPPGKGLE
WMGYIHYSGYTDFNPSLKTRITISRDTSKNQFSLKLSSVTAVDTAVY
YCARKDSGNYFPYWGQGTLVTVSS >1E11.C4 VL nucleic acid sequence
(SEQ ID NO: 3)
GAAATTGTGTTGACGCAGTCTCCAGACTTTCAGTCTGTGACTCCAAA
GGAAAAAGTCACCATCACCTGCAGGGCCAGTCAGAGTATCAGCGACC
ACTTACACTGGTACCAACAGAAACCTGATCAGTCTCCCAAGCTCCTC
ATCAAATATGCTTCCCATGCCATTTCTGGGGTCCCATCGAGGTTCAG
TGGCAGTGGGTCTGGGACAGACTTCACTCTCACCATCAATAGCCTAG
AGGCTGAAGATGCTGCAACGTATTACTGTCAGCAGGGTCACAGTTTT
CCGCTCACTTTCGGCGGAGGGACCAAGGTGGAGATCAAA >1E11.C4 VL amino acid sequence
(SEQ ID NO: 4)
EIVLTQSPDFQSVTPKEKVTITCRASQSISDHLHWYQQKPDQSPKL
LIKYASHAISGVPSRFSGSGSGTDFTLTINSLEAEDAATYYCQQGH
SFPLTFGGGTKVEIK The amino acids encompassing the complementarity determining regions (CDR) are as defined by M. P. Lefranc (See Lefranc, M.-P., Current Protocols in Immunology, J. Wiley and Sons, New York supplement 40, A1.P.1-A.1P.37 (2000) LIGM:230). The heavy chain CDRs of the 1E11.C4 antibody have the following sequences: GFPIGQGYS (SEQ ID NO: 58); IHYSGYT (SEQ ID NO: 26); and ARKDS-GNYFPY (SEQ ID NO: 27). The light chain CDRs of the 1E11.C1 antibody have the following sequences: QSISDH (SEQ ID NO: 37); YAS (SEQ ID NO: 38); and QQGHSF-PLT (SEQ ID NO: 39).

An exemplary TLR4 monoclonal antibody is the 1E11.C5 antibody described herein. As shown below, the 1E11.C5 antibody includes a heavy chain variable region (SEQ ID NO: 75) encoded by the nucleic acid sequence shown in SEQ ID NO: 74, and a light chain variable region (SEQ ID NO: 4) encoded by the nucleic acid sequence shown in SEQ ID NO: 3.

>1E11.C5 VH nucleic acid sequence
(SEQ ID NO: 74)
CAGGTGCAGCTTCAGGAGTCCGGCCCAGGACTGGTGAAGCCTTCGGACA
CCCTGTCCCTCACCTGCGCTGTCTCTGGTTACCCGATCTGGGGGGCTA
TAGCTGGCACTGGATACGGCAGCCCCCAGGGAAGGGACTGGAGTGGATG
GGGTATATCCACTACAGTGGTTACACTGACTTCAACCCCTCCCTCAAG
ACTCGAATCACCATATCACGTGACACGTCCAAGAACCAGTTCTCCCTG
AAGCTGAGCTCTGTGACCGCTGTGGACACTGCAGTGTATTACTGTGCG
AGAAAAGATTCGGGCAACTACTTCCCTTACTGGGGCCAAGGGACTCT
GGTCACTGTCTCTTCCGCCTCCACC >1E11.C5 VH amino acid sequence
(SEQ ID NO: 75)
QVQLQESGPGLVKPSDTLSLTCAVSGYPIWGGYSWHWIRQPPGKGLE
WMGYIHYSGYTDFNPSLKTRITISRDTSKNQFSLKLSSVTAVDTAVY
YCARKDSGNYFPYWGQGTLVTVSS >1E11.C5 VL nucleic acid sequence
(SEQ ID NO: 3)
GAAATTGTGTTGACGCAGTCTCCAGACTTTCAGTCTGTGACTCCAAAG
GAAAAAGTCACCATCACCTGCAGGGCCAGTCAGAGTATCAGCGACCAC
TTACACTGGTACCAACAGAAACCTGATCAGTCTCCCAAGCTCCTCAT
CAAATATGCTTCCCATGCCATTTCTGGGGTCCCATCGAGGTTCAGTG
GCAGTGGGTCTGGGACAGACTTCACTCTCACCATCAATAGCCTAGAG
GCTGAAGATGCTGCAACGTATTACTGTCAGCAGGGTCACAGTTTTCC
GCTCACTTTCGGCGGAGGGACCAAGGTGGAGATCAAA >1E11.C5 VL amino acid sequence
(SEQ ID NO: 4)
EIVLTQSPDFQSVTPKEKVTITCRASQSISDHLHWYQQKPDQSPKLL
IKYASHAISGVPSRFSGSGSGTDFTLTINSLEAEDAATYYCQQGHSF
PLTFGGGTKVEIK The amino acids encompassing the complementarity determining regions (CDR) are as defined by M. P. Lefranc (See Lefranc, M.-P., Current Protocols in Immunology, J. Wiley and Sons, New York supplement 40, A1.P.1-A.1P.37 (2000) LIGM:230). The heavy chain CDRs of the 1E11.C5 antibody have the following sequences: GYPIWGGYS (SEQ ID NO:59); IHYSGYT (SEQ ID NO: 26); and ARKDSGNYFPY (SEQ ID NO: 27). The light chain CDRs of the 1E11.C1 antibody have the following sequences: QSISDH (SEQ ID NO: 37); YAS (SEQ ID NO: 38); and QQGHSFPLT (SEQ ID NO: 39).

An exemplary TLR4 monoclonal antibody is the 1E11.C6 antibody described herein. As shown below, the 1E11.C6 antibody includes a heavy chain variable region (SEQ ID NO: 77) encoded by the nucleic acid sequence shown in SEQ ID NO: 76, and a light chain variable region (SEQ ID NO: 4) encoded by the nucleic acid sequence shown in SEQ ID NO: 3.

>1E11.C5 VH nucleic acid sequence
(SEQ ID NO: 76)
CAGGTGCAGCTTCAGGAGTCCGGCCCAGGACTGGTGAAGCCTTCGGACA
CCCTGTCCCTCACCTGCGCTGTCTCTGGTTACCCCATCGGCGGCGGCT
ATAGCTGGCACTGGATACGGCAGCCCCCAGGGAAGGGACTGGAGTGG
ATGGGGTATATCCACTACAGTGGTTACACTGACTTCAACCCCTCCCTC
AAGACTCGAATCACCATATCACGTGACACGTCCAAGAACCAGTTCTCC
CTGAAGCTGAGCTCTGTGACCGCTGTGGACACTGCAGTGTATTACTGT
GCGAGAAAAGATTCGGGCAACTACTTCCCTTA
CTGGGGCCAAGGGACTCTGGTCACTGTCTCTTCC >1E11.C5 VH amino acid sequence
(SEQ ID NO: 77)
QVQLQESGPGLVKPSDTLSLTCAVSGYPIGGGYSWHWIRQPPGKGLEW
MGYIHYSGYTDFNPSLKTRITISRDTSKNQFSLKLSSVTAVDTAVYY
CARKDSGNYFPYWGQGTLVTVSS >1E11.C5 VL nucleic acid sequence
(SEQ ID NO: 3)
GAAATTGTGTTGACGCAGTCTCCAGACTTTCAGTCTGTGACTCCAAA
GGAAAAAGTCACCATCACCTGCAGGGCCAGTCAGAGTATCAGCGAC
CACTTACACTGGTACCAACAGAAACCTGATCAGTCTCCCAAGCTCCT
CATCAAATATGCTTCCCATGCCATTTCTGGGGTCCCATCGAGGTTC
AGTGGCAGTGGGTCTGGGACAGACTTCACTCTCACCATCAATAGCC
TAGAGGCTGAAGATGCTGCAACGTATTACTGTCAGCAGGGTCACAG
TTTTCCGCTCACTTTCGGCGGAGGGACCAAGGTGGAGATCAAA >1E11.C5 VL amino acid sequence
(SEQ ID NO: 4)
EIVLTQSPDFQSVTPKEKVTITCRASQSISDHLHWYQQKPDQSPKL
LIKYASHAISGVPSRFSGSGSGTDFTLTINSLEAEDAATYYCQQG
HSFPLTFGGGTKVEIK The amino acids encompassing the complementarity determining regions (CDR) are as defined by M. P. Lefranc (See Lefranc, M.-P., Current Protocols in Immunology, J. Wiley and Sons, New York supplement 40, A1.P.1-A.1P.37 (2000) LIGM:230). The heavy chain CDRs of the 1E11.C6 antibody have the following sequences: GYPIGGGYS (SEQ ID NO: 60); IHYSGYT (SEQ ID NO: 26); and ARKDSGNYFPY (SEQ ID NO: 27). The light chain CDRs of the 1E11.C1 antibody have the following sequences: QSISDH (SEQ ID NO: 37); YAS (SEQ ID NO: 38); and QQGHSFPLT (SEQ ID NO: 39).

An exemplary TLR4 monoclonal antibody is the 1E11.E1 antibody described herein. As shown below, the 1E11.E1 antibody includes a heavy chain variable region (SEQ ID NO: 1) encoded by the nucleic acid sequence shown in SEQ ID NO:2, and a light chain variable region (SEQ ID NO: 79) encoded by the nucleic acid sequence shown in SEQ ID NO: 78.

>1E11.E1 VH nucleic acid sequence
(SEQ ID NO: 1)
CAGGTGCAGCTTCAGGAGTCCGGCCCAGGACTGGTGAAGCCTTCGGAC
ACCCTGTCCCTCACCTGCGCTGTCTCTGGTTACTCCATCACCGGTGGTT
ATAGCTGGCACTGGATACGGCAGCCCCCAGGGAAGGGACTGGAGTGGA
TGGGGTATATCCACTACAGTGGTTACACTGACTTCAACCCCTCCCTC
AAGACTCGAATCACCATATCACGTGACACGTCCAAGAACCAGTTCTC
CCTGAAGCTGAGCTCTGTGACCGCTGTGGACACTGCAGTGTATTACT
GTGCGAGAAAAGATTCGGGCAACTACTTCCCTTA
CTGGGGCCAAGGGACTCTGGTCACTGTCTCTTCC >1E11.E1 VH amino acid sequence
(SEQ ID NO: 2)
QVQLQESGPGLVKPSDTLSLTCAVSGYSITGGYSWHWIRQPPGKGLEWM
GYIHYSGYTDFNPSLKTRITISRDTSKNQFSLKLSSVTAVDTAVYYC
ARKDSGNYFPYWGQGTLVTVSS >1E11.E1 VL nucleic acid sequence
(SEQ ID NO: 78)
GAAATTGTGTTGACGCAGTCTCCAGACTTTCAGTCTGTGACTCCAAAGG
AAAAAGTCACCATCACCTGCAGGGCCAGTCAGAGTATCAGCGACCAC
TTACACTGGTACCAACAGAAACCTGATCAGTCTCCCAAGCTCCTCA
TCAAATATGCTTCCCATGCCATTTCTGGGGTCCCATCGAGGTTCAGT
GGCAGTGGGTCTGGGACAGACTTCACTCTCACCATCAATAGCCTAG
AGGCTGAAGATGCTGCAACGTATTACTGTCAGCAGGGGAACGACTT
CCCGGTGACTTTCGGCGGAGGGACCAAGGTGGAGATCAAA >1E11.E1 VL amino acid sequence
(SEQ ID NO: 79)
EIVLTQSPDFQSVTPKEKVTITCRASQSISDHLHWYQQKPDQSPKL
LIKYASHAISGVPSRFSGSGSGTDFTLTINSLEAEDAATYYCQQG
NDFPVTFGGGTKVEIK The amino acids encompassing the complementarity determining regions (CDR) are as defined by M. P. Lefranc (See Lefranc, M.-P., Current Protocols in Immunology, J. Wiley and Sons, New York supplement 40, A1.P.1-A.1P.37 (2000) LIGM:230). The heavy chain CDRs of the 1E11.E1 antibody have the following sequences: GYSITGGYS (SEQ ID NO: 25); IHYSGYT (SEQ ID NO: 26); and ARKDSGNYFPY (SEQ ID NO: 27). The light chain CDRs of the 1E11 antibody have the following sequences: QSISDH (SEQ ID NO: 37); YAS (SEQ ID NO: 38); and QQGNDFPVT (SEQ ID NO: 61).

An exemplary TLR4 monoclonal antibody is the 1E11.E2 antibody described herein. As shown below, the 1E11.E2 antibody includes a heavy chain variable region (SEQ ID NO: 1) encoded by the nucleic acid sequence shown in SEQ ID NO:2, and a light chain variable region (SEQ ID NO: 81) encoded by the nucleic acid sequence shown in SEQ ID NO: 80.

>1E11.E2 VH nucleic acid sequence
(SEQ ID NO: 1)
CAGGTGCAGCTTCAGGAGTCCGGCCCAGGACTGGTGAAGCCTTCGGACA
CCCTGTCCCTCACCTGCGCTGTCTCTGGTTACTCCATCACCGGTGGTTA
TAGCTGGCACTGGATACGGCAGCCCCCAGGGAAGGGACTGGAGTGG
ATGGGGTATATCCACTACAGTGGTTACACTGACTTCAACCCCTCCCTC
AAGACTCGAATCACCATATCACGTGACACGTCCAAGAACCAGTTCTCC
CTGAAGCTGAGCTCTGTGACCGCTGTGGACACTGCAGTGTATTACTGT
GCGAGAAAAGATTCGGGCAACTACTTCCCTTA
CTGGGGCCAAGGGACTCTGGTCACTGTCTCTTCC >1E11.E2 VH amino acid sequence
(SEQ ID NO: 2)
QVQLQESGPGLVKPSDTLSLTCAVSGYSITGGYSWHWIRQPPGKGLEWM
GYIHYSGYTDFNPSLKTRITISRDTSKNQFSLKLSSVTAVDTAVYYC
ARKDSGNYFPYWGQGTLVTVSS >1E11.E2 VL nucleic acid sequence
(SEQ ID NO: 80)
GAAATTGTGTTGACGCAGTCTCCAGACTTTCAGTCTGTGACTCCAAAGG
AAAAAGTCACCATCACCTGCAGGGCCAGTCAGAGTATCAGCGACCAC
TTACACTGGTACCAACAGAAACCTGATCAGTCTCCCAAGCTCCTCAT
CAAATATGCTTCCCATGCCATTTCTGGGGTCCCATCGAGGTTCAGTGGC
AGTGGGTCTGGGACAGACTTCACTCTCACCATCAATAGCCTAGAGGCT
GAAGATGCTGCAACGTATTACTGTCAGCAGGGGTACGACGAGCCGTTC
ACTTTCGGCGGAGGGACCAAGGTGGAGATCAAA >1E11.E2 VL amino acid sequence
(SEQ ID NO: 81)
EIVLTQSPDFQSVTPKEKVTITCRASQSISDHLHWYQQKPDQSPKLL
IKYASHAISGVPSRFSGSGSGTDFTLTINSLEAEDAATYYCQQGY
DEPFTFGGGTKVEIK The amino acids encompassing the complementarity determining regions (CDR) are as defined by M. P. Lefranc (See Lefranc, M.-P., Current Protocols in Immunology, J. Wiley and Sons, New York supplement 40, A1.P.1-A.1P.37 (2000) LIGM:230). The heavy chain CDRs of the 1E11.E2 antibody have the following sequences: GYSITGGYS (SEQ ID NO: 25); IHYSGYT (SEQ ID NO: 26); and ARKDS-GNYFPY (SEQ ID NO: 27). The light chain CDRs of the 1E11 antibody have the following sequences: QSISDH (SEQ ID NO: 37); YAS (SEQ ID NO: 38); and QQGYDEPFT (SEQ ID NO: 62).

An exemplary TLR4 monoclonal antibody is the 1E11.E3 antibody described herein. As shown below, the 1E11.E3 antibody includes a heavy chain variable region (SEQ ID NO: 1) encoded by the nucleic acid sequence shown in SEQ ID NO:2, and a light chain variable region (SEQ ID NO: 83) encoded by the nucleic acid sequence shown in SEQ ID NO: 82.

>1E11.E3 VH nucleic acid sequence
(SEQ ID NO: 1)
CAGGTGCAGCTTCAGGAGTCCGGCCCAGGACTGGTGAAGCCTTCGGACA
CCCTGTCCCTCACCTGCGCTGTCTCTGGTTACTCCATCACCGGTGGTT
ATAGCTGGCACTGGATACGGCAGCCCCCAGGGAAGGGACTGGAGTGGA
TGGGGTATATCCACTACAGTGGTTACACTGACTTCAACCCCTCCCTC
AAGACTCGAATCACCATATCACGTGACACGTCCAAGAACCAGTTCTC
CCTGAAGCTGAGCTCTGTGACCGCTGTGGACACTGCAGTGTATTACT
GTGCGAGAAAAGATTCGGGCAACTACTTCCCTTA
CTGGGGCCAAGGGACTCTGGTCACTGTCTCTTCC >1E11.E3 VH amino acid sequence
(SEQ ID NO: 2)
QVQLQESGPGLVKPSDTLSLTCAVSGYSITGGYSWHWIRQPPGKGLEW
MGYIHYSGYTDFNPSLKTRITISRDTSKNQFSLKLSSVTAVDTAVYY
CARKDSGNYFPYWGQGTLVTVSS >1E11.E3 VL nucleic acid sequence
(SEQ ID NO: 82)
GAAATTGTGTTGACGCAGTCTCCAGACTTTCAGTCTGTGACTCCAAA
GGAAAAAGTCACCATCACCTGCAGGGCCAGTCAGAGTATCAGCGACC
ACTTACACTGGTACCAACAGAAACCTGATCAGTCTCCCAAGCTCCTC
ATCAAATATGCTTCCCATGCCATTTCTGGGGTCCCATCGAGGTTCAG
TGGCAGTGGGTCTGGGACAGACTTCACTCTCACCATCAATAGCCTAG
AGGCTGAAGATGCTGCAACGTATTACTGTCAGCAGGGCTACGACTT
CCCGTTGACTTTCGGCGGAGGGACCAAGGTGGAGATCAAA >1E11.E3 VL amino acid sequence
(SEQ ID NO: 83)
EIVLTQSPDFQSVTPKEKVTITCRASQSISDHLHWYQQKPDQSPKL
LIKYASHAISGVPSRFSGSGSGTDFTLTINSLEAEDAATYYCQQGY
DFPLTFGGGTKVEIK The amino acids encompassing the complementarity determining regions (CDR) are as defined by M. P. Lefranc (See Lefranc, M.-P., Current Protocols in Immunology, J. Wiley and Sons, New York supplement 40, A1.P.1-A.1P.37 (2000) LIGM:230). The heavy chain CDRs of the 1E11.E3 antibody have the following sequences: GYSITGGYS (SEQ ID NO: 25); IHYSGYT (SEQ ID NO: 26); and ARKDS-GNYFPY (SEQ ID NO: 27). The light chain CDRs of the 1E11 antibody have the following sequences: QSISDH (SEQ ID NO: 37); YAS (SEQ ID NO: 38); and QQGYD-FPLT (SEQ ID NO: 63).

An exemplary TLR4 monoclonal antibody is the 1E11.E4 antibody described herein. As shown below, the 1E11.E4 antibody includes a heavy chain variable region (SEQ ID NO: 1) encoded by the nucleic acid sequence shown in SEQ ID NO:2, and a light chain variable region (SEQ ID NO: 85) encoded by the nucleic acid sequence shown in SEQ ID NO: 84.

>1E11.E4 VH nucleic acid sequence
(SEQ ID NO: 1)
CAGGTGCAGCTTCAGGAGTCCGGCCCAGGACTGGTGAAGCCTTCGGACA
CCCTGTCCCTCACCTGCGCTGTCTCTGGTTACTCCATCACCGGTGGTT
ATAGCTGGCACTGGATACGGCAGCCCCCAGGGAAGGGACTGGAGTGGA
TGGGGTATATCCACTACAGTGGTTACACTGACTTCAACCCCTCCCTC
AAGACTCGAATCACCATATCACGTGACACGTCCAAGAACCAGTTCTC
CCTGAAGCTGAGCTCTGTGACCGCTGTGGACACTGCAGTGTATTACT
GTGCGAGAAAAGATTCGGGCAACTACTTCCCTTA
CTGGGGCCAAGGGACTCTGGTCACTGTCTCTTCC >1E11.E4 VH amino acid sequence
(SEQ ID NO: 2)
QVQLQESGPGLVKPSDTLSLTCAVSGYSITGGYSWHWIRQPPGKGLE
WMGYIHYSGYTDFNPSLKTRITISRDTSKNQFSLKLSSVTAVDTAVY
YCARKDSGNYFPYWGQGTLVTVSS >1E11.E4 VL nucleic acid sequence
(SEQ ID NO: 84)
GAAATTGTGTTGACGCAGTCTCCAGACTTTCAGTCTGTGACTCCAAAG
GAAAAAGTCACCATCACCTGCAGGGCCAGTCAGAGTATCAGCGACCAC
TTACACTGGTACCAACAGAAACCTGATCAGTCTCCCAAGCTCCTCATC
AAATATGCTTCCCATGCCATTTCTGGGGTCCCATCGAGGTTCAGTGGC
AGTGGGTCTGGGACAGACTTCACTCTCACCATCAATAGCCTAGAGGCT
GAAGATGCTGCAACGTATTACTGTCAGCAGGGCTACGACTACCCGCTC
ACTTTCGGCGGAGGGACCAAGGTGGAGATCAAA >1E11.E4 VL amino acid sequence
(SEQ ID NO: 85)
EIVLTQSPDFQSVTPKEKVTITCRASQSISDHLHWYQQKPDQSPKLL
IKYASHAISGVPSRFSGSGSGTDFTLTINSLEAEDAATYYCQQGYDY
PLTFGGGTKVEIK The amino acids encompassing the complementarity determining regions (CDR) are as defined by M. P. Lefranc (See Lefranc, M.-P., Current Protocols in Immunology, J. Wiley and Sons, New York supplement 40, A1.P.1-A.1P.37 (2000) LIGM:230). The heavy chain CDRs of the 1E11.E4 antibody have the following sequences: GYSITGGYS (SEQ ID NO: 25); IHYSGYT (SEQ ID NO: 26); and ARKDS-GNYFPY (SEQ ID NO: 27). The light chain CDRs of the 1E11 antibody have the following sequences: QSISDH (SEQ ID NO: 37); YAS (SEQ ID NO: 38); and QQGYDY-PLT (SEQ ID NO: 64).

An exemplary TLR4 monoclonal antibody is the 1E11.E5 antibody described herein. As shown below, the 1E11.E5 antibody includes a heavy chain variable region (SEQ ID NO:1) encoded by the nucleic acid sequence shown in SEQ ID NO:2, and a light chain variable region (SEQ ID NO: 87) encoded by the nucleic acid sequence shown in SEQ ID NO: 86.

>1E11.E5 VH nucleic acid sequence
(SEQ ID NO: 1)
CAGGTGCAGCTTCAGGAGTCCGGCCCAGGACTGGTGAAGCCTTCGGAC
ACCCTGTCCCTCACCTGCGCTGTCTCTGGTTACTCCATCACCGGTGGT
TATAGCTGGCACTGGATACGGCAGCCCCAGGGAAGGGACTGGAGTG
GATGGGGTATATCCACTACAGTGGTTACACTGACTTCAACCCCTCCC
TCAAGACTCGAATCACCATATCACGTGACACGTCCAAGAACCAGTTC
TCCCTGAAGCTGAGCTCTGTGACCGCTGTGGACACTGCAGTGTATTA
CTGTGCGAGAAAAGATTCGGGCAACTACTTCCCTTA
CTGGGGCCAAGGGACTCTGGTCACTGTCTCTTCC >1E11.E5 VH amino acid sequence
(SEQ ID NO: 2)
QVQLQESGPGLVKPSDTLSLTCAVSGYSITGGYSWHWIRQPPGKGLE
WMGYIHYSGYTDFNPSLKTRITISRDTSKNQFSLKLSSVTAVDTAV
YYCARKDSGNYFPYWGQGTLVTVSS >1E11.E5 VL nucleic acid sequence
(SEQ ID NO: 86)
GAAATTGTGTTGACGCAGTCTCCAGACTTTCAGTCTGTGACTCCAAA
GGAAAAAGTCACCATCACCTGCAGGGCCAGTCAGAGTATCAGCGACC
ACTTACACTGGTACCAACAGAAACCTGATCAGTCTCCCAAGCTCCTC
ATCAAATATGCTTCCCATGCCATTTCTGGGGTCCCATCGAGGTTCAGT
GGCAGTGGGTCTGGGACAGACTTCACTCTCACCATCAATAGCCTAGAG
GCTGAAGATGCTGCAACGTATTACTGTCAGCAGGGCTACGAGTTCCC
GTTGACTTTCGGCGGAGGGACCAAGGTGGAGATCAAA >1E11.E5 VL amino acid sequence
(SEQ ID NO: 87)
EIVLTQSPDFQSVTPKEKVTITCRASQSISDHLHWYQQKPDQSPKLL
IKYASHAISGVPSRFSGSGSGTDFTLTINSLEAEDAATYYCQQGYE
FPLTFGGGTKVEIK The amino acids encompassing the complementarity determining regions (CDR) are as defined by M. P. Lefranc (See Lefranc, M.-P., Current Protocols in Immunology, J. Wiley and Sons, New York supplement 40, A1.P.1-A.1P.37 (2000) LIGM:230). The heavy chain CDRs of the 1E11.E5 antibody have the following sequences: GYSITGGYS (SEQ ID NO: 25); IHYSGYT (SEQ ID NO: 26); and ARKDS-GNYFPY (SEQ ID NO: 27). The light chain CDRs of the 1E11 antibody have the following sequences: QSISDH (SEQ ID NO: 37); YAS (SEQ ID NO: 38); and QQGYEF-PLT (SEQ ID NO: 65).

An exemplary TLR4 monoclonal antibody is the 1E11.C2E1 antibody described herein. As shown below, the 1E11.C2E1 antibody includes a heavy chain variable region (SEQ ID NO: 89) encoded by the nucleic acid sequence shown in SEQ ID NO: 88, and a light chain variable region (SEQ ID NO: 91) encoded by the nucleic acid sequence shown in SEQ ID NO: 90.

>1E11.C2E1 VH nucleic acid sequence
(SEQ ID NO: 88)
CAGGTGCAGCTTCAGGAGTCCGGCCCAGGACTGGTGAAGCCTTCGGACAC
CCTGTCCCTCACCTGCGCTGTCTCTGGTTACCCGATCCGGTTCGGCTATA
GCTGGCACTGGATACGGCAGCCCCCAGGGAAGGGACTGGAGTGGATGGGG
TATATCCACTACAGTGGTTACACTGACTTCAACCCCTCCCTCAAGACTCG
AATCACCATATCACGTGACACGTCCAAGAACCAGTTCTCCCTGAAGCTGA
GCTCTGTGACCGCTGTGGACACTGCAGTGTATTACTGTGCGAGAAAAGAT
TCGGGCAACTACTTCCCTTACTGGGGCCAAGGGACTCTGGTCACTGTCTC
TTCC >1E11.C2E1 VH amino acid sequence
(SEQ ID NO: 89)
QVQLQESGPGLVKPSDTLSLTCAVSGYPIRFGYSWHWIRQPPGKGLEWMG
YIHYSGYTDFNPSLKTRITISRDTSKNQFSLKLSSVTAVDTAVYYCARKD
SGNYFPYWGQGTLVTVSS >1E11.C2E1 VL nucleic acid sequence
(SEQ ID NO: 90)
GAAATTGTGTTGACGCAGTCTCCAGACTTTCAGTCTGTGACTCCAAAGGA
AAAAGTCACCATCACCTGCAGGGCCAGTCAGAGTATCAGCGACCACTTAC
ACTGGTACCAACAGAAACCTGATCAGTCTCCCAAGCTCCTCATCAAATAT
GCTTCCCATGCCATTTCTGGGGTCCCATCGAGGTTCAGTGGCAGTGGGTC
TGGGACAGACTTCACTCTCACCATCAATAGCCTAGAGGCTGAAGATGCTG
CAACGTATTACTGTCAGCAGGGGAACGACTTCCCGGTGACTTTCGGCGGA
GGGACCAAGGTGGAGATCAAA >1E11.C2E1 VL amino acid sequence
(SEQ ID NO: 91)
EIVLTQSPDFQSVTPKEKVTITCRASQSISDHLHWYQQKPDQSPKLLIKY
ASHAISGVPSRFSGSGSGTDFTLTINSLEAEDAATYYCQQGNDFPVTFGG
GTKVEIK The amino acids encompassing the complementarity determining regions (CDR) are as defined by M. P. Lefranc (See Lefranc, M.-P., Current Protocols in Immunology, J. Wiley and Sons, New York supplement 40, A1.P.1-A.1P.37 (2000) LIGM:230). The heavy chain CDRs of the 1E11.C2E1 antibody have the following sequences: GYPIR-FGYS (SEQ ID NO: 56); IHYSGYT (SEQ ID NO: 26); and ARKDSGNYFPY (SEQ ID NO: 27). The light chain CDRs of the 1E11 antibody have the following sequences: QSISDH (SEQ ID NO: 37); YAS (SEQ ID NO: 38); and QQGNDFPVT (SEQ ID NO: 61).

An exemplary TLR4 monoclonal antibody is the 1E11.C2E3 antibody described herein. As shown below, the 1E11.C2E3 antibody includes a heavy chain variable region (SEQ ID NO: 93) encoded by the nucleic acid sequence shown in SEQ ID NO: 92, and a light chain variable region (SEQ ID NO: 95) encoded by the nucleic acid sequence shown in SEQ ID NO: 94.

>1E11.C2E3 VH nucleic acid sequence
(SEQ ID NO: 92)
CAGGTGCAGCTTCAGGAGTCCGGCCCAGGACTGGTGAAGCCTTCGGACAC
CCTGTCCCTCACCTGCGCTGTCTCTGGTTACCCGATCCGGTTCGGCTATA
GCTGGCACTGGATACGGCAGCCCCCAGGGAAGGGACTGGAGTGGATGGGG
TATATCCACTACAGTGGTTACACTGACTTCAACCCCTCCCTCAAGACTCG
AATCACCATATCACGTGACACGTCCAAGAACCAGTTCTCCCTGAAGCTGA
GCTCTGTGACCGCTGTGGACACTGCAGTGTATTACTGTGCGAGAAAAGAT
TCGGGCAACTACTTCCCTTACTGGGGCCAAGGGACTCTGGTCACTGTCTC
TTCC >1E11.C2E3 VH amino acid sequence
(SEQ ID NO: 93)
QVQLQESGPGLVKPSDTLSLTCAVSGYPIRFGYSWHWIRQPPGKGLEWMG
YIHYSGYTDFNPSLKTRITISRDTSKNQFSLKLSSVTAVDTAVYYCARKD
SGNYFPYWGQGTLVTVSS >1E11.C2E3 VL nucleic acid sequence
(SEQ ID NO: 94)
GAAATTGTGTTGACGCAGTCTCCAGACTTTCAGTCTGTGACTCCAAAGGA
AAAAGTCACCATCACCTGCAGGGCCAGTCAGAGTATCAGCGACCACTTAC
ACTGGTACCAACAGAAACCTGATCAGTCTCCCAAGCTCCTCATCAAATAT
GCTTCCCATGCCATTTCTGGGGTCCCATCGAGGTTCAGTGGCAGTGGGTC

```
-continued
TGGGACAGACTTCACTCTCACCATCAATAGCCTAGAGGCTGAAGATGCTG
CAACGTATTACTGTCAGCAGGGCTACGACTTCCCGTTGACTTTCGGCGGA
GGGACCAAGGTGGAGATCAAA >1E11.C2E3 VL amino acid sequence
                                        (SEQ ID NO: 95)
EIVLTQSPDFQSVTPKEKVTITCRASQSISDHLHWYQQKPDQSPKLLIKY
ASHAISGVPSRFSGSGSGTDFTLTINSLEAEDAATYYCQQGYDFPLTFGG
GTKVEIK
```

The amino acids encompassing the complementarity determining regions (CDR) are as defined by M. P. Lefranc (See Lefranc, M.-P., Current Protocols in Immunology, J. Wiley and Sons, New York supplement 40, A1.P.1-A.1P.37 (2000) LIGM:230). The heavy chain CDRs of the 1E11.C2E3 antibody have the following sequences: GYPIR-FGYS (SEQ ID NO: 56); IHYSGYT (SEQ ID NO: 26); and ARKDSGNYFPY (SEQ ID NO: 27). The light chain CDRs of the 1E11 antibody have the following sequences: QSISDH (SEQ ID NO: 37); YAS (SEQ ID NO: 38); and QQGYDFPLT (SEQ ID NO: 63).

An exemplary TLR4 monoclonal antibody is the 1E11.C2E4 antibody described herein. As shown below, the 1E11.C2E4 antibody includes a heavy chain variable region (SEQ ID NO: 97) encoded by the nucleic acid sequence shown in SEQ ID NO: 96, and a light chain variable region (SEQ ID NO: 99) encoded by the nucleic acid sequence shown in SEQ ID NO: 98.

```
>1E11.C2E4 VH nucleic acid sequence
                                        (SEQ ID NO: 96)
CAGGTGCAGCTTCAGGAGTCCGGCCCAGGACTGGTGAAGCCTTCGGACAC
CCTGTCCCTCACCTGCGCTGTCTCTGGTTACCCGATCCGGTTCGGCTATA
GCTGGCACTGGATACGGCAGCCCCCAGGGAAGGGACTGGAGTGGATGGGG
TATATCCACTACAGTGGTTACACTGACTTCAACCCCTCCCTCAAGACTCG
AATCACCATATCACGTGACACGTCCAAGAACCAGTTCTCCCTGAAGCTGA
GCTCTGTGACCGCTGTGGACACTGCAGTGTATTACTGTGCGAGAAAAGAT
TCGGGCAACTACTTCCCTTACTGGGGCCAAGGGACTCTGGTCACTGTCTC
TTCC >1E11.C2E4 VH amino acid sequence
                                        (SEQ ID NO: 97)
QVQLQESGPGLVKPSDTLSLTCAVSGYPIRFGYSWHWIRQPPGKGLEWMG
YIHYSGYTDFNPSLKTRITISRDTSKNQFSLKLSSVTAVDTAVYYCARKD
SGNYFPYWGQGTLVTVSS >1E11.C2E4 VL nucleic acid sequence
                                        (SEQ ID NO: 98)
GAAATTGTGTTGACGCAGTCTCCAGACTTTCAGTCTGTGACTCCAAAGGA
AAAAGTCACCATCACCTGCAGGGCCAGTCAGAGTATCAGCGACCACTTAC
ACTGGTACCAACAGAAACCTGATCAGTCTCCCAAGCTCCTCATCAAATAT
GCTTCCCATGCCATTTCTGGGGTCCCATCGAGGTTCAGTGGCAGTGGGTC
TGGGACAGACTTCACTCTCACCATCAATAGCCTAGAGGCTGAAGATGCTG
CAACGTATTACTGTCAGCAGGGCTACGACTACCCGCTCACTTTCGGCGGA
GGGACCAAGGTGGAGATCAAA >1E11.C2E4 VL amino acid sequence
                                        (SEQ ID NO: 99)
EIVLTQSPDFQSVTPKEKVTITCRASQSISDHLHWYQQKPDQSPKLLIKY
ASHAISGVPSRFSGSGSGTDFTLTINSLEAEDAATYYCQQGYDYPLTFGG
GTKVEIK
```

The amino acids encompassing the complementarity determining regions (CDR) are as defined by M. P. Lefranc (See Lefranc, M.-P., Current Protocols in Immunology, J. Wiley and Sons, New York supplement 40, A1.P.1-A.1P.37 (2000) LIGM:230). The heavy chain CDRs of the 1E11.C2E4 antibody have the following sequences: GYPIR-FGYS (SEQ ID NO: 56); IHYSGYT (SEQ ID NO: 26); and ARKDSGNYFPY (SEQ ID NO: 27). The light chain CDRs of the 1E11 antibody have the following sequences: QSISDH (SEQ ID NO: 37); YAS (SEQ ID NO: 38); and QQGYDYPLT (SEQ ID NO: 64).

An exemplary TLR4 monoclonal antibody is the 1E11.C2E5 antibody described herein. As shown below, the 1E11.C2E5 antibody includes a heavy chain variable region (SEQ ID NO: 101) encoded by the nucleic acid sequence shown in SEQ ID NO: 100, and a light chain variable region (SEQ ID NO: 103) encoded by the nucleic acid sequence shown in SEQ ID NO: 102.

```
>1E11.C2E5 VH nucleic acid sequence
                                        (SEQ ID NO: 100)
CAGGTGCAGCTTCAGGAGTCCGGCCCAGGACTGGTGAAGCCTTCGGACAC
CCTGTCCCTCACCTGCGCTGTCTCTGGTTACCCGATCCGGTTCGGCTATA
GCTGGCACTGGATACGGCAGCCCCCAGGGAAGGGACTGGAGTGGATGGGG
TATATCCACTACAGTGGTTACACTGACTTCAACCCCTCCCTCAAGACTCG
AATCACCATATCACGTGACACGTCCAAGAACCAGTTCTCCCTGAAGCTGA
GCTCTGTGACCGCTGTGGACACTGCAGTGTATTACTGTGCGAGAAAAGAT
TCGGGCAACTACTTCCCTTACTGGGGCCAAGGGACTCTGGTCACTGTCTC
TTCC >1E11.C2E5 VH amino acid sequence
                                        (SEQ ID NO: 101)
QVQLQESGPGLVKPSDTLSLTCAVSGYPIRFGYSWHWIRQPPGKGLEWMG
YIHYSGYTDFNPSLKTRITISRDTSKNQFSLKLSSVTAVDTAVYYCARKD
SGNYFPYWGQGTLVTVSS >1E11.C2E5 VL nucleic acid sequence
                                        (SEQ ID NO: 102)
GAAATTGTGTTGACGCAGTCTCCAGACTTTCAGTCTGTGACTCCAAAGGA
AAAAGTCACCATCACCTGCAGGGCCAGTCAGAGTATCAGCGACCACTTAC
ACTGGTACCAACAGAAACCTGATCAGTCTCCCAAGCTCCTCATCAAATAT
GCTTCCCATGCCATTTCTGGGGTCCCATCGAGGTTCAGTGGCAGTGGGTC
TGGGACAGACTTCACTCTCACCATCAATAGCCTAGAGGCTGAAGATGCTG
CAACGTATTACTGTCAGCAGGGCTACGAGTTCCCGTTGACTTTCGGCGGA
GGGACCAAGGTGGAGATCAAA >1E11.C2E5 VL amino acid sequence
                                        (SEQ ID NO: 103)
EIVLTQSPDFQSVTPKEKVTITCRASQSISDHLHWYQQKPDQSPKLLIKY
ASHAISGVPSRFSGSGSGTDFTLTINSLEAEDAATYYCQQGYEFPLTFGG
GTKVEIK
```

The amino acids encompassing the complementarity determining regions (CDR) are as defined by M. P. Lefranc (See Lefranc, M.-P., Current Protocols in Immunology, J. Wiley and Sons, New York supplement 40, A1.P.1-A.1P.37 (2000) LIGM:230). The heavy chain CDRs of the 1E11.C2E5 antibody have the following sequences: GYPIR-FGYS (SEQ ID NO: 56); IHYSGYT (SEQ ID NO: 26); and ARKDSGNYFPY (SEQ ID NO: 27). The light chain CDRs of the 1E11 antibody have the following sequences: QSISDH (SEQ ID NO: 37); YAS (SEQ ID NO: 38); and QQGYEFPLT (SEQ ID NO: 65).

TLR4 antibodies of the invention specifically bind human and/or cynomolgus TLR4/MD-2 complex, wherein the antibody binds to an epitope that includes one or more amino acid residues on human and/or cynomolgus TLR4 between residues 325 and 374 of SEQ ID NO: 23 (human) and SEQ ID NO: 24 (cynomolgus). Alternatively, the monoclonal antibody is an antibody that binds to the same epitope as 1A1, 1A6, 1B12, 1C7, 1C10, 1C12, 1D10, 1E11, 1E11 N103D, 1G12, 1E11.C1, 1E11.C2, 1E11.C3, 1E11.C4, 1E11.C5, 1E11.C6, 1E11.E1, 1E11.E2, 1E11.E3, 1E11.E4, 1E11.E5, 1E11.C2E1, 1E11.C2E3, 1E11.C2E4 and 1E11.C2E5.

The anti-TLR4 antibodies of the invention include an altered antibody in which at least the amino acid residue at EU position 325 and at least the amino acid residue at EU position 328 in the CH2 domain of the Fc portion of the antibody has been modified. For example, at least the amino acid residue at EU position 325 has been substituted with serine, and at least the amino acid residue at EU position 328 has been substituted with phenylalanine.

These anti-TLR4 antibodies with a modified Fc portion elicit modified effector functions e.g., a modified Fc receptor activity, as compared to an unaltered antibody. For example, the human Fc receptor is CD32A. In some embodiments, these anti-TLR4 antibodies elicit a prevention of proinflammatory mediators release following ligation to CD32A as compared to an unaltered antibody. Thus, these anti-TLR4 antibodies elicit a modified Fc receptor activity, such as the prevention of proinflammatory mediators release while retaining the ability to bind a target antigen. In some embodiments, these anti-TLR4 antibodies are neutralizing antibodies, wherein the anti-TLR4 antibody elicits a modified Fc receptor activity, while retaining the ability to neutralize one or more biological activities of a target antigen.

For example, anti-TLR4 antibodies of the invention include monoclonal antibodies that bind the human TLR4/MD-2 receptor complex. This receptor complex is activated by lipopolysaccharide (LPS), the major component of the outer membrane of gram-negative bacteria. The anti-TLR4 antibodies of the invention inhibit receptor activation and subsequent intracellular signaling via LPS. Thus, the anti-TLR4 antibodies neutralize the activation of the TLR4/MD-2 receptor complex. In particular, the invention provides anti-TLR4 antibodies that recognize the TLR4/MD-2 receptor complex expressed on the cell surface. These anti-TLR4 antibodies block LPS-induced IL-8 production. In addition, some anti-TLR4 antibodies of the invention also recognize TLR4 when not complexed with MD-2. The altered antibody is, e.g., a humanized antibody.

DEFINITIONS

Unless otherwise defined, scientific and technical terms used in connection with the present invention shall have the meanings that are commonly understood by those of ordinary skill in the art. Further, unless otherwise required by context, singular terms shall include pluralities and plural terms shall include the singular. Generally, nomenclatures utilized in connection with, and techniques of, cell and tissue culture, molecular biology, and protein and oligo- or polynucleotide chemistry and hybridization described herein are those well-known and commonly used in the art. Standard techniques are used for recombinant DNA, oligonucleotide synthesis, and tissue culture and transformation (e.g., electroporation, lipofection). Enzymatic reactions and purification techniques are performed according to manufacturer's specifications or as commonly accomplished in the art or as described herein. The foregoing techniques and procedures are generally performed according to conventional methods well known in the art and as described in various general and more specific references that are cited and discussed throughout the present specification. See e.g., Sambrook et al. Molecular Cloning: A Laboratory Manual (2d ed., Cold Spring Harbor Laboratory Press, Cold Spring Harbor, N.Y. (1989)). The nomenclatures utilized in connection with, and the laboratory procedures and techniques of, analytical chemistry, synthetic organic chemistry, and medicinal and pharmaceutical chemistry described herein are those well-known and commonly used in the art. Standard techniques are used for chemical syntheses, chemical analyses, pharmaceutical preparation, formulation, and delivery, and treatment of patients.

As utilized in accordance with the present disclosure, the following terms, unless otherwise indicated, shall be understood to have the following meanings:

As used herein, the term "antibody" refers to immunoglobulin molecules and immunologically active portions of immunoglobulin (Ig) molecules, i.e., molecules that contain an antigen binding site that specifically binds (immunoreacts with) an antigen. By "specifically bind" or "immunoreacts with" or "immunospecifically bind" is meant that the antibody reacts with one or more antigenic determinants of the desired antigen and does not react with other polypeptides or binds at much lower affinity ($K_d > 10^{-6}$). Antibodies include, but are not limited to, polyclonal, monoclonal, chimeric, dAb (domain antibody), single chain, $F_{ab}$, $F_{ab'}$ and $F_{(ab')2}$ fragments, scFvs, and an $F_{ab}$ expression library.

The basic antibody structural unit is known to comprise a tetramer. Each tetramer is composed of two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function. In general, antibody molecules obtained from humans relate to any of the classes IgG, IgM, IgA, IgE and IgD, which differ from one another by the nature of the heavy chain present in the molecule. Certain classes have subclasses as well, such as $IgG_1$, $IgG_2$, and others. Furthermore, in humans, the light chain may be a kappa chain or a lambda chain.

The term "monoclonal antibody" (MAb) or "monoclonal antibody composition", as used herein, refers to a population of antibody molecules that contain only one molecular species of antibody molecule consisting of a unique light chain gene product and a unique heavy chain gene product. In particular, the complementarity determining regions (CDRs) of the monoclonal antibody are identical in all the molecules of the population. MAbs contain an antigen binding site capable of immunoreacting with a particular epitope of the antigen characterized by a unique binding affinity for it.

The term "antigen-binding site," or "binding portion" refers to the part of the immunoglobulin molecule that participates in antigen binding. The antigen binding site is formed by amino acid residues of the N-terminal variable ("V") regions of the heavy ("H") and light ("L") chains. Three highly divergent stretches within the V regions of the heavy and light chains, referred to as "hypervariable regions," are interposed between more conserved flanking stretches known as "framework regions," or "FRs". Thus, the term "FR" refers to amino acid sequences which are naturally found between, and adjacent to, hypervariable regions in immunoglobulins. In an antibody molecule, the three hypervariable regions of a light chain and the three hypervariable regions of a heavy chain are disposed relative to each other in three dimensional space to form an antigen-binding surface. The antigen-binding surface is complementary to the three-dimensional surface of a bound antigen, and the three hypervariable regions of each of the heavy and light chains are referred to as "complementarity-determining regions," or "CDRs." The assignment of amino acids to each domain is in accordance with the definitions of Kabat Sequences of Proteins of Immunological Interest (National Institutes of Health, Bethesda, Md. (1987 and 1991)), or Chothia & Lesk J. Mol. Biol. 196:901-917 (1987), Chothia et al. Nature 342:878-883 (1989).

As used herein, the term "epitope" includes any protein determinant capable of specific binding to an immunoglobulin, an scFv, or a T-cell receptor. The term "epitope" includes any protein determinant capable of specific binding to an immunoglobulin or T-cell receptor. Epitopic determinants usually consist of chemically active surface groupings of molecules such as amino acids or sugar side chains and usually have specific three dimensional structural characteristics, as well as specific charge characteristics. For example, antibodies may be raised against N-terminal or C-terminal peptides of a polypeptide. An antibody is the to specifically bind an antigen when the dissociation constant is ≤1 µM; e.g., ≤100 nM, preferably ≤10 nM and more preferably ≤1 nM.

As used herein, the terms "immunological binding," and "immunological binding properties" refer to the non-covalent interactions of the type which occur between an immunoglobulin molecule and an antigen for which the immunoglobulin is specific. The strength, or affinity of immunological binding interactions can be expressed in terms of the dissociation constant ($K_d$) of the interaction, wherein a smaller $K_d$ represents a greater affinity. Immunological binding properties of selected polypeptides can be quantified using methods well known in the art. One such method entails measuring the rates of antigen-binding site/antigen complex formation and dissociation, wherein those rates depend on the concentrations of the complex partners, the affinity of the interaction, and geometric parameters that equally influence the rate in both directions. Thus, both the "on rate constant" ($K_{on}$) and the "off rate constant" ($K_{off}$) can be determined by calculation of the concentrations and the actual rates of association and dissociation. (See Nature 361:186-87 (1993)). The ratio of $K_{off}/K_{on}$ enables the cancellation of all parameters not related to affinity, and is equal to the dissociation constant $K_d$. (See, generally, Davies et al. (1990) Annual Rev Biochem 59:439-473). An antibody of the present invention is the to specifically bind to its target, when the equilibrium binding constant ($K_d$) is ≤1 µM, e.g., ≤100 nM, preferably ≤10 nM, and more preferably ≤1 nM, as measured by assays such as radioligand binding assays or similar assays known to those skilled in the art.

The term "isolated polynucleotide" as used herein shall mean a polynucleotide of genomic, cDNA, or synthetic origin or some combination thereof, which by virtue of its origin the "isolated polynucleotide" (1) is not associated with all or a portion of a polynucleotide in which the "isolated polynucleotide" is found in nature, (2) is operably linked to a polynucleotide which it is not linked to in nature, or (3) does not occur in nature as part of a larger sequence. Polynucleotides in accordance with the invention include the nucleic acid molecules encoding the heavy chain immunoglobulin molecules, and nucleic acid molecules encoding the light chain immunoglobulin molecules described herein.

The term "isolated protein" referred to herein means a protein of cDNA, recombinant RNA, or synthetic origin or some combination thereof, which by virtue of its origin, or source of derivation, the "isolated protein" (1) is not associated with proteins found in nature, (2) is free of other proteins from the same source, e.g., free of marine proteins, (3) is expressed by a cell from a different species, or (4) does not occur in nature.

The term "polypeptide" is used herein as a generic term to refer to native protein, fragments, or analogs of a polypeptide sequence. Hence, native protein fragments, and analogs are species of the polypeptide genus. Polypeptides in accordance with the invention comprise the heavy chain immunoglobulin molecules, and the light chain immunoglobulin molecules described herein, as well as antibody molecules formed by combinations comprising the heavy chain immunoglobulin molecules with light chain immunoglobulin molecules, such as kappa light chain immunoglobulin molecules, and vice versa, as well as fragments and analogs thereof.

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory or otherwise is naturally-occurring.

The term "operably linked" as used herein refers to positions of components so described are in a relationship permitting them to function in their intended manner. A control sequence "operably linked" to a coding sequence is ligated in such a way that expression of the coding sequence is achieved under conditions compatible with the control sequences.

The term "control sequence" as used herein refers to polynucleotide sequences which are necessary to effect the expression and processing of coding sequences to which they are ligated. The nature of such control sequences differs depending upon the host organism in prokaryotes, such control sequences generally include promoter, ribosomal binding site, and transcription termination sequence in eukaryotes, generally, such control sequences include promoters and transcription termination sequence. The term "control sequences" is intended to include, at a minimum, all components whose presence is essential for expression and processing, and can also include additional components whose presence is advantageous, for example, leader sequences and fusion partner sequences. The term "polynucleotide" as referred to herein means a polymeric boron of nucleotides of at least 10 bases in length, either ribonucleotides or deoxynucleotides or a modified form of either type of nucleotide. The term includes single and double stranded forms of DNA.

As used herein, the twenty conventional amino acids and their abbreviations follow conventional usage. See Immunology—A Synthesis (2nd Edition, E. S. Golub and D. R. Gren, Eds., Sinauer Associates, Sunderland Mass. (1991)). Stereoisomers (e.g., D-amino acids) of the twenty conventional amino acids, unnatural amino acids such as α-,α-disubstituted amino acids, N-alkyl amino acids, lactic acid, and other unconventional amino acids may also be suitable components for polypeptides of the present invention. Examples of unconventional amino acids include: 4 hydroxyproline, γ-carboxyglutamate, ε-N,N,N-trimethyllysine, ε-N-acetyllysine, O-phosphoserine, N-acetylserine, N-formylmethionine, 3-methylhistidine, 5-hydroxylysine, σ-N-methylarginine, and other similar amino acids and imino acids (e.g., 4-hydroxyproline). In the polypeptide notation used herein, the left-hand direction is the amino terminal direction and the right-hand direction is the carboxy-terminal direction, in accordance with standard usage and convention.

As applied to polypeptides, the term "substantial identity" means that two peptide sequences, when optimally aligned, such as by the programs GAP or BESTFIT using default gap weights, share at least 80 percent sequence identity, preferably at least 90 percent sequence identity, more preferably at least 95 percent sequence identity, and most preferably at least 99 percent sequence identity.

Preferably, residue positions which are not identical differ by conservative amino acid substitutions.

Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine valine, glutamic-aspartic, and asparagine-glutamine.

As discussed herein, minor variations in the amino acid sequences of antibodies or immunoglobulin molecules are contemplated as being encompassed by the present invention, providing that the variations in the amino acid sequence maintain at least 75%, more preferably at least 80%, 90%, 95%, and most preferably 99%. In particular, conservative amino acid replacements are contemplated. Conservative replacements are those that take place within a family of amino acids that are related in their side chains. Genetically encoded amino acids are generally divided into families: (1) acidic amino acids are aspartate, glutamate; (2) basic amino acids are lysine, arginine, histidine; (3) non-polar amino acids are alanine, valine, leucine, isoleucine, proline, phenylalanine, methionine, tryptophan, and (4) uncharged polar amino acids are glycine, asparagine, glutamine, cysteine, serine, threonine, tyrosine. The hydrophilic amino acids include arginine, asparagine, aspartate, glutamine, glutamate, histidine, lysine, serine, and threonine. The hydrophobic amino acids include alanine, cysteine, isoleucine, leucine, methionine, phenylalanine, proline, tryptophan, tyrosine and valine. Other families of amino acids include (i) serine and threonine, which are the aliphatic-hydroxy family; (ii) asparagine and glutamine, which are the amide containing family; (iii) alanine, valine, leucine and isoleucine, which are the aliphatic family; and (iv) phenylalanine, tryptophan, and tyrosine, which are the aromatic family. For example, it is reasonable to expect that an isolated replacement of a leucine with an isoleucine or valine, an aspartate with a glutamate, a threonine with a serine, or a similar replacement of an amino acid with a structurally related amino acid will not have a major effect on the binding or properties of the resulting molecule, especially if the replacement does not involve an amino acid within a framework site. Whether an amino acid change results in a functional peptide can readily be determined by assaying the specific activity of the polypeptide derivative. Assays are described in detail herein. Fragments or analogs of antibodies or immunoglobulin molecules can be readily prepared by those of ordinary skill in the art. Preferred amino- and carboxy-termini of fragments or analogs occur near boundaries of functional domains. Structural and functional domains can be identified by comparison of the nucleotide and/or amino acid sequence data to public or proprietary sequence databases. Preferably, computerized comparison methods are used to identify sequence motifs or predicted protein conformation domains that occur in other proteins of known structure and/or function. Methods to identify protein sequences that fold into a known three-dimensional structure are known. Bowie et al. Science 253:164 (1991). Thus, the foregoing examples demonstrate that those of skill in the art can recognize sequence motifs and structural conformations that may be used to define structural and functional domains in accordance with the invention.

Preferred amino acid substitutions are those which: (1) reduce susceptibility to proteolysis, (2) reduce susceptibility to oxidation, (3) alter binding affinity for forming protein complexes, (4) alter binding affinities, and (4) confer or modify other physicochemical or functional properties of such analogs. Analogs can include various muteins of a sequence other than the naturally-occurring peptide sequence. For example, single or multiple amino acid substitutions (preferably conservative amino acid substitutions) may be made in the naturally-occurring sequence (preferably in the portion of the polypeptide outside the domain(s) forming intermolecular contacts. A conservative amino acid substitution should not substantially change the structural characteristics of the parent sequence (e.g., a replacement amino acid should not tend to break a helix that occurs in the parent sequence, or disrupt other types of secondary structure that characterizes the parent sequence). Examples of art-recognized polypeptide secondary and tertiary structures are described in Proteins, Structures and Molecular Principles (Creighton, Ed., W. H. Freeman and Company, New York (1984)); Introduction to Protein Structure (C. Branden and J. Tooze, eds., Garland Publishing, New York, N.Y. (1991)); and Thornton et al. Nature 354:105 (1991).

As used herein, the terms "label" or "labeled" refers to incorporation of a detectable marker, e.g., by incorporation of a radiolabeled amino acid or attachment to a polypeptide of biotinyl moieties that can be detected by marked avidin (e.g., streptavidin containing a fluorescent marker or enzymatic activity that can be detected by optical or calorimetric methods). In certain situations, the label or marker can also be therapeutic. Various methods of labeling polypeptides and glycoproteins are known in the art and may be used. Examples of labels for polypeptides include, but are not limited to, the following: radioisotopes or radionuclides (e.g., $^{3}$H, $^{14}$C, $^{15}$N, $^{35}$S, $^{90}$Y, $^{99}$Tc, $^{111}$In, $^{125}$I, $^{131}$I), fluorescent labels (e.g., FITC, rhodamine, lanthanide phosphors), enzymatic labels (e.g., horseradish peroxidase, p-galactosidase, luciferase, alkaline phosphatase), chemiluminescent, biotinyl groups, predetermined polypeptide epitopes recognized by a secondary reporter (e.g., leucine zipper pair sequences, binding sites for secondary antibodies, metal binding domains, epitope tags). In some embodiments, labels are attached by spacer arms of various lengths to reduce potential steric hindrance. The term "pharmaceutical agent or drug" as used herein refers to a chemical compound or composition capable of inducing a desired therapeutic effect when properly administered to a patient.

Other chemistry terms herein are used according to conventional usage in the art, as exemplified by The McGraw-Hill Dictionary of Chemical Terms (Parker, S., Ed., McGraw-Hill, San Francisco (1985)).

As used herein, "substantially pure" means an object species is the predominant species present (i.e., on a molar basis it is more abundant than any other individual species in the composition), and preferably a substantially purified fraction is a composition wherein the object species comprises at least about 50 percent (on a molar basis) of all macromolecular species present.

Generally, a substantially pure composition will comprise more than about 80 percent of all macromolecular species present in the composition, more preferably more than about 85%, 90%, 95%, and 99%. Most preferably, the object species is purified to essential homogeneity (contaminant species cannot be detected in the composition by conventional detection methods) wherein the composition consists essentially of a single macromolecular species.

The term patient includes human and veterinary subjects.

Antibodies

The anti-TLR4 antibodies provided herein recognize human and/or cynomolgus monkey TLR4/MD-2 receptor expressed on the cell surface. The antibodies are capable of blocking, e.g., neutralizing, receptor activation and subsequent intracellular signaling induced TLR4 ligands, e.g., LPS. Antibodies of the invention include antibodies that bind human and cynomolgus monkey TLR4/MD-2 receptor complex and also bind TLR4 independently of the presence of MD-2.

The anti-TLR4 antibodies described herein are antibodies that include at least one specific amino acid substitution in the gamma heavy chain constant region such that the anti-TLR4 antibody elicits alterations in antigen-dependent effector function while retaining binding to antigen as compared to an unaltered antibody. In a preferred embodiment of the anti-TLR4 antibodies, the EU amino acid position 325 of the gamma heavy chain constant region is substituted with serine, and EU amino acid position 328 of the gamma heavy chain constant region is substituted with phenylalanine, such that the EU positions 325 to 328 of the gamma heavy chain constant region of the altered human IgG1 antibody comprise the amino acid sequence SKAF (SEQ ID NO: 42).

In one embodiment, the anti-TLR4 antibodies that recognize human and cynomolgus TLR4/MD2 complex have the ability to inhibit LPS-induced proinflammatory cytokine production Inhibition is determined, for example, in the human whole blood and huTLR4/MD2 transfected HEK 293 cellular assays such as those described in PCT Publication Nos. WO 2005/065015 and WO 2007/110678.

Also included in the invention are antibodies that bind to the same epitope as the anti-TLR4 antibodies described herein. For example, anti-TLR4 antibodies of the invention specifically bind a human and/or cynomolgus TLR4/MD-2 complex, wherein the antibody binds to an epitope that includes one or more amino acid residues on human and/or cynomolgus monkey TLR4 between residues 289 and 375 of SEQ ID NO: 23 (human) and SEQ ID NO: 24 (cynomolgus). For example, TLR4 antibodies specifically binds to an epitope that includes residues selected from the group consisting of at least residues 328 and 329 of SEQ ID NO: 23 (human) and SEQ ID NO: 24 (cynomolgus); at least residues 349 through 351 of SEQ ID NO: 23 (human) and SEQ ID NO: 24 (cynomolgus); and at least residues 369 through 371 of SEQ ID NO: 23 (human) and SEQ ID NO: 24 (cynomolgus).

Various procedures known within the art may be used for the production of polyclonal or monoclonal antibodies directed against a given target, such as, for example, a toll-like receptor, the human and/or cynomolgus TLR4/MD-2 complex, or TLR4 when not complexed to MD-2, or against derivatives, fragments, analogs homologs or orthologs thereof. (See, for example, Antibodies: A Laboratory Manual, Harlow E, and Lane D, 1988, Cold Spring Harbor Laboratory Press, Cold Spring Harbor, N.Y., incorporated herein by reference).

Antibodies are purified by well-known techniques, such as affinity chromatography using protein A or protein G, which provide primarily the IgG fraction of immune serum. Subsequently, or alternatively, the specific antigen which is the target of the immunoglobulin sought, or an epitope thereof, may be immobilized on a column to purify the immune specific antibody by immunoaffinity chromatography. Purification of immunoglobulins is discussed, for example, by D. Wilkinson (The Scientist, published by The Scientist, Inc., Philadelphia Pa., Vol. 14, No. 8 (Apr. 17, 2000), pp. 25-28).

Preferably, the anti-TLR4 antibodies of the invention are monoclonal antibodies. Monoclonal anti-TLR4 antibodies are generated, e.g., by using the procedures set forth in PCT Publication Nos. WO 2005/065015, WO 2007/110678 and/or WO 2009/101479. Anti-TLR4 antibodies are generated, for example, by using the procedures set forth in the Examples provided herein. Anti-TLR4 antibodies are also generated, e.g., by immunizing BALB/c mice with combinations of cell transfectants expressing high levels of a given target on their surface. Hybridomas resulting from myeloma/B cell fusions are then screened for reactivity to the selected target.

Monoclonal antibodies are prepared, for example, using hybridoma methods, such as those described by Kohler and Milstein, Nature, 256:495 (1975). In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes can be immunized in vitro.

The immunizing agent will typically include the protein antigen, a fragment thereof or a fusion protein thereof. Generally, either peripheral blood lymphocytes are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell (Goding, *Monoclonal Antibodies: Principles and Practice*, Academic Press, (1986) pp. 59-103). Immortalized cell lines are usually transformed mammalian cells, particularly myeloma cells of rodent, bovine and human origin. Usually, rat or mouse myeloma cell lines are employed. The hybridoma cells can be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Manassas, Va. Human myeloma and mouse-human heteromyeloma cell lines also have been described for the production of monoclonal antibodies. (See Kozbor, J. Immunol., 133:3001 (1984); Brodeur et al., Monoclonal Antibody Production Techniques and Applications, Marcel Dekker, Inc., New York, (1987) pp. 51-63)).

The culture medium in which the hybridoma cells are cultured can then be assayed for the presence of monoclonal antibodies directed against the antigen. Preferably, the binding specificity of monoclonal antibodies produced by the hybridoma cells is determined by immunoprecipitation or by an in vitro binding assay, such as radioimmunoassay (RIA) or enzyme-linked immunoabsorbent assay (ELISA). Such techniques and assays are known in the art. The binding affinity of the monoclonal antibody can, for example, be determined by the Scatchard analysis of Munson and Pollard, Anal. Biochem., 107:220 (1980). Moreover, in therapeutic applications of monoclonal antibodies, it is important to identify antibodies having a high degree of specificity and a high binding affinity for the target antigen.

After the desired hybridoma cells are identified, the clones can be subcloned by limiting dilution procedures and grown by standard methods. (See Goding, *Monoclonal Antibodies: Principles and Practice*, Academic Press, (1986) pp. 59-103). Suitable culture media for this purpose include, for example, Dulbecco's Modified Eagle's Medium and RPMI-1640 medium. Alternatively, the hybridoma cells can be grown in vivo as ascites in a mammal.

The monoclonal antibodies secreted by the subclones can be isolated or purified from the culture medium or ascites fluid by conventional immunoglobulin purification procedures such as, for example, protein A-Sepharose, hydroxylapatite chromatography, gel electrophoresis, dialysis, or affinity chromatography.

Monoclonal antibodies can also be made by recombinant DNA methods, such as those described in U.S. Pat. No. 4,816,567. DNA encoding the monoclonal antibodies of the invention can be readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA can be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also can be modified, for example, by substituting the coding sequence for human heavy and light chain constant domains in place of the homologous murine sequences (see U.S. Pat. No. 4,816,567; Morrison, Nature 368, 812-13 (1994)) or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody.

Monoclonal antibodies of the invention include humanized antibodies or human antibodies. These antibodies are suitable for administration to humans without engendering an immune response by the human against the administered immunoglobulin. Humanized forms of antibodies are chimeric immunoglobulins, immunoglobulin chains or fragments thereof (such as Fv, Fab, Fab', F(ab')$_2$ or other antigen-binding subsequences of antibodies) that are principally comprised of the sequence of a human immunoglobulin, and contain minimal sequence derived from a non-human immunoglobulin. Humanization is performed, e.g., by following the method of Winter and co-workers (Jones et al., Nature, 321:522-525 (1986); Riechmann et al., Nature, 332:323-327 (1988); Verhoeyen et al., Science, 239:1534-1536 (1988)), by substituting rodent CDRs or CDR sequences for the corresponding sequences of a human antibody. (See also U.S. Pat. No. 5,225,539). In some instances, Fv framework residues of the human immunoglobulin are replaced by corresponding non-human residues. Humanized antibodies also comprise, e.g., residues which are found neither in the recipient antibody nor in the imported CDR or framework sequences. In general, the humanized antibody includes substantially all of at least one, and typically two, variable domains, in which all or substantially all of the CDR regions correspond to those of a non-human immunoglobulin and all or substantially all of the framework regions are those of a human immunoglobulin consensus sequence. The humanized antibody optimally also includes at least a portion of an immunoglobulin constant region (Fc), typically that of a human immunoglobulin (Jones et al., 1986; Riechmann et al., 1988; and Presta, Curr. Op. Struct. Biol., 2:593-596 (1992)).

Fully human antibodies are antibody molecules in which the entire sequence of both the light chain and the heavy chain, including the CDRs, arise from human genes. Such antibodies are termed "human antibodies", or "fully human antibodies" herein. Monoclonal antibodies can be prepared by using trioma technique; the human B-cell hybridoma technique (see Kozbor, et al., 1983 Immunol Today 4: 72); and the EBV hybridoma technique to produce monoclonal antibodies (see Cole, et al., 1985 In: MONOCLONAL ANTIBODIES AND CANCER THERAPY, Alan R. Liss, Inc., pp. 77-96). Monoclonal antibodies may be utilized and may be produced by using human hybridomas (see Cote, et al., 1983. Proc Natl Acad Sci USA 80: 2026-2030) or by transforming human B-cells with Epstein Barr Virus in vitro (see Cole, et al., 1985 In: MONOCLONAL ANTIBODIES AND CANCER THERAPY, Alan R. Liss, Inc., pp. 77-96).

In addition, human antibodies can also be produced using additional techniques, including phage display libraries. (See Hoogenboom and Winter, J. Mol. Biol., 227:381 (1991); Marks et al., J. Mol. Biol., 222:581 (1991)). Similarly, human antibodies can be made by introducing human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in Marks et al., Bio/Technology 10, 779-783 (1992); Lonberg et al., Nature 368 856-859 (1994); Morrison, Nature 368, 812-13 (1994); Fishwild et al, Nature Biotechnology 14, 845-51 (1996); Neuberger, Nature Biotechnology 14, 826 (1996); and Lonberg and Huszar, Intern. Rev. Immunol. 13 65-93 (1995).

Human antibodies may additionally be produced using transgenic nonhuman animals which are modified so as to produce fully human antibodies rather than the animal's endogenous antibodies in response to challenge by an antigen. (See PCT publication WO94/02602). The endogenous genes encoding the heavy and light immunoglobulin chains in the nonhuman host have been incapacitated, and active loci encoding human heavy and light chain immunoglobulins are inserted into the host's genome. The human genes are incorporated, for example, using yeast artificial chromosomes containing the requisite human DNA segments. An animal which provides all the desired modifications is then obtained as progeny by crossbreeding intermediate transgenic animals containing fewer than the full complement of the modifications. An example of such a nonhuman animal is a mouse termed the Xenomouse™ as disclosed in PCT publications WO 96/33735 and WO 96/34096. This animal produces B cells which secrete fully human immunoglobulins. The antibodies can be obtained directly from the animal after immunization with an immunogen of interest, as, for example, a preparation of a polyclonal antibody, or alternatively from immortalized B cells derived from the animal, such as hybridomas producing monoclonal antibodies. Additionally, the genes encoding the immunoglobulins with human variable regions can be recovered and expressed to obtain the antibodies directly, or can be further modified to obtain analogs of antibodies such as, for example, single chain Fv (scFv) molecules.

An example of a method of producing a nonhuman host, exemplified as a mouse, lacking expression of an endogenous immunoglobulin heavy chain is disclosed in U.S. Pat. No. 5,939,598. It can be obtained by a method, which includes deleting the J segment genes from at least one endogenous heavy chain locus in an embryonic stem cell to prevent rearrangement of the locus and to prevent formation of a transcript of a rearranged immunoglobulin heavy chain locus, the deletion being effected by a targeting vector containing a gene encoding a selectable marker; and producing from the embryonic stem cell a transgenic mouse whose somatic and germ cells contain the gene encoding the selectable marker.

One method for producing an antibody of interest, such as a human antibody, is disclosed in U.S. Pat. No. 5,916,771. This method includes introducing an expression vector that contains a nucleotide sequence encoding a heavy chain into one mammalian host cell in culture, introducing an expression vector containing a nucleotide sequence encoding a light chain into another mammalian host cell, and fusing the two cells to form a hybrid cell. The hybrid cell expresses an antibody containing the heavy chain and the light chain.

In a further improvement on this procedure, a method for identifying a clinically relevant epitope on an immunogen and a correlative method for selecting an antibody that binds specifically to the relevant epitope with high affinity are disclosed in PCT publication WO 99/53049.

The antibody can be expressed by a vector containing a DNA segment encoding the single chain antibody described above.

These can include vectors, liposomes, naked DNA, adjuvant-assisted DNA. gene gun, catheters, etc. Vectors include chemical conjugates such as described in WO 93/64701, which has targeting moiety (e.g., a ligand to a cellular surface receptor), and a nucleic acid binding moiety (e.g., polylysine), viral vector (e.g., a DNA or RNA viral vector), fusion proteins such as described in PCT/US 95/02140 (WO 95/22618) which is a fusion protein containing a target moiety (e.g., an antibody specific for a target cell) and a nucleic acid binding moiety (e.g., a protamine), plasmids, phage, etc. The vectors can be chromosomal, non-chromosomal or synthetic.

Preferred vectors include viral vectors, fusion proteins and chemical conjugates. Retroviral vectors include moloney murine leukemia viruses. DNA viral vectors are preferred. These vectors include pox vectors such as orthopox or avipox vectors, herpesvirus vectors such as a herpes simplex I virus (HSV) vector (see Geller, A. I. et al., J. Neurochem, 64:487 (1995); Lim, F., et al., in DNA Cloning: Mammalian Systems, D. Glover, Ed. (Oxford Univ. Press, Oxford England) (1995); Geller, A. I. et al., Proc Natl. Acad. Sci.: U.S.A. 90:7603 (1993); Geller, A. I., et al., Proc Natl. Acad. Sci USA 87:1149 (1990), Adenovirus Vectors (see LeGal LaSalle et al., Science, 259:988 (1993); Davidson, et al., Nat. Genet 3:219 (1993); Yang, et al., J. Virol. 69:2004 (1995) and Adeno-associated Virus Vectors (see Kaplitt, M. G. et al., Nat. Genet. 8:148 (1994).

Pox viral vectors introduce the gene into the cells cytoplasm. Avipox virus vectors result in only a short term expression of the nucleic acid. Adenovirus vectors, adeno-associated virus vectors and herpes simplex virus (HSV) vectors are preferred for introducing the nucleic acid into neural cells. The adenovirus vector results in a shorter term expression (about 2 months) than adeno-associated virus (about 4 months), which in turn is shorter than HSV vectors. The particular vector chosen will depend upon the target cell and the condition being treated. The introduction can be by standard techniques, e.g., infection, transfection, transduction or transformation. Examples of modes of gene transfer include e.g., naked DNA, $CaPO_4$ precipitation, DEAE dextran, electroporation, protoplast fusion, lipofection, cell microinjection, and viral vectors.

The vector can be employed to target essentially any desired target cell. For example, stereotaxic injection can be used to direct the vectors (e.g., adenovirus, HSV) to a desired location. Additionally, the particles can be delivered by intracerebroventricular (icy) infusion using a minipump infusion system, such as a SynchroMed Infusion System. A method based on bulk flow, termed convection, has also proven effective at delivering large molecules to extended areas of the brain and may be useful in delivering the vector to the target cell. (See Bobo et al., Proc. Natl. Acad. Sci. USA 91:2076-2080 (1994); Morrison et al., Am. J. Physiol. 266:292-305 (1994)). Other methods that can be used include catheters, intravenous, parenteral, intraperitoneal and subcutaneous injection, and oral or other known routes of administration.

Bispecific antibodies are antibodies that have binding specificities for at least two different antigens. In the present case, one of the binding specificities is for a target such as TLR4, MD2, human and/or cynomolgus TLR4/MD2 complex or any fragment thereof. The second binding target is any other antigen, and advantageously is a cell-surface protein or receptor or receptor subunit.

Methods for making bispecific antibodies are known in the art. Traditionally, the recombinant production of bispecific antibodies is based on the co-expression of two immunoglobulin heavy-chain/light-chain pairs, where the two heavy chains have different specificities (Milstein and Cuello, Nature, 305:537-539 (1983)). Because of the random assortment of immunoglobulin heavy and light chains, these hybridomas (quadromas) produce a potential mixture of ten different antibody molecules, of which only one has the correct bispecific structure. The purification of the correct molecule is usually accomplished by affinity chromatography steps. Similar procedures are disclosed in WO 93/08829, published 13 May 1993, and in Traunecker et al., EMBO J., 10:3655-3659 (1991).

Antibody variable domains with the desired binding specificities (antibody-antigen combining sites) can be fused to immunoglobulin constant domain sequences. The fusion preferably is with an immunoglobulin heavy-chain constant domain, comprising at least part of the hinge, CH2, and CH3 regions. It is preferred to have the first heavy-chain constant region (CH1) containing the site necessary for light-chain binding present in at least one of the fusions. DNAs encoding the immunoglobulin heavy-chain fusions and, if desired, the immunoglobulin light chain, are inserted into separate expression vectors, and are co-transfected into a suitable host organism. For further details of generating bispecific antibodies see, for example, Suresh et al., Methods in Enzymology, 121:210 (1986).

According to another approach described in WO 96/27011, the interface between a pair of antibody molecules can be engineered to maximize the percentage of heterodimers which are recovered from recombinant cell culture. The preferred interface includes at least a part of the CH3 region of an antibody constant domain. In this method, one or more small amino acid side chains from the interface of the first antibody molecule are replaced with larger side chains (e.g., tyrosine or tryptophan). Compensatory "cavities" of identical or similar size to the large side chain(s) are created on the interface of the second antibody molecule by replacing large amino acid side chains with smaller ones (e.g., alanine or threonine). This provides a mechanism for increasing the yield of the heterodimer over other unwanted end-products such as homodimers.

Techniques for generating bispecific antibodies from antibody fragments have been described in the literature. For example, bispecific antibodies can be prepared using chemical linkage. The bispecific antibodies produced can be used as agents for the selective immobilization of enzymes.

Various techniques for making and isolating bispecific antibody fragments directly from recombinant cell culture have also been described. For example, bispecific antibodies have been produced using leucine zippers. Kostelny et al., J. Immunol. 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., Proc. Natl. Acad. Sci. USA 90:6444-6448 (1993) has provided an alternative mechanism for making bispecific antibody fragments. The fragments comprise a heavy-chain variable domain ($V_H$) connected to a light-chain variable domain ($V_L$) by a linker which is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (sFv) dimers has also been reported. See, Gruber et al., J. Immunol. 152:5368 (1994).

Antibodies with more than two valencies are contemplated. For example, trispecific antibodies can be prepared. Tutt et al., J. Immunol. 147:60 (1991).

Exemplary bispecific antibodies can bind to two different epitopes, at least one of which originates in the protein antigen of the invention. Alternatively, an anti-antigenic arm of an immunoglobulin molecule can be combined with an arm which binds to a triggering molecule on a leukocyte such as a T-cell receptor molecule (e.g., CD2, CD3, CD28, or B7), or Fc receptors for IgG (FcγR), such as FcγRI (CD64), FcγRII (CD32) and FcγRIII (CD16) so as to focus cellular defense mechanisms to the cell expressing the particular antigen. Bispecific antibodies can also be used to direct cytotoxic agents to cells which express a particular antigen. These antibodies possess an antigen-binding arm and an arm which binds a cytotoxic agent or a radionuclide chelator, such as EOTUBE, DPTA, DOTA, or TETA. Another bispecific antibody of interest binds the protein antigen described herein and further binds tissue factor (TF).

Heteroconjugate antibodies are also within the scope of the present invention. Heteroconjugate antibodies are composed of two covalently joined antibodies. Such antibodies have, for example, been proposed to target immune system cells to unwanted cells (see U.S. Pat. No. 4,676,980), and for treatment of HIV infection (see WO 91/00360; WO 92/200373; EP 03089). It is contemplated that the antibodies can be prepared in vitro using known methods in synthetic protein chemistry, including those involving crosslinking agents. For example, immunotoxins can be constructed using a disulfide exchange reaction or by forming a thioether bond. Examples of suitable reagents for this purpose include iminothiolate and methyl-4-mercaptobutyrimidate and those disclosed, for example, in U.S. Pat. No. 4,676,980.

It can be desirable to modify the antibody of the invention with respect to effector function, so as to enhance, e.g., the effectiveness of the antibody in treating diseases and disorders associated with aberrant LPS signaling. For example, cysteine residue(s) can be introduced into the Fc region, thereby allowing interchain disulfide bond formation in this region. The homodimeric antibody thus generated can have improved internalization capability and/or increased complement-mediated cell killing and antibody-dependent cellular cytotoxicity (ADCC). (See Caron et al., J. Exp Med., 176: 1191-1195 (1992) and Shopes, J. Immunol., 148: 2918-2922 (1992)). Alternatively, an antibody can be engineered that has dual Fc regions and can thereby have enhanced complement lysis and ADCC capabilities. (See Stevenson et al., Anti-Cancer Drug Design, 3: 219-230 (1989)).

The invention also pertains to immunoconjugates comprising an antibody conjugated to a cytotoxic agent such as a toxin (e.g., an enzymatically active toxin of bacterial, fungal, plant, or animal origin, or fragments thereof), or a radioactive isotope (i.e., a radioconjugate).

Enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, sapaonaria officinalis inhibitor, gelonin, mitogellin, restrictocin, phenomycin, enomycin, and the tricothecenes. A variety of radionuclides are available for the production of radioconjugated antibodies. Examples include $^{212}$Bi, $^{131}$I, $^{131}$In, $^{90}$Y, and $^{186}$Re.

Conjugates of the antibody and cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutaredehyde), bis-azido compounds (such as bis(p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al., Science 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. (See WO94/11026).

Those of ordinary skill in the art will recognize that a large variety of possible moieties can be coupled to the resultant antibodies of the invention. (See, for example, "Conjugate Vaccines", Contributions to Microbiology and Immunology, J. M. Cruse and R. E. Lewis, Jr (eds), Carger Press, New York, (1989), the entire contents of which are incorporated herein by reference).

Coupling may be accomplished by any chemical reaction that will bind the two molecules so long as the antibody and the other moiety retain their respective activities. This linkage can include many chemical mechanisms, for instance covalent binding, affinity binding, intercalation, coordinate binding and complexation. The preferred binding is, however, covalent binding. Covalent binding can be achieved either by direct condensation of existing side chains or by the incorporation of external bridging molecules. Many bivalent or polyvalent linking agents are useful in coupling protein molecules, such as the antibodies of the present invention, to other molecules. For example, representative coupling agents can include organic compounds such as thioesters, carbodiimides, succinimide esters, diisocyanates, glutaraldehyde, diazobenzenes and hexamethylene diamines. This listing is not intended to be exhaustive of the various classes of coupling agents known in the art but, rather, is exemplary of the more common coupling agents. (See Killen and Lindstrom, Jour. Immun. 133:1335-2549 (1984); Jansen et al., Immunological Reviews 62:185-216 (1982); and Vitetta et al., Science 238:1098 (1987).

Preferred linkers are described in the literature. (See, for example, Ramakrishnan, S. et al., Cancer Res. 44:201-208 (1984) describing use of MBS (M-maleimidobenzoyl-N-hydroxysuccinimide ester). See also, U.S. Pat. No. 5,030,719, describing use of halogenated acetyl hydrazide derivative coupled to an antibody by way of an oligopeptide linker. Particularly preferred linkers include: (i) EDC (1-ethyl-3-(3-dimethylamino-propyl)carbodiimide hydrochloride; (ii) SMPT (4-succinimidyloxycarbonyl-alpha-methyl-alpha-(2-pridyl-dithio)-toluene (Pierce Chem. Co., Cat. (21558G); (iii) SPDP (succinimidyl-6 [3-(2-pyridyldithio)propionamido]hexanoate (Pierce Chem. Co., Cat #21651G); (iv) Sulfo-LC-SPDP (sulfosuccinimidyl 6 [3-(2-pyridyldithio)-propianamide]hexanoate (Pierce Chem. Co. Cat. #2165-G); and (v) sulfo-NHS (N-hydroxysulfo-succinimide: Pierce Chem. Co., Cat. #24510) conjugated to EDC.

The linkers described above contain components that have different attributes, thus leading to conjugates with differing physio-chemical properties. For example, sulfo-NHS esters of alkyl carboxylates are more stable than sulfo-NHS esters of aromatic carboxylates. NHS-ester containing linkers are less soluble than sulfo-NHS esters. Further, the linker SMPT contains a sterically hindered disulfide bond, and can form conjugates with increased stability. Disulfide linkages, are in general, less stable than other linkages because the disulfide linkage is cleaved in vitro, resulting in less conjugate available. Sulfo-NHS, in particular, can enhance the stability of carbodimide couplings. Carbodimide couplings (such as EDC) when used in conjunction with sulfo-NHS, forms esters that are more resistant to hydrolysis than the carbodimide coupling reaction alone.

The antibodies disclosed herein can also be formulated as immunoliposomes. Liposomes containing the antibody are prepared by methods known in the art, such as described in Epstein et al., Proc. Natl. Acad. Sci. USA, 82: 3688 (1985); Hwang et al., Proc. Natl. Acad. Sci. USA, 77: 4030 (1980); and U.S. Pat. Nos. 4,485,045 and 4,544,545. Liposomes with enhanced circulation time are disclosed in U.S. Pat. No. 5,013,556.

Particularly useful liposomes can be generated by the reverse-phase evaporation method with a lipid composition comprising phosphatidylcholine, cholesterol, and PEG-derivatized phosphatidylethanolamine (PEG-PE). Liposomes are extruded through filters of defined pore size to yield liposomes with the desired diameter. Fab' fragments of the antibody of the present invention can be conjugated to the liposomes as described in Martin et al., J. Biol. Chem., 257: 286-288 (1982) via a disulfide-interchange reaction.

Use of Anti-TLR4 Antibodies

It will be appreciated that administration of therapeutic entities in accordance with the invention will be administered with suitable carriers, excipients, and other agents that are incorporated into formulations to provide improved transfer, delivery, tolerance, and the like. A multitude of appropriate formulations can be found in the formulary known to all pharmaceutical chemists: Remington's Pharmaceutical Sciences (15th ed, Mack Publishing Company, Easton, Pa. (1975)), particularly Chapter 87 by Blaug, Seymour, therein. These formulations include, for example, powders, pastes, ointments, jellies, waxes, oils, lipids, lipid (cationic or anionic) containing vesicles (such as Lipofectin™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. Any of the foregoing mixtures may be appropriate in treatments and therapies in accordance with the present invention, provided that the active ingredient in the formulation is not inactivated by the formulation and the formulation is physiologically compatible and tolerable with the route of administration. See also Baldrick P. "Pharmaceutical excipient development: the need for preclinical guidance." Regul. Toxicol Pharmacol. 32(2):210-8 (2000), Wang W. "Lyophilization and development of solid protein pharmaceuticals." Int. J. Pharm. 203(1-2):1-60 (2000), Charman WN "Lipids, lipophilic drugs, and oral drug delivery-some emerging concepts." J Pharm Sci. 89(8):967-78 (2000), Powell et al. "Compendium of excipients for parenteral formulations" PDA J Pharm Sci Technol. 52:238-311 (1998) and the citations therein for additional information related to formulations, excipients and carriers well known to pharmaceutical chemists.

Therapeutic formulations of the invention, which include an anti-TLR4 antibody of the invention, are used to treat or alleviate a symptom associated with an immune-related disorder. The present invention also provides methods of treating or alleviating a symptom associated with an immune-related disorder. A therapeutic regimen is carried out by identifying a subject, e.g., a human patient suffering from (or at risk of developing) an immune-related disorder, using standard methods. For example, anti-TLR4 antibodies of the invention are useful therapeutic tools in the treatment of autoimmune diseases and/or inflammatory disorders. In certain embodiments, the use of anti-TLR4 antibodies that modulate, e.g., inhibit, neutralize, or interfere with, TLR signaling is contemplated for treating autoimmune diseases and/or inflammatory disorders.

Autoimmune diseases include, for example, Acquired Immunodeficiency Syndrome (AIDS, which is a viral disease with an autoimmune component), alopecia greata, ankylosing spondylitis, antiphospholipid syndrome, autoimmune Addison's disease, autoimmune hemolytic anemia, autoimmune hepatitis, autoimmune inner ear disease (AIED), autoimmune lymphoproliferative syndrome (ALPS), autoimmune thrombocytopenic purpura (ATP), Behcet's disease, cardiomyopathy, celiac sprue-dermatitis hepetiformis; chronic fatigue immune dysfunction syndrome (CFIDS), chronic inflammatory demyelinating polyneuropathy (CIPD), cicatricial pemphigold, cold agglutinin disease, crest syndrome, Crohn's disease, Degos' disease, dermatomyositis-juvenile, discoid lupus, essential mixed cryoglobulinemia, fibromyalgia-fibromyositis, Graves' disease, Guillain-Barré syndrome, Hashimoto's thyroiditis, idiopathic pulmonary fibrosis, idiopathic thrombocytopenia purpura (ITP), IgA nephropathy, insulin-dependent diabetes mellitus, juvenile chronic arthritis (Still's disease), juvenile rheumatoid arthritis, Ménière's disease, mixed connective tissue disease, multiple sclerosis, myasthenia gravis, pernacious anemia, polyarteritis nodosa, polychondritis, polyglandular syndromes, polymyalgia rheumatica, polymyositis and dermatomyositis, primary agammaglobulinemia, primary biliary cirrhosis, psoriasis, psoriatic arthritis, Raynaud's phenomena, Reiter's syndrome, rheumatic fever, rheumatoid arthritis, sarcoidosis, scleroderma (progressive systemic sclerosis (PSS), also known as systemic sclerosis (SS)), Sjögren's syndrome, stiff-man syndrome, systemic lupus erythematosus, Takayasu arteritis, temporal arteritis/giant cell arteritis, ulcerative colitis, uveitis, vitiligo and Wegener's granulomatosis.

Inflammatory disorders include, for example, chronic and acute inflammatory disorders. Examples of inflammatory disorders include Alzheimer's disease, asthma, atopic allergy, allergy, atherosclerosis, bronchial asthma, eczema, glomerulonephritis, graft vs. host disease, hemolytic anemias, osteoarthritis, sepsis, stroke, transplantation of tissue and organs, vasculitis, diabetic retinopathy and ventilator induced lung injury.

For example, anti-TLR4 antibodies are useful in the treatment of acute inflammation and sepsis induced by microbial products (e.g., LPS) and exacerbations arising from this acute inflammation, such as, for example, chronic obstructive pulmonary disease and asthma (see O'Neill, Curr. Opin. Pharmacol. 3: 396-403 (2003), hereby incorporated by reference in its entirety). Such antibodies are also useful in treating neurodegenerative autoimmune diseases. (Lehnardt et al., Proc. Natl. Acad. Sci. USA 100: 8514-8519 (2003), hereby incorporated by reference in its entirety).

In addition, the antibodies of the invention are also useful as therapeutic reagents in the treatment of diseases, such as, for example, osteoarthritis, which are caused by stress, for example, cellular stress, which, in turn, induces endogenous soluble "stress" factors that trigger TLR4. Endogenous soluble stress factor include e.g., Hsp60 (see Ohashi et al., J. Immunol. 164: 558-561 (2000)) and fibronectin (see Okamura et al., J. Biol. Chem. 276: 10229-10233 (2001) and heparin sulphate, hyaluronan, gp96, β-Defensin-2 or surfactant protein A (see e.g., Johnson et al., Crit. Rev. Immunol., 23(1-2):15-44 (2003), each of which is hereby incorporated by reference in its entirety). The antibodies of the invention are also useful in the treatment of a variety of disorders associated with stress, such as for example, cellular stress that is associated with subjects and patients placed on respirators, ventilators and other respiratory-assist devices. For example, the antibodies of the invention are useful in the treatment of ventilator-induced lung injury ("VILI"), also referred to as ventilation-associated lung injury ("VALI").

Other disease areas in which inhibiting TLR4 function could be beneficial include, for example, chronic inflammation (e.g., chronic inflammation associated with allergic conditions and asthma), autoimmune diseases (e.g., inflammatory bowel disorder) and atherosclerosis (see O'Neill, Curr. Opin. Pharmacol. 3: 396-403 (2003), hereby incorporated by reference in its entirety).

Symptoms associated with these immune-related disorders include, for example, inflammation, fever, general malaise, fever, pain, often localized to the inflamed area, rapid pulse rate, joint pain or aches (arthralgia), rapid breathing or other abnormal breathing patterns, chills, confusion, disorientation, agitation, dizziness, cough, dyspnea, pulmonary infections, cardiac failure, respiratory failure, edema, weight gain, mucopurulent relapses, cachexia, wheezing, headache, and abdominal symptoms such as, for example, abdominal pain, diarrhea or constipation.

Efficaciousness of treatment is determined in association with any known method for diagnosing or treating the particular immune-related disorder. Alleviation of one or more symptoms of the immune-related disorder indicates that the antibody confers a clinical benefit.

Methods for the screening of antibodies that possess the desired specificity include, but are not limited to, enzyme linked immunosorbent assay (ELISA) and other immunologically mediated techniques known within the art.

Antibodies directed against a target such as TLR2, CD14, TLR4, MD2, the TLR4/MD-2 complex or any toll-like receptor (or a fragment thereof) may be used in methods known within the art relating to the localization and/or quantitation of these targets, e.g., for use in measuring levels of these targets within appropriate physiological samples, for use in diagnostic methods, for use in imaging the protein, and the like). In a given embodiment, antibodies specific any of these targets, or derivative, fragment, analog or homolog thereof, that contain the antibody derived antigen binding domain, are utilized as pharmacologically active compounds (referred to hereinafter as "Therapeutics").

An anti-TLR4 antibody of the invention can be used to isolate a particular target using standard techniques, such as immunoaffinity, chromatography or immunoprecipitation. Anti-TLR4 antibodies of the invention (or a fragment thereof) can be used diagnostically to monitor protein levels in tissue as part of a clinical testing procedure, e.g., to determine the efficacy of a given treatment regimen. Detection can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^{3}H$.

Antibodies of the invention, including polyclonal, monoclonal, humanized and fully human antibodies, may be used as therapeutic agents. Such agents will generally be employed to treat or prevent a disease or pathology associated with aberrant expression or activation of a given target in a subject. An antibody preparation, preferably one having high specificity and high affinity for its target antigen, is administered to the subject and will generally have an effect due to its binding with the target. Administration of the antibody may abrogate or inhibit or interfere with the signaling function of the target. Administration of the antibody may abrogate or inhibit or interfere with the binding of the target with an endogenous ligand to which it naturally binds. For example, the antibody binds to the target and neutralizes LPS-induced proinflammatory cytokine production.

A therapeutically effective amount of an antibody of the invention relates generally to the amount needed to achieve a therapeutic objective. As noted above, this may be a binding interaction between the antibody and its target antigen that, in certain cases, interferes with the functioning of the target. The amount required to be administered will furthermore depend on the binding affinity of the antibody for its specific antigen, and will also depend on the rate at which an administered antibody is depleted from the free volume other subject to which it is administered. Common ranges for therapeutically effective dosing of an antibody or antibody fragment of the invention may be, by way of nonlimiting example, from about 0.1 mg/kg body weight to about 50 mg/kg body weight. Common dosing frequencies may range, for example, from twice daily to once a week.

Antibodies or a fragment thereof of the invention can be administered for the treatment of a variety of diseases and disorders in the form of pharmaceutical compositions. Principles and considerations involved in preparing such compositions, as well as guidance in the choice of components are provided, for example, in Remington: The Science And Practice Of Pharmacy 19th ed. (Alfonso R. Gennaro, et al., editors) Mack Pub. Co., Easton, Pa.: 1995; Drug Absorption Enhancement: Concepts, Possibilities, Limitations, And Trends, Harwood Academic Publishers, Langhorne, Pa., 1994; and Peptide And Protein Drug Delivery (Advances In Parenteral Sciences, Vol. 4), 1991, M. Dekker, New York.

Where antibody fragments are used, the smallest inhibitory fragment that specifically binds to the binding domain of the target protein is preferred. For example, based upon the variable-region sequences of an antibody, peptide molecules can be designed that retain the ability to bind the target protein sequence. Such peptides can be synthesized chemically and/or produced by recombinant DNA technology. (See, e.g., Marasco et al., Proc. Natl. Acad. Sci. USA, 90: 7889-7893 (1993)). The formulation can also contain more than one active compound as necessary for the particular indication being treated, preferably those with complementary activities that do not adversely affect each other. Alternatively, or in addition, the composition can comprise an agent that enhances its function, such as, for example, a cytotoxic agent, cytokine, chemotherapeutic agent, or growth-inhibitory agent. Such molecules are suitably present in combination in amounts that are effective for the purpose intended.

The active ingredients can also be entrapped in microcapsules prepared, for example, by coacervation techniques or by interfacial polymerization, for example, hydroxymethylcellulose or gelatin-microcapsules and poly-(methylmethacrylate) microcapsules, respectively, in colloidal drug delivery systems (for example, liposomes, albumin microspheres, microemulsions, nano-particles, and nanocapsules) or in macroemulsions.

The formulations to be used for in vivo administration must be sterile. This is readily accomplished by filtration through sterile filtration membranes.

Sustained-release preparations can be prepared. Suitable examples of sustained-release preparations include semipermeable matrices of solid hydrophobic polymers containing the antibody, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods.

An antibody according to the invention can be used as an agent for detecting the presence of a given target (or a protein fragment thereof) in a sample. In some embodiments, the antibody contains a detectable label. Antibodies are polyclonal, or more preferably, monoclonal. An intact antibody, or a fragment thereof (e.g., $F_{ab}$, scFv, or $F_{(ab)2}$) is used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently-labeled secondary antibody and end-labeling of a DNA probe with biotin such that it can be detected with fluorescently-labeled streptavidin. The term "biological sample" is intended to include tissues, cells and biological fluids isolated from a subject, as well as tissues, cells and fluids present within a subject. Included within the usage of the term "biological sample", therefore, is blood and a fraction or component of blood including blood serum, blood plasma, or lymph. That is, the detection method of the invention can be used to detect an analyte mRNA, protein, or genomic DNA in a biological sample in vitro as well as in vivo. For example, in vitro techniques for detection of an analyte mRNA include Northern hybridizations and in situ hybridizations. In vitro techniques for detection of an analyte protein include enzyme linked immunosorbent assays (ELISAs), Western blots, immunoprecipitations, and immunofluorescence. In vitro techniques for detection of an analyte genomic DNA include Southern hybridizations. Procedures for conducting immunoassays are described, for example in "ELISA: Theory and Practice: Methods in Molecular Biology", Vol. 42, J. R. Crowther (Ed.) Human Press, Totowa, N.J., 1995; "Immunoassay", E. Diamandis and T. Christopoulus, Academic Press, Inc., San Diego, Calif., 1996; and "Practice and Theory of Enzyme Immunoassays", P. Tijssen, Elsevier Science Publishers, Amsterdam, 1985. Furthermore, in vivo techniques for detection of an analyte protein include introducing into a subject a labeled anti-analyte protein antibody. For example, the antibody can be labeled with a radioactive marker whose presence and location in a subject can be detected by standard imaging techniques.

Pharmaceutical Compositions

The antibodies or soluble chimeric polypeptides of the invention (also referred to herein as "active compounds"), and derivatives, fragments, analogs and homologs thereof, can be incorporated into pharmaceutical compositions suitable for administration. Such compositions typically comprise the antibody or soluble chimeric polypeptide and a pharmaceutically acceptable carrier. As used herein, the term "pharmaceutically acceptable carrier" is intended to include any and all solvents, dispersion media, coatings, antibacterial and antifungal agents, isotonic and absorption delaying agents, and the like, compatible with pharmaceutical administration. Suitable carriers are described in the most recent edition of Remington's Pharmaceutical Sciences, a standard reference text in the field, which is incorporated herein by reference. Preferred examples of such carriers or diluents include, but are not limited to, water, saline, ringer's solutions, dextrose solution, and 5% human serum albumin. Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (i.e., topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid (EDTA); buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The pharmaceutical compositions can be included in a container, pack, or dispenser together with instructions for administration.

The invention will be further described in the following examples, which do not limit the scope of the invention described in the claims.

EXAMPLES

Example 1

Generation of Stable Cynomolgus Monkey TLR4 and Human TLR4/MD-2 TLR4 Transfectants Stable cynomolgus monkey TLR4 and human TLR4/MD-2 transfectants were generated in CHO-K1 cells based on sequences described below.

```
>Human TLR4 amino acid sequence
                                         (SEQ ID NO: 23)
MMSASRLAGTLIPAMAFLSCVRPESWEPCVEVVPNITYQCMELNFYKIPD
NLPFSTKNLDLSFNPLRHLGSYSFFSFPELQVLDLSRCEIQTIEDGAYQS
LSHLSTLILTGNPIQSLALGAFSGLSSLQKLVAVETNLASLENFPIGHLK
TLKELNVAHNLIQSFKLPEYFSNLTNLEHLDLSSNKIQSIYCTDLRVLHQ
MPLLNLSLDLSLNPMNFIQPGAFKEIRLHKLTLRNNFDSLNVMKTCIQGL
AGLEVHRLVLGEFRNEGNLEKFDKSALEGLCNLTIEEFRLAYLDYYLDDI
IDLFNCLTNVSSFSLVSVTIERVKDFSYNFGWQHLELVNCKFGQFPTLKL
KSLKRLTFTSNKGGNAFSEVDLPSLEFLDLSRNGLSFKGCCSQSDFGTTS
LKYLDLSFNGVITMSSNFLGLEQLEHLDFQHSNLKQMSEFSVFLSLRNLI
YLDISHTHTRVAFNGIFNGLSSLEVLKMAGNSFQENFLPDIFTELRNLTF
LDLSQCQLEQLSPTAFNSLSSLQVLNMSHNNFFSLDTFPYKCLNSLQVLD
YSLNHIMTSKKQELQHFPSSLAFLNLTQNDFACTCEHQSFLQWIKDQRQL
LVEVERMECATPSDKQGMPVLSLNITCQMNKTIIGVSVLSVLVVSVVAVL
VYKFYPHLMLLAGCIKYGRGENIYDAFVIYSSQDEDWVRNELVKNLEEGV
PPFQLCLHYRDFIPGVAIAANIIHEGFHKSRKVIVVVSQHFIQSRWCIFE
YEIAQTWQFLSSRAGIIFIVLQKVEKTLLRQQVELYRLLSRNTYLEWEDS
VLGRHIFWRRLRKALLDGKSWNPEGTVGTGCNWQEATSI >Cynomolgus monkey TLR4 amino acid sequence 1
                                         (SEQ ID NO: 24)
MTSALRLAGTLIPAMAFLSCVRPESWEPCVEVVPNITYQCMELKFYKIPD
NIPFSTKNLDLSFNPLRHLGSYSFLRFPELQVLDLSRCEIQTIEDGAYQS
LSHLSTLILTGNPIQSLALGAFSGLSSLQKLVAVETNLASLENFPIGHLK
TLKELNVAHNLIQSFKLPEYFSNLTNLEHLDLSSNKIQNIYCKDLQVLHQ
MPLSNLSLDLSLNPINFIQPGAFKEIRLHKLTLRSNFDDLNVMKTCIQGL
AGLEVHRLVLGEFRNERNLEEFDKSSLEGLCNLTIEEFRLTYLDCYLDNI
IDLFNCLANVSSFSLVSVNIKRVEDFSYNFRWQHLELVNCKFEQFPTLEL
KSLKRLTFTANKGGNAFSEVDLPSLEFLDLSRNGLSFKGCCSQSDFGTTS
LKYLDLSFNDVITMSSNFLGLEQLEHLDFQHSNLKQMSQFSVFLSLRNLI
YLDISHTHTRVAFNGIFDGLLSLKVLKMAGNSFQENFLPDIFTDLKNLTF
LDLSQCQLEQLSPTAFDTLNKLQVLNMSHNNFFSLDTFPYKCLPSLQVLD
YSLNHIMTSNNQELQHFPSSLAFLNLTQNDFACTCEHQSFLQWIKDQRQL
LVEAERMECATPSDKQGMPVLSLNITCQMNKTIIGVSVFSVLVVSVVAVL
VYKFYPHLMLLAGCIKYGRGENIYDAFVIYSSQDEDWVRNELVKNLEEGV
PPFQLCLHYRDFIPGVAIAANIIHEGFHKSRKVIVVVSQHFIQSRWCIFE
YEIAQTWQFLSSRAGIIFIVLQKVEKTLLRQQVELYRLLSRNTYLEWEDS
VLGQHIFWRRLRKALLDGKSWNPEEQ
```

For CHO-K1 cells, human TLR4 cDNA encoding an N-terminal c-Myc epitope tag and cynomolgus monkey TLR4 cDNA were cloned into pCDNA3.1(−) hygro (Invitrogen), and human MD-2 cDNA encoding C-terminal c-Myc and Protein C epitope tags was cloned into pCDNA3 (Invitrogen). Human TLR4 and Human MD2 constructs were co-transfected into CHO cells using Fugene 6™ reagent (Roche), according to the manufacturer's guidelines. Antibiotic resistant cells were selected in culture medium containing 500 µg/mL G418 and 250 µg/mL hygromycin B (both from Invitrogen). Cynomolgus monkey TLR4 construct was transfected into CHO cells using Fugene 6™ reagent (Roche), according to the manufacturer's guideline and cultured as described above.

To select for cells expressing the human TLR4/MD-2 complex or cynomolgus monkey TLR4, $1 \times 10^7$ CHO cells/mL were incubated in 1×PBS supplemented with 1% BSA and either 10 µg/mL anti-protein C monoclonal antibody (Roche) or 10 µg/mL anti-TLR4 protein 106 monoclonal antibody (NovImmune SA). Cells were washed once and then incubated in the same buffer with PE-conjugated goat anti-mouse IgG (H+L) antibody (1:200 dilution; Anwara). Cells were subsequently incubated with anti-PE microbeads (Miltenyi Biotec) and passed through a Midi MACS LS column. Cells retained on the column were eluted and placed back in culture with antibiotic selection. Rounds of sorting were continued until uniformly positive populations of cells expressing the human TLR4/MD-2 complex and cynomolgus monkey TLR4 were obtained.

Example 2

CDRs Randomization of 15C1 Antibody and Cell Surface Selections

The humanized anti-TLR4 antibody 15C1 (as described in U.S. patent application Ser. No. 11/151,916, now issued as U.S. Pat. No. 7,674,884, shown herein as SEQ ID NOs: 43 and 4 below) was subjected to sequence randomization in order to obtain antibodies binding to cynomolgus monkey and/or human TLR4 and able to neutralize LPS-induced pro-inflammatory cytokine production mediated by TLR4.

```
>15C1 VH amino acid sequence
                                         (SEQ ID NO: 43)
QVQLQESGPGLVKPSDTLSLTCAVSGYSITGGYSWHWIRQPPGKGLEWMG
YIHYSGYTDFNPSLKTRITISRDTSKNQFSLKLSSVTAVDTAVYYCARKD
PSDAFPYWGQGTLVTVSS >15C1 VL amino acid sequence
                                         (SEQ ID NO: 4)
EIVLTQSPDFQSVTPKEKVTITCRASQSISDHLHWYQQKPDQSPKLLIKY
ASHAISGVPSRFSGSGSGTDFTLTINSLEAEDAATYYCQQGHSFPLTFGG
GTKVEIK
```

The $V_H$ (SEQ ID NO: 43) and $V_L$ (SEQ ID NO: 4) regions of the humanized 15C1 antibody were cloned into the pNDS vector described in Ravn et al. (Nucleic Acids Res. 2010 November; 38(21):e193). Briefly, the $V_H$ region was cloned in frame of the PelB leader sequence using a NcoI restriction site in 5' and a XhoI restriction site in 3'. Then, the $V_L$ region was inserted in frame of a linker sequence using SalI restriction enzyme in 5' and NotI restriction enzyme in 3' to form a construct coding for the 15C1 scFv fused in its C-terminal part to the 6×His and c-Myc tags and the pIII protein.

Then, stretches of 5 residues in the CDR3 of the heavy chain (SEQ ID NO: 44) or light chain (SEQ ID NO: 48) were randomized in order to generate 6 libraries (Library size ranging from $5 \times 10^7$ to $2 \times 10^8$). The different libraries generated are shown below in Table 3 and Table 4 where X represents any amino acid.

TABLE 3

| 15C1 CDRH3 randomization libraries. | | | | | | | | | |
|---|---|---|---|---|---|---|---|---|---|
| 15C1 CDRH3 (SEQ ID NO: 44) | A | R | K | D | P | S | D | A | F | P | Y |
| LIBRARY 1 (SEQ ID NO: 45) | A | R | X | X | X | X | X | A | F | P | Y |
| LIBRARY 2 (SEQ ID NO: 46) | A | R | K | D | P | S | X | X | X | X | X |
| LIBRARY 3 (SEQ ID NO: 47) | A | R | K | D | X | X | X | X | X | P | Y |

TABLE 4

15C1 CDRL3 randomization libraries.

| | | | | | | | | |
|---|---|---|---|---|---|---|---|---|
| 15C1 CDRL3 (SEQ ID NO: 48) | Q | Q | G | H | S | F | P | L | T |
| LIBRARY 4 (SEQ ID NO: 49) | Q | Q | X | X | X | X | X | L | T |
| LIBRARY 5 (SEQ ID NO: 50) | Q | Q | G | H | X | X | X | X | X |
| LIBRARY 6 (SEQ ID NO: 51) | Q | Q | X | X | X | X | P | X | T |

Five selection rounds were performed using these libraries and screening for variants with desired activities was performed using scFv periplasmic extracts. Briefly, aliquots of 15C1 modified scFv phage libraries ($10^{12}$ Pfu) were blocked with PBS containing 3% (w/v) skimmed milk for one hour at room temperature on a rotary mixer. Blocked phages were then deselected for one hour at 37° C./5% $CO_2$ on CHO cells (in a T75 flask 80% confluence) that had been previously blocked with PBS containing 2% (w/v) skimmed milk. Deselected phages were then incubated on CHO cells expressing cynomolgus monkey TLR4 for three hours at room temperature with gentle shaking Cells were then washed ten times with PBS. Bound phages were eluted by adding 1 mL of 75 mM citric acid followed by neutralization with 280 µl of Tris-HCl pH 9. Then, 10 mL of exponentially growing TG1 were added to the T75 flask and incubating for one hour at 37° C. with slow shaking. An aliquot of the infected TG1 was serial diluted to titer the selection output. Infected TG1 were spun at 3000 rpm for 15 minutes and re-suspended in 0.5 mL 2×TY-AG (2×TY media containing 100 µg/mL ampicillin and 2% glucose) and spread on 2×TYAG agar Bioassay plates. After overnight incubation at 30° C. 10 mL of 2×TYAG was added to the plates and the cells were scraped form the surface and transferred to a 50 mL polypropylene tube. 2×TYAG containing 50% glycerol was added to the cell suspension to obtain a final concentration of 17% glycerol. Aliquots of the selection round were kept at −80° C.

Example 3

Screening of 15C1 scFv Variants

General procedures for construction and handling of human scFv libraries are described in Vaughan et al., (Nat. Biotech. 1996, 14:309-314), hereby incorporated by reference in its entirety. Libraries of 15C1 scFv variants were screened against cynomolgus monkey TLR4 according to the following procedure.

ScFv Periplasmic Preparation for Screening

After five rounds of selections on CHO cells expressing cynomolgus monkey TLR4 at the membrane, single clones were picked into a deep well microtiter plate containing 0.9 mL of 2×TYAG media (0.1% glucose) per well and grown at 37° C. for 5-6 h (250 rpm). 100 µl per well of 0.2 mM IPTG in 2×TY medium were then added to give a final concentration of 0.02 mM IPTG. Plates were then incubated overnight at 30° C. with shaking at 250 rpm. The deep-well plates were centrifuged at 2,500 rpm for 10 min and the supernatant carefully removed. The pellets were re-suspended in 150 µl TES buffer (50 mM Tris/HCl (pH 8), 1 mM EDTA (pH 8), 20% sucrose, complemented with Complete protease inhibitor, Roche). A hypotonic shock was produced by adding 150 µl of diluted TES buffer (1:5 TES:water dilution) and incubation on ice for 30 min. Plates were then centrifuged at 4000 rpm for 10 minutes to remove cells and debris. The supernatants were carefully transferred into another microtiter plate and kept on ice for immediate testing in screening assays Monoclonal Phage Preparation for Screening Single clones were picked into a microtiter plate containing 150 µl of 2×TYAG media (2% glucose) per well and grown at 37° C. (100-120 rpm) for 5-6 h. M13KO7 helper phage was added to each well to obtain a multiplicity of infection (MOI) of 10 (i.e., 10 phage for each cell in the culture) and incubated at 37° C. (100 rpm) for 1 h. Following growth, plates were centrifuged at 3,200 rpm for 10 min. Supernatant was carefully removed, cells re-suspended in 150 µl 2×TYAK medium and grown overnight at 30° C. (120 rpm). The plates were then centrifuged 10 minutes at 3000 rpm and the phage containing supernatant was then concentrated by PEG precipitation. Briefly, phages were precipitated by adding ⅓ volume of cold PEG 8000 20%, NaCl 2.5M to the phage containing supernatant. The mix was incubated on ice for 1 h and then centrifuged 15 min 8000 rpm at 4° C. The phage pellet was re-suspended in 500 µl of TE buffer.

ScFv Screening

In brief, CHO-K1 cells and stably transfected CHO-K1 expressing cynomolgus monkey TLR4 were distributed into FMAT® 384-well optical plates (Applied Biosystems) at a density of 5,000 cells per well (in 50 µl of DMEM F12, 10% FCS, 2 mM Gln), 24 hours before the screening assay. At day 0, cells were mixed with a small volume of scFv periplasmic preparation (40 µl per well) and 10 µl of Penta-His Alexa Fluor 647 conjugate (1:200 dilution, QIAGEN). After an incubation period of 1 to 8 hours, the fluorescence of the cells was measured in an 8200 Cellular Detection System analyzer (Applied Biosystems). ScFv clones binding to CHO-K1 expressing cynomolgus monkey TLR4 but not to wt CHO-K1 cells were retained and subjected to further analyses. Selected clones were the 1A1, 1A6, 1B12, 1C7, 1C10, 1C12, 1D10, 1E11 and 1G12.

Monoclonal Phage Binding to Cynomolgus Monkey and Human TLR4

$10^5$ CHO cells or CHO cells expressing the cynomolgus monkey TLR4 were incubated in phosphate-buffered saline, 2% bovine serum albumin with different concentrations of precipitated monoclonal phages expressing scFvs selected by FMAT (1A1, 1A6, 1B12, 1C7, 1C10, 1C12, 1D10, 1E11, 1G12). As control, the parent 15C1 scFv was also expressed as monoclonal phage for binding test. Cells were then washed and incubated in the same buffer with monoclonal antibody to M13, fd, F1 filamentous phages-FITC (1:50; Acris antibodies). Cells were finally analyzed using a FACS calibur cytometer (BD Biosciences). FIG. 1 shows FACS analysis of these cells following antibody staining, which revealed that 1A1, 1A6, 1B12, 1C7, 1C10, 1C12, 1D10, 1E11 and 1G12 recognized cells expressing cynomolgus monkey TLR4 alone, contrary to 15C1 which doesn't bind to these cells. Moreover, these results suggest that the tested scFvs are specific of the cynomolgus monkey TLR4 protein as they did not bind to the native CHO cells.

Figure 2:
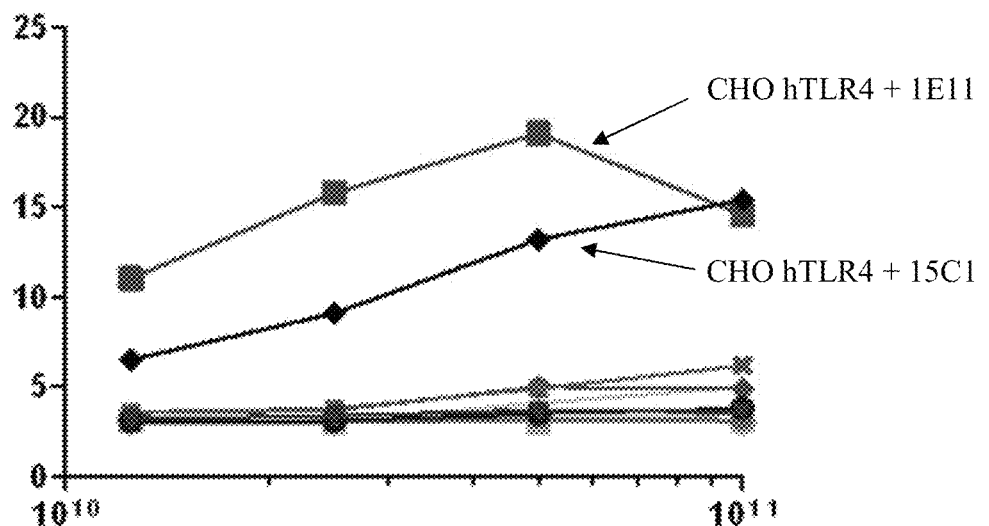
FIG. 2 is a graph depicting the binding by monoclonal phages expressing scFvs, referred to herein as "1A1, 1A6, 1B12, 1C7, 1C10, 1C12, 1D10, 1E11, 1G12, 15C1", to the human TLR4/MD2 complex. Specificity of binding is shown by flow cytometry using CHO cells mock transfected or transfected with human TLR4/MD2. The results using mock-transfected cells are shown with grey symbols (key on right), while the results using human TLR4/MD2 transfected cells are shown in other colored symbols (key on left).

Similarly, $10^5$ CHO cells or CHO cells expressing the human TLR4/MD2 complex were incubated in phosphate-buffered saline, 2% bovine serum albumin with different concentrations of the precipitated monoclonal phages expressing scFvs as described above. FIG. 2 shows FACS analysis of these cells following antibody staining, which revealed that 1E11 recognized cells expressing human TLR4/MD2 complex, similarly to 15C1 but not 1A1, 1A6, 1B12, 1C7, 1C10, 1C12, 1D10 and 1G12. These results suggest that 1A1, 1A6, 1B12, 1C7, 1C10, 1C12, 1D10 and 1G12 scFvs are specific of cynomolgus monkey TLR4 and that 1E11 is cross-reactive for human and cynomolgus monkey TLR4.

Example 4

Reformatting scFv into IgG Format and IgG Binding to Cynomolgus Monkey and Human TLR4

Reformatting, Production and Purification

The $V_H$ and $V_L$ sequence of selected scFvs (1A1, 1A6, 1B12, 1C7, 1C10, 1C12, 1D10, 1E11, 1G12) were amplified with specific oligonucleotides introducing a leader sequence at the 5' end. The amplified $V_H$ and $V_L$ sequences were cloned into mammalian expression vector in frame with human IgG1 constant and Kappa constant domains, respectively. The constructions were verified by sequencing before transfection into mammalian cells.

The $V_H$ and $V_L$ cDNA sequences in their appropriate expression vectors were transfected into mammalian cells using the Fugene 6 Transfection Reagent (Roche, Basel, Switzerland). Briefly, Peak cells were cultured in 6-well plates at a concentration of 6×10$^5$ cells per well in 2 mL culture media containing fetal bovine serum. The expression vectors, encoding the candidate $V_H$ and $V_L$ sequences, were co-transfected into the cells using the Fugene 6 Transfection Reagent according to manufacturer's instructions. One day following transfection, the culture media was aspirated, and 3 mL of fresh serum-free media was added to cells and cultured for three days at 37° C. Following three days culture period, the supernatant was harvested for IgG purified on protein G-Sepharose 4B fast flow columns (Sigma, St. Louis, Mo.) according to manufacturer's instructions. Briefly, supernatants from transfected cells were incubated overnight at 4° C. with ImmunoPure (G) IgG binding buffer (Pierce, Rockford Ill.). Samples were then passed over Protein G-Sepharose 4B fast flow columns and the IgG consequently purified using elution buffer. The eluted IgG fraction was then dialyzed against PBS and the IgG content quantified by absorption at 280 nm. Purity and IgG integrity were verified by SDS-PAGE.

The nucleic acid and amino acid sequences of the IgG1 reformatted 1E11 antibody is shown below:

>1E11 Heavy Chain Amino Acid Sequence
(SEQ ID NO: 40)
QVQLQESGPGLVKPSDTLSLTCAVSGYSITGGYSWHWIRQPPGKGLEWMG
YIHYSGYTDFNPSLKTRITISRDTSKNQFSLKLSSVTAVDTAVYYCARKD
SGNYFPYWGQGTLVTVSSASTKGPSVFPLAPSSKSTSGGTAALGCLVKDY
FPEPVTVSWNSGALTSGVHTFPAVLQSSGLYSLSSVVTVPSSSLGTQTYI
CNVNHKPSNTKVDKRVEPKSCDKTHTCPPCPAPELLGGPSVFLFPPKPKD
TLMISRTPEVTCVVVDVSHEDPEVKFNWYVDGVEVHNAKTKPREEQYNST
YRVVSVLTVLHQDWLNGKEYKCKVSNKALPAPIEKTISKAKGQPREPQVY
TLPPSREEMTKNQVSLTCLVKGFYPSDIAVEWESNGQPENNYKTTPPVLD
SDGSFFLYSKLTVDKSRWQQGNVFSCSVMHEALHNHYTQKSLSLSPG >1E11 Light Chain Amino Acid Sequence
(SEQ ID NO: 41)
EIVLTQSPDFQSVTPKEKVTITCRASQSISDHLHWYQQKPDQSPKLLIKY
ASHAISGVPSRFSGSGSGTDFTLTINSLEAEDAATYYCQQGHSFPLTFGG
GTKVEIKRTVAAPSVFIFPPSDEQLKSGTASVVCLLNNFYPREAKVQWKV
DNALQSGNSQESVTEQDSKDSTYSLSSTLTLSKADYEKHKVYACEVTHQG
LSSPVTKSFNRGEC >1E11 Light Chain Nucleic Acid Sequence
(SEQ ID NO: 52)
ATGAGTGTGCCCACTCAGGTCCTGGGGTTGCTGCTGCTGTGGCTTACAGA
TGCCAGATGTGAAATTGTGTTGACGCAGTCTCCAGACTTTCAGTCTGTGA
CTCCAAAGGAAAAAGTCACCATCACCTGCAGGGCCAGTCAGAGTATCAGC
GACCACTTACACTGGTACCAACAGAAACCTGATCAGTCTCCCAAGCTCCT
CATCAAATATGCTTCCCATGCCATTTCTGGGGTCCCATCGAGGTTCAGTG
GCAGTGGGTCTGGGACAGACTTCACTCTCACCATCAATAGCCTAGAGGCT
GAAGATGCTGCAACGTATTACTGTCAGCAGGGTCACAGTTTTCCGCTCAC
TTTCGGCGGAGGGACCAAGGTGGAGATCAAACGTACGGTGGCTGCACCAT
CTGTCTTCATCTTCCCGCCATCTGATGAGCAGTTGAAATCTGGAACTGCC
TCTGTTGTGTGCCTGCTGAATAACTTCTATCCCAGAGAGGCCAAAGTACA
GTGGAAGGTGGATAACGCCCTCCAATCGGGTAACTCCCAGGAGAGTGTCA
CAGAGCAGGACAGCAAGGACAGCACCTACAGCCTCAGCAGCACCCTGACG
CTGAGCAAAGCAGACTACGAGAAACACAAAGTCTACGCCTGCGAAGTCAC
CCATCAGGGCCTGAGCTCGCCCGTCACAAAGAGCTTCAACAGGGGAGAGT
GTTAA >1E11 Heavy Chain Nucleic Acid Sequence
(SEQ ID NO: 53)
ATGGAATGGAGCTGGGTCTTTCTCTTCTTCCTGTCAGTAACTACAGGTGT
CCACCAGGTGCAGCTTCAGGAGTCCGGCCCAGGACTGGTGAAGCCTTCGG
ACACCCTGTCCCTCACCTGCGCTGTCTCTGGTTACTCCATCACCGGTGGT
TATAGCTGGCACTGGATACGGCAGCCCCCAGGGAAGGGACTGGAGTGGAT
GGGGTATATCCACTACAGTGGTTACACTGACTTCAACCCCTCCCTCAAGA
CTCGAATCACCATATCACGTGACACGTCCAAGAACCAGTTCTCCCTGAAG
CTGAGCTCTGTGACCGCTGTGGACACTGCAGTGTATTACTGTGCGAGAAA
AGATCCGTCCGACGCCTTTCCTTACTGGGGCCAAGGGACTCTGGTCACTG
TCTCTTCCGCCTCCACCAAGGGCCCATCGGTCTTCCCCCTGGCACCCTCC
TCCAAGAGCACCTCTGGGGGCACAGCGGCCCTGGGCTGCCTGGTCAAGGA
CTACTTCCCCGAACCGGTGACAGTCGTGGAACTCAGGAGCCCTGACCA
GCGGCGTGCACACCTTCCCGGCTGTCCTACAGTCCTCAGGACTCTACTCC
CTCAGCAGCGTGGTGACTGTGCCCTCCAGCAGCTTGGGCACCCAGACCTA
CATCTGCAACGTGAATCACAAGCCCAGCAACACCAAGGTGGACAAGAGAG
TTGAGCCCAAATCTTGTGACAAAACTCACACATGCCCACCGTGCCCAGCA
CCTGAACTCCTGGGGGGACCGTCAGTCTTCCTCTTCCCCCCAAAACCCAA
GGACACCCTCATGATCTCCCGGACCCCTGAGGTCACATGCGTGGTGGTGG
ACGTGAGCCACGAAGACCCTGAGGTCAAGTTCAACTGGTACGTGGACGGC
GTGGAGGTGCATAATGCCAAGACAAAGCCGCGGGAGGAGCAGTACAACAG
CACGTACCGTGTGGTCAGCGTCCTCACCGTCCTGCACCAGGACTGGCTGA
ATGGCAAGGAGTACAAGTGCAAGGTCTCCAACAAAGCCCTCCCAGCCCCC
ATCGAGAAAACCATCTCCAAAGCCAAAGGGCAGCCCCGAGAACCACAGGT
GTATACCCTGCCCCCATCTCGGGAGGAGATGACCAAGAACCAGGTCAGCC
TGACTTGCCTGGTCAAAGGCTTCTATCCCAGCGACATCGCCGTGGAGTGG
GAGAGCAACGGGCAGCCGGAGAACAACTACAAGACCACGCCTCCCGTGCT
GGACTCCGACGGCTCCTTCTTCCTCTATAGCAAGCTCACCGTGGACAAGT
CCAGGTGGCAGCAGGGGAACGTCTTCTCATGCTCCGTGATGCATGAGGCT
CTGCACAACCACTACACGCAGAAGAGCCTCTCCCTGTCTCCGGGTTAA Monoclonal Antibody Binding to Cynomolgus Monkey and Human TLR4

Figure 3:
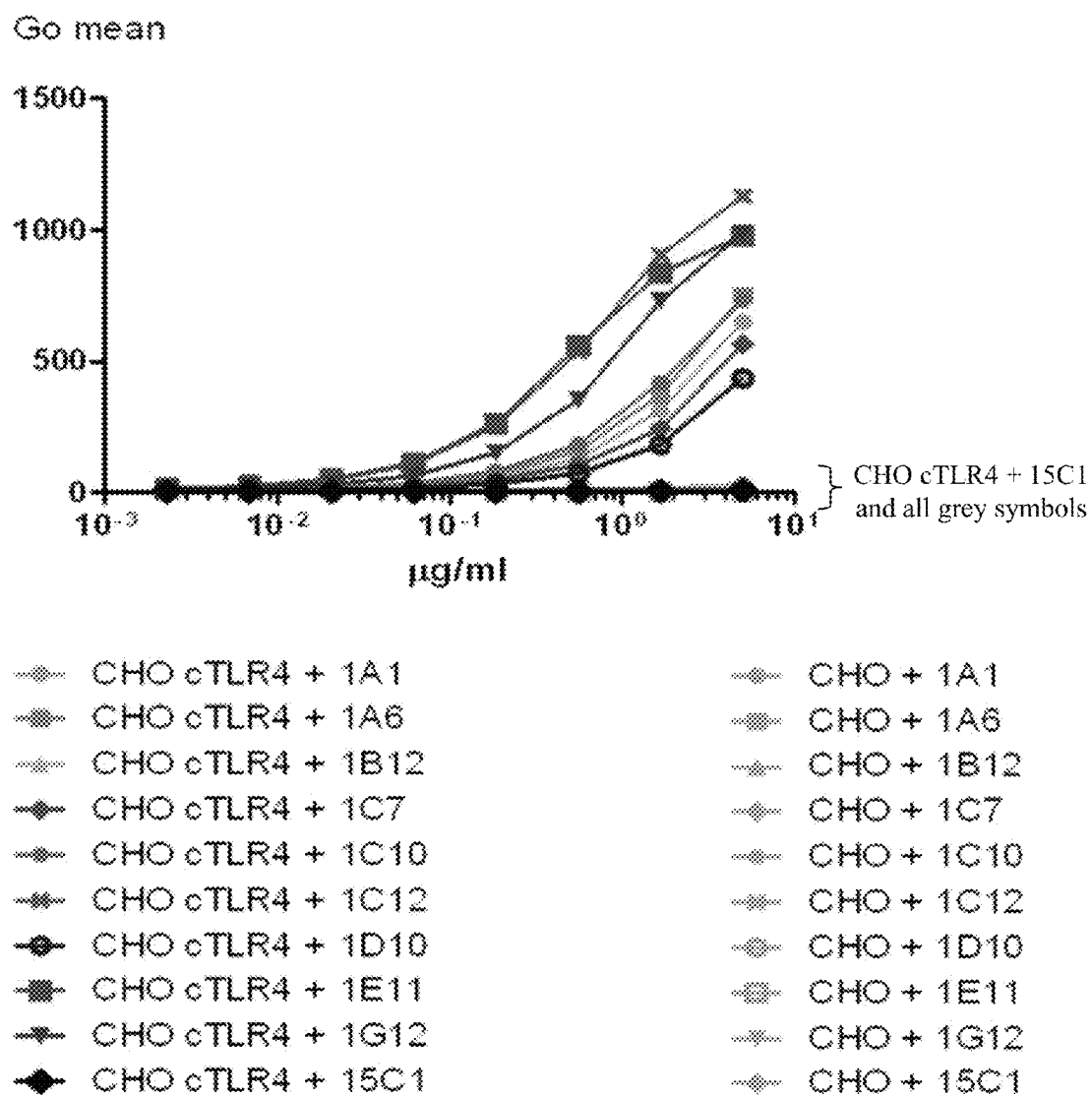
FIG. 3 is a graph depicting the binding by purified antibodies, referred to herein as "1A1, 1A6, 1B12, 1C7, 1C10, 1C12, 1D10, 1E11, 1G12, 15C1", to the cynomolgus monkey TLR4. Specificity of binding is shown by flow cytometry using CHO cells mock transfected or transfected with cynomolgus monkey TLR4/MD2. The results using mock-transfected cells are shown with grey symbols (key on right), while the results using cynomolgus monkey TLR4/MD2 transfected cells are shown in other colored symbols (key on left).

10$^5$ CHO cells or CHO cells expressing the cynomolgus monkey TLR4 were incubated in phosphate-buffered saline, 2% bovine serum albumin with different concentrations of purified antibodies selected by FMAT (1A1, 1A6, 1B12, 1C7, 1C10, 1C12, 1D10, 1E11, 1G12) with 15C1 as control. Cells were washed in phosphate-buffered saline, 2% bovine serum albumin and incubated in Alexa Fluor® 647 goat anti human IgG (H+L) (1:200; Invitrogen). Cells were analyzed using a FACS calibur cytometer (BD Biosciences). FIG. 3 shows FACS analysis of these cells following antibody staining, which revealed that 1A1, 1A6, 1B12, 1C7, 1C10, 1C12, 1D10, 1E11 and 1G12 Mabs recognized cells expressing cynomolgus monkey TLR4 alone, contrary to 15C1 which doesn't bind to these cells. Moreover, these results confirm that these antibodies were specific of the TLR4 protein as they did not bind to the native CHO cells.

Figure 4:
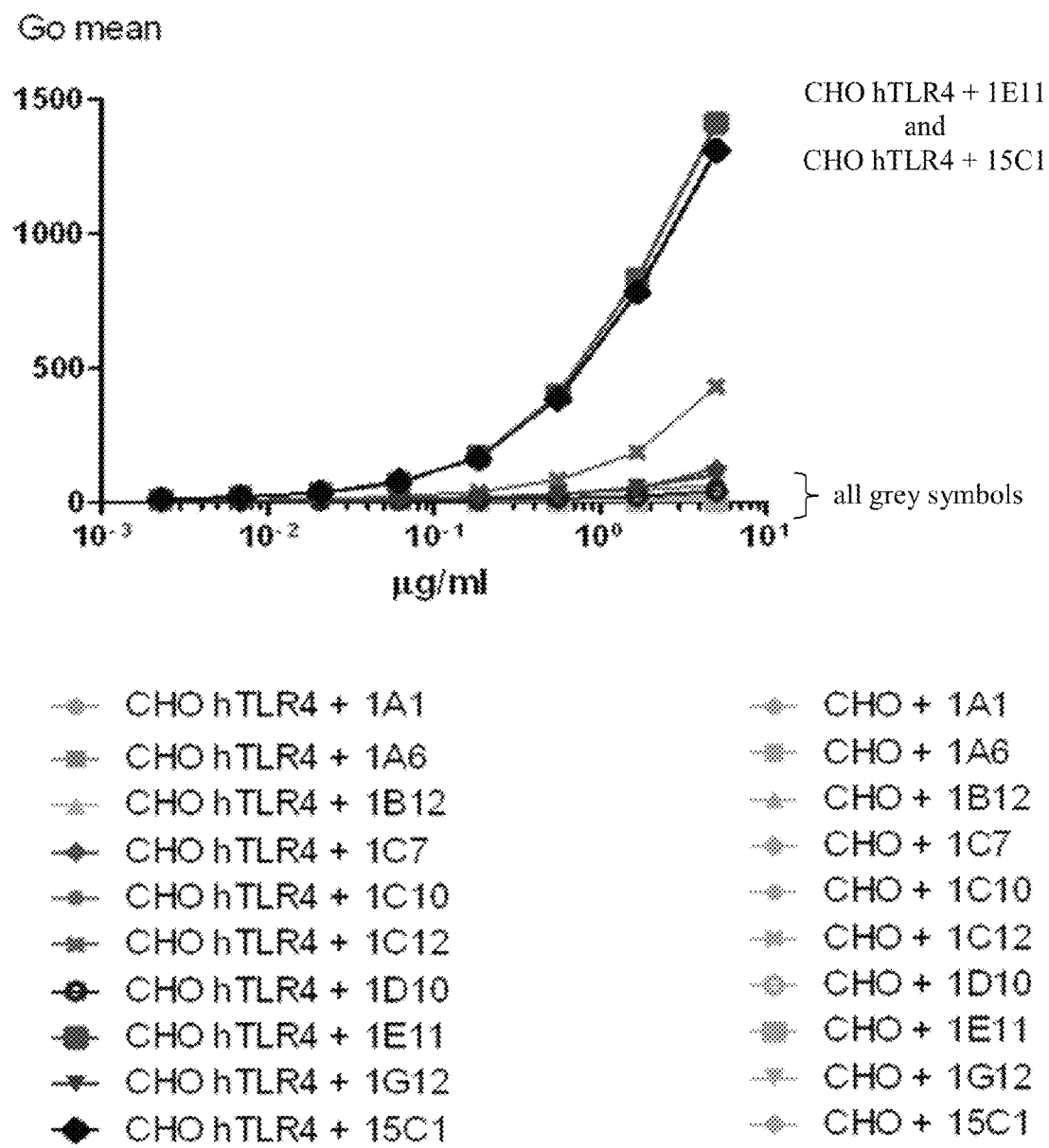
FIG. 4 is a graph depicting the binding by purified antibodies, referred to herein as "1A1, 1A6, 1B12, 1C7, 1C10, 1C12, 1D10, 1E11, 1G12, 15C1", to the human TLR4/MD2 complex. Specificity of binding is shown by flow cytometry CHO cells mock transfected or transfected with human TLR4/MD2. The results using mock-transfected cells are shown with grey symbols (key on right), while the results using human TLR4/MD2 transfected cells are shown in other colored symbols (key on left).

Similar experiments were conducted with CHO cells or CHO cells expressing the human TLR4/MD2 complex. FIG. 4 shows FACS analysis of these cells following antibody staining, which revealed that 1E11 Mab recognized cells expressing human TLR4/MD2 complex, similarly to 15C1 Mab but that 1A1, 1A6, 1B12, 1C7, 1C10, 1D10 and 1G12 Mabs are unable to bind to the human protein. 1C12 Mab was also able to bind to human TLR4 but with a lower potency compared to 1E11 and 15C1 Mabs. These results confirm that 1E11 and 1C12 are cross-reactive monoclonal antibodies able to bind to both human and cynomolgus monkey TLR4 alone or in complex with MD2. These results also confirm that that 1A1, 1A6, 1B12, 1C7, 1C10, 1D10 and 1G12 are specific anti-cynomolgus monkey TLR4 monoclonal antibodies.

Example 5

Analysis of Paratope-Epitope Specificity Between Anti-TLR4 Antibodies and TLR4

Figures 5, 6:
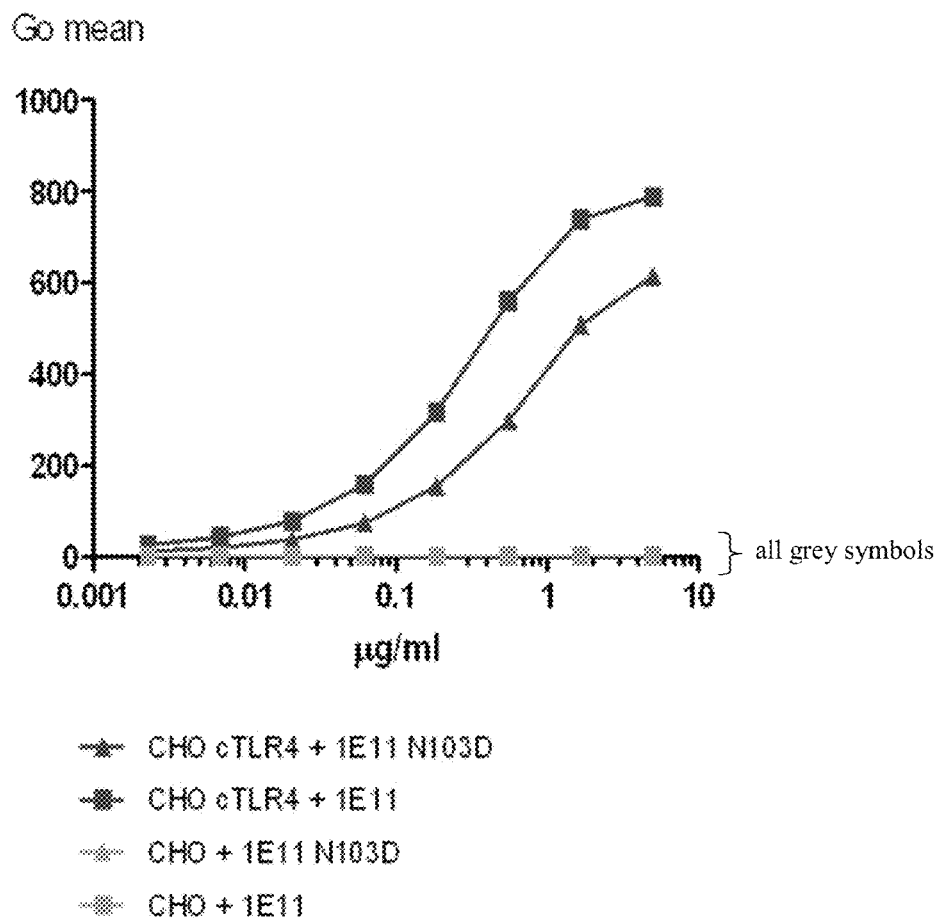
FIG. 5 an illustration of the antibody paratope/TLR4 epitope potential amino acid contact. The CDRH3 sequence of the human specific TLR4 antibody, 15C1, (SEQ ID NO: 44) can make salt bridge interaction with lysine 349 of human TLR4 (SEQ ID NO: 23). CDRH3 sequence of cynomolgus-monkey specific TLR41G12 MAb (SEQ ID NO: 36) can make salt bridge interaction with glutamic acid 349 of cynomolgus monkey TLR4 (SEQ ID NO: 24). CDRH3 sequence of cynomolgus-monkey/human specific TLR41E11 MAb can make hydrogen bonds with both lysine 349 of human TLR4 (SEQ ID NO: 23) and glutamic acid 349 of cynomolgus monkey TLR4 (SEQ ID NO: 24).
FIG. 6 is a graph depicting the binding by purified antibodies, referred to herein as "1E11, 1E11 N103D", to the cynomolgus monkey TLR4. Specificity of binding is shown by flow cytometry using CHO cells mock transfected or transfected with cynomolgus monkey TLR4/MD2. The results using mock-transfected cells are shown with grey symbols, while the results using cynomolgus monkey TLR4/MD2 transfected cells are shown in other colored symbols.

FIG. 5 shows an illustration of the antibody paratope/TLR4 epitope potential amino acid contact which determines the antibody/TLR4 specificities. The Human TLR4 and the cynomolgus monkey TLR4 have only one different amino acid into the regions known to be important for the binding (see Irene Dunne-Siegrist et al. J Biol Chem, 2007 Nov. 30; 282(48):34817-27). Effectively, the human TLR4 has a lysine (positively charged amino acid) at the position 349 whereas the cynomolgus monkey TLR4 has a glutamic acid (negatively charged amino acid) at this position. These results suggest that a salt bridge occurs between the amino acid 103 of the heavy chain of the selected antibodies and the amino acid 349 of TLR4. Moreover, the cross reactive antibodies (1E11 and 1C12) have an asparagine or a glutamine at the position 103 which may serve both as hydrogen donor to glutamic acid and hydrogen acceptor to lysine. These specific amino acids may allow antibody cross reactivity to both the human and cynomolgus monkey TLR4.

Figure 7:
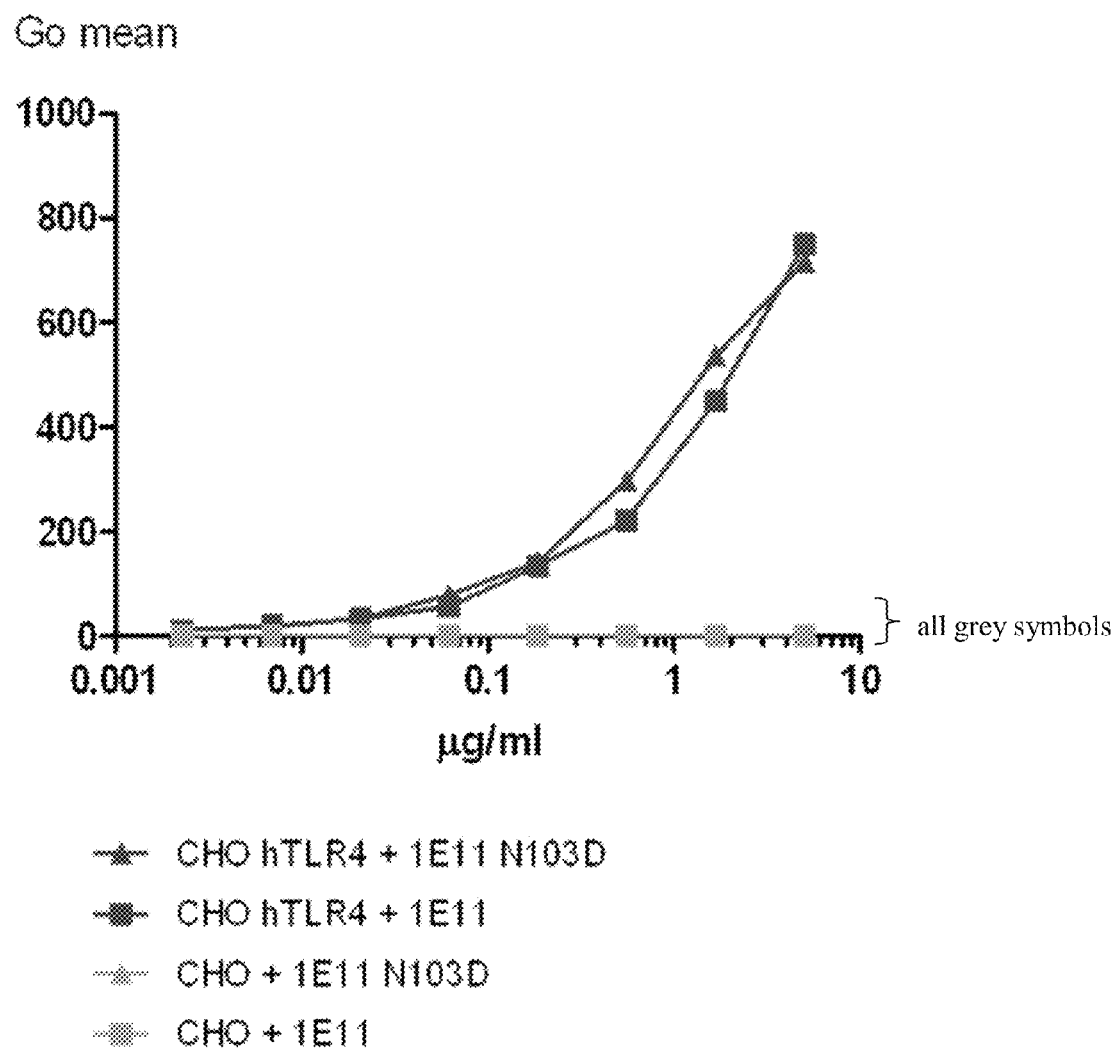
FIG. 7 is a graph depicting the binding by purified antibodies, referred to herein "1E11, 1E11 N103D", to the human TLR4/MD2 complex. Specificity of binding is shown by flow cytometry using CHO cells mock transfected or transfected with human TLR4. The results using mock-transfected cells are shown with grey symbols, while the results using human TLR4/MD2 transfected cells are shown in other colored symbols.

Site directed mutagenesis was performed at position 103 in the 1E11 antibody to introduce the N103D mutation. Vector containing the verified VH sequence of 1E11 N103D was then co-transfected with VL sequence into mammalian cells using the Fugene 6 Transfection Reagent (Roche, Basel, Switzerland) as described previously. Then, $10^5$ CHO cells or CHO cells expressing the cynomolgus monkey TLR4 were incubated in phosphate-buffered saline, 2% bovine serum albumin with different concentrations of purified antibodies (1E11 and 1E11 N103D). Cells were washed in phosphate-buffered saline, 2% bovine serum albumin and incubated in Alexa Fluor® 647 goat anti human IgG (H+L) (1:200; Invitrogen) and were finally analyzed using a FACS calibur cytometer (BD Biosciences). FIG. 6 shows the results of the analysis of these cells following antibody staining, which revealed that 1E11 and 1E11 N103D Mabs recognized cells expressing cynomolgus monkey TLR4 alone. However, binding of 1E11 N103D Mab to cynomolgus monkey is significantly lower compared to 1E11. Similarly, $10^5$ CHO cells or CHO cells expressing the human TLR4/MD2 complex were incubated in phosphate-buffered saline, 2% bovine serum albumin with different concentrations of purified antibodies (1E11 and 1E11 N103D) and then binding of antibodies to these cells were monitored by FACS. FIG. 7 represents FACS analysis of these cells following antibody staining, which revealed that 1E11 and 1E11 N103D Mabs both recognized cells expressing human TLR4 with the same potency. Taken together, these results suggest that position 103 is crucial for the binding of 1E11 to human and cynomolgus monkey TLR4. More precisely, these data indicate that a CDRH3 motif could be designed in order to induce species cross-reactivity of an anti TLR4 antibody.

TABLE 5

Cross-reactivity of anti-TLR4 antibodies.
CDRH3 motif = CARKDSG[N, Q, D][Y, L]FPY
(SEQ ID NO: 54)

| Clone ID | Heavy CDR3 | Species specificity |
|---|---|---|
| 1A1 | ARKDSGRLLPY (SEQ ID NO: 28) | Cynomolgus monkey |
| 1A6 | ARKDSGKWLPY (SEQ ID NO: 29) | |
| 1B12 | ARKDSGHLMPY (SEQ ID NO: 30) | |
| 1C7 | ARKDSGHNYPY (SEQ ID NO: 31) | |
| 1C10 | ARKDSGKNFPY (SEQ ID NO: 32) | |
| 1G12 | ARKDSGRYWPY (SEQ ID NO: 36) | |
| 1D10 | ARKDSGHNLPY (SEQ ID NO: 34) | |
| 15C1 | ARKDPSDAFPY (SEQ ID NO: 44) | Human |
| 1E11 | ARKDSGNYFPY (SEQ ID NO: 27) | Human and cynomolgus monkey |
| 1E11 N103D | ARKDSGDYFPY (SEQ ID NO: 35) | |
| 1C12 | ARKDSGQLFPY (SEQ ID NO: 33) | |

Example 6

Figure 8:
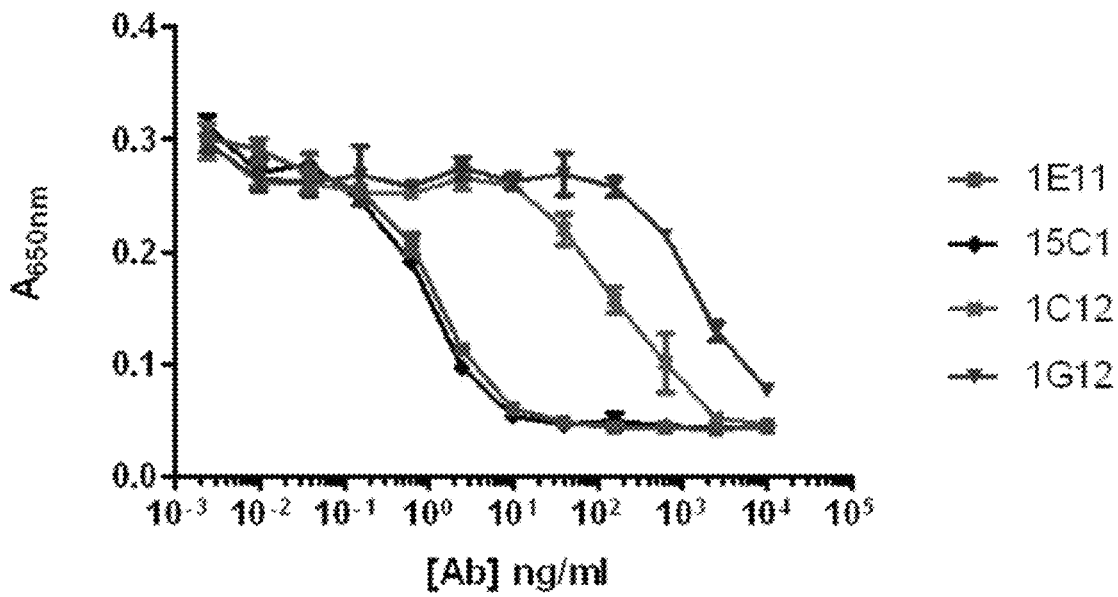
FIG. 8 is a graph depicting the inhibition of LPS-induced downstream signaling cascade of TLR4, NF-κB, by purified antibodies, referred to herein "1E11, 15C1, 1C12, 1G12". THP1-blue-CD14 cell line is derived from human monocytic cell line expressing the human TLR4/MD2 complex and stably transfected with a reporter gene which facilitates the monitoring of TLR-induced NF-κB/AP-1 activation. Cells were incubated with 1E11, 15C1, 1C12 and 1G12 at the indicated concentrations and subsequently incubated with LPS (10 ng/mL). Levels of secreted embryonic alkaline phosphatase were assessed 24 hours post LPS-treatment by measuring the absorbance at 650 nm using a microplate reader.

Inhibition of LPS-Induced Downstream Signaling Cascade of TLR4: NFκB, by Purified Antibodies THP1-Blue™-CD14 cells (Invivogen), which express human TLR4/MD2 complex, were plated in 96 well plates at $10^5$ cells/well in 30 μl of HEK-Blue detection medium (Invivogen). TLR4 antibodies were diluted in 30 μl of medium to the appropriate concentration and added to the cells for 30 min at 37° C. Then, LPS was diluted at 10 ng/mL in 30 μl of medium, added to the cells, and left to incubate 24 h at 37° C. The absorbance was measured at 650 nm using a microplate reader. FIG. 8 shows the results of the inhibition of LPS-induced downstream signaling cascade of TLR4 by selected Mabs (1E11, 15C1, 1C12 and 1G12). 1E11 showed inhibition potency of LPS induced TLR4 signaling comparable to 15C1. 1C12 showed lower inhibition capacities compared to 1E11 and 1G12 did not affect the LPS-induced downstream signaling cascade of human TLR4 confirming its specificity for cynomolgus monkey TLR4.

Example 7

CDRs Randomization of 1E11 Antibody and Cell Surface Selections

The cross-reactive 1E11 antibody sequence (heavy chain sequence of SEQ ID NO: 40 and light chain sequence of SEQ ID NO: 41) has the same binding and blocking potency than 15C1. This antibody was subjected to sequence randomization in order to obtain antibodies binding to human and cynomolgus monkey TLR4 with higher affinity compared to the parental antibody and 15C1 and able to neutralize LPS-induced pro-inflammatory cytokine production mediated by TLR4.

>1E11 Light Chain Amino Acid Sequence
(SEQ ID NO: 41)
EIVLTQSPDFQSVTPKEKVTITCRASQSISDHLHWYQQKPDQSPKLLIKY
ASHAISGVPSRFSGSGSGTDFTLTINSLEAEDAATYYCQQGHSFPLTFGG
GTKVEIKRTVAAPSVFIFPPSDEQLKSGTASVVCLLNNFYPREAKVQWKV
DNALQSGNSQESVTEQDSKDSTYSLSSTLTLSKADYEKHKVYACEVTHQG
LSSPVTKSFNRGEC >1E11 Heavy Chain Amino Acid Sequence
(SEQ ID NO: 40)
QVQLQESGPGLVKPSDTLSLTCAVSGYSITGGYSWHWIRQPPGKGLEWMG
YIHYSGYTDFNPSLKTRITISRDTSKNQFSLKLSSVTAVDTAVYYCARKD
SGNYFPYWGQGTLVTVSSASTKGPSVFPLAPSSKSTSGGTAALGCLVKDY
FPEPVTVSWNSGALTSGVHTFPAVLQSSGLYSLSSVVTVPSSSLGTQTYI
CNVNHKPSNTKVDKRVEPKSCDKTHTCPPCPAPELLGGPSVFLFPPKPKD
TLMISRTPEVTCVVVDVSHEDPEVKFNWYVDGVEVHNAKTKPREEQYNST
YRVVSVLTVLHQDWLNGKEYKCKVSNKALPAPIEKTISKAKGQPREPQVY
TLPPSREEMTKNQVSLTCLVKGFYPSDIAVEWESNGQPENNYKTTPPVLD
SDGSFFLYSKLTVDKSRWQQGNVFSCSVMHEALHNHYTQKSLSLSPG >1E11 Light Chain Nucleic Acid Sequence
(SEQ ID NO: 52)
ATGAGTGTGCCCACTCAGGTCCTGGGGTTGCTGCTGCTGTGGCTTACAGA
TGCCAGATGTGAAATTGTGTTGACGCAGTCTCCAGACTTTCAGTCTGTGA
CTCCAAAGGAAAAAGTCACCATCACCTGCAGGGCCAGTCAGAGTATCAGC
GACCACTTACACTGGTACCAACAGAAACCTGATCAGTCTCCCAAGCTCCT
CATCAAATATGCTTCCCATGCCATTTCTGGGGTCCCATCGAGGTTCAGTG
GCAGTGGGTCTGGGACAGACTTCACTCTCACCATCAATAGCCTAGAGGCT
GAAGATGCTGCAACGTATTACTGTCAGCAGGGTCACAGTTTTCCGCTCAC
TTTCGGCGGAGGGACCAAGGTGGAGATCAAACGTACGGTGGCTGCACCAT
CTGTCTTCATCTTCCCGCCATCTGATGAGCAGTTGAAATCTGGAACTGCC
TCTGTTGTGTGCCTGCTGAATAACTTCTATCCCAGAGAGGCCAAAGTACA
GTGGAAGGTGGATAACGCCCTCCAATCGGGTAACTCCCAGGAGAGTGTCA
CAGAGCAGGACAGCAAGGACAGCACCTACAGCCTCAGCAGCACCCTGACG
CTGAGCAAAGCAGACTACGAGAAACACAAAGTCTACGCCTGCGAAGTCAC
CCATCAGGGCCTGAGCTCGCCCGTCACAAAGAGCTTCAACAGGGGAGAGT
GTTAA >1E11 Heavy Chain Nucleic Acid Sequence
(SEQ ID NO: 53)
ATGGAATGGAGCTGGGTCTTTCTCTTCTTCCTGTCAGTAACTACAGGTGT
CCACCAGGTGCAGCTTCAGGAGTCCGGCCCAGGACTGGTGAAGCCTTCG
ACACCCTGTCCCTCACCTGCGCTGTCTCTGGTTACTCCATCACCGGTGGT
TATAGCTGGCACTGGATACGGCAGCCCCCAGGGAAGGGACTGGAGTGGAT
GGGGTATATCCACTACAGTGGTTACACTGACTTCAACCCCTCCCTCAAGA
CTCGAATCACCATATCACGTGACACGTCCAAGAACCAGTTCTCCCTGAAG
CTGAGCTCTGTGACCGCTGTGGACACTGCAGTGTATTACTGTGCGAGAAA
AGATCCGTCCGACGCCTTTCCTTACTGGGGCCAAGGGACCTGGTCACTG
TCTCTTCCGCCTCCACCAAGGGCCCATCGGTCTTCCCCCTGGCACCCTCC
TCCAAGAGCACCTCTGGGGGCACAGCGGCCCTGGGCTGCCTGGTCAAGGA
CTACTTCCCCGAACCGGTGACAGTCTCGTGGAACTCAGGAGCCCTGACCA
GCGGCGTGCACACCTTCCCGGCTGTCCTACAGTCCTCAGGACTCTACTCC
CTCAGCAGCGTGGTGACTGTGCCCTCCAGCAGCTTGGGCACCCAGACCTA
CATCTGCAACGTGAATCACAAGCCCAGCAACACCAAGGTGGACAAGAGAG
TTGAGCCCAAATCTTGTGACAAAACTCACACATGCCCACCGTGCCCAGCA
CCTGAACTCCTGGGGGGACCGTCAGTCTTCCTCTTCCCCCCAAAACCCAA
GGACACCCTCATGATCTCCCGGACCCCTGAGGTCACATGCGTGGTGGTGG
ACGTGAGCCACGAAGACCCTGAGGTCAAGTTCAACTGGTACGTGGACGGC
GTGGAGGTGCATAATGCCAAGACAAAGCCGCGGGAGGAGCAGTACAACAG
CACGTACCGTGTGGTCAGCGTCCTCACCGTCCTGCACCAGGACTGGCTGA
ATGGCAAGGAGTACAAGTGCAAGGTCTCCAACAAAGCCCTCCCAGCCCCC
ATCGAGAAACCATCTCCAAAGCCAAAGGGCAGCCCCGAGAACCACAGGT
GTATACCCTGCCCCCATCTCGGGAGGAGATGACCAAGAACCAGGTCAGCC
TGACTTGCCTGGTCAAAGGCTTCTATCCCAGCGACATCGCCGTGGAGTGG
GAGAGCAACGGGCAGCCGGAGAACAACTACAAGACCACGCCTCCCGTGCT
GGACTCCGACGGCTCCTTCTTCCTCTATAGCAAGCTCACCGTGGACAAGT
CCAGGTGGCAGCAGGGGAACGTCTTCTCATGCTCCGTGATGCATGAGGCT
CTGCACAACCACTACACGCAGAAGAGCCTCTCCCTGTCTCCGGGTTAA The $V_H$ (SEQ ID NO:1) and $V_L$ (SEQ ID NO:2) regions of the 1E11 antibody were cloned into the pNDS vector described in Ravn et al. (Nucleic Acids Res. 2010 November; 38(21):e193). Briefly, the $V_H$ region was cloned in frame of the PelB leader sequence using a NcoI restriction site in 5' and a XhoI restriction site in 3'. Then, the $V_L$ region was inserted in frame of a linker sequence using SalI restriction enzyme in 5' and NotI restriction enzyme in 3' to form a construct coding for the 15C1 scFv fused in its C-terminal part to the 6×His and c-Myc tags and the pIII protein. Then, 5 residues in the CDRH1 of the heavy chain (SEQ ID NO: 25) or light chain (SEQ ID NO: 48) were randomized in order to generate 5 libraries (Library size ranging from 5×10⁷ to 2×10⁸). The different libraries generated are shown below in Table 6 and Table 7 where X represents any amino acid.

TABLE 6

| 1E11 CDRH1 randomization libraries. | | | | | | | |
|---|---|---|---|---|---|---|---|
| 1E11 CDRH1 (SEQ ID NO: 25) | G | Y | S | I | T | G | G | Y |
| LIBRARY 1 (SEQ ID NO: 104) | G | X | X | I | X | X | X | Y |
| LIBRARY 2 (SEQ ID NO: 105) | G | Y | X | I | X | X | X | X |

TABLE 7

| 1E11 CDRL3 randomization libraries. | | | | | | | |
|---|---|---|---|---|---|---|---|
| 1E11 CDRL3 (SEQ ID NO: 48) | Q | Q | G | H | S | F | P | L | T |
| LIBRARY 3 (SEQ ID NO: 49) | Q | Q | X | X | X | X | X | L | T |
| LIBRARY 4 (SEQ ID NO: 50) | Q | Q | G | H | X | X | X | X | X |
| LIBRARY 5 (SEQ ID NO: 51) | Q | Q | X | X | X | X | P | X | T |

Five selection rounds were performed using these libraries and screening for variants with desired activities was performed using scFv periplasmic extracts. Briefly, aliquots of 1E11 modified scFv phage libraries ($10^{12}$ Pfu) were blocked with PBS containing 3% (w/v) skimmed milk for one hour at room temperature on a rotary mixer. Blocked phages were then deselected for one hour at 37° C./5% $CO_2$ on CHO cells (in a T75 flask 80% confluence) that had been previously blocked with PBS containing 2% (w/v) skimmed milk. Deselected phages were then mixed with increasing concentration of 15C1 antibody and incubated on CHO cells expressing human TLR4 for three hours at room temperature with gentle shaking Cells were then washed ten times with PBS. Bound phages were eluted by adding 1 mL of 75 mM citric acid followed by neutralization with 280 µl of Tris-HCl pH 9. Then, 10 mL of exponentially growing TG1 were added to the T75 flask and incubating for one hour at 37° C. with slow shaking. An aliquot of the infected TG1 was serial diluted to titer the selection output. Infected TG1 were spun at 3000 rpm for 15 minutes and re-suspended in 0.5 mL 2×TY-AG (2×TY media containing 100 µg/mL ampicillin and 2% glucose) and spread on 2×TYAG agar Bioassay plates. After overnight incubation at 30° C. 10 mL of 2×TYAG was added to the plates and the cells were scraped form the surface and transferred to a 50 mL polypropylene tube. 2×TYAG containing 50% glycerol was added to the cell suspension to obtain a final concentration of 17% glycerol. Aliquots of the selection round were kept at −80° C. After five rounds of selections on CHO cells expressing human TLR4 at the membrane in competition with 15C1 antibody, 50 single clones were picked into a deep well microtiter plate containing 0.9 mL of 2×TYAG media (0.1% glucose) per well and grown at 37° C. for 5-6 h (250 rpm). Plasmids encoding scFv were then purified and analyzed by Sanger sequencing.

Example 8

Identification of Affinity Matured Variants of 1E11

Clones isolated after the last round of selection were sequenced and analyzed. After alignment, sequence consensuses in CDRH1 or CDRL3 were identified. Enriched scFv sequences with specific amino acid consensus were then selected. The 1E11.C1, 1E11.C2, 1E11.C3, 1E11.C4, 1E11.C5 and 1E11.C6 scFvs have specific CDRH1 sequences. The 1E11.E1, 1E11.E2, 1E11.E3, 1E11.E4 and 1E11.E5 scFvs which have specific CDRL3 sequences were also identified. The $V_H$ and $V_L$ sequence of selected scFvs were amplified with specific oligonucleotides introducing a leader sequence at the 5' end. The amplified $V_H$ and $V_L$ sequences were cloned into mammalian expression vector in frame with human IgG1 constant and Kappa constant domains, respectively. The constructions were verified by sequencing before transfection into mammalian cells. The nucleic acid and amino acid sequences of the IgG1 reformatted 1E11.C1 antibody are shown below:

```
>1E11.C1 Light Chain Amino Acid Sequence
                                    (SEQ ID NO: 106)
EIVLTQSPDFQSVTPKEKVTITCRASQSISDHLHWYQQKPDQSPKLLIKY
ASHAISGVPSRFSGSGSGTDFTLTINSLEAEDAATYYCQQGHSFPLTFGG
GTKVEIKRTVAAPSVFIFPPSDEQLKSGTASVVCLLNNFYPREAKVQWKV
DNALQSGNSQESVTEQDSKDSTYSLSSTLTLSKADYEKHKVYACEVTHQG
LSSPVTKSFNRGEC >1E11.C1 Heavy Chain Amino Acid Sequence
                                    (SEQ ID NO: 108)
QVQLQESGPGLVKPSDTLSLTCAVSGFPIRYGYSWHWIRQPPGKGLEWMG
YIHYSGYTDFNPLKTRITISRDTSKNQFSLKLSSVTAVDTAVYYCARKDS
GNYFPYWGQGTLVTVSSASTKGPSVFPLAPSSKSTSGGTAALGCLVKDYF
PEPVTVSWNSGALTSGVHTFPAVLQSSGLYSLSSVVTVPSSSLGTQTYIC
NVNHKPSNTKVDKRVEPKSCDKTHTCPPCPAPELLGGPSVFLFPPKPKDT
LMISRTPEVTCVVVDVSHEDPEVKFNWYVDGVEVHNAKTKPREEQYNSTY
RVVSVLTVLHQDWLNGKEYKCKVSNKALPAPIEKTISKAKGQPREPQVYT
LPPSREEMTKNQVSLTCLVKGFYPSDIAVEWESNGQPENNYKTTPPVLDS
DGSFFLYSKLTVDKSRWQQGNVFSCSVMHEALHNHYTQKSLSLSPG >1E11.C1 Light Chain Nucleic Acid Sequence
                                    (SEQ ID NO: 107)
ATGAGTGTGCCCACTCAGGTCCTGGGGTTGCTGCTGCTGTGGCTTACAGA
TGCCAGATGTGAAATTGTGTTGACGCAGTCTCCAGACTTTCAGTCTGTGA
CTCCAAAGGAAAAAGTCACCATCACCTGCAGGGCCAGTCAGAGTATCAGC
GACCACTTACACTGGTACCAACAGAAACCTGATCAGTCTCCCAAGCTCCT
CATCAAATATGCTTCCCATGCCATTTCTGGGGTCCCATCGAGGTTCAGTG
GCAGTGGGTCTGGGACAGACTTCACTCTCACCATCAATAGCCTAGAGGCT
GAAGATGCTGCAACGTATTACTGTCAGCAGGGTCACAGTTTTCCGCTCAC
TTTCGGCGGAGGGACCAAGGTGGAGATCAAACGTACGGTGGCTGCACCAT
CTGTCTTCATCTTCCCGCCATCTGATGAGCAGTTGAAATCTGGAACTGCC
TCTGTTGTGTGCCTGCTGAATAACTTCTATCCCAGAGAGGCCAAAGTACA
GTGGAAGGTGGATAACGCCCTCCAATCGGGTAACTCCCAGGAGAGTGTCA
CAGAGCAGGACAGCAAGGACAGCACCTACAGCCTCAGCAGCACCCTGACG
CTGAGCAAAGCAGACTACGAGAAACACAAAGTCTACGCCTGCGAAGTCAC
CCATCAGGGCCTGAGCTCGCCCGTCACAAAGAGCTTCAACAGGGGAGAGT
GTTAA >1E11.C1 Heavy Chain Nucleic Acid Sequence
                                    (SEQ ID NO: 109)
ATGGAATGGAGCTGGGTCTTTCTCTTCTTCCTGTCAGTAACTACAGGTGT
CCACCAGGTGCAGCTTCAGGAGTCCGGCCCAGGACTGGTGAAGCCTTCGG
ACACCCTGTCCCTCACCTGCGCTGTCTCTGGTTTCCCGATCCGCTACGGG
TATAGCTGGCACTGGATACGGCAGCCCCCAGGGAAGGGACTGGAGTGGAT
GGGGTATATCCACTACAGTGGTTACACTGACTTCAACCCCTCCCTCAAGA
CTCGAATCACCATATCACGTGACACGTCCAAGAACCAGTTCTCCCTGAAG
CTGAGCTCTGTGACCGCTGTGGACACTGCAGTGTATTACTGTGCGAGAAA
AGATTCGGGCAACTACTTCCCTTACTGGGGCCAAGGGACTCTGGTCACTG
TCTCTTCCGCCTCCACCAAGGGCCCATCGGTCTTCCCCCTGGCACCCTCC
TCCAAGAGCACCTCTGGGGGCACAGCGGCCCTGGGCTGCCTGGTCAAGGA
CTACTTCCCCGAACCGGTGACAGTCTCGTGGAACTCAGGAGCCCTGACCA
GCGGCGTGCACACCTTCCCGGCTGTCCTACAGTCCTCAGGACTCTACTCC
CTCAGCAGCGTGGTGACTGTGCCCTCCAGCAGCTTGGGCACCCAGACCTA
```

-continued

```
CATCTGCAACGTGAATCACAAGCCCAGCAACACCAAGGTGGACAAGAGAG
TTGAGCCCAAATCTTGTGACAAAACTCACACATGCCCACCGTGCCCAGCA
CCTGAACTCCTGGGGGGACCGTCAGTCTTCCTCTTCCCCCCAAAACCCAA
GGACACCCTCATGATCTCCCGGACCCCTGAGGTCACATGCGTGGTGGTGG
ACGTGAGCCACGAAGACCCTGAGGTCAAGTTCAACTGGTACGTGGACGGC
GTGGAGGTGCATAATGCCAAGACAAAGCCGCGGGAGGAGCAGTACAACAG
CACGTACCGTGTGGTCAGCGTCCTCACCGTCCTGCACCAGGACTGGCTGA
ATGGCAAGGAGTACAAGTGCAAGGTCTCCAACAAAGCCCTCCCAGCCCCC
ATCGAGAAAACCATCTCCAAAGCCAAAGGGCAGCCCCGAGAACCACAGGT
GTATACCCTGCCCCCATCTCGGGAGGAGATGACCAAGAACCAGGTCAGCC
TGACTTGCCTGGTCAAAGGCTTCTATCCCAGCGACATCGCCGTGGAGTGG
GAGAGCAACGGGCAGCCGGAGAACAACTACAAGACCACGCCTCCCGTGCT
GGACTCCGACGGCTCCTTCTTCCTCTATAGCAAGCTCACCGTGGACAAGT
CCAGGTGGCAGCAGGGGAACGTCTTCTCATGCTCCGTGATGCATGAGGCT
CTGCACAACCACTACACGCAGAAGAGCCTCTCCCTGTCTCCGGGTTAA
```

The $V_H$ and $V_L$ cDNA sequences in their appropriate expression vectors were transfected into mammalian cells using the Fugene 6 Transfection Reagent (Roche, Basel, Switzerland). Briefly, Peak cells were cultured in 6-well plates at a concentration of $6\times10^5$ cells per well in 2 mL culture media containing fetal bovine serum. The expression vectors, encoding the candidate $V_H$ and $V_L$ sequences, were co-transfected into the cells using the Fugene 6 Transfection Reagent according to manufacturer's instructions. One day following transfection, the culture media was aspirated, and 3 mL of fresh serum-free media was added to cells and cultured for three days at 37° C. Following three days culture period, the supernatant was harvested for IgG purified on protein G-Sepharose 4B fast flow columns (Sigma, St. Louis, Mo.) according to manufacturer's instructions. Briefly, supernatants from transfected cells were incubated overnight at 4° C. with ImmunoPure (G) IgG binding buffer (Pierce, Rockford Ill.). Samples were then passed over Protein G-Sepharose 4B fast flow columns and the IgG consequently purified using elution buffer. The eluted IgG fraction was then dialyzed against PBS and the IgG content quantified by absorption at 280 nm. Purity and IgG integrity were verified by SDS-PAGE. Relative binding potency of 1E11 variants was assessed by competitive ELISA. Briefly, 15C1 antibody was coated overnight in a 96-well Maxisorp plate and then blocked with PBS-BSA. The 15C1 reference antibody and affinity matured variants of 1E11 were added to the plate at a fixed concentration and a 3.5-fold serial dilution of the samples was performed. Then, soluble histidine-tagged form of human TLR4/MD2 complex was added to the plate at a fixed concentration. After incubation one hour at 37° C., the plate was washed and a solution of Penta-His-HRP antibody was distributed, this step was followed by an additional incubation time of one hour at 37° C. Finally, the plate was washed and TMB was added for colorimetric revelation, the enzymatic reaction is stopped by $H_2SO_4$ solution. The results were determined according to the absorbance at 450 nm. The relative binding potency was calculated by dividing the reference $EC_{50}$ with affinity matured variants $EC_{50}$ (Table 8).

Figure 9:
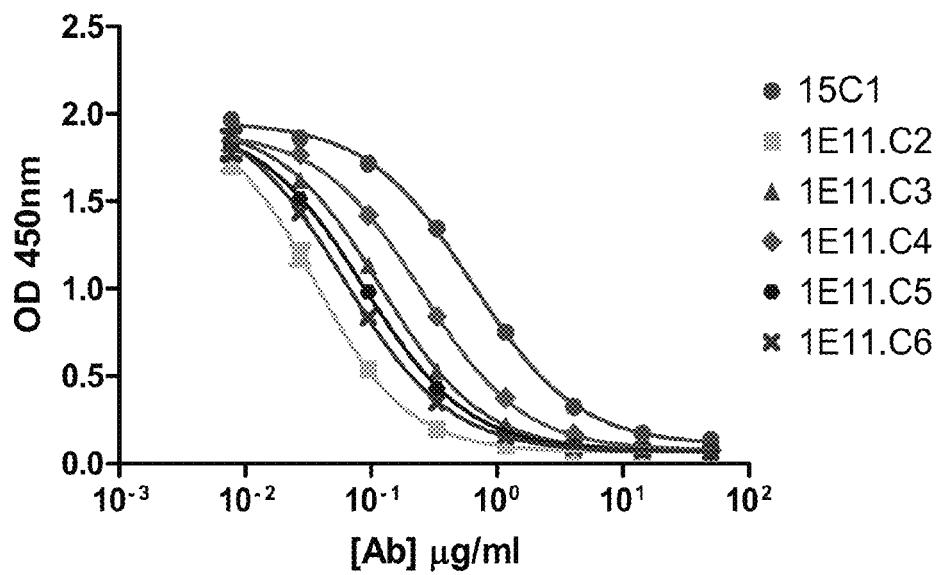
FIG. 9 is a graph depicting the binding potency of purified antibodies with CDRH1 mutations, referred to herein "15C1, 1E11.C2, 1E11.C3, 1E11.C4, 1E11.C5, 1E11.C6", to the human TLR4/MD2 complex. Binding potency is determined by competitive ELISA. The results obtained with parental antibody 15C1 are shown with circle symbols, while the results using 1E11.C2, 1E11.C3, 1E11.C4, 1E11.C5 and 1E11.C6 antibodies are shown in other colored and shaped symbols.
Figure 10:
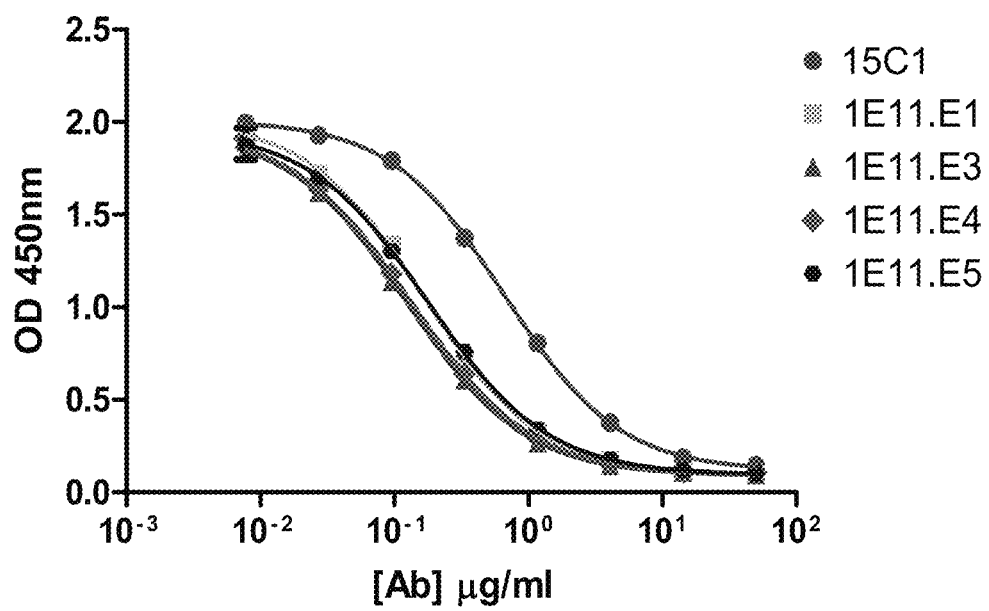
FIG. 10 is a graph depicting the binding potency of purified antibodies with CDRH1 mutations, referred to herein "15C1, 1E11.E1, 1E11.E3, 1E11.E4, 1E11.E5", to the human TLR4/MD2 complex. Binding potency is determined by competitive ELISA. The results obtained with parental antibody 15C1 are shown with circle symbols, while the results using 1E11.E1, 1E11.E3, 1E11.E4 and 1E11.E5 antibodies are shown in other colored and shaped symbols.

All selected Mabs with mutations in their CDRH1 (1E11.C1, 1E11.C2, 1E11.C3, 1E11.C4, 1E11.C5, 1E11.C6) were positive for binding human TLR4 with relative binding potency ranging from 3 to 17 fold-increase compared to the parental antibody 15C1 (FIG. 9 and Table 8). Selected Mabs with mutations in their CDRL3 (1E11.E1, 1E11.E2, 1E11.E3, 1E11.E4 and 1E11.E5) were also positive for binding human TLR4 with relative binding potency ranging from 2 to 5 fold-increase compared to the parental antibody 15C1 (FIG. 10 and Table 8).

To test for an additive binding effect by combining heavy and light chain variants, the 1E11.C2 variant with modified CDRH1, which had the highest binding potency, was chosen. The heavy chain of this variant was associated with the light chain of the 1E11.E1, 1E11.E3, 1E11.E4 and 1E11.E5 which were modified in the CDRL3. The 1E11.C2 VH region was cloned with the VL of 1E11.E1, 1E11.E3, 1E11.E4 and 1E11.E5 into mammalian expression vectors as described above. After expression and purification, the new 1E11 variants called 1E11.C2E1, 1E11.C2E3, 1E11.C2E4 and 1E11.C2E5 were tested by competitive ELISA to determine their binding potency.

Figure 11:
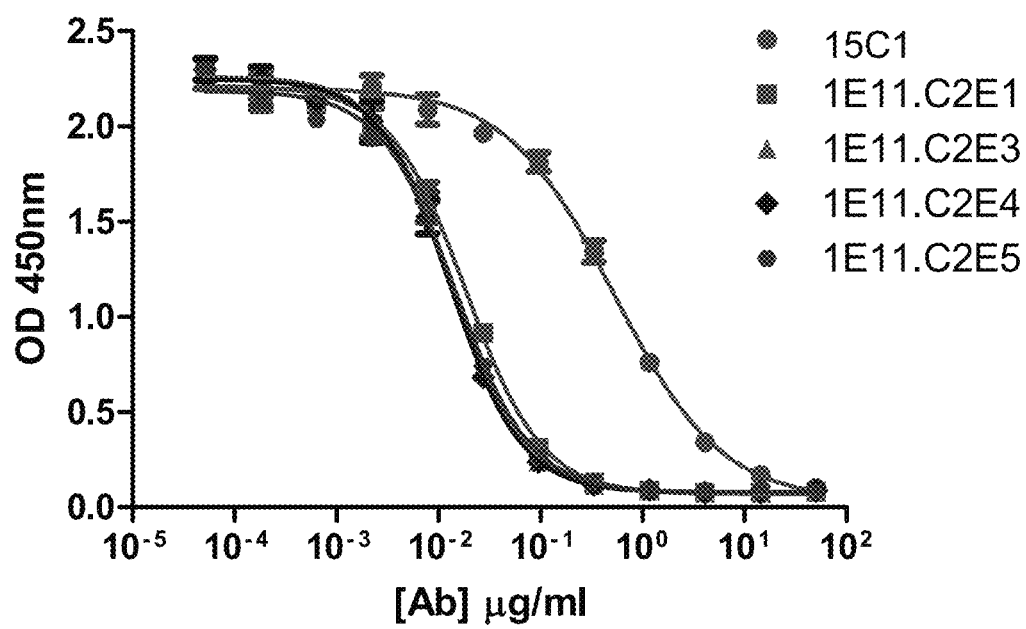
FIG. 11 is a graph depicting the binding potency of purified antibodies with CDRH1 mutations, referred to herein "15C1, 1E11.C2E1, 1E11.C2E3, 1E11.C2E4, 1E11.C2E5", to the human TLR4/MD2 complex. Binding potency is determined by competitive ELISA. The results obtained with parental antibody 15C1 are shown with circle symbols, while the results using 1E11.C2E1, 1E11.C2E3, 1E11.C2E4 and 1E11.C2E5 antibodies are shown in other colored and shaped symbols.
Figure 12:
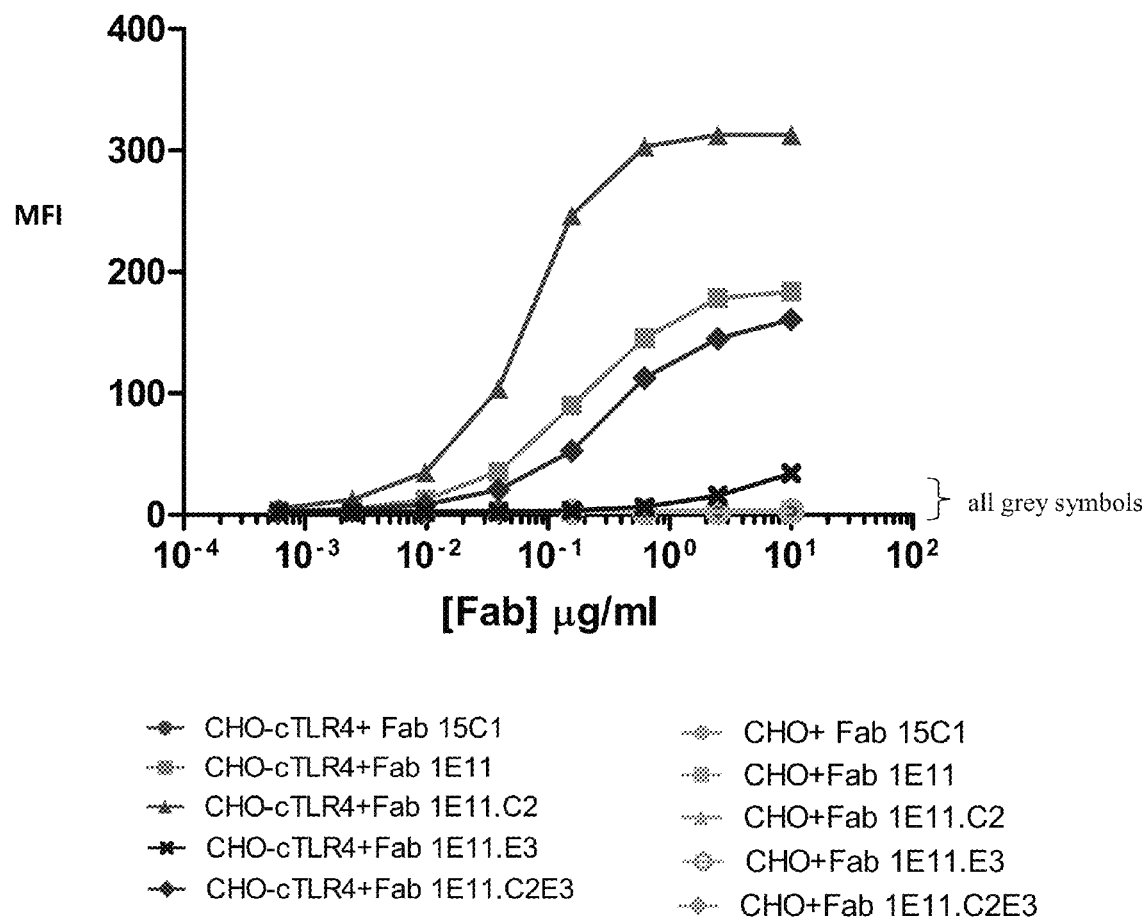
FIG. 12 is a graph depicting the binding by purified Fab, referred to herein as "Fab 15C1, Fab 1E11, Fab 1E11.C2, Fab 1E11.E3 and Fab 1E11.C2E3", to the cynomolgus monkey TLR4/MD2 complex. Specificity of binding is shown by flow cytometry CHO cells mock transfected or transfected with the cynomolgus monkey TLR4/MD2. The results using mock-transfected cells are shown with grey symbols (key on right), while the results using the cynomolgus monkey TLR4/MD2 transfected cells are shown in other colored symbols (key on left).

All selected Mabs (1E11.C2E1, 1E11.C2E3, 1E11.C2E4 and 1E11.C2E5) were positive for binding human TLR4 with binding potency ranging from 29 to 40 fold increase compared to the parental antibody 15C1 (FIG. 11 and Table 8).

TABLE 8

$EC_{50}$ values of antibodies binding to human TLR4 determined by ELISA and relative binding potency increase of 1E11 affinity matured variants

| 15C1 Reference $EC_{50}$ ug/mL | | | 0.63 | | | |
|---|---|---|---|---|---|---|
| 1E11 variants (CDRH1) | 1E11.C1 | 1E11.C2 | 1E11.C3 | 1E11.C4 | 1E11.C5 | 1E11.C6 |
| $EC_{50}$ ug/mL | 0.052 | 0.036 | 0.119 | 0.251 | 0.087 | 0.061 |
| Relative binding potency increase | 12 | 17 | 5 | 2.5 | 7 | 10 |
| 1E11 variants (CDRL3) | 1E11.E1 | 1E11.E2 | 1E11.E3 | 1E11.E4 | 1E11.E5 | |
| $EC_{50}$ ug/mL | 0.157 | 0.315 | 0.126 | 0.130 | 0.152 | |
| Relative binding potency increase | 4 | 2 | 5 | 5 | 4 | |
| 1E11 variants (CDRH1/CDRL3) | 1E11.C2E1 | 1E11.C2E3 | 1E11.C2E4 | 1E11.C2E5 | | |
| $EC_{50}$ ug/mL | 0.021 | 0.016 | 0.015 | 0.017 | | |
| Relative binding potency increase | 29 | 39 | 40 | 36 | | |

Binding tests were also conducted with cynomolgus monkey TLR4. Interestingly, mutations in the CDRH1 (C1, C2, C3, C4, C5 and C6) increase binding of 1E11 modified antibody to cynomolgus monkey TLR4, but mutations in CDRL3 (E1, E2, E3, E4 and E5) decrease or almost abolish antibody binding to this molecule (Table 9 and FIG. 12).

TABLE 9

Cross-reactivity of affinity matured anti-TLR4 antibodies.

| Clone ID | Heavy CDR1 | Heavy CDR3 | Light CDR3 | Species binding potential |
|---|---|---|---|---|
| 1E11 | GYSITGGYS (SEQ ID NO: 25) | ARKDSGNYFPY (SEQ ID NO: 27) | QQGHSFPLT (SEQ ID NO: 39) | Human: + Cynomolgus monkey: + |
| 1E11.C1 | GFPIRYGYS (SEQ ID NO: 55) | ARKDSGNYFPY (SEQ ID NO: 27) | QQGHSFPLT (SEQ ID NO: 39) | Human: ++ Cynomolgus monkey: ++ |
| 1E11.C2 | GYPIRFGYS (SEQ ID NO: 56) | ARKDSGNYFPY (SEQ ID NO: 27) | QQGHSFPLT (SEQ ID NO: 39) | |
| 1E11.C3 | GYPIRHGYS (SEQ ID NO: 57) | ARKDSGNYFPY (SEQ ID NO: 27) | QQGHSFPLT (SEQ ID NO: 39) | |
| 1E11.C4 | GFPIGQGYS (SEQ ID NO: 58) | ARKDSGNYFPY (SEQ ID NO: 27) | QQGHSFPLT (SEQ ID NO: 39) | |
| 1E11.C5 | GYPIWGGYS (SEQ ID NO: 59) | ARKDSGNYFPY (SEQ ID NO: 27) | QQGHSFPLT (SEQ ID NO: 39) | |
| 1E11.C6 | GYPIGGGYS (SEQ ID NO: 60) | ARKDSGNYFPY (SEQ ID NO: 27) | QQGHSFPLT (SEQ ID NO: 39) | |
| 1E11.E1 | GYSITGGYS (SEQ ID NO: 25) | ARKDSGNYFPY (SEQ ID NO: 27) | QQGNDFPVT (SEQ ID NO: 61) | Human: + Cynomolgus monkey: +/- |
| 1E11.E2 | GYSITGGYS (SEQ ID NO: 25) | ARKDSGNYFPY (SEQ ID NO: 27) | QQGYDEPFT (SEQ ID NO: 62) | |
| 1E11.E3 | GYSITGGYS (SEQ ID NO: 25) | ARKDSGNYFPY (SEQ ID NO: 27) | QQGYDFPLT (SEQ ID NO: 63) | |
| 1E11.E4 | GYSITGGYS (SEQ ID NO: 25) | ARKDSGNYFPY (SEQ ID NO: 27) | QQGYDYPLT (SEQ ID NO: 64) | |
| 1E11.E5 | GYSITGGYS (SEQ ID NO: 25) | ARKDSGNYFPY (SEQ ID NO: 27) | QQGYEFPLT (SEQ ID NO: 65) | |

TABLE 9-continued

Cross-reactivity of affinity matured anti-TLR4 antibodies.

| Clone ID | Heavy CDR1 | Heavy CDR3 | Light CDR3 | Species binding potential |
|---|---|---|---|---|
| 1E11.C2E1 | GYPIRFGYS (SEQ ID NO: 56) | ARKDSGNYFPY (SEQ ID NO: 27) | QQGNDFPVT (SEQ ID NO: 61) | Human: +++ Cynomolgus monkey: + |
| 1E11.C2E3 | GYPIRFGYS (SEQ ID NO: 56) | ARKDSGNYFPY (SEQ ID NO: 27) | QQGYDFPLT (SEQ ID NO: 63) | |
| 1E11.C2E4 | GYPIRFGYS (SEQ ID NO: 56) | ARKDSGNYFPY (SEQ ID NO: 27) | QQGYDYPLT (SEQ ID NO: 64) | |
| 1E11.C2E5 | GYPIRFGYS (SEQ ID NO: 56) | ARKDSGNYFPY (SEQ ID NO: 27) | QQGYEFPLT (SEQ ID NO: 65) | |
| Consensus | G(F/Y)PI(R/G/W)(Y/F/G)GYS (SEQ ID NO: 110) | ARKDSG(N/Q/D/E)(hydrophobic)(hydrophobic)PY (SEQ ID NO: 111) | QQG(Y/N)(D/E)(F/Y)P(hydrophobic)T (SEQ ID NO: 112) | |

It is therefore possible to predict antibody binding specificity depending on its CDR compositions and based on the relative binding potency and TLR4 cross-reactivity.

Effectively, antibodies having the heavy chain CDRs composed of CDR1 sequence GYSITGGYS (SEQ ID NO: 25) or a CDR1 with the consensus sequence G(F/Y)PI(R/G/W)(Y/F/G)GYS (SEQ ID NO: 110); CDR2 sequence IHYSGYT (SEQ ID NO: 26); CDR3 with the consensus sequence ARKDSG(N/Q/D/E)($X_1$)($X_2$)PY (SEQ ID NO: 111) where $X_1$ and $X_2$ are each independently any hydrophobic amino acid, and the light chain CDRs composed of CDR1 sequence QSISDH (SEQ ID NO: 37); CDR2 sequence YAS (SEQ ID NO: 38); and CDR3 sequence QQGHSFPLT (SEQ ID NO: 39), are human/cynomolgus monkey TLR4 cross-reactive.

Antibodies having the heavy chain CDRs composed of CDR1 with the consensus sequence G(F/Y)PI(R/G/W)(Y/F/G)GYS (SEQ ID NO: 110), CDR2 sequence IHYSGYT (SEQ ID NO: 26), CDR3 with the consensus sequence ARKDSG(N/Q/D/E)($X_1$)($X_2$)PY (SEQ ID NO: 111) where $X_1$ and $X_2$ are each independently any hydrophobic amino acid, and the light chain CDRs composed of CDR1 sequence QSISDH (SEQ ID NO: 37); CDR2 sequence YAS (SEQ ID NO: 38); CDR3 sequence QQGHSFPLT (SEQ ID NO: 39) or CDR3 with the consensus sequence QQG(Y/N)(D/E)(F/Y)PXT (SEQ ID NO: 112, where X is any hydrophobic amino acid), are human/cynomolgus monkey TLR4 cross-reactive with increased binding potency to human TLR4 compared to the 15C1 parental antibody.

Example 9

Inhibition of LPS-Activation of TLR4

Figure 13:
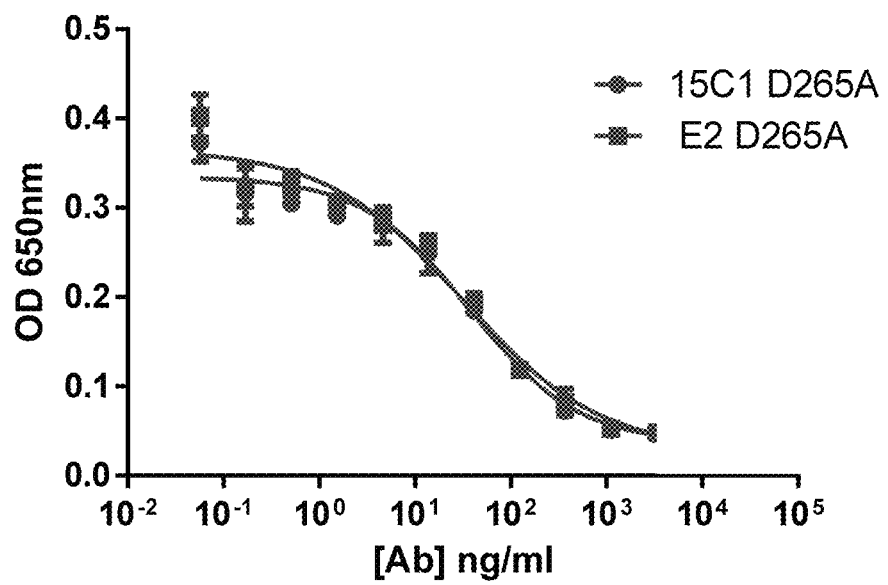
FIG. 13 is a graph depicting the inhibition of LPS-induced downstream signaling cascade of TLR4, NF-κB, by purified antibodies, referred to herein "15C1, 1E11.E2". THP1-blue-CD14 cell line is derived from human monocytic cell line expressing the human TLR4/MD2 complex and stably transfected with a reporter gene which facilitates the monitoring of TLR-induced NF-κB/AP-1 activation. Cells were incubated with 15C1 and 1E11.E2 at the indicated concentrations and subsequently incubated with LPS (10 ng/mL). Levels of secreted embryonic alkaline phosphatase were assessed 24 hours post LPS-treatment by measuring the absorbance at 650 nm using a microplate reader.

LPS-induced activation of TLR4 results in the activation of the NFκB signaling pathway. To test the inhibition of this signaling pathway, THP1-Blue™-CD14 cells (Invivogen), which express human TLR4/MD2 complex were used and stably transfected with a reporter gene with NFκB responsive elements. TLR4 antibodies were tested in this assay as described earlier. FIG. 13 shows the results of the inhibition of LPS-induced downstream signaling cascade of TLR4 by selected Mabs (15C1 and 1E11.E2). Interestingly, despite a 2 fold increase in binding potency of 1E11.E2 compared to the parental 15C1, this antibody did not show increased inhibition potency of LPS induced TLR4 signaling compared to 15C1.

In vivo, TLR4 activation by LPS results in the production of IL-6 by macrophages. To test 1E11, 1E11.C2 and 1E11.C2E3 potency ex vivo, these antibodies were produced as described previously and tested in human and cynomolgus monkey whole blood assay. This experiment consists to measure the inhibition of IL-6 production when LPS-activation of TLR4 is blocked.

Briefly, blood was diluted in an equal amount of RPMI 1640 and spread in U-bottom 96-well plates. Dilutions of antibodies (9 concentrations between 20 μg/mL and 305 pg/mL, final concentrations) were prepared in RPMI 1640 and added in triplicate to blood. One hour later, LPS (0.25 ng/mL final concentration in RPMI 0.1% FCS) was added to wells and incubated 24 h at 37° C. and 5% of $CO_2$. After incubation, supernatants were harvested carefully and frozen for further analysis. IL-6 levels were measured in supernatants according to the instruction of the Milliplex kit for use with the Luminex 200 reader. Raw data were obtained and analyzed by the Milliplex Analyst software.

Figure 14:
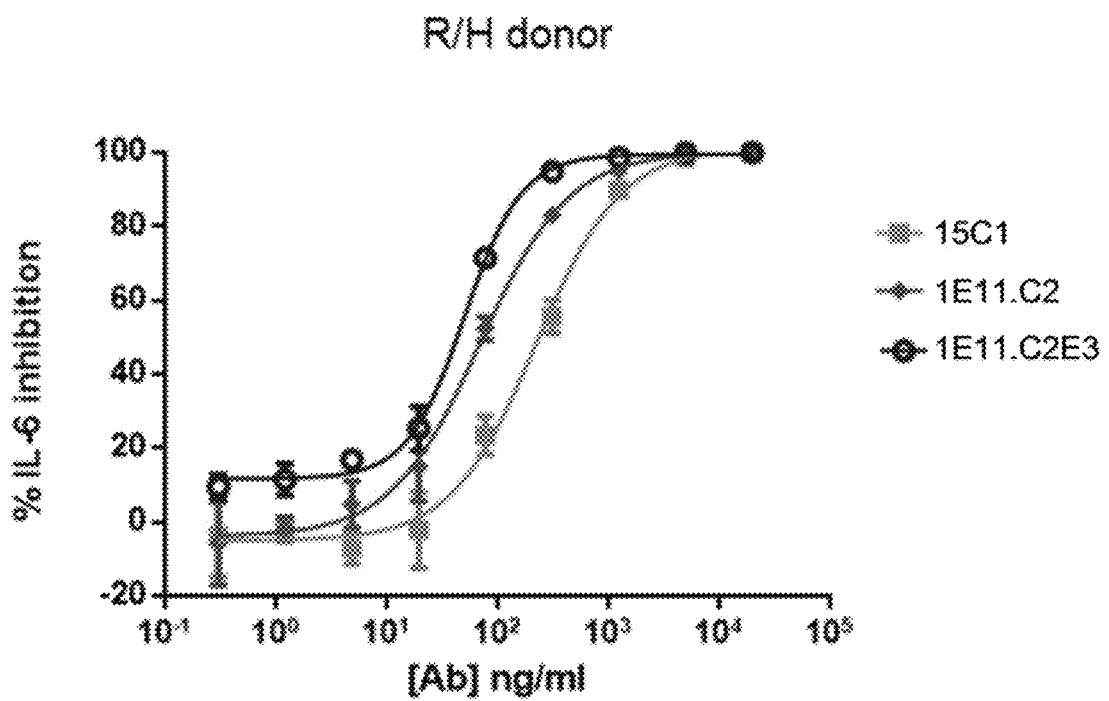
FIG. 14 is a graph depicting the inhibition of IL-6 production induced by TLR4 activation in human whole blood assay by purified antibodies, referred to herein "15C1, 1E11C2, 1E11.C2E3". Human blood was diluted with decreased concentration of antibodies and subsequently incubated with LPS. Levels of IL-6 were assessed 24 hours post LPS-treatment using Milliplex kit. The results are represented as percentage of IL-6 inhibition. The data obtained with parental antibody 15C1 are shown with orange symbols, while the results using 1E11.C2 and 1E11.C2E3 antibodies are shown in other colored symbols.

In human whole blood assay, the $IC_{50}$ of 1E11.C2 and 1E11.C2E3 were of 70 ng/mL and 50 ng/mL, respectively. In comparison to 15C1, the parental antibody which has an $IC_{50}$ of approximately 220 ng/mL, these antibodies are 3-fold and 5-fold better, respectively, at blocking human TLR4 (FIG. 14). Interestingly for 1E11.C2, a 17 fold increase in binding potency translated in a 3-fold increase in blocking potency while, for 1E11.C2E3, a 40-fold increase in binding potency correlated with a 5-fold increase in blocking potency.

In cynomolgus monkey whole blood assay conducted with 2 animal samples, the 1E11.C2 antibody blocked TLR4-activation by LPS with an $IC_{50}$ of approximately 500 ng/mL (FIG. 15).

Other Embodiments

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. An isolated antibody that specifically binds Toll-like receptor 4 (TLR4), wherein the antibody comprises a heavy chain with three complementarity determining regions (CDRs) comprising a variable heavy chain complementarity determining region 1 (CDRH1) amino acid sequence of GYSITGGYS (SEQ ID NO: 25); a variable heavy chain complementarity determining region 2 (CDRH2) amino acid sequence of IHYSGYT (SEQ ID NO: 26); and a variable heavy chain complementarity determining region 3 (CDRH3) amino acid sequence of ARKDSG($X_1$)($X_2$)($X_3$)PY (SEQ ID NO: 111), where $X_1$ is N, Q, D or E, $X_2$ is any hydrophobic amino acid, and $X_3$ is any hydrophobic amino acid; and a light chain with three CDRs comprising a variable light chain complementarity determining region 1 (CDRL1) amino acid sequence of QSISDH (SEQ ID NO: 37); a variable light chain complementarity determining region 2 (CDRL2) amino acid sequence of YAS (SEQ ID NO: 38); and a variable light chain complementarity determining region 3 (CDRL3) amino acid sequence of QQGHSFPLT (SEQ ID NO: 39).

2. The isolated antibody of claim 1, wherein the antibody further comprises an amino acid substitution in the gamma heavy chain constant region at EU amino acid position 325 and an amino acid substitution at EU amino acid position 328, wherein the amino acid substituted at EU amino acid position 325 is serine, and wherein the amino acid substituted at EU amino acid position 328 is phenylalanine.

3. An isolated antibody that specifically binds Toll-like receptor 4 (TLR4), wherein the antibody comprises a heavy chain with three complementarity determining regions (CDRs) comprising a variable heavy chain complementarity determining region 1 (CDRH1) amino acid sequence of G($X_1$)PI($X_2$)($X_3$)GYS (SEQ ID NO: 110), where $X_1$ is F or Y, $X_2$ is R, G or W, $X_3$ is Y, F or G; a variable heavy chain complementarity determining region 2 (CDRH2) amino acid sequence of IHYSGYT (SEQ ID NO: 26); and a variable heavy chain complementarity determining region 3 (CDRH3) amino acid sequence of ARKDSG($X_1$)($X_2$)($X_3$)PY (SEQ ID NO: 111), where $X_1$ is N, Q, D or E, $X_2$ is any hydrophobic amino acid, and $X_3$ is any hydrophobic amino acid; and a light chain with three CDRs comprising a variable light chain complementarity determining region 1 (CDRL1) amino acid sequence of QSISDH (SEQ ID NO: 37); a variable light chain complementarity determining region 2 (CDRL2) amino acid sequence of YAS (SEQ ID NO: 38); and a variable light chain complementarity determining region 3 (CDRL3) comprising the amino acid sequence of QQG($X_1$)($X_2$)($X_3$)P($X_4$)T (SEQ ID NO: 112), where $X_1$ is Y or N, $X_2$ is D or E, $X_3$ is F or Y, and $X_4$ is any hydrophobic amino acid, or the amino acid sequence of QQGHSFPLT (SEQ ID NO: 39).

4. The isolated antibody of claim 3, wherein the antibody further comprises an amino acid substitution in the gamma heavy chain constant region at EU amino acid position 325 and an amino acid substitution at EU amino acid position 328, wherein the amino acid substituted at EU amino acid position 325 is serine, and wherein the amino acid substituted at EU amino acid position 328 is phenylalanine.

5. An isolated antibody that specifically binds Toll-like receptor 4 (TLR4), wherein the antibody comprises a heavy chain with three complementarity determining regions (CDRs) comprising a variable heavy chain complementarity determining region 1 (CDRH1) amino acid sequence of G($X_1$)PI($X_2$)($X_3$)GYS (SEQ ID NO: 110), where $X_1$ is F or Y, $X_2$ is R, G or W, $X_3$ is Y, F or G; a variable heavy chain complementarity determining region 2 (CDRH2) amino acid sequence of IHYSGYT (SEQ ID NO: 26); and a variable heavy chain complementarity determining region 3 (CDRH3) amino acid sequence of ARKDSG($X_1$)($X_2$)($X_3$)PY (SEQ ID NO: 111), where $X_1$ is N, Q, D or E, $X_2$ is any hydrophobic amino acid, and $X_3$ is any hydrophobic amino acid; and a light chain with three CDRs comprising a variable light chain complementarity determining region 1 (CDRL1) amino acid sequence of QSISDH (SEQ ID NO: 37); a variable light chain complementarity determining region 2 (CDRL2) amino acid sequence of YAS (SEQ ID NO: 38); and a variable light chain complementarity determining region 3 (CDRL3) comprising the amino acid sequence of QQG($X_1$)($X_2$)($X_3$)P($X_4$)T (SEQ ID NO: 112), where $X_1$ is Y or N, $X_2$ is D or E, X3 is F or Y, and $X_4$ is any hydrophobic amino acid, or the amino acid sequence of QQGHSFPLT (SEQ ID NO: 39).

6. The isolated antibody of claim 5, wherein the antibody further comprises an amino acid substitution in the gamma heavy chain constant region at EU amino acid position 325 and an amino acid substitution at EU amino acid position 328, wherein the amino acid substituted at EU amino acid position 325 is serine, and wherein the amino acid substituted at EU amino acid position 328 is phenylalanine.

7. An isolated antibody that specifically binds to Toll-like receptor 4 (TLR4), wherein the antibody comprises a heavy chain with three complementarity determining regions (CDRs) comprising a variable heavy chain complementarity determining region 1 (CDRH1) amino acid sequence of G($X_1$)PI($X_2$)($X_3$)GYS (SEQ ID NO: 110), where $X_1$ is F or Y, $X_2$ is R, G or W, $X_3$ is Y, F or G; a variable heavy chain complementarity determining region 2 (CDRH2) amino acid sequence of IHYSGYT (SEQ ID NO: 26); and a variable heavy chain complementarity determining region 3 (CDRH3) amino acid sequence of ARKDSG($X_1$)($X_2$)($X_3$)PY (SEQ ID NO: 111), where $X_1$ is N, Q, D or E, $X_2$ is any hydrophobic amino acid, and $X_3$ is any hydrophobic amino acid; and a light chain with three CDRs comprising a variable light chain complementarity determining region 1 (CDRL1) amino acid sequence of QSISDH (SEQ ID NO: 37); a variable light chain complementarity determining region 2 (CDRL2) amino acid sequence of YAS (SEQ ID NO: 38); and a variable light chain complementarity determining region 3 (CDRL3) amino acid sequence of QQG ($X_1$)($X_2$)($X_3$)P($X_4$)T (SEQ ID NO: 112), where $X_1$ is Y or N, $X_2$ is D or E, $X_3$ is F or Y, and $X_4$ is any hydrophobic amino acid.

8. The isolated antibody of claim 7, wherein the antibody comprises a CDRH1 amino acid sequence of GYSITGGYS (SEQ ID NO: 25); GFPIRYGYS (SEQ ID NO: 55), GYPIRFGYS (SEQ ID NO: 56), GYPIRHGYS (SEQ ID NO: 57), GFPIGQGYS (SEQ ID NO: 58), GYPIWGGYS (SEQ ID NO: 59) or GYPIGGGYS (SEQ ID NO: 60); a CDRH2 amino acid sequence of IHYSGYT (SEQ ID NO: 26); and a CDRH3 amino acid sequence selected from the group consisting of ARKDSGNYFPY (SEQ ID NO: 27); ARKDSGQLFPY (SEQ ID NO: 33); and ARKDSGDYFPY (SEQ ID NO: 35); a CDRL1 amino acid sequence of QSISDH (SEQ ID NO: 37); a CDRL2 amino acid sequence of YAS (SEQ ID NO: 38); and a CDRL3 amino acid sequence of QQGHSFPLT (SEQ ID NO: 39), QQGNDFPVT (SEQ ID NO: 61), QQGYDEPFT (SEQ ID NO: 62), QQGYDFPLT (SEQ ID NO: 63), QQGYDYPLT (SEQ ID NO: 64) or QQGYEFPLT (SEQ ID NO: 65).

9. The isolated antibody of claim 8, wherein the antibody further comprises an amino acid substitution in the gamma heavy chain constant region at EU amino acid position 325 and an amino acid substitution at EU amino acid position 328, wherein the amino acid substituted at EU amino acid position 325 is serine, and wherein the amino acid substituted at EU amino acid position 328 is phenylalanine.

10. The isolated antibody of claim 7, wherein the antibody comprises a heavy chain variable amino acid sequence selected from the group consisting of SEQ ID NOs: 2, 6, 8, 10, 12, 14, 16, 18, 20, 22, 67, 69, 71, 73, 75 or 77 and comprises a light chain variable amino acid comprising the amino acid sequence of SEQ ID NO: 4, 79, 81, 83, 85 or 87.

11. The isolated antibody of claim 7, wherein the antibody comprises a combination of a variable heavy chain amino acid sequence and a variable light chain amino acid sequence selected from the group consisting of:
  (a) a heavy chain variable region comprising the amino acid sequence of SEQ ID NO: 6 and a light chain variable region comprising the amino acid sequence of SEQ ID NO: 4;
  (b) a heavy chain variable region comprising the amino acid sequence of SEQ ID NO: 8 and a light chain variable region comprising the amino acid sequence of SEQ ID NO: 4;
  (c) a heavy chain variable region comprising the amino acid sequence of SEQ ID NO: 10 and a light chain variable region comprising the amino acid sequence of SEQ ID NO: 4;
  (d) a heavy chain variable region comprising the amino acid sequence of SEQ ID NO: 12 and a light chain variable region comprising the amino acid sequence of SEQ ID NO: 4;
  (e) a heavy chain variable region comprising the amino acid sequence of SEQ ID NO: 14 and a light chain variable region comprising the amino acid sequence of SEQ ID NO: 4;
  (f) a heavy chain variable region comprising the amino acid sequence of SEQ ID NO: 16 and a light chain variable region comprising the amino acid sequence of SEQ ID NO: 4;
  (g) a heavy chain variable region comprising the amino acid sequence of SEQ ID NO: 18 and a light chain variable region comprising the amino acid sequence of SEQ ID NO: 4;
  (h) a heavy chain variable region comprising the amino acid sequence of SEQ ID NO: 2 and a light chain variable region comprising the amino acid sequence of SEQ ID NO: 4;
  (i) a heavy chain variable region comprising the amino acid sequence of SEQ ID NO: 20 and a light chain variable region comprising the amino acid sequence of SEQ ID NO: 4;
  (j) a heavy chain variable region comprising the amino acid sequence of SEQ ID NO: 22 and a light chain variable region comprising the amino acid sequence of SEQ ID NO: 4;
  (k) a heavy chain variable region comprising the amino acid sequence of SEQ ID NO: 67 and a light chain variable region comprising the amino acid sequence of SEQ ID NO: 4;
  (l) a heavy chain variable region comprising the amino acid sequence of SEQ ID NO: 69 and a light chain variable region comprising the amino acid sequence of SEQ ID NO: 4;
  (m) a heavy chain variable region comprising the amino acid sequence of SEQ ID NO: 71 and a light chain variable region comprising the amino acid sequence of SEQ ID NO: 4;
  (n) a heavy chain variable region comprising the amino acid sequence of SEQ ID NO: 73 and a light chain variable region comprising the amino acid sequence of SEQ ID NO: 4;
  (o) a heavy chain variable region comprising the amino acid sequence of SEQ ID NO: 75 and a light chain variable region comprising the amino acid sequence of SEQ ID NO: 4;

(p) a heavy chain variable region comprising the amino acid sequence of SEQ ID NO: 77 and a light chain variable region comprising the amino acid sequence of SEQ ID NO: 4;

(q) a heavy chain variable region comprising the amino acid sequence of SEQ ID NO: 2 and a light chain variable region comprising the amino acid sequence of SEQ ID NO: 79;

(r) a heavy chain variable region comprising the amino acid sequence of SEQ ID NO: 2 and a light chain variable region comprising the amino acid sequence of SEQ ID NO: 81;

(s) a heavy chain variable region comprising the amino acid sequence of SEQ ID NO: 2 and a light chain variable region comprising the amino acid sequence of SEQ ID NO: 83;

(t) a heavy chain variable region comprising the amino acid sequence of SEQ ID NO: 2 and a light chain variable region comprising the amino acid sequence of SEQ ID NO: 85;

(u) a heavy chain variable region comprising the amino acid sequence of SEQ ID NO: 2 and a light chain variable region comprising the amino acid sequence of SEQ ID NO: 87

(v) a heavy chain variable region comprising the amino acid sequence of SEQ ID NO: 69 and a light chain variable region comprising the amino acid sequence of SEQ ID NO: 79;

(w) a heavy chain variable region comprising the amino acid sequence of SEQ ID NO: 69 and a light chain variable region comprising the amino acid sequence of SEQ ID NO: 83;

(x) a heavy chain variable region comprising the amino acid sequence of SEQ ID NO: 69 and a light chain variable region comprising the amino acid sequence of SEQ ID NO: 85; and (y) a heavy chain variable region comprising the amino acid sequence of SEQ ID NO: 69 and a light chain variable region comprising the amino acid sequence of SEQ ID NO: 87.

12. The isolated antibody of claim 11, wherein the antibody further comprises an amino acid substitution in the gamma heavy chain constant region at EU amino acid position 325 and an amino acid substitution at EU amino acid position 328, wherein the amino acid substituted at EU amino acid position 325 is serine, and wherein the amino acid substituted at EU amino acid position 328 is phenylalanine.

13. The isolated antibody of claim 7, wherein the antibody comprises a combination of CDRH1, CDRH2, CDRH3, CDRL1, CDRL2, and CDRL3 sequences selected from the group consisting of:

(a) a CDRH1 amino acid sequence of GYSITGGYS (SEQ ID NO: 25); a CDRH2 amino acid sequence of IHYSGYT (SEQ ID NO: 26); a CDRH3 amino acid sequence of ARKDSGNYFPY (SEQ ID NO: 27); a CDRL1 amino acid sequence of QSISDH (SEQ ID NO: 37); a CDRL2 amino acid sequence of YAS (SEQ ID NO: 38); and a CDRL3 amino acid sequence of QQGHSFPLT (SEQ ID NO: 39);

(b) a CDRH1 amino acid sequence of GYSITGGYS (SEQ ID NO: 25); a CDRH2 amino acid sequence of IHYSGYT (SEQ ID NO: 26); a CDRH3 amino acid sequence of ARKDSGRLLPY (SEQ ID NO: 28); a CDRL1 amino acid sequence of QSISDH (SEQ ID NO: 37); a CDRL2 amino acid sequence of YAS (SEQ ID NO: 38); and a CDRL3 amino acid sequence of QQGHSFPLT (SEQ ID NO: 39);

(b) a CDRH1 amino acid sequence of GYSITGGYS (SEQ ID NO: 25); a CDRH2 amino acid sequence of IHYSGYT (SEQ ID NO: 26); a CDRH3 amino acid sequence of ARKDSGKWLPY (SEQ ID NO: 29); a CDRL1 amino acid sequence of QSISDH (SEQ ID NO: 37); a CDRL2 amino acid sequence of YAS (SEQ ID NO: 38); and a CDRL3 amino acid sequence of QQGHSFPLT (SEQ ID NO: 39);

(c) a CDRH1 amino acid sequence of GYSITGGYS (SEQ ID NO: 25); a CDRH2 amino acid sequence of IHYSGYT (SEQ ID NO: 26); a CDRH3 amino acid sequence of ARKDSGHLMPY (SEQ ID NO: 30); a CDRL1 amino acid sequence of QSISDH (SEQ ID NO: 37); a CDRL2 amino acid sequence of YAS (SEQ ID NO: 38); and a CDRL3 amino acid sequence of QQGHSFPLT (SEQ ID NO: 39);

(d) a CDRH1 amino acid sequence of GYSITGGYS (SEQ ID NO: 25); a CDRH2 amino acid sequence of IHYSGYT (SEQ ID NO: 26); a CDRH3 amino acid sequence of ARKDSGHNYPY (SEQ ID NO: 31); a CDRL1 amino acid sequence of QSISDH (SEQ ID NO: 37); a CDRL2 amino acid sequence of YAS (SEQ ID NO: 38); and a CDRL3 amino acid sequence of QQGHSFPLT (SEQ ID NO: 39);

(e) a CDRH1 amino acid sequence of GYSITGGYS (SEQ ID NO: 25); a CDRH2 amino acid sequence of IHYSGYT (SEQ ID NO: 26); a CDRH3 amino acid sequence of ARKDSGKNFPY (SEQ ID NO: 32); a CDRL1 amino acid sequence of QSISDH (SEQ ID NO: 37); a CDRL2 amino acid sequence of YAS (SEQ ID NO: 38); and a CDRL3 amino acid sequence of QQGHSFPLT (SEQ ID NO: 39);

(f) a CDRH1 amino acid sequence of GYSITGGYS (SEQ ID NO: 25); a CDRH2 amino acid sequence of IHYSGYT (SEQ ID NO: 26); a CDRH3 amino acid sequence of ARKDSGQLFPY (SEQ ID NO: 33); a CDRL1 amino acid sequence of QSISDH (SEQ ID NO: 37); a CDRL2 amino acid sequence of YAS (SEQ ID NO: 38); and a CDRL3 amino acid sequence of QQGHSFPLT (SEQ ID NO: 39);

(g) a CDRH1 amino acid sequence of GYSITGGYS (SEQ ID NO: 25); a CDRH2 amino acid sequence of IHYSGYT (SEQ ID NO: 26); a CDRH3 amino acid sequence of ARKDSGHNLPY (SEQ ID NO: 34); a CDRL1 amino acid sequence of QSISDH (SEQ ID NO: 37); a CDRL2 amino acid sequence of YAS (SEQ ID NO: 38); and a CDRL3 amino acid sequence of QQGHSFPLT (SEQ ID NO: 39);

(h) a CDRH1 amino acid sequence of GYSITGGYS (SEQ ID NO: 25); a CDRH2 amino acid sequence of IHYSGYT (SEQ ID NO: 26); a CDRH3 amino acid sequence of ARKDSGKYFPY (SEQ ID NO: 35); a CDRL1 amino acid sequence of QSISDH (SEQ ID NO: 37); a CDRL2 amino acid sequence of YAS (SEQ ID NO: 38); and a CDRL3 amino acid sequence of QQGHSFPLT (SEQ ID NO: 39);

(i) a CDRH1 amino acid sequence of GYSITGGYS (SEQ ID NO: 25); a CDRH2 amino acid sequence of IHYSGYT (SEQ ID NO: 26); a CDRH3 amino acid sequence of ARKDSGRYWPY (SEQ ID NO: 36); a CDRL1 amino acid sequence of QSISDH (SEQ ID NO: 37); a CDRL2 amino acid sequence of YAS (SEQ ID NO: 38); and a CDRL3 amino acid sequence of QQGHSFPLT (SEQ ID NO: 39);

(j) a CDRH1 amino acid sequence of GFPIRYGYS (SEQ ID NO: 55); a CDRH2 amino acid sequence of IHYSGYT (SEQ ID NO: 26); a CDRH3 amino acid sequence of ARKDSGNYFPY (SEQ ID NO: 27); a CDRL1 amino acid sequence of QSISDH (SEQ ID NO: 37); a CDRL2 amino acid sequence of YAS (SEQ ID NO: 38); and a CDRL3 amino acid sequence of QQGHSFPLT (SEQ ID NO: 39);

(l) a CDRH1 amino acid sequence of GYPIRFGYS (SEQ ID NO: 56); a CDRH2 amino acid sequence of IHYSGYT (SEQ ID NO: 26); a CDRH3 amino acid sequence of ARKDSGNYFPY (SEQ ID NO: 27); a CDRL1 amino acid sequence of QSISDH (SEQ ID NO: 37); a CDRL2 amino acid sequence of YAS (SEQ ID NO: 38); and a CDRL3 amino acid sequence of QQGHSFPLT (SEQ ID NO: 39);

(m) a CDRH1 amino acid sequence of GYPIRHGYS (SEQ ID NO: 57); a CDRH2 amino acid sequence of IHYSGYT (SEQ ID NO: 26); a CDRH3 amino acid sequence of ARKDSGNYFPY (SEQ ID NO: 27); a CDRL1 amino acid sequence of QSISDH (SEQ ID NO: 37); a CDRL2 amino acid sequence of YAS (SEQ ID NO: 38); and a CDRL3 amino acid sequence of QQGHSFPLT (SEQ ID NO: 39);

(n) a CDRH1 amino acid sequence of GFPIGQGYS (SEQ ID NO: 58); a CDRH2 amino acid sequence of IHYSGYT (SEQ ID NO: 26); a CDRH3 amino acid sequence of ARKDSGNYFPY (SEQ ID NO: 27); a CDRL1 amino acid sequence of QSISDH (SEQ ID NO: 37); a CDRL2 amino acid sequence of YAS (SEQ ID NO: 38); and a CDRL3 amino acid sequence of QQGHSFPLT (SEQ ID NO: 39);

(o) a CDRH1 amino acid sequence of GYPIWGGYS (SEQ ID NO: 59); a CDRH2 amino acid sequence of IHYSGYT (SEQ ID NO: 26); a CDRH3 amino acid sequence of ARKDSGNYFPY (SEQ ID NO: 27); a CDRL1 amino acid sequence of QSISDH (SEQ ID NO: 37); a CDRL2 amino acid sequence of YAS (SEQ ID NO: 38); and a CDRL3 amino acid sequence of QQGHSFPLT (SEQ ID NO: 39);

(p) a CDRH1 amino acid sequence of GYPIGGGYS (SEQ ID NO: 60); a CDRH2 amino acid sequence of IHYSGYT (SEQ ID NO: 26); a CDRH3 amino acid sequence of ARKDSGNYFPY (SEQ ID NO: 27); a CDRL1 amino acid sequence of QSISDH (SEQ ID NO: 37); a CDRL2 amino acid sequence of YAS (SEQ ID NO: 38); and a CDRL3 amino acid sequence of QQGHSFPLT (SEQ ID NO: 39);

(q) a CDRH1 amino acid sequence of GYSITGGYS (SEQ ID NO: 25); a CDRH2 amino acid sequence of IHYSGYT (SEQ ID NO: 26); a CDRH3 amino acid sequence of ARKDSGNYFPY (SEQ ID NO: 27); a CDRL1 amino acid sequence of QSISDH (SEQ ID NO: 37); a CDRL2 amino acid sequence of YAS (SEQ ID NO: 38); and a CDRL3 amino acid sequence of QQGNDFPVT (SEQ ID NO: 61);

(r) a CDRH1 amino acid sequence of GYSITGGYS (SEQ ID NO: 25); a CDRH2 amino acid sequence of IHYSGYT (SEQ ID NO: 26); a CDRH3 amino acid sequence of ARKDSGNYFPY (SEQ ID NO: 27); a CDRL1 amino acid sequence of QSISDH (SEQ ID NO: 37); a CDRL2 amino acid sequence of YAS (SEQ ID NO: 38); and a CDRL3 amino acid sequence of QQGYDEPFT (SEQ ID NO: 62);

(s) a CDRH1 amino acid sequence of GYSITGGYS (SEQ ID NO: 25); a CDRH2 amino acid sequence of IHYSGYT (SEQ ID NO: 26); a CDRH3 amino acid sequence of ARKDSGNYFPY (SEQ ID NO: 27); a CDRL1 amino acid sequence of QSISDH (SEQ ID NO: 37); a CDRL2 amino acid sequence of YAS (SEQ ID NO: 38); and a CDRL3 amino acid sequence of QQGYDFPLT (SEQ ID NO: 63);

(t) a CDRH1 amino acid sequence of GYSITGGYS (SEQ ID NO: 25); a CDRH2 amino acid sequence of IHYSGYT (SEQ ID NO: 26); a CDRH3 amino acid sequence of ARKDSGNYFPY (SEQ ID NO: 27); a CDRL1 amino acid sequence of QSISDH (SEQ ID NO: 37); a CDRL2 amino acid sequence of YAS (SEQ ID NO: 38); and a CDRL3 amino acid sequence of QQGYDYPLT (SEQ ID NO: 64);

(u) a CDRH1 amino acid sequence of GYSITGGYS (SEQ ID NO: 25); a CDRH2 amino acid sequence of IHYSGYT (SEQ ID NO: 26); a CDRH3 amino acid sequence of ARKDSGNYFPY (SEQ ID NO: 27); a CDRL1 amino acid sequence of QSISDH (SEQ ID NO: 37); a CDRL2 amino acid sequence of YAS (SEQ ID NO: 38); and a CDRL3 amino acid sequence of QQGYEFPLT (SEQ ID NO: 65);

(v) a CDRH1 amino acid sequence of GYPIRFGYS (SEQ ID NO: 56); a CDRH2 amino acid sequence of IHYSGYT (SEQ ID NO: 26); a CDRH3 amino acid sequence of ARKDSGNYFPY (SEQ ID NO: 27); a CDRL1 amino acid sequence of QSISDH (SEQ ID NO: 37); a CDRL2 amino acid sequence of YAS (SEQ ID NO: 38); and a CDRL3 amino acid sequence of QQGNDFPVT (SEQ ID NO: 61);

(w) a CDRH1 amino acid sequence of GYPIRFGYS (SEQ ID NO: 56); a CDRH2 amino acid sequence of IHYSGYT (SEQ ID NO: 26); a CDRH3 amino acid sequence of ARKDSGNYFPY (SEQ ID NO: 27); a CDRL1 amino acid sequence of QSISDH (SEQ ID NO: 37); a CDRL2 amino acid sequence of YAS (SEQ ID NO: 38); and a CDRL3 amino acid sequence of QQGYDFPLT (SEQ ID NO: 63);

(x) a CDRH1 amino acid sequence of GYPIRFGYS (SEQ ID NO: 56); a CDRH2 amino acid sequence of IHYSGYT (SEQ ID NO: 26); a CDRH3 amino acid sequence of ARKDSGNYFPY (SEQ ID NO: 27); a CDRL1 amino acid sequence of QSISDH (SEQ ID NO: 37); a CDRL2 amino acid sequence of YAS (SEQ ID NO: 38); and a CDRL3 amino acid sequence of QQGYDYPLT (SEQ ID NO: 64); and (y) a CDRH1 amino acid sequence of GYPIRFGYS (SEQ ID NO: 56); a CDRH2 amino acid sequence of IHYSGYT (SEQ ID NO: 26); a CDRH3 amino acid sequence of ARKDSGNYFPY (SEQ ID NO: 27); a CDRL1 amino acid sequence of QSISDH (SEQ ID NO: 37); a CDRL2 amino acid sequence of YAS (SEQ ID NO: 38); and a CDRL3 amino acid sequence of QQGYEFPLT (SEQ ID NO: 65).

* * * * *